US009605243B2

(12) United States Patent
D'Amour et al.

(10) Patent No.: US 9,605,243 B2
(45) Date of Patent: Mar. 28, 2017

(54) MARKERS OF DEFINITIVE ENDODERM

(71) Applicant: ViaCyte, Inc., San Diego, CA (US)

(72) Inventors: Kevin Allen D'Amour, San Diego, CA (US); Alan D. Agulnick, San Diego, CA (US); Emmanuel Edward Baetge, Encinitas, CA (US)

(73) Assignee: ViaCyte, Inc., San Diego, CA (US)

( * ) Notice: Subject to any disclaimer, the term of this patent is extended or adjusted under 35 U.S.C. 154(b) by 0 days.

(21) Appl. No.: 14/066,441

(22) Filed: Oct. 29, 2013

(65) Prior Publication Data

US 2014/0134726 A1   May 15, 2014

Related U.S. Application Data

(63) Continuation of application No. 12/093,590, filed as application No. PCT/US2006/043932 on Nov. 13, 2006, now Pat. No. 8,586,357, and a continuation-in-part of application No. 11/021,618, filed on Dec. 23, 2004, now Pat. No. 7,510,876.

(60) Provisional application No. 60/736,598, filed on Nov. 14, 2005, provisional application No. 60/532,004, filed on Dec. 23, 2003, provisional application No. 60/586,566, filed on Jul. 9, 2004, provisional application No. 60/587,942, filed on Jul. 14, 2004.

(51) Int. Cl.
*C12N 5/00* (2006.01)
*C12N 5/071* (2010.01)
*C12N 5/073* (2010.01)

(52) U.S. Cl.
CPC ......... *C12N 5/0617* (2013.01); *C12N 5/0603* (2013.01); *C12N 2501/16* (2013.01)

(58) Field of Classification Search
CPC .................................................. C12N 5/0617
USPC ........................................................ 435/377
See application file for complete search history.

(56) References Cited

U.S. PATENT DOCUMENTS

| 4,683,195 | A | 7/1987 | Mullis |
| 4,683,202 | A | 7/1987 | Mullis |
| 4,816,567 | A | 3/1989 | Cabilly et al. |
| 5,453,357 | A | 9/1995 | Hogan |
| 5,670,372 | A | 9/1997 | Hogan |
| 5,690,926 | A | 11/1997 | Hogan |
| 5,817,637 | A | 10/1998 | Weiner et al. |
| 5,830,876 | A | 11/1998 | Weiner et al. |
| 5,843,780 | A | 12/1998 | Thomson |
| 5,866,366 | A | 2/1999 | Kallender |
| 5,869,620 | A | 2/1999 | Whitlow et al. |
| 6,015,671 | A | 1/2000 | Field |
| 6,090,592 | A | 7/2000 | Adams et al. |
| 6,090,622 | A | 7/2000 | Gearhart et al. |
| 6,117,635 | A | 9/2000 | Nazarenko et al. |
| 6,117,986 | A | 9/2000 | Nardone et al. |
| 6,165,993 | A | 12/2000 | Herrmann et al. |
| 6,200,806 | B1 | 3/2001 | Thomson |
| 6,251,671 | B1 | 6/2001 | Hogan et al. |
| 6,261,281 | B1 | 7/2001 | Mathiesen et al. |
| 6,458,589 | B1 | 10/2002 | Rambhatla et al. |
| 6,506,574 | B1 | 1/2003 | Rambhatla et al. |
| 6,872,389 | B1 | 3/2005 | Faris |
| 6,921,811 | B2 | 7/2005 | Zamora et al. |
| 7,033,831 | B2 | 4/2006 | Fisk et al. |
| 7,153,684 | B1 | 12/2006 | Hogan |
| 7,256,042 | B2 | 8/2007 | Rambhatla et al. |
| 7,326,572 | B2 | 2/2008 | Fisk et al. |
| 7,510,876 | B2 | 3/2009 | D'Amour et al. |
| 7,534,608 | B2 | 5/2009 | Martinson et al. |
| 7,541,185 | B2 | 6/2009 | D'Amour et al. |
| 8,586,357 | B2 | 11/2013 | D'Amour et al. |
| 2002/0072117 | A1 | 6/2002 | Xu et al. |
| 2002/0090723 | A1 | 7/2002 | Carpenter et al. |
| 2003/0138948 | A1 | 7/2003 | Fisk et al. |
| 2003/0138949 | A1 | 7/2003 | Bhushan et al. |
| 2003/0175956 | A1 | 9/2003 | Bodnar et al. |
| 2003/0190748 | A1 | 10/2003 | Thomson |
| 2003/0224411 | A1 | 12/2003 | Stanton et al. |
| 2004/0127406 | A1 | 7/2004 | Presnell et al. |
| 2004/0229350 | A1 | 11/2004 | Strelchenko et al. |
| 2005/0079159 | A1 | 4/2005 | Shastri et al. |
| 2005/0158853 | A1 | 7/2005 | D'Amour et al. |
| 2006/0003446 | A1 | 1/2006 | Keller et al. |
| 2006/0019387 | A1 | 1/2006 | Faris |
| 2006/0040385 | A1 | 2/2006 | Itskovitz-Eldor et al. |
| 2006/0040387 | A1 | 2/2006 | Fisk et al. |
| 2006/0128018 | A1 | 6/2006 | Zwaka et al. |
| 2006/0148081 | A1 | 7/2006 | Kelly et al. |
| 2006/0276420 | A1 | 12/2006 | Keller et al. |

(Continued)

FOREIGN PATENT DOCUMENTS

EP   0 543 942       6/1993
EP   1 298 201 A     4/2003

(Continued)

OTHER PUBLICATIONS

Hoshi et al. (2007, Endocrinology, vol. 148(9), pp. 4251-4258).*
Armelin HA., (1973, PNAS, vol. 70(9), pp. 2702-2706).*
Smolich et al., (1993, Mol. Biol. Cell, vol. 4, pp. 1267-1275).*
Fayet et al. (2002, Thyroid, vol. 12(7), pp. 539-546).*
2008, Ireland KA., Visualizing Human Biology, 3rd Ed., Wiley and Sons Inc., 3 pages total.*
Reubinoff et al. (2000, Nature Biotechnology, vol. 18, pp. 399-404).*

(Continued)

*Primary Examiner* — Thaian N Ton
*Assistant Examiner* — David A Montanari
(74) *Attorney, Agent, or Firm* — Klarquist Sparkman, LLP

(57) ABSTRACT

Disclosed herein are reagent-cell complexes comprising one or more definitive endoderm cells. Also described herein are compositions for detecting definitive endoderm. Method of enriching, isolating and/or purifying definitive endoderm cells are also disclosed.

2 Claims, 38 Drawing Sheets

(56) References Cited

U.S. PATENT DOCUMENTS

| | | |
|---|---|---|
| 2007/0154984 A1 | 7/2007 | D'Amour et al. |
| 2007/0281355 A1 | 12/2007 | Dalton et al. |
| 2009/0253202 A1 | 10/2009 | D'Amour et al. |

FOREIGN PATENT DOCUMENTS

| | | |
|---|---|---|
| EP | 1 627 912 | 2/2006 |
| JP | 2004504834 | 2/2004 |
| WO | WO 98/18943 | 5/1998 |
| WO | WO 98/30679 | 7/1998 |
| WO | WO 99/13915 | 3/1999 |
| WO | WO 00/29442 | 5/2000 |
| WO | WO 02/10347 | 2/2002 |
| WO | WO 02/34880 | 5/2002 |
| WO | WO 02/059278 | 8/2002 |
| WO | WO 03/050249 | 6/2003 |
| WO | WO 03/100026 | 12/2003 |
| WO | WO 2004/098490 | 11/2004 |
| WO | WO 2005/017131 | 2/2005 |
| WO | WO 2005/033294 | 4/2005 |
| WO | WO 2005/045001 | 5/2005 |
| WO | WO 2005/063971 | 7/2005 |
| WO | WO 2005/097977 | 10/2005 |
| WO | WO 2005/097980 A2 | 10/2005 |
| WO | WO 2005/116073 | 12/2005 |
| WO | WO 2006/016999 | 2/2006 |
| WO | WO 2006/017134 | 2/2006 |
| WO | WO 2006/020919 | 2/2006 |
| WO | WO 2006/034873 | 4/2006 |
| WO | WO 2006/083782 | 8/2006 |
| WO | WO 2007/002210 A2 | 1/2007 |
| WO | WO-2007/059007 A2 | 5/2007 |
| WO | WO-2007/059007 A3 | 5/2007 |
| WO | WO 2007/088372 | 8/2007 |

OTHER PUBLICATIONS

Reijo et al. (2009, Differentiation, vol. 78, pp. 18-23).*
Van den Wijngaard et al. (1995, Genomics, vol. 27, pp. 559-560).*
D'Amour et al. (e-Published Oct. 28, 2005, Nature Biotechnology, vol. 23(12), pp. 1534-1541).*
Serls et al. (Jan. 2005, Development, vol. 132, pp. 35-47).*
Abe K et al., "Endoderm-Specific Gene Expression in Embryonic Stem Cells Differentiated to Embryoid Bodies." Experimental Cell Research. vol. 229. No. 1, p. 27-34, 1996.
Activin A, Product Information from SIGMA-Aldrich.
Alexander, J., and Stainier, D.Y. (1999). A molecular pathway leading to endoderm formation in zebrafish. Curr Biol 9, 1147-1157.
Alexander, J., Rothenberg, M., Henry, G.L., and Stainier, D.Y. (1999). Casanova plays an early and essential role in endoderm formation in zebrafish. Dev Biol 215, 343-357.
Ang et al., "HNF-3beta is essential for node and notochord formation in mouse development," Cell, (1994) 78:561-574.
Ang et al., "The Formation and Maintenance of the Definitive Endoderm Lineage in the Mouse: Involvement of HNF3/forkhead Proteins." Development, 119:1301-1315. (1993).
Aoki, T.O., Mathieu, J., Saint-Etienne, L., Rebagliati, M.R., Peurieras, N., and Rosa, F. M. (2002). Regulation of nodal signalling and mesendoderm formation by TARAM-A, a TGFbeta-related type I receptor. Dev Biol 241, 273-288.
Arnold et al., "Brachyury is a target gene of the Wnt/beta-catenin signaling pathway," Mech. Dev., (2000) 91:249-258.
Assady et al., "Insulin production by human embryonic stem cells," Diabetes (2001) 50(8): 1691-7.
Bachiller et al., "The organizer factors chordin and noggin are required for mouse forebrain development," Nature, (2000) 403:658-661.
Bain et al., "Embryonic Stem Cells Express Neuronal Properties in Vitro." Developmental Biology. 168:342-357 (1995).
Barbacci, et al. "Variant Hepatocyte Nuclear Factor 1 Is Required for Visceral Endoderm Specification" (1999) Development 126:4795-4805.

Barringer et al., "Blunt-end and single-strand ligations by Escherichia coli ligase: influence on an in vitro amplification schemem," Gene, (1990) 89(1):117-22.
Barry et al. "Production of monoclonal antibodies by genetic immunization." Biotechniques 16 : 616-620. (1994).
Battle et al., "The transcription factor snail is a repressor of E-cadherin gene expression in epithelial tumour cells," Nat. Cell. Biol., (2000) 2:84-89.
Beck, S., Le Good, J.A., Guzman, M., Ben Haim, N., Roy, K., Beermann, F., and Constam, D.B. (2002). Extra-embryonic proteases regulate Nodal signaling during gastrulation. Nat Cell Biol 4, 981-985.
Beddington, R.S., Rashbass, P., and Wilson, V. (1992). Brachyury—a gene affecting mouse gastrulation and easly organogenesis. Dev Suppl, 157-165.
Bendall et al., "IGF and FGF cooperatively establish regulatory stem cell niche of pluripotent human cells in vitro," Nature (2007) 448:1015-1021.
Blum et al., "Gastrulation in the mouse: the role of the homebox gene igoosecoid," Cell, (1992) 69:1097-1106.
Bongso, A., Fong, C.Y., Ng, S.C., and Ratnam, S. (1994). Isolation and culture of inner cell mass cells from human blastocysts. Hum Reprod 9, 2110-2117.
Bordonaro et al., "Cell type—a promoter-dependent modulation of the Wnt signaling pathway by sodium butyrate," Int. J. Cancer (2002) 97(1):42-51.
Bost et al., "Retinoic Acid Activation of the ERK Pathway is Required for Embryonic Stem Cell Commitment into the Adipocyte Lineage." Biochem. J. 361:621-627. (2002).
Brennan et al., "Nodal signalling in the epiblast patterns the early mouse embryo," Nature, (2001) 411:965-969.
Brunt, "Amplifying genes: PCR and its alternatives," Biotechnology, (1990) 8(4):291-4.
Candia et al., "Differential localization of mox-1 and mox-2 proteins indicates distinct roles during development," Int. J. Dev. Biol. (1996), 40:1179-1184.
Candia et al., "Mox-1 and Mox-2 define a novel homeobox gene subfamily and are differentially expressed during early mesodermal patterning in mouse embryos," Development (1992), 116:783-797.
Cereghini, et al. "Expression Patterns of vHNF1 and HNF1 Homeoproteins in Early Postimplantation Embryos Suggest Distinct and Sequential Developmental Roles" (1992) Development 116:783-797.
Chang, H., Brown, C.W., and Matzuk, M.M (2002). Genetic analysis of the mammalian transforming growth factor-beta superfamily. Endocr Rev 23, 787-823.
Chen et al., "Retinoic acid signaling is essential for pancreas development and promotes endocrine at the expense of exocrine cell differentiation in xenopus," Developmental Biology, (2004) 271:144-160.
Chen et al., "Suppression of ES cell differentiation by retinol (vitamin A) via the overexpression of Nanog," Differentiation (2007) 75(8):682-93.
Chin et al., "Induced pluripotent stem cells and embryonic stem cells are distinguished by gene expression signatures," Cell Stem Cell (2009) 5(1):111-23.
Ciani et al., "WNTs in the vertebrate nervous system: from patterning to neuronal connectivity," Nat. Rev. Neurosci. (2005) 6(5):351-62.
Ciruna et al., "Chimeric analysis of fibroblast growth factor receptor-1 (Fgfr1) Function: a role for FGFR1 in morphogenetic movement through the primitive streak," Development, (1997) 124:2829-2841.
Ciruna et al., "FGF signaling regulates mesoderm cell fate specification and morphogenetic movement at the primitive streak," Development, (1997) 124:2829-2841.
Clackson et al., "Making antibody fragments using phage display libraries," Nature, (1991) 352(6336):624-8.
Collombat et al., "Specifying pancreatic endocrine cell fates," Mech. Dev. (2006) 123(7):501-12.
Conley et al. "Bmps Regulate Differentiation of a Putative Visceral Endoderm Layer Within Human Embryonic Stem-Cell-Derived Embryoid Bodies" (2007) Biochem Cell Biol 85: 121-132.

(56) References Cited

OTHER PUBLICATIONS

Conlon, F.L., Lyons, K.M., Takaesu, N., Barth, K.S., Kispert, A., Herrmann, B., and Robertson, E.J. (1994). A primary requirement for nodal in the formation and maintenance of the primitive streak in the mouse. Development 120, 1919-1928.

Costagliola et al. (1998) Genetic immunization against the human thyrotropin receptor causes thyroiditis and allows production of monoclonal antibodies recognizing the native receptor. J. Immunol. 160: 1458-1465.

Czyz et al. "Embryonic Stem Cell Differentiation: The Role of Extracellular Factors" (2001)Differentiation 68(4-5):167-174.

Daheron et al. "LIF/STAT3 Signaling Fails to Maintain Self-Renewal of Human Embryonic Stem Cells" Stem Cells 22, 770-8 (2004).

D'Amour et al. "Production of Pancreatic Hormone-Expressing Endocrine Cells From Human Embryonic Stem Cells" (Nov. 1, 2006) Nature Biotechnology 24, 1392-1401.

D'Amour, et al., "Efficient Differentiation of Human Embryonic Stem Cells to Definitive Endoderm" *Nature Biotechnology* (2005) 23(12): 1534-1541.

Dang et al., "Controlled, scalable embryonic stem cell differentiation culture," Stem Cells, (2004) 22:275-282.

Dani et al., "Differentiation of Embryonic Stem Cells into Adipocytes in Vitro." Journal of Cell Science. 110:1279-1285. (1997).

Database UniProt, "1-acyl-sn-glycerol-3-phosphate acyltransferase gmma (EC 2.3.1.51) (1-AGP acyltransferase 3) (1-AGPAT 3) (Lyspohosphatidic acid acyltransfearse gamma) (LPAAT-gamma) (1-acylglycerol-3-phosphate 0-acyltransfearse 3)" retrieved from EBI accession No. UNIPROT: Q9NRZ7 on Oct. 1, 2000.

De Caestecker, "The transforming growth factor-beta superfamily of receptors," *Cytokine Growth Factor* (2004) Rev 15:1-11.

Defelice Mario et al., "TTF-1 Phosphorylation is required for peripheral lung Morphogenesis, Perinatal Survival, and Tissue-Specific Gene Expression." The Journal of Biological Chemistry. 278:37, pp. 35574-35583. (2003).

Dougan, S.T., Warga, R.M., Kane, D.A., Schier, A.F., and Talbot, W.S. (2003). The role of the zebrafish nodal-related genes squint and Cyclops in patterning of mesendoderm. Development 130, 1837-1851.

Dudas et al., "The homeobox transcription factor Prox1 is highly conserved in embryonic hepatoblasts and in adult and transformed hepatocytes, but is absent from bile duct epithelium," *Ant. Embryol. (Berl.)* (2004).

Edlund, H., "Factors Controlling Pancreatic Cell Differentiation and Function," Diabetologia, Sep. 2001, vol. 44, No. 9, pp. 1071-1079.

Elghanian et al., "Selective Colorimetric Detection of Polynucleotides Based on the Distance-Dependent Optical Properties of Gold Nanoparticles," *Science*, (1997) 277(5329):1078-1081.

Elms et al., "Overlapping and distinct expression domain of Zic2 and Zic3 during mouse gastrulation," *Gene Expression Patterns*, (2004) 4:505-511.

Falasca, L. et al., "Retinoic Acid Treatment Induces Apoptosis or Expression of a More Differentiated Phenotype on Different Fractions of Cultured Fetal Rat Hepatocytes," Hepatology, 1998, vol. 28, No. 3, pp. 727-737.

Fehling et al., "Development and Disease: Tracking Mesoderm Induction and its Specification to the Hemangioblast during Embryonic Stem Cell Differentiation." Development. 130:4217-4227. (2003).

Feldman, B., Gates, M.A., Egan, E.S., Dougan, S.T., Rennebeck, G., Sirotkin, H. I., Schier, A.F., and Talbot, W.S. (1998). Zebrafish organizer development and germ-layer formation require nodal-related signals. Nature 395, 181-185.

Feng, Y., Broder, C.C., Kennedy, P.E., and Berger, E.A. (1996). HIV-1 entry cofactor: functional cDNA cloning of a seven-transmembrane, G protein-coupled receptor. Science 272, 872-877.

Freund, et al., "Insulin redirect differentiation from cardiogenic mesoderm and endoderm to neuroectoderm in differentiating human embryonic stem cells," *Stem Cells* (2007), published online Dec. 20, 2007.

Futaki, S., Hayashi, Y., Yamashita, M., Yagi, K., Bono, H., Hayashizaki, Y., Okazaki, Y., and Sekiguchi, K. (2003). Molecular basis of constitutive production of basement membrane components: Gene expression profiles of engelbreth-holm-swarm tumor and F9 embryonal carcinoma cells. J Biol. Chem.

Gardner, "Stem cells and regenerative medicine: principles, prospects and problems," *C.R. Biol.* (2007) 330(6-7):465-73.

Goumans et al., "Mouse Embryonic Stem Cells with Aberrant Transforming Growth Factor Beta signaling Exhibit Impaired Differentiation in Vitro and In Vivo." Differentiation. 63:103-113. (1998).

Grapin-Botton, A., and Melton, D. A. (2000). Endoderm development: from patterning to organogenesis. Trends Genet 16, 124-130.

Guatelli et al., "Isothermal, in vitro amplification of nucleic acids by a multienzyme reaction modeled after retroviral replication," *Proc. Natl. Acad. Sci. USA*, (1990) 87(5):1874-8.

Gupta et al., "Pharmacological evidence for complex and multiple site interaction of CXCR4 with SDF-1alpha: implications for development of selective CXCR4 antagonists", Immunol. Lett., (2001), 78(1):29-34.

Haegel, et al., "Lack of β-catenin Affects Mouse Development at Gastrulation" *Development* (1995) 121: 3529-3537.

Hallonet, et al., "Maintenance of the Specification of the Anterior Definitive Endoderm and Forebrain Depends on the Axial Mesendoderm: A Study Using HNF3β/Foxa2 Conditional Mutants" *Dev Biol* (2002) 243: 20-33.

Hamazaki et al. "Hepatic Maturation in Differentiating Embryonic Stem Cells in Vitro." Febs Letter, Elsevier Science Publishers, Amsterdam, NL, vol. 497, No. 1: 15-19.

Hansson, et al. "Artifactual Insulin Release from Differentiated Embryonic Stem Cells" (2004) Diabetes 53:2603-2609.

Harris, T. M., and Childs, G. (2002). Global gene expression patterns during differentiation of F9 embryonal carcinoma cells into parietal endoderm. Funct Integr Geneomics 2, 105-119.

Harrison, et al., "Pancreas Dorsal Lobe Agenesis and Abnormal Islets of Langerhans in Hlxb9-deficient Mice" *Nature Genetics* (1999) 23: 71-75.

Haumaitre, et al. "Functions of HNF1 Family Members in Differentiation of the Visceral Endoderm Cell Lineage" (2003) J. Biol. Chem. 278 (42): 40933-40942.

Henry, et al., "Mixer, a Homeobox Gene Required for Endoderm Development" *Science* (1998) 281: 91-96.

Herrmann, et al., "Cloning of the T Gene Required in Mesoderm Formation in the Mouse" *Nature* (1990) 343: 617-622.

Hogan, B.L. (1996). Bone morphogenetic proteins in development. Curr Opin Genet Dev 6, 432-438.

Holland et al., "Experimental control of pancreatic development and maintenance," Proc Natl Acad Sci USA (2002) 99(19):12 236-12 241.

Houard, N., et al. "HNF-6-Independent Differentiation of Mouse Embryonic Stem Cells into Insulin-Producing Cells" (2003) Diabetologia 46:378-385.

Houde et al., "Intestinal epithelial cell differentiation involves activation of p38 mitogen-activated protein kinase that regulates the homeobox transcription factor CDX2," *J. Biol. Chem.* (2005) 276(24):21885-94.

Howe, C.C., Overton, G.C., Sawicki, J., Solter, D., Stein, P., and Strickland, S. (1988). Expression of SPARC/osteonectin transcript in murine embryos and gonads. Differentiation 37, 20-25.

Hudson, C., Clements, D., Friday, R. V., Stott, D., and Woodland, H.R. (1997). Xsox17alpha and -beta mediate endoderm formation in Xenopus. Cell 91, 397-405.

Huelsken, et al., "Requirement for β-Catenin in Anterior-Posterior Axis Formation in Mice" *J Cell Biol* (2000) 148: 567-578.

Humphrey et al. "Maintenance of Pluripotency in Human Embryonic Stem Cells is STAT3 Independent" (2004) Stem Cells 22: 522-30.

(56) References Cited

OTHER PUBLICATIONS

Imada, M., Imada, S., Iwasaki, H., Kume, A., Yamaguchi, H., and Moore, E.E. (1987). Fetomodulin: Marker surface protein of fetal development which is modulatable by cyclic AMP. Dev Biol 122, 483-491.

International Search Report and Written Opinion issued in PCT/US2006/043932, mailed Jul. 6, 2007.

Itskovitz-Eldor, et al., Differentiation of Human Embryonic Stem Cells into Embryoid Bodies Comprising the Three Embryonic Germ Layers, Molecular Medicine, 6, 88-95, 2000.

Jain, K. et al., "Glucose Control and Long-Term Survival in Breeding/Worcester Rats After Intraperitoneal Implantation of Hydrophilic Macrobeads containing Porcine Islets without Immunosuppression," Transplantation, 1999, vol. 68, No. 11, pp. 1693-1700.

Johannesson et al., "FGF4 and retionic acid direct differentiation of hESCs into PDX-1 expressing foregut endoderm in a time and concentration-dependent manner," *PLoS One* (2009) 4(3):e4794.

Jones et al. "Differences Between Human and Mouse Alpha-Fetoprotein Expression During Early Development" (2001) J. Anat. 198: 555-9.

Jonsson, J., et al., "Insulin-promoter-factor 1 is required for pancreas development in mice", Nature, vol. 371. pp. 606-609, (1994).

Kahan, B.W., et al. "Pancreatic Precursors and Differentiated Islet Cell Types from Murine Embryonic Stem Cells: An In Vitro Model to Study Islet Differentiation." Diabetes. Aug. 2003, vol. 52, No. 8, pp. 2016-2024.

Kalinichenko, et al., "The Forkhead Box F1 Transcription Factor is Expressed in Brain and Head Mesenchyme During Mouse Embryonic Development" Gene Expr Patterns (2003) 3: 153-158.

Kanai-Azuma, M., Kanai, Y., Gad, J.M., Tajima, Y., Taya, C., Kurohmaru, M., Sanai, Y., Yonekawa, H., Yazaki, K., Tam, P.P., and Hayashi, Y. (2002). Depletion of definitive gut endoderm in Sox17-null mutant mice. Development 129, 2367-2379.

Katoh, M. (2002). Expression of human SOX7 in normal tissues and tumors. Int J Mol Med 9, 363-368.

Kawahira, et al., "Hedghog Signaling Regulates Expansion of Pancreatic Epithelial Cells" *Developmental Biology* (2005) 280: 111-121.

Kawaji, et al., "Exploration of Novel Motifs Derived from Mouse cDNA Sequences" *Genome Research* (2002) 12: 367-378.

Keller GM, "In vitro differentiation of embryonic stem cells," Curr Op Cell Biol (1995) 7:862-869.

Khoo, et al., "Growth and Differentiation of Embryoid Bodies Derived from Human Embryonic Stem Cells: Effect of Glucose and Basic Fibroblast Growth Factor", Biology of Reproduction (2005) 73: 1147-1156.

Kieffer, T.J., and J.F. Habener, "The Glucagon-Like Peptides," Endocrinology Reviews, Dec. 1999, vol. 20, No. 6, pp. 876-913.

Kikuchi, Y., Agathon, A., Alexander, J., Thisse, C., Waldron, S., Yelon, D., Thisse, B., and Stainier, D.Y. (2001). Casanova encodes a novel Sox-related protein necessary and sufficient for early endoderm formation in zebrafish. Genes Dev 15, 1493-1505.

Kilpatrick et al. (1998). Gene gun delivered DNA-based immunizations mediate rapid production of murine monoclonal antibodies to the Flt-3 receptor. Hybridoma 17: 569-576.

Kim, C.H., and Brozmeyer, H.E. (1999). Chemokines: signal lamps for trafficking of T and B cells for development and effector function. J Leukoc Biol 65, 6-15.

Kim, et al., Pancreas development is promoted by cyclopamine, a Hedgehog signaling inhibitor, Proc. Natl. Acad. Sci. USA vol. 95, pp. 13036-13041, Oct. 1998.

Kimelman, D., and Griffin, K. J. (2000). Vertebrae mesendoderm induction and patterning, Curr Opin Genet Dev 10, 350-356.

Kimmel et al., "Preparation of cDNA and the generation of cDNA libraries: overview," *Methods Enzymol.*, (1987) 152:307-16.

Kinder, et al., "The Organizer of the Mouse Gastrula is Composed of a Dynamic Population of Progenitor Cells for the Axial Mesoderm" Development (2001) 128: 3623-3634.

Köhler et al., "Continuous cultures of fused cells secreting antibody of predefined specificity," Nature, (1975) 256(5517):495-7.

Krasemann et al. (1999). Generation of monoclonal antibodies against proteins with an unconventional nucleic acid-based immunization strategy. J. Biotechnol. 73: 119-129.

Kubo, A., Shinozaki, K., Shannon, J. M., Kouskoff, V., Kennedy, M., Woo, S., Fehlong, H.J., and Keller, G. (2004). Development of definitive endoderm from embryonic stem cells in culture. Development 131, 1651-1652.

Kumar, A., Novoselov, V., Celeste, A. J., Wolfman, N.M., ten Dijke, P., and Kuehn, M. R. (2001). Nodal signaling uses activin and transforming growth factor-beta receptor-regulated Smads. J Biol Chem 276, 656-661.

Kuo et al., "Roles of histone acetyltransferases and deacetylases in gene regulation", *BioEssays*, (1998) 20:615-626.

Kwoh et al., "Transcription-based amplification system and detection of amplified human immunodeficiency virus type 1 with a bead-based sandwich hybridization format," *Proc. Natl. Acad. Sci. USA*, (1989) 86(4):1173-7.

Labosky, P.A., Barlow, D. P., and Hogan, B. L. (1994). Embryonic germ cell lines and their derivation from mouse primordial germ cells. Ciba Found Symp 182, 157-168; discussion 168-178.

Labosky, P.A., Barlow, D. P., and Hogan, B. L. (1994). Mourse embryonic germ (EG) cell lines: transmission through the germline and differences in the methylation imprint of insulin-like growth factor 2 receptor (Igf2r) gene compared with embryonic stem (ES) cell lines. Development 120, 3197-3204.

Landegren et al., "A ligase-mediated gene detection technique," *Science*, (1988) 241(4869):1077-80.

Latif, Z.A. et al., "A Simple Method of Staining Fresh and Cultured Islets," Transplantation, 1998, vol. 45, No. 4, pp. 827-830.

Lawson, et al., "Bmp4 is Required for the Generation of Primordial Germ Cells in the Mouse Embryo" Genes Dev (1999) 13: 424-436.

Lickert, H., Kutsch, S., Kanzler, B., Tamai, Y., Taketo, M.M., and Kemler, R. (2002). Formation of multiple hearts in mice following deletion of beta-catenin in the embryonic endoderm. Dev Cell 3, 171-181.

Liu, et al., "Requirement for Wnt3 in Vertebrate Axis Formation" Nat Genet (1999) 22: 361-365.

Loebel et al., "A gut feeling," *Nat. Biotechnol.* (2005) 23(12):1491-2.

Loebel et al., "Lineage choice and differentiation in mouse embryos and embryonic stem cells," Developmental Biology 264 pp. 1-14 Dec. 2003.

Lomell et al., "Quantitative assays based on the use of replicatable hybridization probes," *J. Clin. Chem.*, (1989) 35(9):1826-31.

Lowe et al., "Genetic dissection of nodal function in patterning the mouse embryo," *Development*, (2001) 128:1831-1843.

Lu, C.C., Brennanm J., and Robortson, E. J., (2001). From fertilization to gastrulation: axis formation in the mouse embryo. Curr Opin Genet Dev 11, 384-392.

Lumelsky, N. et al., "Differentiation of Embryonic Stem Cells to Insulin-Secreting Structures Similar to Pancreatic Islets," Science vol. 292, pp. 1389-1394 (2001).

Ma, Q., Jones, D., and Springer, T. A. (1999). The chemokine receptor CXCR4 is required for the retention of B lineage and granulocytic precursors within the bone marrow microenvironment, Immunity 10, 463-471.

Mark et al., "Function of retinoid nuclear receptors: lessons from genetic and pharmacological dissections of the retinoic acid signaling pathway during mouse embryogenesis," *Annu. Rev. Pharmacol. Toxicol.* (2006) 46:451-80.

Martin, et al., "Dorsal Pancreas Agenesis in Retinoic Acid-Deficient Raldh2 Mutant Mice" Developmental Biology (2005) 284: 399-411.

Maruoka, et al., "Comparison of the Expression of Three Highly Related Genes, Fgf8, Fgf17 and Fgf18, in the Mouse Embryo" Mech Dev (1998) 74: 175-177.

Matsuda T, et al. "STAT3 Activation is Sufficient to Maintain an Undifferentiated State of Mouse Embryonic Stem Cells" (Aug. 2, 1999) EMBO J, 18(15):4261-9.

McGrath et al. "Expression of Homeobox Genes, Including and Insulin Promoting Factor, in the Murine Yolk Sac at the Time of Hematopoietic Initiation" (1997) Mol Reprod Dev 48: 145-153.

(56) References Cited

OTHER PUBLICATIONS

McGrath, K.E., Koniski, A. D., Maltby, K. M., McGann, J.K. And Palis, J. (1999). Embryonic expression and function of the chemokine SDF-1 and its receptor, CXCR4. Dev Biol. 213, 442-456.

McLean et al. "Activin A Efficiently Specifies Definitive Endoderm from Human Embryonic Stem Cells Only When Phosphtidylinositol 3-Kinase Signaling Is Suppressed" (2007) Stem Cells 25: 29-38.

Micallef Suzanne, et al. "Retinoic Acid Induces Pdx1-positive Endoderm in Differentiating mouse embryonic stem cells." Diabetes. Feb. 2005, vol. 54, No. 2, pp. 301-305.

Millonig, et al. "Molecular Analysis of the Distal Enhancer of the Mouse Alpha-Fetoprotein Gene" (1995) Mol. Cell Biol. 15: 3848-3856.

Milne, et al. "Generation of Insulin-Expressing Cells from Mouse Embryonic Stem Cells" (2005) Biochemical and Biophysical Research Communications 328:399-403.

Miyazono. K., Kusanagi, K., and Inoue, H. (2001). Divergence and convergenence of TGF-beta/BMP signaling. J Cell Physiol 187, 265-276.

Mizusawa et al., "Differentiation Phenotypes of Pancreatic Islet Beta- and Alpha-Cells are Closely Related with Homeotic Genes and a Group of Defferentially Expressed Genes." Gene: An Int. Journal on Genes and Genomes. 331:53-63. (2004).

Molotkov, et al., "Retinoic Acid Generated by Raldh2 in Mesoderm Is Required for Mouse Dorsal Endodermal Pancreas Development" Development Dynamics (2005) 232: 950-957.

Moriya, N. et al., "In Vitro Pancreas Formation from Xenopus Ectoderm Treated with Activin and Retinoic Acid," Develop. Growth Differ., vol. 42, pp. 593-602 (2000).

Nagai, et al., "The Expression of the Mouse Zic1, Zic2, and Zic3 Gene Suggests an Essential Role for Zic Genes in Body Pattern Formation" Dev Biol (1997) 182: 299-313.

Nagasawa, T., Hirota, S., Tachibaba, K., Takakura, N., Nichikawa, S., Kitamura, Y., Yoshida, N., Kikutani, H., and Kishimito, T. (1996). Defects of B-cell lymphopoiesis and bone-marrow myelopoiesis in mice lacking the CXC chemokine PBSF/SDF-1. Nature 382, 635-638.

Nakagawa, et al., "Recruitment and Activation of Rac1 by the Formation of E-cadherin-mediated Cell-cell Adhesion Sites" J. Cell Science (2001) 114(10): 1829-1838.

Nieto, et al., "Cloning and Developmental Expression of Sna, a Murine Homologue of the *Drosophila* snail Gene" Development (1992) 116: 227-237.

Nieto, M.A., The Snail Superfamily of Zinc-Finger Transcription Factors Nat Rev Mol Cell Biol (2002) 3: 155-166.

Niimi, et al. "SOX7 and SOX17 Regulate the Parietal Endoderm-Specific Enhancer Activity of Mouse Laminin Alpha1 Gene." (2004) J. Biol. Chem. 279 (36): 38055-38061.

Niswander, L. & Martin, G.R., "Fgf-4 Expression During Gastrulation, Myogenesis, Limb and Tooth Development in the Mouse" Development (1992) 114: 755-768.

Niwa, H. (2001). Molecular mechanism to maintain stem cell renewal of ES cells. Cell Struct Funct 26, 137-148.

O'Hare, M.J. et al., "Conditional Immortilization of Freshly Isolated Human Mammary Fibroblast and Endothelial Cells," Proc. Nat. Acad. Sci., vol. 98, pp. 646-651 (2001).

Offield, et al., "PDX-1 is Required for Pancreatic Outgrowth and Differentiation of the Rostral Duodenum" Development (1996) 122: 983-995.

Ogura, H., Aruga, J., and Mikoshiba, K. (2001). Behavioral abnormalities of Zic1 and Zic2 mutant mice: implications as models for human neurological disorders, Behav Genet 31,317-324.

Ohlsson et al., "Embryonic stem cells express growth hormone receptors: regulation by retenoic acid," *Endocrinology* (1993) 133(6):2897-2903.

Ormestad, et al., "Differences in the Embryonic Expression Patterns of Mouse Foxf1 and -2 Match Their Distinct Mutant Phenotypes" Developmental Dynamics (2004) 229: 328-333.

Pearce, J.J. & Evans, M.J., "Mml, a Mouse Mix-like Gene Expressed in the Primitive Streak" Mech Dev (1999) 87: 189-192.

Pera, et al., "Regulation of Human Embryonic Stem Cell Differentiation by BMP-2 and its Antagonist Noggin" J Cell Sci (2004) 117: 1269-1280.

Perea-Gomez, et al., "Initiation of Gastrulation in the Mouse Embryo is Preceded by an Apparent Shift in the Orientation of the Anterior-Posterior Axis" Curr Biol (2004) 14: 197-207.

Pesce, M. & Scholer, H.R., "Oct-4: Gatekeeper in the Beginnings of Mammalian Development" Stem Cells (2001) 19: 271-278.

Pevny, et al., "A Role for SOX1 in Neural Determination" Development (1998) 125: 1967-1978.

Phillips et al., "Differentiation of Embryonic Stem Cells for Pharmacological Studies on Adipose Cells." Pharmacological Research. 47:263-268. (2003).

Price et al., "Serum-free media for neural cell cultures," *Protocols for Neural Cell Culture, 3rd Ed.*, Fedoroff and Richardson (Eds.) Humana Press, Totowa, New Jersey 255-264.

Rajagopal, et al. "Insulin Staining of ES Cell Progeny from Insulin Uptake" (2003) Science 299:363.

Rambhatla et al., "Generation of hepatocyte-like celIIs from human embryonic stem cells," *Cell Transplantation* (2003) 12:1-11.

Ramiya et al., "Reversal of insulin-dependent diabetes using islets generated in vitro from pancreatic stem cells," *Nature Medicine* (2000) 6:278-282.

Reubinoff, B.E., Pera, M.F., Fong, C.Y. Tounson, A., and Bongso, A. (2000). Embryonic stem cell lines from human blastocysts: somatic differentiation in vitro. Nat Biotechnol 18, 399-404.

Reue, "mRNA quantitation techniques: considerations for experimental design and application," *The Journal of Nutrition*, (1998) 128(11):2038-2044.

Robb, L. & Tam, P.P., "Gastrula Organiser and Embryonic Patterning in the Mouse" Seminars in Cell & Dev. Biol. (2004) 15: 543-554.

Robertson, "Teratocarcinomas and embryonic stem cells: A practical approach," IRL Press 1987.

Roche et al. "Ectodermal commitment of insulin-producing cells derived from mouse embryonic stem cells" Faseb J (2005) 19: 1341-3.

Rodaway, A., and Patient, R. (2001). Mesendoderm, an ancient germ layer? Cell 105, 169-172.

Rodaway, A., Takeda, K., Koshida, S., Broadbent, J., Price, B., Smith, J.C., Patient, R., and Holder, N. (1999). Induction of the mesendoderm in the zebrafish germ ring by yolk cell-derived TGF-beta family signals and discrimination of mesoderm and endoderm by FGF. Development 126, 3067-3078.

Rohr, K.B., Schulte-Merker, S., and Tautz, D. (1999). Zebrafish zic1 expression in brain and somites is affected by BMP and hedgehog signaling. Mech Dev 85, 147-159.

Rossant, J. & Tam, P.P., "Emerging Asymmetry and Embryonic Patterning in Early Mouse Development" Dev Cell (2004) 7: 155-164.

Saarma et al., "GDNF—a stranger in the TGF—superfamily?" Eur. J. Biochem. (2000) 267(24):6968-71.

Sander, M. and M.S. German, "The Beta Cell Transcription Factors and Development of the Pancreas," Journal of Molecular Medicine, May 1997, vol. 75, No. 5, pp. 327-340.

Sasaki et al., "Differential expression of multiple fork head related genes during gastrulation and axial pattern formation in the mouse embryo", *Development*, (1993) 118:47-59.

Schier, A. F. (2003). Nodal signaling in vertebrate development. Annu Rev Cell Dev Biol 19, 589-621.

Schmolke et al. (1998). Identification of hepatitis G virus particles in human serum by E2-specific monoclonal antibodies generated by DNA immunization. J. Virol. 72: 4541-4545.

Schoenwolf, G.C., and Smith, J. L. (2000). Gastrulation and early mesodermal patterning in vertebrates. Methods Mol Biol 135, 113-125.

Schuldiner et al. (2000). Effects of Eight Growth Factors on the Differentiation of Cell Derived from Human Embryonic Stem Cells. Proc. Natl. Sci., vol. 97, 11307-11312.

(56) References Cited

OTHER PUBLICATIONS

Schwartz, et al. "Defined Conditions for Development of Functional Hepatic Cells from Human Embryonic Stem Cells" Stem Cells and Development (2005) 14(6): 643-655.
Segev et al., "Differentiation of human embryonic stem cells into insulin-producing clusters," Stem Cells (2004) 22:265-274.
Shalaby, et al., "Failure of Blood-Island Formation and Vasculogenesis in Flk-1-deficient Mice" Nature (1995) 376: 62-66.
Shamblott et al., "Human embryonic germ cell derivatives express a broad range of developmentally distinct markers and proliferate exensively in vitro," Proc. Natl. Acad. Sci. USA (2001) 98(1):113-8.
Shamblott, M.J., Axelman, J., Wang, S., Bugg, E. M., Littlefield, J.W., Donovan, P. J., Blumenthal, P. D., Huggins, G. R., and Gearhart, J.D. (1998). Derivation of pluripotent stem cells from cultured human primordial germ cells. Proc Natl Acad Sci USA 95, 13726-13731.
Shapiro, A. M., Lakey, J.R., Ryan, E. A., Korbuttm G. S., Toth, E., Warnock, G. L., Kneteman, N.M., and Rajotte, R. V. (2000). Islet transplantation in seven patients with type 1 diabetes mellitus using a glucocorticoid-free immunosuppressive regimen. N Engl J Med 343, 230-238.
Shapiro, A. M., Ryan, E. A., and Lakey, J. R. (2001) Pancreatic islet transplantation in the treatment of diabetes mellitus. Best Pract Res Clin Endocrinol Metab 15, 241-264.
Shapiro, J., Ryan, E., Warnock, G. L., Kneteman, N. M., Lakey, J., Korbutt, G. S., and Rajotte, R. V. (2001) Could fewer islet cells be transplanted in type 1 diabetes? Insulin independence should be dominant force in islet transplantation. Bmj 322, 861.
Shi et al., "Inducing embryonic stem cells to differentiate into pancreatic beta cells by a novel three-step approach with activin A and all-trans retinoic acid," Stem Cells (2005) 23:656-662.
Shiozawa, M., Hiraoka, Y., Komatsu, N., Ogawa, M., Sakai, Y., and Aiso, D. (1996). Cloning and characterization of Xenopus laevis xSox 7 xDNA. Biochim Biophys Acta 1309, 73-76.
Shirahashi, et al., "Differentiation of Human and Mouse Embryonic Stem Cells Along a Hepatocyte Lineage" Cell Transplantation (2004) 13: 197-211.
Shiraki, "TGF-beta signaling potentiates differentiation of embryonic stem cells to PDx-1 expressing endodermal cells," Genes to Cells (2005) 21:405-412.
Shook, D. & Keller, R., "Mechanisms, Mechanics and Function of Epithelial-Mesenchymal Transitions in Early Development" Mech Dev (2003) 120: 1351-1383.
Sinner, et al., "Sox17 and β-Catenin Cooperate to Regulate the Transcription of Endodermal Genes" Development (2004) 131: 3069-3080.
Skoudy, A., et al. "Transforming Growth Factor (TGF) beta, Fibroblast Growth Factor (FGF) and Retinoid Signaling Pathways Promote Pancreatic Exocrine Gene Expression in Mouse Embryonic Stem Cells." The Biochemical Journal. May 1, 2004, vol. 379, No. Pt 3, pp. 749-756.
Smith, J. (1997). Brachyury and the T-box genes. Curr Opin Genet Dev 7, 474-480.
Smith, J. C., Armes, N. A., Conlon, F. L., Tada, M., Umbhauer, M., and Weston, K.M. (1997). Upstream and downstream from Brachyury, a gene required for vertebrae mesoderm formation. Cold Springs Harb Symp Quant Biol 62, 337-346.
Sooknanan et al., "NASBA: a detection and amplification system uniquely suited for RNA," Nature Biotechnology, (1995) 13:563-564.
Soon-Shiong, P., "Treatment of Type I Diabetes using Encapsulated Islets," Advanced Drug Delivery Reviews, 1999, vol. 35, pp. 259-270.
Soria, et al. "Insulin-Secreting Cells Derived from Embryonic Stem Cells Normalize Glycemia in Streptozotocin-Induced Diabetic Mice." Diabetes, New York, NY, vol. 49, No. 2: 157-162.
Stafford, D. and Prince, V. (2002). Retinoic Acid Signaling Is Required for a Critical Early Step in Zebrafish Pancreatic Development, Current Biology, vol. 12, 1215-1220, Jul. 23, 2002.
Stafford, D. and Prince, V., "The Role of Retinoid Signaling in Pancreas Differentiation" Pancreatic Development, Proliferation and Stem Cells, Meeting Abstract, Oct. 18-19, 2001, National Institute of Health.
Stafford, et al., "A Conserved Role for Retoid Signaling in Vertebrate Pancreas Development" Dev Genes Evol. (2004) 214: 432-441.
Stainier, D.Y.R., "A Glimpse into the Molecular Entrails of Endoderm Formation" Genes Dev (2002) 16: 893-907.
Stemmler, et al., "Analysis of Regulatory Elements of E-Cadherin with Reporter Gene Constructs in Transgenic Mouse Embryos" Developmental Dynamics (2003) 227: 238-245.
Stoffers, et al., "Early-onset Type-II Diabetes Mellitus (MODY4) Linked to IPF1" Nature Genetics (1997) 17: 138-139.
Stoffers, et al., "Pancreatic Agenesis Attributable to a Single Nucleotide Deletion in the Human IPF1 Gene Coding Sequence" Nature Genetics (1997) 15: 106-110.
Sun et al., "Conditional inactiviation of Fgf4 reveals complexity of signaling during limb bud development," Nat. Genet., (2000) 25:83-86.
Sun, et al., "Targeted Disruption of Fgf8 Causes Failure of Cell Migration in the Gastrulating Mouse Embryo" Genes Dev (1999) 13: 1834-1846.
Suzuki, M. et al. Cloned Cells Develop Renal Cortical Collecting Tubles. Nephron. 1994, vol. 68, pp. 118-124.
Tada, et al. "Characterization of Mesendoderm: A Diverging Point of the Definitive Endoderm and Mesoderm in Embryonic Stem Cell Differentiation Culture." (2005) Development 132: 4363-4374.
Takahashi et al., "Induction of pluripotent stem cells from adult human fibroblasts by defined factors," Cell (2007) 131(5):861-72.
Takash, W., Canizares, J., Bonneaud, N., Poulat, F., Mattei, M.G., Jay, P., and Berta, P. (2001). SOX7 transcription factor: sequence, chromosomal localization, expression, transactivation and interference with Wnt signaling. Nucleic Acids Res 29, 4274-4283.
Tam et al., "Early endoderm development in vertebrate: lineage differentiation and morphogenetic function," Curr. Opin. Genet. Dev. (2003) 13(4):393-400.
Tam et al., "Gene function in mouse embryogenesis: get set for gastrulation," Nat. Rev. Genet. (2007) 8(5):368-81.
Taniguchi, K., Hiraoka, Y., Ogawa, M.,Sakai, Y., Kido, S., and Aiso, S. (1999). Isolation and characterization of a mouse Sry-related cDNA, mSox7. Biochim Biophys Act 1445, 225-231.
Technau, U. (2001). Brachyury, the blastopore and the evolution of the mesoderm. Bioessays 23, 788-794.
Terskikh et al., ""Peptabody": a new type of high avidity binding protein," Proc. Natl. Acad. Sci. USA, (1997) 94(5):1663-8.
Thelwell et al., "Mode of action and application of Scorpion primers to mutation detection," Nucleic Acids Res., (2000) 28(19):3752-61.
Thisse et al., "Antivin, a novel and divergent member of the TGF—superfamily, negatively regulates mesoderm induction," Development (1999) 126(2):229-40.
Thomas, et al., "The Murine Gene, Traube, Is Essential for the Growth of Preimplantation Embryos" Dev Biol (2000) 227: 324-342.
Thomson, J.A., Itskovitz-Eldor, J., Shapiro, S. S., Waknitz, M. A., Swiergiel, J. J., Marshall, V. S., and Jones, J. M. (1998). Embryonic stem cell lines derived from human blastocysts, Science 282, 1145-1147.
Tiedemann et al., "Pluripotent cells (stem cells) and Their Determination and Differentiation in Early Vertebrate Embryogenesis." Develop. Growth Differ. 43:469-502, (2001).
Tremblay, K. D., Hoodless, P. A., Bikoff, E. K., and Robertson, E. J. (2000). Formation of the definitive endoderm in mouse is a Smad2-dependent process. Development 127, 3079-3090.
Trueba et al., "PAX8, TITF1, and FOXE1 gene expression patterns during human development: new insights into human thyroid deevlopment and thyroid dysgenesis-associated malformations," J. Clin. Endocrinol. Metab. (2005) 90(1):455-62.
Tyagi et al., "Molecular beacons: probes that fluoresce upon hybridization," Nat. Biotechnol., (1996) 14(3):303-8.
Ulivieri et al. (1996). Generation of a monoclonal antibody to a defined portion of the Heliobacter pylori vacuolating cytotoxin by DNA immunization. J. Biotechnol. 51: 191-194.

(56) References Cited

OTHER PUBLICATIONS

Urbach et al. "Modeling Lesch-Nyhan Disease by Gene Targeting in Human Embryonic Stem Cells" (2004) Stem Cells 22:635-641.
Valdimarsdottir et al., "Functions of the TFGb superfamily in human embryonic stem cells," *APMIS* (2005) 113(11-12):773-89.
Vallier et al. "Nodal Inhibits Differentiation of Human Embryonic Stem Cells Along the Neuroectodermal Default Pathway" (2004) Developmental Biology 275, 403-421.
Vallier et al. "Activin/Nodal and FGF Pathways Cooperate to Maintain Pluripotency of Human Embryonic Stem Cells" (2005) J Cell Sci. 118: 4495-509.
Vandescompele, J., De Preter, K., Pattyn, F., Poppe, B., Van Roy, N., De Paepe, A., and Speleman, F. (2002). Accurate normalization of real-time quantitative RT-PCR data by geometric averaging of multiple internal control genes. Genome Biol 3, RESEARCH0034.
Varlet, I., Collignon, J., and Robertson, E. J. (1997). Nodal expression in the primitive endoderm is required for specification of the anterior axis during mouse gastrulation. Development 124, 1033-1044.
Vincent, S. D., Dunn, N. R., Hayashi, D. P., and Robertson, E. J, (2003). Cell fate decisions within the mouse organizer are governed by graded nodal signals. Genes Dev 17, 1646-1662.
Vogel, G. Stem Cells are Coaxed to Produce Insulin. Science. Apr. 27, 2001, vol. 292, pp. 615-616.
Wang et al., "Self-renewal of human embryonic stem cells requires insulin-like growth factor-1 receptor and ERBB2 receptor signaling," *Blood* (2007) 110:4110-4119.
Wei et al. "Transcriptome Profiling of Human and Murine ESCs Identifies Divergent Paths Required to Maintain the Stem Cell State"(2005) Stem Cells 23:166-185.
Weiler-Guettler, H., Aird, W. C., Rayburn, H., Husain, M., and Rosenberg, R. D. (1996). Developmentally regulated gene expression of thrombomodulin in postimplantation mouse embryos. Development 122, 2271-2281.
Weiler-Guettler, H., Yu, K., Soff, G., Gudas, L. J., and Rosenberg, R. D. (1992). Thrombomodulatin gene regulation by cAMP and retinoic acid in F9 embryonal carcinoma cells. Proceedings of the National Academy of Sciences of the United States of America 89, 2155-2159.
Weinstein, D.C. et al. The winged-helix transcription factor HNF-3 beta is required for notochord development in the mouse embryo. Cell 78, 575-588 (1994).
Wells, J.M., and Melton, D. A. (1999). Vertebrate endoderm development. Annu Rev Cell Dev Biol 15, 393-410.
Wells, J.M., and Melton, D.A. (2000). Early mouse endoderm is patterned by soluble factors from adjacent germ layers. Development 127, 1563-1572.
Wilding et al., "The role of pdx1 and HNF6 in proliferation and differentiation of endorine precursors," (2005) Diabetes Metab Res Rev. 20(2):114-23.
Wiles and Johansson, "Embryonic Stem Cell Development in a Chemically Defined Medium," Experimental Cell Research (1999) 247:241-248.
Willert, et al., Wnt Proteins are lipid-modified and can act as stem cell growth factors, Nature, 423, 448-452, 2003.
Willison, K. (1990). The mouse Brachyury gene and mesoderm formation. Trends Genet 6, 104-105.
Wilson et al., "Streptozotocin interactions with pancreatic beta cells and the induction of insulin-dependent diabetes," *Current Topics Microbiol. Immunol.* (1990) 158:27-54.
Wu et al., "The ligation amplification reaction (LAR)—amplification of specific DNA sequences using sequential rounds of template-dependent ligation.," *Genomics*, (1989): 4(4):560-9.
Xu et al., "BMP4 initiates human embryonic stem cell differentiation to trophoblast," *Nature Biotechnology* (2002) 20:1261-1264.
Xu et al., "Feeder-free growth of undifferentiated human embryonic stem cells," *Nat. Biotechnol.* (2001) 19(10):971.
Xu et al., "Characterization and Enrichment of Cardiomyocytes Derived From Human Embryonic Stem Cells." Cellular Biology. 91:501-508. (2002).
Yamaguchi, et al., "flk-1, an flt-related Receptor Tyrosine Kinase is an Early Marker for Endothelial Cell Precursors" Development (1993) 118: 489-498.
Yamaguchi, et al., "T (Brachyury) is a Direct Target of Wnt3a During Paraxial Mesoderm Specification" Genes Dev (1999) 13: 3185-3190.
Yang, et al., "Disabled-2 is Essential for Endodermal Cell Positioning and Structure Formation During Mouse Embryogenesis" Dev Biol (2002) 251: 27-44.
Yasunaga, et al. "Induction and Monitoring of Definitive and Visceral Endoderm Differentiation of Mouse ES Cells." (2005) Nature Biotechnology 23(12):1542-1550.
Ying et al., "BMP induction of Id proteins suppresses differentiation and sustains embryonic stem cell self-renewal in collaboration with STAT3," *Cell* (2003) 115:281-292.
Yu et al., "Human induced pluripotent stem cells free of vector and transgene sequences," *Science* (2007) 324: 797-801.
Yusuf et al., "Expression of chemokine receptor CXCR4 during chick embryo development," *Anat. Embryol (Berl)* (2005) 210(1):35-41.
Zhang et al., "Highly efficient differentiation of human ES cells and IPS cells into mature pancreatic insulin-producing cells," *Cell Research* (2009): 429-438.
Zhao, G. Q. (2003). Consequences of knocking out BMP signaling in the mouse. Genesis 35, 43-56.
Zhou, X., Sasaki, H., Lowe, L., Hogan, B.L., and Kuehn, M. R. (1993). Nodal is a novel TGF-beta-like gene expressed in the mouse node during gastrulation. Nature 361, 543-547.
Zwaka, et al. "Homologous Recombination in Human Embryonic Stem Cells" Nature Biotechnology (2003) vol. 21.

\* cited by examiner

MARKERS OF DEFINITIVE ENDODERM

RELATED APPLICATIONS

This application is a continuation application of U.S. application Ser. No. 12/093,590, entitled MARKERS OF DEFINITIVE ENDODERM, filed Jul. 21, 2008, now U.S. Pat. No. 8,586,357, issued Nov. 19, 2013, which is a U.S. national phase application under 35 U.S.C. .sctn.371 of International Application No. PCT/US2006/043932, entitled MARKERS OF DEFINITIVE ENDODERM, filed Nov. 13, 2006, designating the United States and published in English on May 24, 2007 as WO2007/059007, which is a nonprovisional application claiming priority under 35 U.S.C. .sctn.119(e) to U.S. Provisional Patent Application No. 60/736,598, entitled MARKERS OF DEFINITIVE ENDODERM, filed Nov. 14, 2005; this application is also a continuation-in-part of U.S. patent application Ser. No. 11/021,618, entitled DEFINITIVE ENDODERM, filed Dec. 23, 2004, now U.S. Pat. No. 7,510,876, issued Mar. 31, 2009, which claims priority under 35 U.S.C. .sctn.119(e) as a nonprovisional application to U.S. Provisional Patent Application No. 60/587,942, entitled CHEMOKINE CELL SURFACE RECEPTOR FOR THE ISOLATION OF DEFINITIVE ENDODERM, filed Jul. 14, 2004; and U.S. Provisional Patent Application No. 60/586,566, entitled CHEMOKINE CELL SURFACE RECEPTOR FOR THE ISOLATION OF DEFINITIVE ENDODERM, filed Jul. 9, 2004, and U.S. Provisional Patent Application No. 60/532,004, entitled DEFINITIVE ENDODERM, filed Dec. 23, 2003. The disclosure of each of the foregoing priority applications is incorporated herein by reference in its entirety

REFERENCE TO A SEQUENCE LISTING, A TABLE OR A COMPUTER PROGRAM LISTING APPENDIX SUBMITTED AS AN ASCII TEXT FILE

The Sequence Listing written in file 96183-892092 ST25.TXT, created on Jan. 21, 2014, 5,914 bytes, machine format IBM-PC, MS Windows operating system, is hereby incorporated by reference.

FIELD OF THE INVENTION

The present invention relates to the fields of medicine and cell biology. In particular, the present invention relates to the identification and isolation of definitive endoderm cells.

BACKGROUND

Human pluripotent stem cells, such as embryonic stem (ES) cells and embryonic germ (EG) cells, were first isolated in culture without fibroblast feeders in 1994 (Bongso et al., 1994) and with fibroblast feeders (Hogan, 1997). Later, Thomson, Reubinoff and Shamblott established continuous cultures of human ES and EG cells using mitotically inactivated mouse feeder layers (Reubinoff et al., 2000; Shamblott et al., 1998; Thomson et al., 1998).

Human ES and EG cells (hESCs) offer unique opportunities for investigating early stages of human development as well as for therapeutic intervention in several disease states, such as diabetes mellitus and Parkinson's disease. For example, the use of insulin-producing β-cells derived from hESCs would offer a vast improvement over current cell therapy procedures that utilize cells from donor pancreases for the treatment of diabetes. However, presently it is not known how to generate an insulin-producing β-cell from hESCs. As such, current cell therapy treatments for diabetes mellitus, which utilize islet cells from donor pancreases, are limited by the scarcity of high quality islet cells needed for transplant. Cell therapy for a single Type I diabetic patient requires a transplant of approximately $8 \times 10^8$ pancreatic islet cells. (Shapiro et al., 2000; Shapiro et al., 2001a; Shapiro et al., 2001b). As such, at least two healthy donor organs are required to obtain sufficient islet cells for a successful transplant. Human embryonic stem cells offer a source of starting material from which to develop substantial quantities of high quality differentiated cells for human cell therapies.

Two properties that make hESCs uniquely suited to cell therapy applications are pluripotence and the ability to maintain these cells in culture for prolonged periods. Pluripotency is defined by the ability of hESCs to differentiate to derivatives of all 3 primary germ layers (endoderm, mesoderm, ectoderm) which, in turn, form all somatic cell types of the mature organism in addition to extraembryonic tissues (e.g. placenta) and germ cells. Although pluripotency imparts extraordinary utility upon hESCs, this property also poses unique challenges for the study and manipulation of these cells and their derivatives. Owing to the large variety of cell types that may arise in differentiating hESC cultures, the vast majority of cell types are produced at very low efficiencies. Additionally, success in evaluating production of any given cell type depends critically on defining appropriate markers. Achieving efficient, directed differentiation is of great importance for therapeutic application of hESCs.

In order to use hESCs as a starting material to generate cells that are useful in cell therapy applications, it would be advantageous to overcome the foregoing problems. For example, it would be useful to identify and isolate cell types, such as definitive endoderm, that can later differentiate into pancreatic islet/β-cells, as well as other useful cell types.

SUMMARY OF THE INVENTION

Embodiments of the present invention relate to methods for producing a cell population enriched in definitive endoderm cells. The method can include the following steps: providing a cell population including definitive endoderm cells with a reagent that binds to a marker selected from Table 3, and separating definitive endoderm cells bound to the reagent from cells that are not bound to the reagent, thereby producing a cell population enriched in definitive endoderm cells. In some embodiments, the marker is selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192. In preferred embodiments, the marker is selected from the group consisting of CALCR, CMKOR1, CXCR4, GPR37, NTN4, RTN4RL1, SEMA3E, SLC40A1, SLC5A9 and TRPA1. The reagent used to produce a cell population enriched in definitive endoderm can be an antibody, such as a polyclonal or monoclonal antibody that binds to one of the markers described herein.

In certain embodiments, the method of producing a cell population enriched for definitive endoderm cells can also include the following steps: obtaining a cell population comprising pluripotent human cells; providing the cell population with at least one growth factor of the TGFβ superfamily in an amount sufficient to promote differentiation of said pluripotent cells to definitive endoderm cells; and allowing sufficient time for definitive endoderm cells to form. In further embodiments, the at least one growth factor can be selected from the following: Nodal, activin A, activin B and combinations thereof. In some embodiments, the at least one growth factor can be provided to said cell population at a concentration ranging from about 1 ng/ml to about 1000 ng/ml. In further preferred embodiments, the at least one growth factor can be provided in a concentration of at least about 100 ng/ml. In other preferred embodiments, the cell population can be grown in a medium including less than about 10% serum. In yet other preferred embodiments, the pluripotent human cells can be human embryonic stem cells.

Additional embodiments of the invention relate to other methods of producing a cell population enriched in definitive endoderm cells, which can include the steps of: obtaining a population of pluripotent cells, wherein at least one cell of the pluripotent cell population includes a nucleic acid encoding a fluorescent protein or a biologically active fragment thereof, which has been operably linked to a promoter that controls the expression of a marker selected from Table 3; differentiating the pluripotent cells so as to produce definitive endoderm cells, wherein the definitive endoderm cells express said fluorescent protein; and separating the definitive endoderm cells from cells that do not substantially express said fluorescent protein. In preferred embodiments, the marker is selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192. In other embodiments, the marker is selected from the group consisting of CALCR, CMKOR1, CXCR4, GPR37, NTN4, RTN4RL1, SEMA3E, SLC40A1, SLC5A9 and TRPA1. Methods known in the art, such as fluorescence activated cell sorting (FACS), can be used to separate the fluorescently-tagged definitive endoderm cells from cells that do not substantially express said fluorescent protein.

In some embodiments, the step of differentiating the pluripotent cells can include providing the cell population with at least one growth factor of the TGFβ superfamily in an amount sufficient to promote differentiation of said pluripotent cells to definitive endoderm cells, and allowing sufficient time for definitive endoderm cells to form. For example, in some embodiments, the cell population can be provided with at least one growth factor selected from the group consisting of Nodal, activin A, activin B and combinations thereof. In preferred embodiments, the at least one growth factor can be provided to said cell population at a concentration ranging from about 1 ng/ml to about 1000 ng/ml. In other preferred embodiments, the at least one growth factor can be provided in a concentration of at least about 100 ng/ml. In still other preferred embodiments, the cell population can be grown in a medium including less than about 10% serum. In yet other preferred embodiments, the pluripotent human cells can be human embryonic stem cells.

In some embodiments, methods, such as affinity-based separation or magnetic-based separation, are used to enrich, isolate or substantially purify preparations of definitive endoderm cells which bind to the reagent.

In accordance with the methods described herein, embodiments of the present invention relate to compositions useful for the enrichment and isolation of definitive endoderm cells. Some embodiments relate to an ex vivo reagent-cell complex. The ex vivo complex can include a human definitive endoderm cell expressing a marker selected from Table 3 and a reagent bound to the marker. The definitive endoderm cell of the ex vivo reagent-cell complex is a multipotent cell that can differentiate into cells of the gut tube or organs derived therefrom. In certain embodiments, the marker expressed by the human definitive endoderm cell is selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192. In preferred embodiments, the definitive endoderm cell expresses a cell-surface marker selected from the group consisting of CALCR, CMKOR1, CXCR4, GPR37, NTN4, RTN4RL1, SEMA3E, SLC40A1, SLC5A9 and TRPA1.

The reagent of the reagent-cell complex can be, for example, an antibody. In preferred embodiments, the bound marker in the reagent-cell complex can be a cell-surface marker selected from the group consisting of CALCR, CMKOR1, CXCR4, GPR37, NTN4, RTN4RL1, SEMA3E, SLC40A1, SLC5A9 and TRPA1.

In accordance with the embodiments described herein, aspects of the present invention relate to compositions of cell populations that include human cells wherein at least about 10% of the cells are reagent-cell complexes, wherein the complex can include a human definitive endoderm cell expressing a marker selected from Table 3, and wherein the definitive endoderm cell is a multipotent cell that can differentiate into cells of the gut tube or organs derived therefrom. In such embodiments, the marker is expressed by the definitive endoderm cell, wherein the marker is selected from Table 3, and a reagent bound to the marker. In some embodiments, the marker bound by the reagent in the reagent-cell complex is selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192. In preferred embodiments, the marker bound by the reagent is selected from the group consisting of CALCR, CMKOR1, CXCR4, GPR37, NTN4, RTN4RL1, SEMA3E, SLC40A1, SLC5A9 and TRPA1. In further embodiments, the expression of one or more of the markers selected from Table 3 in definitive endoderm cells can be greater than expression of a marker selected from the group consisting of OCT4, AFP, Thrombomodulin (TM), SPARC and SOX7.

In some embodiments, the cell population includes human cells wherein at least about 20% of the cells are reagent-cell complexes as described herein. In other embodiments, the cell population includes human cells wherein at least about 40% of the cells are reagent-cell complexes as described herein. In yet other embodiments, the cell population includes human cells wherein at least about 60% of the cells are reagent-cell complexes as described herein. In yet other embodiments, the cell population includes human cells wherein at least about 80% of the cells are reagent-cell complexes as described herein. In yet other embodiments, the cell population includes human cells wherein at least about 95% of the cells are reagent-cell complexes as described herein.

Additionally, embodiments of the present invention also relate to isolated antibodies that bind to markers that are differentially expressed in definitive endoderm cells. For example, some embodiments relate to any of the markers shown in Table 3. In preferred embodiments, the antibody binds to a polypeptide encoded by AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192. In other preferred embodiments, the antibody binds to a marker that is expressed on the cell surface, such as for example, CALCR, CMKOR1, CXCR4, GPR37, NTN4, RTN4RL1, SEMA3E, SLC40A1, SLC5A9 and TRPA1.

Antibodies described herein can be either polyclonal or monoclonal. Further, in certain embodiments, the antibodies can be single chain, and/or modified, for example to incorporate a label.

Other embodiments of the present invention relate to compositions for the identification of definitive endoderm. The composition can include a first oligonucleotide that hybridizes to a first marker, wherein the first marker is selected from Table 3; and a second oligonucleotide that hybridizes to a second marker, wherein the second marker is selected from Table 3, and wherein the second marker is different from the first marker. In preferred embodiments, the first marker and the second marker can be selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706, AW772192, OCT4, AFP, Thrombomodulin (TM), SPARC and SOX7. In other preferred embodiments, the first marker and the second marker can be selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192. In still other preferred embodiments, the first marker and second marker are selected from the group consisting of CALCR, CMKOR1, CXCR4, GPR37, NTN4, RTN4RL1, SEMA3E, SLC40A1, SLC5A9 and TRPA1. The compositions above can also include a polymerase, such as an RNA-dependent DNA polymerase and/or a DNA-dependent DNA polymerase. In certain embodiments, at least one oligonucleotide includes a label. In some embodiments, the marker can be a nucleic acid, for example DNA or RNA.

Other embodiments relate to methods of detecting definitive endoderm cells that can include the steps of detecting the presence of definitive endoderm cells in a cell population by detecting expression of at least one marker selected from Table 3 in cells of the cell population. In preferred embodiments, the at least one marker can be selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192. In other preferred embodiments, the method can also include detection of expression of at least one marker selected from the group consisting of OCT4, AFP, TM, SPARC and SOX7 in cells of the cell population. In some embodiments, the expression of the at least one marker selected from Table 3 can be greater than expression of the at least one marker selected from the group consisting of OCT4, AFP, TM, SPARC and SOX7 in the definitive endoderm cells. In further embodiments, the method can also include detecting expression of at least one marker selected from the group consisting of SOX17 and CXCR4, wherein expression of the at least one marker selected from Table 3 and expression of the at least one marker selected from the group consisting of SOX17 and CXCR4 is greater than expression of the at least one marker selected from the group consisting of OCT4, AFP, TM, SPARC and SOX7 in the definitive endoderm cells. In some embodiments, the expression of the at least one marker is determined by quantitative polymerase chain reaction (Q-PCR). In other embodiments, the expression of the at least one marker is determined by immunocytochemistry.

Other embodiments relate to methods of identifying a differentiation factor capable of promoting the differentiation of human definitive endoderm cells in a cell population including human cells. Methods can include the steps of: obtaining a cell population including human definitive endoderm cells, providing a candidate differentiation factor to the cell population, determining expression of a marker selected from Table 3 in the cell population at a first time point, determining expression of the same marker in the cell population at a second time point, wherein the second time point is subsequent to the first time point and wherein the second time point is subsequent to providing said cell population with said candidate differentiation factor and determining if expression of the marker in the cell population at the second time point is increased or decreased as compared to expression of the marker in the cell population at the first time point, wherein an increase or decrease in expression of said marker in the cell population indicate can that said candidate differentiation factor is capable of promoting the differentiation of said human definitive endoderm cells. In preferred embodiments, the marker is selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192. In other embodiments, the human definitive endoderm cells include at least about 10% of the human cells in the cell population. In preferred embodiments, the human definitive endoderm cells include about 90% of the human cells in said cell population. In yet other embodiments, the human definitive endoderm cells can differentiate into cells, tissues or organs derived from the gut tube in response to the candidate differentiation factor.

In embodiments described herein, the first time point can be prior to providing the candidate differentiation factor to the cell population, whereas in other embodiments, the first time point can be at approximately the same time as providing the candidate differentiation factor to the cell population. In still other embodiments, the first time point can be subsequent to providing the candidate differentiation factor to the cell population. In some embodiments, expression of the marker can be determined by quantitative polymerase chain reaction (Q-PCR), whereas in other embodiments, expression of the marker can be determined by immunocytochemistry.

Candidate differentiation factors can include known and unknown factors, and may be small molecules, polypeptides, or the like. In certain embodiments, the candidate differentiation factor can include a growth factor. In some embodiments, the candidate differentiation factor can be provided to the cell population at a concentration of between about 1 ng/ml to about 1 mg/ml. In preferred embodiments, the candidate differentiation factor can be provided to the cell population at a concentration of about 100 ng/ml Some embodiments of the present invention relate to cell cultures comprising definitive endoderm cells, wherein the definitive endoderm cells are multipotent cells that can differentiate into cells of the gut tube or organs derived from the gut tube. In accordance with certain embodiments, the definitive endoderm cells are mammalian cells, and in a preferred embodiment, the definitive endoderm cells are human cells. In some embodiments of the present invention, definitive endoderm cells express or fail to significantly express certain markers. In some embodiments, one or more markers selected from Table 3 are expressed in definitive endoderm cells. In other embodiments, one or more markers selected from the group consisting of OCT4, alpha-fetoprotein (AFP), Thrombomodulin (TM), SPARC and SOX7 are not significantly expressed in definitive endoderm cells.

In accordance with other embodiments of the present invention, methods of producing definitive endoderm from pluripotent cells are described. In some embodiments, pluripotent cells are derived from a morula. In some embodiments, pluripotent cells are stem cells. Stem cells used in these methods can include, but are not limited to, embryonic stem cells. Embryonic stem cells can be derived from the embryonic inner cell mass or from the embryonic gonadal ridges. Embryonic stem cells can originate from a variety of animal species including, but not limited to, various mammalian species including humans. In a preferred embodiment, human embryonic stem cells are used to produce definitive endoderm. In certain embodiments the hESCs are maintained on a feeder layer. In such embodiments, the feeder layer cells can be cells, such as fibroblasts, which are obtained from humans, mice or any other suitable organism.

In some embodiments of the present invention, the compositions comprising definitive endoderm cells and hESCs also includes one or more growth factors. Such growth factors can include growth factors from the TGFβ superfamily. In such embodiments, the one or more growth factors comprise the Nodal/Activin and/or the BMP subgroups of the TGFβ superfamily of growth factors. In some embodiments, the one or more growth factors are selected from the group consisting of Nodal, Activin A, Activin B, BMP4, Wnt3a or combinations of any of these growth factors In certain jurisdictions, there may not be any generally accepted definition of the term "comprising." As used herein, the term "comprising" is intended to represent "open" language which permits the inclusion of any additional elements. With this in mind, additional embodiments of the present inventions are described with reference to the numbered paragraphs below:

1. An isolated antibody that binds to a marker selected from Table 3.

2. The antibody of paragraph 1, wherein said marker is selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192.

3. The antibody of paragraph 2, wherein said marker comprises a polypeptide selected from the group consisting of CALCR, CMKOR1, CXCR4, GPR37, NTN4, RTN4RL1, SEMA3E, SLC40A1, SLC5A9 and TRPA1.

4. The antibody of paragraph 1, wherein said antibody is polyclonal.

5. The antibody of paragraph 1, wherein said antibody is monoclonal.

6. The antibody of paragraph 1, wherein said antibody is a single-chain antibody.

7. The antibody of paragraph 1, wherein said antibody is labeled.

8. An ex vivo reagent-cell complex comprising a human definitive endoderm cell expressing a marker selected from Table 3, said definitive endoderm cell being a multipotent cell that can differentiate into cells of the gut tube or organs derived therefrom, and a reagent bound to said marker.

9. The reagent-cell complex of paragraph 8, wherein said marker is selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192.

10. The reagent-cell complex of paragraph 9, wherein said marker comprises a polypeptide selected from the group consisting of CALCR, CMKOR1, CXCR4, GPR37, NTN4, RTN4RL1, SEMA3E, SLC40A1, SLC5A9 and TRPA1.

11. The reagent-cell complex of paragraph 10, wherein said reagent comprises an antibody.

12. The reagent-cell complex of paragraph 10, wherein said reagent comprises a ligand for a receptor.

13. A cell population comprising human cells wherein at least about 10% of said cells form reagent-cell complexes according to paragraph 8.

14. A cell population comprising human cells wherein at least about 20% of said cells form reagent-cell complexes according to paragraph 8.

15. A cell population comprising human cells wherein at least about 40% of said cells form reagent-cell complexes according to paragraph 8.

16. A cell population comprising human cells wherein at least about 60% of said cells form reagent-cell complexes according to paragraph 8.

17. A cell population comprising human cells wherein at least about 80% of said cells form reagent-cell complexes according to paragraph 8.

18. A cell population comprising human cells wherein at least about 95% of said cells form reagent-cell complexes according to paragraph 8.

19. The cell population of any one of paragraphs 13-18, wherein said marker is selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192.

20. The cell population of paragraph 19, wherein expression of said marker is greater than expression of a marker selected from the group consisting of OCT4, AFP, Thrombomodulin (TM), SPARC and SOX7 in definitive endoderm cells.

21. The cell population of paragraph 19, wherein said marker comprises a polypeptide selected from the group consisting of CALCR, CMKOR1, CXCR4, GPR37, NTN4, RTN4RL1, SEMA3E, SLC40A1, SLC5A9 and TRPA1.

22. The cell population of paragraph 20, wherein said reagent comprises an antibody.

23. The cell population of paragraph 20, wherein said reagent comprises a ligand for a receptor.

24. A composition for the identification of definitive endoderm, said composition comprising a first oligonucleotide that hybridizes to a first marker, wherein said first marker is selected from the group consisting of Table 3, OCT4, AFP, Thrombomodulin (TM), SPARC and SOX7, and a second oligonucleotide that hybridizes to a second marker, wherein said second marker is selected from the group consisting of Table 3, OCT4, AFP, Thrombomodulin (TM), SPARC and SOX7, and wherein said second marker is different from said first marker.

25. The composition of paragraph 24, wherein said first marker and said second marker are selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706, AW772192, OCT4, AFP, Thrombomodulin (TM), SPARC and SOX7.

26. The composition of paragraph 25, wherein said first marker and said second marker are selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192.

27. The composition of paragraph 24, wherein said marker is a nucleic acid.

28. The composition of paragraph 27, wherein said nucleic acid is DNA.

29. The composition of paragraph 27, wherein said nucleic acid is RNA.

30. The composition of paragraph 24, wherein at least one oligonucleotide comprises a label.

31. The composition of paragraph 24 further comprising a polymerase.

32. The composition of paragraph 31, wherein the polymerase comprises a DNA-dependent DNA polymerase.

33. The composition of paragraph 31, wherein the polymerase comprises an RNA-dependent DNA polymerase.

34. The method of paragraph 33, wherein the RNA-dependent DNA polymerase comprises Moloney Murine Leukemia Virus reverse transcriptase or Avian Myeloblastosis Virus (AMV) reverse transcriptase.

35. A method for producing a cell population enriched in definitive endoderm cells, said method comprising the steps of providing a cell population comprising definitive endoderm cells with a reagent that binds to a marker selected from Table 3, and separating definitive endoderm cells bound to said reagent from cells that are not bound to said reagent, thereby producing a cell population enriched in definitive endoderm cells.

36. The method of paragraph 35, wherein said marker is selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192.

37. The method of paragraph 36, wherein the marker is selected from the group consisting of CALCR, CMKOR1, CXCR4, GPR37, NTN4, RTN4RL1, SEMA3E, SLC40A1, SLC5A9 and TRPA1.

38. The method of paragraph 37, wherein said reagent comprises an antibody or a ligand for a receptor.

39. The method of paragraph 35 further comprising the steps of obtaining a cell population comprising pluripotent human cells, providing said cell population with at least one growth factor of the TGFβ superfamily in an amount sufficient to promote differentiation of said pluripotent cells to definitive endoderm cells, and allowing sufficient time for definitive endoderm cells to form.

40. The method of paragraph 39, wherein said at least one growth factor is selected from the group consisting of Nodal, activin A, activin B and combinations thereof.

41. The method of paragraph 40, wherein said at least one growth factor is provided to said cell population at a concentration ranging from about 1 ng/ml to about 1000 ng/ml.

42. The method of paragraph 41, wherein said at least one growth factor is provided in a concentration of at least about 100 ng/ml 43. The method of paragraph 39, wherein said cell population is grown in a medium comprising less than about 10% serum.

44. The method of paragraph 39, wherein said pluripotent human cells are human embryonic stem cells.

45. A method of producing a cell population enriched in definitive endoderm cells, said method comprising the steps of obtaining a population of pluripotent cells, wherein at least one cell of said pluripotent cell population comprises a nucleic acid encoding a fluorescent protein or a biologically active fragment thereof, which has been operably linked to a promoter that controls the expression of a marker selected from Table 3, differentiating said pluripotent cells so as to produce definitive endoderm cells, wherein said definitive endoderm cells express said fluorescent protein, and separating said definitive endoderm cells from cells that do not substantially express said fluorescent protein.

46. The method of paragraph 45, wherein said marker is selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192.

47. The method of paragraph 45, wherein fluorescence activated cell sorting (FACS) is used to separate said definitive endoderm cells from said cells that do not substantially express said fluorescent protein.

48. The method of paragraph 45, wherein said step of differentiating said pluripotent cells further comprises providing said cell population with at least one growth factor of the TGFβ superfamily in an amount sufficient to promote differentiation of said pluripotent cells to definitive endoderm cells, and allowing sufficient time for definitive endoderm cells to form.

49. The method of paragraph 48, wherein said at least one growth factor is selected from the group consisting of Nodal, activin A, activin B and combinations thereof.

50. The method of paragraph 49, wherein said at least one growth factor is provided to said cell population at a concentration ranging from about 1 ng/ml to about 1000 ng/ml.

51. The method of paragraph 50, wherein said at least one growth factor is provided in a concentration of at least about 100 ng/ml 52. The method of paragraph 45, wherein said cell population is grown in a medium comprising less than about 10% serum.

53. The method of paragraph 45, wherein said pluripotent human cells are human embryonic stem cells.

54. A method of detecting definitive endoderm cells, said method comprising detecting the presence of definitive endoderm cells in a cell population by detecting expression of at least one marker selected from Table 3 in cells of said cell population.

55. The method of paragraph 54, wherein said at least one marker is selected from a group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192.

56. The method of paragraph 54 further comprising detecting expression of at least one marker selected from the group consisting of OCT4, AFP, TM, SPARC and SOX7 in cells of said cell population, wherein the expression of said at least one marker selected from Table 3 is greater than the expression of said at least one marker selected from the group consisting of: OCT4, AFT, TM, SPARC and SOX7 in said definitive endoderm cells.

57. The method of Paragraph 54, further comprising detecting expression of at least one marker selected from the group consisting of SOX17 and CXCR4, and at least one marker from Table 3 other than SOX17 and CXCR4, wherein expression of said at least one marker selected from Table 3 other than SOX17 and CXCR4 and expression of said at least one marker selected from the group consisting of SOX17 and CXCR4 is greater than the expression of said at least one marker selected from the group consisting of OCT4, AFP, TM, SPARC and SOX7 in said definitive endoderm cells.

58. The method of paragraph 54, wherein expression of said at least one marker is determined by quantitative polymerase chain reaction (Q-PCR).

59. The method of paragraph 54, wherein expression of said at least one marker is determined by immunocytochemistry.

60. A method of identifying a differentiation factor capable of promoting the differentiation of human definitive endoderm cells in a cell population comprising human cells, said method comprising the steps of obtaining a cell population comprising human definitive endoderm cells, providing a candidate differentiation factor to said cell population, determining expression of a marker selected from Table 3 in said cell population at a first time point, determining expression of the same marker in said cell population at a second time point, wherein said second time point is subsequent to said first time point and wherein said second time point is subsequent to providing said cell population with said candidate differentiation factor, and determining if expression of the marker in said cell population at said second time point is increased or decreased as compared to expression of the marker in said cell population at said first time point, wherein an increase or decrease in expression of said marker in said cell population indicates that said candidate differentiation factor is capable of promoting the differentiation of said human definitive endoderm cells.

61. The method of paragraph 60, wherein said marker is selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192.

62. The method of paragraph 60, wherein said human definitive endoderm cells comprise at least about 10% of the human cells in said cell population.

63. The method of paragraph 60, wherein said human definitive endoderm cells comprise at least about 90% of the human cells in said cell population.

64. The method of paragraph 60, wherein said human definitive endoderm cells differentiate into cells, tissues or organs derived from the gut tube in response to said candidate differentiation factor.

65. The method of paragraph 60, wherein said first time point is prior to providing said candidate differentiation factor to said cell population.

66. The method of paragraph 60, wherein said first time point is at approximately the same time as providing said candidate differentiation factor to said cell population.

67. The method of paragraph 60, wherein said first time point is subsequent to providing said candidate differentiation factor to said cell population.

68. The method of paragraph 60, wherein expression of said marker is determined by quantitative polymerase chain reaction (Q-PCR).

69. The method of paragraph 60, wherein expression of said marker is determined by immunocytochemistry.

70. The method of paragraph 60, wherein said candidate differentiation factor comprises a small molecule.

71. The method of paragraph 60, wherein said candidate differentiation factor comprises a polypeptide.

72. The method of paragraph 60, wherein said candidate differentiation factor comprises a growth factor.

73. The method of paragraph 60, wherein said candidate differentiation factor is provided to said cell population at a concentration of between about 1 ng/ml to about 1 mg/ml.

74. The method of paragraph 73, wherein said candidate differentiation factor is provided to said cell population at a concentration of about 100 ng/ml.

It will be appreciated that the methods and compositions described above relate to cells cultured in vitro. However, the above-described in vitro differentiated cell compositions may be used for in vivo applications.

Additional embodiments of the present invention may also be found in U.S. Provisional Patent Application No. 60/532,004, entitled DEFINITIVE ENDODERM, filed Dec. 23, 2003; U.S. Provisional Patent Application No. 60/566,293, entitled PDX1 EXPRESSING ENDODERM, filed Apr. 27, 2004; U.S. Provisional Patent Application No. 60/586,566, entitled CHEMOKINE CELL SURFACE RECEPTOR FOR THE ISOLATION OF DEFINITIVE ENDODERM, filed Jul. 9, 2004; U.S. Provisional Patent Application No. 60/587,942, entitled CHEMOKINE CELL SURFACE RECEPTOR FOR THE ISOLATION OF DEFINITIVE ENDODERM, filed Jul. 14, 2004; U.S. patent application Ser. No. 11/021,618, entitled DEFINITIVE ENDODERM, filed Dec. 23, 2004, and U.S. patent application Ser. No. 11/115,868, entitled PDX1 EXPRESSING ENDODERM, filed Apr. 26, 2005, U.S. patent application Ser. No. 11/165,305, entitled METHODS FOR IDENTIFYING FACTORS FOR DIFFERENTIATING DEFINITIVE ENDODERM, filed Jun. 23, 2005, the disclosures of which are incorporated herein by reference in their entireties.

DETAILED DESCRIPTION

Figure 1:
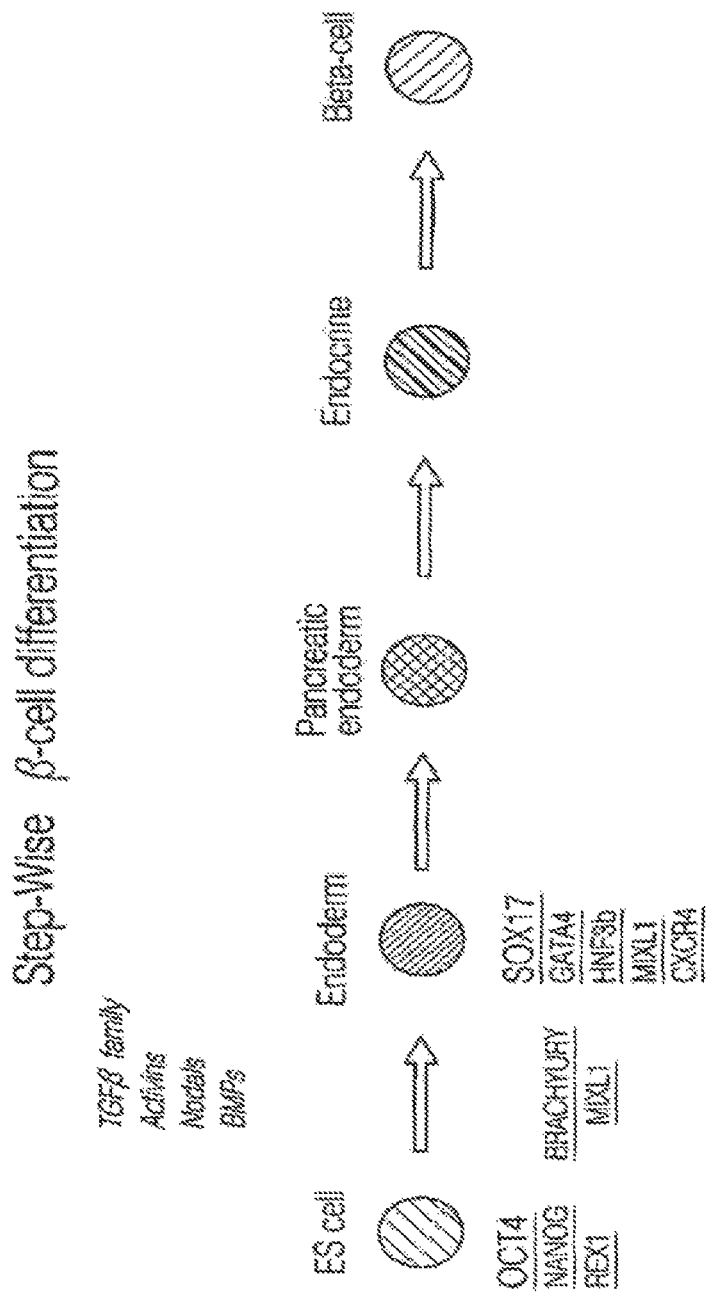
FIG. 1 is a schematic of a proposed differentiation pathway for the production of beta-cells from hESCs. The first step in the pathway commits the ES cell to the definitive endoderm lineage and represents an early step in the further differentiation of ES cells to pancreatic endoderm, endocrine endoderm, or islet/beta-cell. Some factors useful for mediating this transition are members of the TGFβ family which include, but are not limited to, activins, nodals and BMPs. Exemplary markers for defining the definitive endoderm target cell are SOX17, GATA4, HNF3b, MIXL1 and CXCR4.

A crucial stage in early human development termed gastrulation occurs 2-3 weeks after fertilization. Gastrulation is extremely significant because it is at this time that the three primary germ layers are first specified and organized (Lu et al., 2001; Schoenwolf and Smith, 2000). The ectoderm is responsible for the eventual formation of the outer coverings of the body and the entire nervous system whereas the heart, blood, bone, skeletal muscle and other connective tissues are derived from the mesoderm. Definitive endoderm is defined as the germ layer that is responsible for formation of the entire gut tube which includes the esophagus, stomach and small and large intestines, and the organs which derive from the gut tube such as the lungs, liver, thymus, parathyroid and thyroid glands, gall bladder and pancreas (Grapin-Botton and Melton, 2000; Kimelman and Griffin, 2000; Tremblay et al., 2000; Wells and Melton, 1999; Wells and Melton, 2000). A very important distinction should be made between the definitive endoderm and the completely separate lineage of cells termed primitive endoderm. The primitive endoderm is primarily responsible for formation of extra-embryonic tissues, mainly the parietal and visceral endoderm portions of the placental yolk sac and the extracellular matrix material of Reichert's membrane.

During gastrulation, the process of definitive endoderm formation begins with a cellular migration event in which mesendoderm cells (cells competent to form mesoderm or endoderm) migrate through a structure called the primitive streak. Definitive endoderm is derived from cells, which migrate through the anterior portion of the streak and through the node (a specialized structure at the anterior-most region of the streak). As migration occurs, definitive endoderm populates first the most anterior gut tube and culminates with the formation of the posterior end of the gut tube.

In vivo analyses of the formation of definitive endoderm, such as the studies in Zebrafish and *Xenopus* by Conlon et al., 1994; Feldman et al., 1998; Zhou et al., 1993; Aoki et al., 2002; Dougan et al., 2003; Tremblay et al., 2000; Vincent et al., 2003; Alexander et al., 1999; Alexander and Stainier, 1999; Kikuchi et al., 2001; Hudson et al., 1997 and in mouse by Kanai-Azuma et al., 2002 lay a foundation for how one might attempt to approach the development of a specific germ layer cell type in the culture dish using human embryonic stem cells. There are two aspects associated with in vitro ESC culture that pose major obstacles in the attempt to recapitulate development in the culture dish. First, organized germ layer or organ structures are not produced. The majority of germ layer and organ specific genetic markers will be expressed in a heterogeneous fashion in the differentiating hESC culture system. Therefore it is difficult to evaluate formation of a specific tissue or cell type due to this lack of organ specific boundaries. Almost all genes expressed in one cell type within a particular germ layer or tissue type are expressed in other cells of different germ layer or tissue types as well. Without specific boundaries there is considerably less means to assign gene expression specificity with a small sample of 1-3 genes. Therefore one must examine considerably more genes, some of which should be present as well as some that should not be expressed in the particular cell type of the organ or tissue of interest. Second, the timing of gene expression patterns is crucial to movement down a specific developmental pathway.

To further complicate matters, it should be noted that stem cell differentiation in vitro is rather asynchronous, likely considerably more so than in vivo. As such, one group of cells may be expressing genes associated with gastrulation, while another group may be starting final differentiation. Furthermore, manipulation of hESC monolayers or embryoid bodies (EBs) with or without exogenous factor application may result in profound differences with respect to overall gene expression pattern and state of differentiation. For these reasons, the application of exogenous factors must be timed according to gene expression patterns within a heterogeneous cell mixture in order to efficiently move the culture down a specific differentiation pathway. It is also beneficial to consider the morphological association of the cells in the culture vessel. The ability to uniformly influence hESCs when formed into so called embryoid bodies may be less optimal than hESCs grown and differentiated as monolayers and or hESC colonies in the culture vessel.

As an effective way to deal with the above-mentioned problems, some embodiments of the present invention contemplate combining a method for differentiating cells with a method for the enrichment, isolation and/or purification and identification of intermediate cell types in the differentiation pathway.

Definitions

Certain terms and phrases as used throughout this application have the meanings provided as follows:

As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer.

As used herein, "multipotent" or "multipotent cell" refers to a cell type that can give rise to a limited number of other particular cell types. Multipotent cells are committed to one or more, but not all, embryonic and/or extraembryonic cell fates. Thus, in contrast to pluripotent cells, multipotent cells cannot give rise to each of the three embryonic cell lineages as well as extraembryonic cells.

In some embodiments, hESCs can be derived from a "preimplantation embryo." As used herein, "preimplantation embryo" refers to an embryo between the stages of fertilization and implantation. Implantation generally takes place 7-8 days after fertilization. However, implantation may take place about 1, about 2, about 3, about 4, about 5, about 6, about 7, about 8, about 9, about 10, about 11, about 12, about 13, about 14 or greater than about 14 days after fertilization. In some embodiments, a preimplantation embryo has not progressed beyond the blastocyst stage.

As used herein, "expression" refers to the production of a material or substance as well as the level or amount of production of a material or substance. Thus, determining the expression of a specific marker refers to detecting either the relative or absolute amount of the marker that is expressed or simply detecting the presence or absence of the marker.

As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein or a small molecule (for example, molecules having a molecular weight of less than 10,000 amu)

When used in connection with cell cultures and/or cell populations, the term "portion" means any non-zero amount of the cell culture or cell population, which ranges from a single cell to the entirety of the cell culture or cells population.

With respect to cells in cell cultures or in cell populations, the phrase "substantially free of" means that the specified cell type of which the cell culture or cell population is free, is present in an amount of less than about 5% of the total number of cells present in the cell culture or cell population.

"Stringency" of hybridization reactions is readily determinable by those skilled in the art, and generally is an empirical calculation based upon oligonucleotide length and composition, washing temperature, sand salt concentration. In general, longer oligonucleotides may anneal at relatively high temperatures, while shorter oligonucleotides generally anneal at lower temperatures. Hybridization generally depends on the ability of denatured nucleic acid to reanneal when complementary strands are present in an environment below their melting temperature. The higher the degree of desired homology between the oligonucleotide and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions," as used herein, are identified by those that: (1) employ low ionic strength and high temperature for washing, for example 0.015M sodium chloride/0.0015M sodium citrate/0.1% SDS at 50° C.; (2) employ during hybridization a denaturing agent, such as formamide, for example 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C., or (3) for example, employ 50% formamide, 5×SSC (0.75M NaCl, 0.075 M sodium citrate) 50 mM sodium phosphate (pH 6.8), 0.1% sodium pyrophosphate, 5×Denhardt's solution, sonicated salmon sperm DNA (50 µg/mL) 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

As used herein, the term "label" refers to, for example, radioactive, fluorescent, biological or enzymatic tags or labels of standard use in the art. A label can be conjugated, or otherwise bound, to nucleic acids, polypeptides, such as antibodies, or small molecules. For example, oligonucleotides of the present invention can be labeled subsequent to synthesis, by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. Alternatively, when fluorescently-labeled oligonucleotide probes are used, fluorescein, lissamine, phycoerythirin, rhodamine (Perkin Elmer Cetus), Cy2, Cy3, Cy3.5, Cy5, Cy5.5, Cy7, FluorX (Amersham) and others, can be attached to nucleic acids. Non-limiting examples of detectable labels that may be conjugated to polypeptides such as antibodies include but are not limited to radioactive labels, such as $^{3}$H, $^{11}$C, $^{14}$C, $^{18}$F, $^{32}$P, $^{35}$S, $^{64}$Cu, $^{76}$Br, $^{86}$Y, $^{99}$Tc, $^{111}$In, $^{123}$I, $^{125}$I, or $^{177}$Lu, enzymes, such as horseradish peroxidase, fluorophores, chromophores, chemiluminescent agents, chelating complexes, dyes, colloidal gold or latex particles.

Definitive Endoderm Cells and Processes Related Thereto

Embodiments Described Herein Relate to the Production, Identification, and isolation and/or enrichment of definitive endoderm cells in culture by differentiating pluripotent cells, such as stem cells. As described above, definitive endoderm cells do not differentiate into tissues produced from ectoderm or mesoderm, but rather, differentiate into the gut tube as well as organs that are derived from the gut tube. In certain preferred embodiments, the definitive endoderm cells are derived from hESCs. Such processes can provide the basis for efficient production of human endodermal derived tissues such as pancreas, liver, lung, stomach, intestine, thyroid and thymus. For example, production of definitive endoderm may be the first step in differentiation of a stem cell to a functional insulin-producing β-cell. To obtain useful quantities of insulin-producing β-cells, high efficiency of differentiation is desirable for each of the differentiation steps that occur prior to reaching the pancreatic islet/β-cell fate. Since differentiation of stem cells to definitive endoderm cells represents an early step towards the production of functional pancreatic islet/β-cells (as shown in FIG. 1), high efficiency of differentiation at this step is particularly desirable.

In view of the desirability of efficient differentiation of pluripotent cells to definitive endoderm cells, some aspects of the differentiation processes described herein relate to in vitro methodology that results in approximately 50-80% conversion of pluripotent cells to definitive endoderm cells. Typically, such methods encompass the application of culture and growth factor conditions in a defined and temporally specified fashion. Further enrichment of the cell population for definitive endoderm cells can be achieved by isolation and/or purification of the definitive endoderm cells from other cells in the population by using a reagent that specifically binds to definitive endoderm cells. As such, some embodiments described herein relate to definitive endoderm cells as well as methods for producing and isolating and/or purifying such cells.

In order to determine the amount of definitive endoderm cells in a cell culture or cell population, a method of distinguishing this cell type from the other cells in the culture or in the population is desirable. Accordingly, certain embodiments described herein relate to cell markers whose presence, absence and/or relative expression levels are specific for definitive endoderm and methods for detecting and determining the expression of such markers.

In some embodiments described herein, the presence, absence and/or level of expression of a marker is determined by quantitative PCR (Q-PCR). For example, the amount of transcript produced by certain genetic markers, such as one or more markers selected from Table 3 is determined by quantitative Q-PCR. In other embodiments, immunohistochemistry is used to detect the proteins expressed by the above-mentioned genes. In a preferred embodiment, immunohistochemistry is used to detect one or more cell surface markers selected from the group consisting of CALCR, CMKOR1, CXCR4, GPR37, NTN4, RTN4RL1, SEMA3E, SLC40A1, SLC5A9 and TRPA1. In still other embodiments, Q-PCR and immunohistochemcial techniques are both used to identify and determine the amount or relative proportions of markers, such as those selected from Table 3.

By using methods, such as those described above, to determine the expression of one or more appropriate markers, it is possible to identify definitive endoderm cells, as well as determine the proportion of definitive endoderm cells in a cell culture or cell population. For example, in some embodiments of the present invention, the definitive endoderm cells or cell populations that are produced express one or more markers selected from Table 3 at a level of about 2 orders of magnitude greater than non-definitive endoderm cell types or cell populations. In certain embodiments, the non-definitive endoderm cell types consist only of hESCs. In other embodiments, the definitive endoderm cells or cell populations that are produced express one or more markers selected from Table 3 at a level of more than 2 orders of magnitude greater than non-definitive endoderm cell types or cell populations. In particular embodiments, the non-definitive endoderm cell types consist only of hESCs. In still other embodiments, the definitive endoderm cells or cell populations that are produced express one or more of the markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 at a level of about 2 or more than 2 orders of magnitude greater than non-definitive endoderm cell types or cell populations. In certain embodiments, the non-definitive endoderm cell types consist only of hESCs. In some embodiments described herein, definitive endoderm cells do not substantially express PDX1.

Embodiments described herein also relate to definitive endoderm compositions. For example, some embodiments relate to cell cultures comprising definitive endoderm, whereas others relate to cell populations enriched in definitive endoderm cells. Some preferred embodiments relate to cell cultures which comprise definitive endoderm cells, wherein at least about 50-80% of the cells in culture are definitive endoderm cells. An especially preferred embodiment relates to cells cultures comprising human cells, wherein at least about 50-80% of the human cells in culture are definitive endoderm cells. Because the efficiency of the differentiation procedure can be adjusted by modifying certain parameters, which include but are not limited to, cell growth conditions, growth factor concentrations and the timing of culture steps, the differentiation procedures described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% conversion of pluripotent cells to definitive endoderm. In other preferred embodiments, conversion of a pluripotent cell population, such as a stem cell population, to substantially pure definitive endoderm cell population is contemplated.

The compositions and methods described herein have several useful features. For example, the cell cultures and cell populations comprising definitive endoderm as well as the methods for producing such cell cultures and cell populations are useful for modeling the early stages of human development. Furthermore, the compositions and methods described herein can also serve for therapeutic intervention in disease states, such as diabetes mellitus. For example, since definitive endoderm serves as the source for only a limited number of tissues, it can be used in the development of pure tissue or cell types.

Production of Definitive Endoderm from Pluripotent Cells

Processes for differentiating pluripotent cells to produce cell cultures and enriched cell populations comprising definitive endoderm is described below and in U.S. patent Ser. No. 11/021,618, entitled DEFINITIVE ENDODERM, filed Dec. 23, 2004, the disclosure of which is incorporated herein by reference in its entirety. In some of these processes, the pluripotent cells used as starting material are stem cells. In certain processes, definitive endoderm cell cultures and enriched cell populations comprising definitive endoderm cells are produced from embryonic stem cells. A preferred method for deriving definitive endoderm cells utilizes human embryonic stem cells as the starting material for definitive endoderm production. Such pluripotent cells can be cells that originate from the morula, embryonic inner cell mass or those obtained from embryonic gonadal ridges. Human embryonic stem cells can be maintained in culture in a pluripotent state without substantial differentiation using methods that are known in the art. Such methods are described, for example, in U.S. Pat. Nos. 5,453,357, 5,670,372, 5,690,926 5,843,780, 6,200,806 and 6,251,671 the disclosures of which are incorporated herein by reference in their entireties.

In some processes for producing definitive endoderm cells, hESCs are maintained on a feeder layer. In such processes, any feeder layer which allows hESCs to be maintained in a pluripotent state can be used. One commonly used feeder layer for the cultivation of human embryonic stem cells is a layer of mouse fibroblasts. More recently, human fibroblast feeder layers have been developed for use in the cultivation of hESCs (see US Patent Application No. 2002/0072117, the disclosure of which is incorporated herein by reference in its entirety). Alternative processes for producing definitive endoderm permit the maintenance of pluripotent hESC without the use of a feeder layer. Methods of maintaining pluripotent hESCs under feeder-free conditions have been described in US Patent Application No. 2003/0175956, the disclosure of which is incorporated herein by reference in its entirety.

The human embryonic stem cells used herein can be maintained in culture either with or without serum. In some embryonic stem cell maintenance procedures, serum replacement is used. In others, serum free culture techniques, such as those described in US Patent Application No. 2003/0190748, the disclosure of which is incorporated herein by reference in its entirety, are used.

Stem cells are maintained in culture in a pluripotent state by routine passage until it is desired that they be differentiated into definitive endoderm. In some processes, differentiation to definitive endoderm is achieved by providing to the stem cell culture a growth factor of the TGFβ superfamily in an amount sufficient to promote differentiation to definitive endoderm. Growth factors of the TGFβ superfamily which are useful for the production of definitive endoderm are selected from the Nodal/Activin or BMP subgroups. In some preferred differentiation processes, the growth factor is selected from the group consisting of Nodal, activin A, activin B and BMP4. Additionally, the growth factor Wnt3a and other Wnt family members are useful for the production of definitive endoderm cells. In certain differentiation processes, combinations of any of the above-mentioned growth factors can be used.

With respect to some of the processes for the differentiation of pluripotent stem cells to definitive endoderm cells, the above-mentioned growth factors are provided to the cells so that the growth factors are present in the cultures at concentrations sufficient to promote differentiation of at least a portion of the stem cells to definitive endoderm cells. In some processes, the above-mentioned growth factors are present in the cell culture at a concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, at least about 1000 ng/ml, at least about 2000 ng/ml, at least about 3000 ng/ml, at least about 4000 ng/ml, at least about 5000 ng/ml or more than about 5000 ng/ml.

In certain processes for the differentiation of pluripotent stem cells to definitive endoderm cells, the above-mentioned growth factors are removed from the cell culture subsequent to their addition. For example, the growth factors can be removed within about one day, about two days, about three days, about four days, about five days, about six days, about seven days, about eight days, about nine days or about ten days after their addition. In a preferred processes, the growth factors are removed about four days after their addition.

Cultures of definitive endoderm cells can be grown in medium containing reduced serum or no serum. Under certain culture conditions, serum concentrations can range from about 0.05% v/v to about 20% v/v. For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In some processes, definitive endoderm cells are grown without serum or with serum replacement. In still other processes, definitive endoderm cells are grown in the presence of B27. In such processes, the concentration of B27 supplement can range from about 0.1% v/v to about 20% v/v.

Monitoring the Differentiation of Pluripotent Cells to Definitive Endoderm

The progression of the hESC culture to definitive endoderm can be monitored by determining the expression of markers characteristic of definitive endoderm. In some processes, the expression of certain markers is determined by detecting the presence or absence of the marker. Alternatively, the expression of certain markers can be determined by measuring the level at which the marker is present in the cells of the cell culture or cell population. In such processes, the measurement of marker expression can be qualitative or quantitative. One method of quantitating the expression of markers that are produced by marker genes is through the use of quantitative PCR (Q-PCR). Methods of performing Q-PCR are well known in the art. Other methods which are known in the art can also be used to quantitate marker gene expression. For example, the expression of a marker gene product can be detected by using antibodies specific for the marker gene product of interest. In certain processes, the expression of marker genes characteristic of definitive endoderm as well as the lack of significant expression of marker genes characteristic of hESCs and other cell types is determined.

As described further in the Examples below, a reliable marker of definitive endoderm is the SOX17 gene. As such, the definitive endoderm cells produced by the processes described herein express the SOX17 marker gene, thereby producing the SOX17 gene product. Other markers of definitive endoderm are markers selected from Table 3. Since definitive endoderm cells express the SOX17 marker gene at a level higher than that of the SOX7 marker gene, which is characteristic of primitive and visceral endoderm (see Table 1), in some processes, the expression of both SOX17 and SOX7 is monitored. In other processes, expression of the both the SOX17 marker gene and the OCT4 marker gene, which is characteristic of hESCs, is monitored. Additionally, because definitive endoderm cells express the SOX17 marker gene at a level higher than that of the AFP, SPARC or Thrombomodulin (TM) marker genes, the expression of these genes can also be monitored.

Another marker of definitive endoderm is the CXCR4 gene. The CXCR4 gene encodes a cell surface chemokine receptor whose ligand is the chemoattractant SDF-1. The principal roles of the CXCR4 receptor-bearing cells in the adult are believed to be the migration of hematopoetic cells to the bone marrow, lymphocyte trafficking and the differentiation of various B cell and macrophage blood cell lineages [Kim, C., and Broxmeyer, H. J. Leukocyte Biol. 65, 6-15 (1999)]. The CXCR4 receptor also functions as a coreceptor for the entry of HIV-1 into T-cells [Feng, Y., et al. Science, 272, 872-877 (1996)]. In an extensive series of studies carried out by [McGrath, K. E. et al. Dev. Biology 213, 442-456 (1999)], the expression of the chemokine receptor CXCR4 and its unique ligand, SDF-1 [Kim, C., and Broxmyer, H., J. Leukocyte Biol. 65, 6-15 (1999)], were delineated during early development and adult life in the mouse. The CXCR4/SDF1 interaction in development became apparent when it was demonstrated that if either gene was disrupted in transgenic mice [Nagasawa et al. Nature, 382, 635-638 (1996)], Ma, Q., et al Immunity, 10, 463-471 (1999) it resulted in late embryonic lethality. McGrath et al. demonstrated that CXCR4 is the most abundant chemokine receptor messenger RNA detected during early gastrulating embryos (E7.5) using a combination of RNase protection and in situ hybridization methodologies. In the gastrulating embryo, CXCR4/SDF-1 signaling appears to be mainly involved in inducing migration of primitive-streak germlayer cells and is expressed on definitive endoderm, mesoderm and extraembryonic mesoderm present at this time. In E7.2-7.8 mouse embryos, CXCR4 and alpha-fetoprotein are mutually exclusive indicating a lack of expression in visceral endoderm [McGrath, K. E. et al. Dev. Biology 213, 442-456 (1999)].

Since definitive endoderm cells produced by differentiating pluripotent cells express the CXCR4 marker gene, expression of CXCR4 can be monitored in order to track the production of definitive endoderm cells. Additionally, definitive endoderm cells produced by the methods described herein express other markers of definitive endoderm including, but not limited to, one or more markers selected from Table 3. Since definitive endoderm cells express the CXCR4 marker gene at a level higher than that of the SOX7 marker gene, the expression of both CXCR4 and SOX7 can be monitored. In other processes, expression of both the CXCR4 marker gene and the OCT4 marker gene, is monitored. Additionally, because definitive endoderm cells express the CXCR4 marker gene at a level higher than that of the AFP, SPARC or Thrombomodulin (TM) marker genes, the expression of these genes can also be monitored.

It will be appreciated that in some embodiments described herein, the expression of one or more markers selected from Table 3 in definitive endoderm cells is increased as compared to the expression of one or more markers selected from the group consisting of OCT4, SPARC, AFP, TM and SOX7 in definitive endoderm cells. In preferred embodiments, the expression of one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 in definitive endoderm cells is increased as compared to the expression of one or more markers selected from the group consisting of OCT4, SPARC, AFP, TM and SOX7 in definitive endoderm cells.

It will be appreciated that expression of CXCR4 in endodermal cells does not preclude the expression of SOX17. Furthermore, the expression of one or more markers selected from Table 3 in definitive endoderm does not preclude the expression of other markers selected from Table 3. As such, definitive endoderm cells produced by the processes described herein will substantially express SOX17, CXCR4 and one or more other markers selected from Table 3, but will not substantially express AFP, TM, SPARC or PDX1.

It will be appreciated that the expression of SOX17, CXCR4 and/or one or more other markers selected from Table 3 is induced over a range of different levels in definitive endoderm cells depending on the differentiation conditions. As such, in some embodiments described herein, the expression of SOX17, CXCR4 and/or one or more other markers selected from Table 3 in definitive endoderm cells or cell populations is at least about 2-fold higher to at least about 10,000-fold higher than the expression of SOX17, CXCR4 and/or one or more other markers selected from Table 3 in non-definitive endoderm cells or cell populations, for example pluripotent stem cells. In other embodiments, the expression of SOX17, CXCR4 and/or one or more other markers selected from Table 3 in definitive endoderm cells or cell populations is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of SOX17, CXCR4 and/or one or more other markers selected from Table 3 in non-definitive endoderm cells or cell populations, for example pluripotent stem cells. In some embodiments, the expression of SOX17, CXCR4 and/or one or more other markers selected from Table 3 in definitive endoderm cells or cell populations is infinitely higher than the expression of SOX17, CXCR4 and/or one or more other markers selected from Table 3 in non-definitive endoderm cells or cell populations, for example pluripotent stem cells. In preferred embodiments of the above-described processes, the expression of one or more markers selected from Table 3, including one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192, in definitive endoderm cells or cell populations is increased as compared to the expression of one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 in non-definitive endoderm cells or cell populations.

Additionally, it will be appreciated that there is a range of differences between the expression level of SOX17, CXCR4 and/or one or more other markers selected from Table 3 and the expression levels of the OCT4, SPARC, AFP, TM and/or SOX7 markers in definitive endoderm cells. As such, in some embodiments described herein, the expression of SOX17, CXCR4 and/or one or more other markers selected from Table 3 is at least about 2-fold higher to at least about 10,000-fold higher than the expression of OCT4, SPARC, AFP, TM and/or SOX7 markers. In other embodiments, the expression of SOX17, CXCR4 and/or one or more other markers selected from Table 3 is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of OCT4, SPARC, AFP, TM and/or SOX7 markers. In some embodiments, OCT4, SPARC, AFP, TM and/or SOX7 markers are not significantly expressed in definitive endoderm cells.

Enrichment, Isolation and/or Purification of Definitive Endoderm

With respect to aspects of the present invention, definitive endoderm cells can be enriched, isolated and/or purified by contacting a cell population that includes definitive endoderm cells with a reagent that binds to a marker, which is expressed in definitive endoderm cells but not substantially expressed in one or more non-definitive endoderm cell types, and separating cells bound by the reagent from cells that are not bound by the reagent.

In some embodiments, the marker can be any marker that is expressed in definitive endoderm cells but not substantially expressed in one or more non-definitive endoderm cell types. Such markers include, but are not limited to, markers that are more highly expressed in definitive endoderm cells than hESCs, mesoderm cells, ectoderm cells, and/or extra-embryonic endoderm cells. Non-limiting examples of useful markers expressed in definitive endoderm cells, but not substantially expressed in one or more non-definitive endoderm cell types, are provided in Table 3. Certain preferred markers include one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 (highly expressed markers described in Table 4). Other preferred markers include one or more markers selected from the group consisting of CALCR, CMKOR1, CXCR4, GPR37, NTN4, RTN4RL1, SEMA3E, SLC40A1, SLC5A9 and TRPA1 (cell surface markers described in Table 5).

In some embodiments, the reagent can be any type of affinity tag that is specific, or at least partially specific, for definitive endoderm cells, such as antibodies, ligands or other binding agents that are specific, or at least partially specific, to a marker molecule, such as a polypeptide, that is present in definitive endoderm cells but which is not substantially present in other cell types that are found in a cell culture produced by the methods described herein.

Reagents that bind to definitive endoderm associated markers described herein can form reagent-cell complexes with definitive endoderm cells. In some embodiments, subsequent to providing a cell population with a reagent that binds to a marker, unbound reagent can be removed from the composition by washing, stirring, and/or filtering. One example of reagent-cell complex is an antibody-antigen complex. In preferred embodiments of such complexes, the antigen marker can be localized to the cell surface. Another example of a reagent-cell complex is a receptor-ligand complex, wherein the receptor is expressed in definitive endoderm cells but not substantially expressed in one or more non-definitive endoderm cell types. In preferred embodiments, the ligand can bind to the receptor-binding domain without appreciably affecting the receptor activity. In still other preferred embodiments, the ligand is attached to another molecule so as to facilitate easy manipulation of the reagent cell complex. For example, in cases where the ligand is a small molecule, the ligand can be linked to a macromolecule, such as a carbohydrate, a protein or a synthetic polymer. In some embodiments, the macromolecules can be coupled to, for example, labels, particles, such as magnetic particles, or surfaces, such as a solid support. Table 5 lists several polypeptides which are localized at the cell surface, including receptors, which are expressed in definitive endoderm cells but not substantially expressed in one or more non-definitive endoderm cell types.

In some embodiments of the present invention, an antibody is prepared for use as an affinity tag for the enrichment, isolation and/or purification of definitive endoderm cells. Methods for making antibodies, for example, the methods described in Kohler, G., and C. Milstein. 1975. Continuous cultures of fused cells secreting antibody of predefined specificity. *Nature* 256:495-497, the disclosure of which is incorporated herein by reference in its entirety, are well known in the art. Additionally, antibodies and fragments can be made by other standardized methods (See, for example, E. Harlow et al., Antibodies, A Laboratory Manual, Cold Spring Harbor Laboratory, Cold Spring Harbor, N.Y., 1988). The isolation, identification, and molecular construction of antibodies has been developed to such an extent that the choices are almost inexhaustible. Therefore, examples of methods for making various antibodies, antibody fragments and/or antibody complexes will be provided with the understanding that this only represents a sampling of what is known to those of ordinary skill in the art.

Antibodies can be whole immunoglobulin (IgG) of any class, e.g., IgG, IgM, IgA, IgD, IgE, chimeric antibodies or hybrid antibodies with dual or multiple antigen or epitope specificities, or fragments, such as F(ab')$_2$, Fab', Fab and the like, including hybrid fragments. It will be understood that any immunoglobulin or any natural, synthetic, or genetically engineered protein that acts like an antibody by binding to marker of definitive endoderm can be used.

Preparations of polyclonal antibodies can be made using standard methods which are well known in the art. Antibodies can include antiserum preparations from a variety of commonly used animals, e.g., goats, primates, donkeys, swine, rabbits, horses, hens, guinea pigs, rats, or mice, and even human antisera after appropriate selection and purification. Animal antisera are raised by inoculating the animals with immunogenic epitopes from one or more recombinantly-expressed polypeptide markers selected from Table 3. The animals are then bled and the serum or an immunoglobulin-containing serum fraction is recovered.

Hybridoma-derived monoclonal antibodies (human, monkey, rat, mouse, or the like) are also suitable for use in the present invention. Monoclonal antibodies typically display a high degree of specificity. Such antibodies are readily prepared by conventional procedures for the immunization of mammals with preparations such as, the immunogenic epitopes of one or more markers selected from Table 3, fusion of immune lymph or spleen cells with an immortal myeloma cell line, and isolation of specific hybridoma clones. In addition to the foregoing procedure, alternate method of preparing monoclonal antibodies are also useful. Such methods can include interspecies fusions and genetic engineering manipulations of hypervariable regions.

In one embodiment of the present invention, the antibody is a single chain Fv region. Antibody molecules have two generally recognized regions, in each of the heavy and light chains. These regions are the so-called "variable" region which is responsible for binding to the specific antigen in question, and the so-called "constant" region which is responsible for biological effector responses such as complement binding, binding to neutrophils and macrophages, etc. The constant regions have been separated from the antibody molecule and variable binding regions have been obtained. Fragments containing the variable region, but lacking the constant region, are sufficient for antigen binding.

The variable regions of an antibody are composed of a light chain and a heavy chain. Light and heavy chain variable regions have been cloned and expressed in foreign hosts, while maintaining their binding ability. Therefore, it is possible to generate a single chain structure from the multiple chain aggregate (the antibody), such that the single chain structure will retain the three-dimensional architecture of the multiple chain aggregate.

In some embodiments, single polypeptide chain Fv fragments having the characteristic binding ability of multichain variable regions of antibody molecules can be used to bind one or markers selected from Table 3. Such single chain fragments can be produced, for example, following the methods described in U.S. Pat. No. 5,260,203, the disclosure of which is incorporated herein by reference in its entirety, using a computer based system and method to determine chemical structures. These chemical structures are used for converting two naturally aggregated but chemically separated light and heavy polypeptide chains from an antibody variable region into a single polypeptide chain which will fold into a three dimensional structure very similar to the original structure of the two polypeptide chains. The two regions may be linked using an amino acid sequence as a bridge.

The single polypeptide chain obtained from this method can then be used to prepare a genetic sequence that encodes it. The genetic sequence can then be replicated in appropriate hosts, further linked to control regions, and transformed into expression hosts, where it is expressed. The resulting single polypeptide chain binding protein, upon refolding, has the binding characteristics of the aggregate of the original two (heavy and light) polypeptide chains of the variable region of the antibody.

In a further embodiment, the antibodies used herein can multivalent forms of single-chain antigen-binding proteins. Multivalent forms of single-chain antigen-binding proteins have additional utility beyond that of the monovalent single-chain antigen-binding proteins. In particular, a multivalent antigen-binding protein has more than one antigen-binding site which results in an enhanced binding affinity. The multivalent antibodies can be produced using the method disclosed in U.S. Pat. No. 5,869,620, the disclosure of which is incorporated herein by reference in its entirety. The method involves producing a multivalent antigen-binding protein by linking at least two single-chain molecules, each single chain molecule having two binding portions of the variable region of an antibody heavy or light chain linked into a single chain protein. In this way the antibodies can have binding sites for different parts of an antigen or have binding sites for multiple antigens.

In another embodiment, the antibody can be an oligomer. The oligomer is produced as in WO98/18943, the disclosure of which is incorporated herein by reference in its entirety, by first isolating a specific ligand from a phage-display library. Oligomers overcome the problem of the isolation of mostly low affinity ligands from these libraries, by oligomerizing the low-affinity ligands to produce high affinity oligomers. The oligomers are constructed by producing a fusion protein with the ligand fused to a semi-rigid hinge and a coiled coil domain from, for example, Cartilage Oligomeric Matrix Protein (COMP). When the fusion protein is expressed in a host cell, it self assembles into oligomers.

Preferably, the oligomers are peptabodies (Terskikh et al., Biochemistry 94:1663-1668 (1997)). Peptabodies can be exemplified as IgM antibodies which are pentameric with each binding site having low-affinity binding, but able to bind in a high affinity manner as a complex. Peptabodies are made using phage-display random peptide libraries. A short peptide ligand from the library is fused via a semi-rigid hinge at the N-terminus of a COMP pentamerization domain. The fusion protein is expressed in bacteria where it assembles into a pentameric antibody which shows high affinity for its target. Depending on the affinity of the ligand, an antibody with very high affinity can be produced.

Several generally applicable methods for using antibodies in affinity-based isolation and purification methods are known in the art. Such methods can be implemented for use with the antibodies and cells described herein. In preferred embodiments, an antibody which binds to one of the cell surface markers selected from the group consisting of CALCR, CMKOR1, CXCR4, GPR37, NTN4, RTN4RL1, SEMA3E, SLC40A1, SLC5A9 and TRPA1 is attached to a magnetic bead then allowed to bind to definitive endoderm cells in a cell culture which has been enzymatically treated to reduce intercellular and substrate adhesion, to form reagent-cell complexes. The reagent-cell complexes are then exposed to a movable magnetic field which is used to separate reagent-bound definitive endoderm cells from unbound cells. Once the definitive endoderm cells are physically separated from other cells in culture, the antibody binding is disrupted and the cells are replated in appropriate tissue culture medium, thereby producing a population of cells enriched for definitive endoderm.

Other methods of enrichment, isolation and/or purification using antibodies to form antibody-cell complexes are contemplated. For example, in some embodiments, a primary antibody which binds to a marker expressed in definitive endoderm cells, but not substantially expressed in one or more non-definitive endoderm cell types, is incubated with a definitive endoderm-containing cell culture that has been treated to reduce intercellular and substrate adhesion, to form antibody-cell complexes. In preferred embodiments, the primary antibody comprises one or more antibodies that bind to a cell surface polypeptide selected from the group consisting of CALCR, CMKOR1, CXCR4, GPR37, NTN4, RTN4RL1, SEMA3E, SLC40A1, SLC5A9 and TRPA. The cells are then washed, centrifuged and resuspended. The cell suspension is then incubated with a secondary antibody, such as an FITC-conjugated antibody that is capable of binding to the primary antibody of the reagent-cell complex. The cells are then washed, centrifuged and resuspended in buffer. The cell suspension is then analyzed and sorted using a fluorescence activated cell sorter (FACS). Antibody-bound cells are collected separately from cells that are not bound by the antibody, thereby resulting in the isolation of such cell types. If desired, the enriched cell compositions can be further purified by using an alternate affinity-based method or by additional rounds of sorting using the same or different markers that are specific for definitive endoderm.

Additional methods of enrichment, isolation and/or purification related to using a ligand-based reagent to form ligand-cell complexes. For example, ligand-cell complexes can include a ligand-based reagent and receptor that is expressed on definitive endoderm but not substantially expressed in one or more non-definitive endoderm cell types. In such embodiments, ligand-based reagents are used as an affinity tag for the enrichment, isolation and/or purification of definitive endoderm cells. By way of example, the chemokine SDF-1, which is a ligand for CXCR4, or other molecules based on SDF-1 is a useful reagent in the enrichment, isolation and/or purification methods described herein. Likewise, SDF-1 fragments, SDF-1 fusions or SDF-1 mimetics that retain the ability to form reagent-cell complexes are useful in the enrichment, isolation and/or purification methods described herein. In some embodiments, the ligand is a ligand that binds to one of the cell surface markers selected from the group consisting of CALCR, CMKOR1, CXCR4, GPR37, NTN4, RTN4RL1, SEMA3E, SLC40A1, SLC5A9 and TRPA1. In preferred embodiments, a ligand that binds to one of the cell surface markers selected from the group consisting of CALCR, CMKOR1, CXCR4, GPR37, NTN4, RTN4RL1, SEMA3E, SLC40A1, SLC5A9 and TRPA1 is attached directly to a macromolecule or a solid support. In other preferred embodiments, a ligand that binds to one of the cell surface markers selected from the group consisting of CALCR, CMKOR1, CXCR4, GPR37, NTN4, RTN4RL1, SEMA3E, SLC40A1, SLC5A9 and TRPA1 is attached via a linker to a macromolecule or a solid support. In such embodiments, non-bound cells can be removed from the ligand-cell complexes by washing.

Alternatively, in some embodiments of the processes described herein, definitive endoderm cells are fluorescently labeled by recombinant expression of a fluorescent polypeptide or fragment thereof in definitive endoderm cells. For example, a nucleic acid encoding green fluorescent protein (GFP) or a nucleic acid encoding a different expressible fluorescent marker gene is used to label definitive endoderm cells. Various fluorescent marker genes are known in the art, such as luciferase, enhanced green fluorescent protein (EGFP), DS-Red monomer fluorescent protein (Clontech) and others. Any such markers can be used with the enrichment, isolation and/or purification methods described herein. For example, in some embodiments, at least one copy of a nucleic acid encoding GFP or a biologically active fragment thereof is introduced into a pluripotent cell, preferably a human embryonic stem cell, downstream of the promoter of any of the marker genes described herein that are expressed in definitive endoderm cells, but not substantially expressed in one or more non-definitive endoderm cell types, including those listed in Table 3, such that the expression of the GFP gene product or biologically active fragment thereof is under control of the marker gene's promoter. In some embodiments, the entire coding region of the nucleic acid, which encodes the marker, is replaced by a nucleic acid encoding GFP or a biologically active fragment thereof. In other embodiments, the nucleic acid encoding GFP or a biologically active fragment thereof is fused in frame with at least a portion of the nucleic acid encoding the marker, thereby generating a fusion protein. In such embodiments, the fusion protein retains a fluorescent activity similar to GFP.

The fluorescently-tagged cells produced by the above-described methods are then differentiated to definitive endoderm cells using the differentiation methods described herein. Because definitive endoderm cells express the fluorescent marker gene, whereas non-endoderm cells do not, these two cell types can be separated. In some embodiments, cell suspensions comprising a mixture of fluorescently-labeled definitive endoderm cells and unlabeled non-definitive endoderm cells are sorted using a FACS. Definitive endoderm cells are collected separately from non-definitive endoderm cells, thereby resulting in the isolation of such cell types. If desired, the isolated cell compositions can be further purified by additional rounds of sorting using the same or different markers that are specific for definitive endoderm cells.

Using the methods and compositions described herein, enriched, isolated and/or purified populations of definitive endoderm cells and/or tissues can be produced in vitro from hESC cultures or cell populations which have undergone differentiation for from about 1 hour to greater than about 144 hours. In some embodiments, the cells undergo random differentiation. In a preferred embodiment, however, the cells are directed to differentiate primarily into definitive endoderm cells. Some preferred enrichment, isolation and/or purification methods relate to the in vitro production of definitive endoderm cells from human embryonic stem cells.

Using the methods described herein, cell populations or cell cultures can be enriched in definitive endoderm cell content by at least about 2- to about 1000-fold as compared to untreated or unenriched cell populations or cell cultures. In some embodiments, definitive endoderm cells can be enriched by at least about 5- to about 500-fold as compared to untreated or unenriched cell populations or cell cultures. In other embodiments, definitive endoderm cells can be enriched from at least about 10- to about 200-fold as compared to untreated or unenriched cell populations or cell cultures. In still other embodiments, definitive endoderm cells can be enriched from at least about 20- to about 100-fold as compared to untreated or unenriched cell populations or cell cultures. In yet other embodiments, definitive endoderm cells can be enriched from at least about 40- to about 80-fold as compared to untreated or unenriched cell populations or cell cultures. In certain embodiments, definitive endoderm cells can be enriched from at least about 2- to about 20-fold as compared to untreated or unenriched cell populations or cell cultures.

In preferred embodiments, definitive endoderm cells are enriched, isolated and/or purified from other non-definitive endoderm cells after the stem cell cultures are induced to differentiate towards the definitive endoderm lineage. It will be appreciated that the above-described enrichment, isolation and purification procedures can be used with such cultures at any stage of differentiation.

In addition to the procedures just described, definitive endoderm cells may also be isolated by other techniques for cell isolation. Additionally, definitive endoderm cells may also be enriched or isolated by methods of serial subculture in growth conditions which promote the selective survival or selective expansion of said definitive endoderm cells.

Compositions Comprising Definitive Endoderm

Cell compositions produced by the above-described methods include cell cultures comprising definitive endoderm and cell populations enriched in definitive endoderm.

For example, cell cultures which comprise definitive endoderm cells, wherein at least about 50-80% of the cells in culture are definitive endoderm cells, can be produced. Because the efficiency of the differentiation process can be adjusted by modifying certain parameters, which include but are not limited to, cell growth conditions, growth factor concentrations and the timing of culture steps, the differentiation procedures described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% conversion of pluripotent cells to definitive endoderm. In processes in which isolation of definitive endoderm cells is employed, for example, by using an affinity reagent that binds to a marker selected from the group consisting of CALCR, CMKOR1, CXCR4, GPR37, NTN4, RTN4RL1, SEMA3E, SLC40A1, SLC5A9 and TRPA1, a substantially pure definitive endoderm cell population can be recovered.

Some embodiments described herein relate to compositions, such as cell populations and cell cultures, that comprise both pluripotent cells, such as stem cells, and definitive endoderm cells. For example, using the methods described herein, compositions comprising mixtures of hESCs and definitive endoderm cells can be produced. In some embodiments, compositions comprising at least about 5 definitive endoderm cells for about every 95 pluripotent cells are produced. In other embodiments, compositions comprising at least about 95 definitive endoderm cells for about every 5 pluripotent cells are produced. Additionally, compositions comprising other ratios of definitive endoderm cells to pluripotent cells are contemplated. For example, compositions comprising at least about 1 definitive endoderm cell for about every 1,000,000 pluripotent cells, at least about 1 definitive endoderm cell for about every 10,000 pluripotent cells, at least about 1 definitive endoderm cell for about every 100,000 pluripotent cells, at least about 1 definitive endoderm cell for about every 1000 pluripotent cells, at least about 1 definitive endoderm cell for about every 500 pluripotent cells, at least about 1 definitive endoderm cell for about every 100 pluripotent cells, at least about 1 definitive endoderm cell for about every 10 pluripotent cells, at least about 1 definitive endoderm cell for about every 5 pluripotent cells, at least about 1 definitive endoderm cell for about every 2 pluripotent cells, at least about 2 definitive endoderm cells for about every 1 pluripotent cell, at least about 5 definitive endoderm cells for about every 1 pluripotent cell, at least about 10 definitive endoderm cells for about every 1 pluripotent cell, at least about 20 definitive endoderm cells for about every 1 pluripotent cell, at least about 50 definitive endoderm cells for about every 1 pluripotent cell, at least about 100 definitive endoderm cells for about every 1 pluripotent cell, at least about 1000 definitive endoderm cells for about every 1 pluripotent cell, at least about 10,000 definitive endoderm cells for about every 1 pluripotent cell, at least about 100,000 definitive endoderm cells for about every 1 pluripotent cell and at least about 1,000,000 definitive endoderm cells for about every 1 pluripotent cell are contemplated. In some embodiments, the pluripotent cells are human pluripotent stem cells. In certain embodiments the stem cells are derived from a morula, the inner cell mass of an embryo or the gonadal ridges of an embryo. In certain other embodiments, the pluripotent cells are derived from the gondal or germ tissues of a multicellular structure that has developed past the embryonic stage.

Some embodiments described herein relate to cell cultures or cell populations comprising from at least about 5% definitive endoderm cells to at least about 95% definitive endoderm cells. In some embodiments the cell cultures or cell populations comprise mammalian cells. In preferred embodiments, the cell cultures or cell populations comprise human cells. For example, certain specific embodiments relate to cell cultures comprising human cells, wherein from at least about 5% to at least about 95% of the human cells are definitive endoderm cells. Other embodiments relate to cell cultures comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or greater than 90% of the human cells are definitive endoderm cells. In embodiments where the cell cultures or cell populations comprise human feeder cells, the above percentages are calculated without respect to the human feeder cells in the cell cultures or cell populations.

Further embodiments described herein relate to compositions, such as cell cultures or cell populations, comprising human cells, such as human definitive endoderm cells, wherein the expression of SOX17, CXCR4 and/or one or more other markers selected from Table 3 is greater than the expression of the OCT4, SPARC, alpha-fetoprotein (AFP), Thrombomodulin (TM) and/or SOX7 marker in at least about 5% of the human cells. In other embodiments, the expression of SOX17, CXCR4 and/or one or more other markers selected from Table 3 is greater than the expression of the OCT4, SPARC, AFP, TM and/or SOX7 marker in at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells or in greater than 95% of the human cells. In embodiments where the cell cultures or cell populations comprise human feeder cells, the above percentages are calculated without respect to the human feeder cells in the cell cultures or cell populations. In certain embodiments, the definitive endoderm cells expressing SOX17, CXCR4 and/or one or more other markers selected from Table 3 do not express significant levels or amounts of PDX1 (PDX1-negative).

It will be appreciated that some embodiments described herein relate to compositions, such as cell cultures or cell populations, comprising human cells, such as human definitive endoderm cells, wherein the expression of one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 is greater than the expression of the OCT4, SPARC, AFP, TM and/or SOX7 markers in from at least about 5% to greater than at least about 95% of the human cells. In other embodiments, the expression of one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 is greater than the expression of the OCT4, SPARC, AFP, TM and/or SOX7 marker in at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells or in greater than 95% of the human cells. In embodiments where the cell cultures or cell populations comprise human feeder cells, the above percentages are calculated without respect to the human feeder cells in the cell cultures or cell populations. In certain embodiments, the definitive endoderm cells expressing one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 do not express significant levels or amounts of PDX1 (PDX1-negative).

Additional embodiments described herein relate to compositions, such as cell cultures or cell populations, comprising mammalian endodermal cells, such as human endoderm cells, wherein the expression of SOX17, CXCR4 and/or one or more other markers selected from Table 3 is greater than the expression of the OCT4, SPARC, AFP, TM and/or SOX7 marker in at least about 5% of the endodermal cells. In other embodiments, the expression of SOX17, CXCR4 and/or one or more other markers selected from Table 3 is greater than the expression of the OCT4, SPARC, AFP, TM and/or SOX7 marker in at least about 10% of the endodermal cells, in at least about 15% of the endodermal cells, in at least about 20% of the endodermal cells, in at least about 25% of the endodermal cells, in at least about 30% of the endodermal cells, in at least about 35% of the endodermal cells, in at least about 40% of the endodermal cells, in at least about 45% of the endodermal cells, in at least about 50% of the endodermal cells, in at least about 55% of the endodermal cells, in at least about 60% of the endodermal cells, in at least about 65% of the endodermal cells, in at least about 70% of the endodermal cells, in at least about 75% of the endodermal cells, in at least about 80% of the endodermal cells, in at least about 85% of the endodermal cells, in at least about 90% of the endodermal cells, in at least about 95% of the endodermal cells or in greater than 95% of the endodermal cells. In certain embodiments, the mammalian endodermal cells expressing SOX17, CXCR4 and/or one or more other markers selected from Table 3 do not express significant levels or amounts of PDX1 (PDX1-negative).

It will be appreciated that some embodiments described herein relate to compositions, such as cell cultures or cell populations comprising mammalian endodermal cells, wherein the expression of one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 is greater than the expression of the OCT4, SPARC, AFP, TM and/or SOX7 markers in from at least about 5% to greater than at least about 95% of the endodermal cells. In other embodiments, the expression of one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 is greater than the expression of the OCT4, SPARC, AFP, TM and/or SOX7 marker in at least about 10% of the endodermal cells, in at least about 15% of the endodermal cells, in at least about 20% of the endodermal cells, in at least about 25% of the endodermal cells, in at least about 30% of the endodermal cells, in at least about 35% of the endodermal cells, in at least about 40% of the endodermal cells, in at least about 45% of the endodermal cells, in at least about 50% of the endodermal cells, in at least about 55% of the endodermal cells, in at least about 60% of the endodermal cells, in at least about 65% of the endodermal cells, in at least about 70% of the endodermal cells, in at least about 75% of the endodermal cells, in at least about 80% of the endodermal cells, in at least about 85% of the endodermal cells, in at least about 90% of the endodermal cells, in at least about 95% of the endodermal cells or in greater than 95% of the endodermal cells. In certain embodiments, the mammalian endodermal cells expressing one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 do not express significant levels or amounts of PDX1 (PDX1-negative).

Further embodiments described herein relate to compositions, such as cell cultures or cell populations, comprising human cells, such as human definitive endoderm cells, wherein the expression of SOX17, CXCR4 and/or one or more other markers selected from Table 3 is greater than the expression of the OCT4, SPARC, alpha-fetoprotein (AFP), Thrombomodulin (TM) and/or SOX7 marker in at least about 5% of the human cells. In other embodiments, the expression of SOX17, CXCR4 and/or one or more other markers selected from Table 3 is greater than the expression of the OCT4, SPARC, AFP, TM and/or SOX7 marker in at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells or in greater than 95% of the human cells. In embodiments where the cell cultures or cell populations comprise human feeder cells, the above percentages are calculated without respect to the human feeder cells in the cell cultures or cell populations. In certain embodiments, the definitive endoderm cells expressing SOX17, CXCR4 and/or one or more other markers selected from Table 3 do not express significant levels or amounts of PDX1 (PDX1-negative).

It will be appreciated that some embodiments described herein relate to compositions, such as cell cultures or cell populations, comprising human cells, such as human definitive endoderm cells, wherein the expression of one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2 FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 is greater than the expression of the OCT4, SPARC, AFP, TM and/or SOX7 markers in from at least about 5% to greater than at least about 95% of the human cells. In other embodiments, the expression of one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 is greater than the expression of the OCT4, SPARC, AFP, TM and/or SOX7 marker in at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells or in greater than 95% of the human cells. In embodiments where the cell cultures or cell populations comprise human feeder cells, the above percentages are calculated without respect to the human feeder cells in the cell cultures or cell populations. In certain embodiments, the definitive endoderm cells expressing one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 do not express significant levels or amounts of PDX1 (PDX1-negative).

Using the methods described herein, compositions comprising definitive endoderm cells substantially free of other cell types can be produced. In some embodiments described herein, the definitive endoderm cell populations or cell cultures produced by the methods described herein are substantially free of cells that significantly express the OCT4, SOX7, AFP, SPARC, TM, ZIC1 or BRACH marker genes.

Some embodiments described herein relate to enriched, isolated and/or purified compositions, such as cell cultures or cell populations, comprising human cells, such as human definitive endoderm cells, wherein the expression of SOX17, CXCR4 and/or one or more other markers selected from Table 3 is greater than the expression of the OCT4, SPARC, alpha-fetoprotein (AFP), Thrombomodulin (TM) and/or SOX7 marker in at least about 96% of the human cells, in at least about 97% of the human cells, in at least about 98% of the human cells, in at least about 99% of the human cells or in at least about 100% of the human cells. In certain embodiments, enriched, isolated and/or purified compositions of definitive endoderm cells expressing SOX17, CXCR4 and/or one or more other markers selected from Table 3 do not express significant levels or amounts of PDX1 (PDX1-negative).

It will be appreciated that some embodiments described herein relate to enriched, isolated and/or purified compositions, such as cell cultures or cell populations, comprising human cells, such as human definitive endoderm cells, wherein the expression of one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 is greater than the expression of the OCT4, SPARC, AFP, TM and/or SOX7 markers in from at least about 96%, in at least about 97% of the human cells, in at least about 98% of the human cells, in at least about 99% of the human cells or in at least about 100% of the human cells. In certain embodiments, the enriched, isolated and/or purified definitive endoderm cells expressing one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 do not express significant levels or amounts of PDX1 (PDX1-negative).

In one embodiment, a description of a definitive endoderm cell based on the expression of marker genes is, SOX17 high, MIXL1 high, AFP low, SPARC low, Thrombomodulin low, SOX7 low, CXCR4 high. In other embodiments, a description of a definitive endoderm cell based on the expression of marker genes is one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 high; AFP low; SPARC low; Thrombomodulin low and SOX7 low.

Reagent-Cell Complexes

Some aspects of the present invention relate to compositions, such as cell cultures and/or cell population, that comprise complexes of one or more definitive endoderm cells bound to one or more reagents (reagent-cell complexes). For example, cell cultures and/or cell populations comprising reagent-cell complexes, wherein at least about 5 to at least about 100% of the definitive endoderm cells in culture are in the form of reagent-cell complexes, can be produced. In other embodiments, cell cultures and/or cell populations can be produced which comprise at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99% or at least about 100% reagent-cell complexes. In some embodiments, the reagent cell complexes comprise one or more definitive endoderm cells bound to one or more antibodies that bind to a marker selected from Table 3. In preferred embodiments, the reagent cell complexes comprise one or more definitive endoderm cells bound to one or more antibodies that bind to a marker selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192. In other preferred embodiments, the reagent cell complexes comprise one or more definitive endoderm cells bound to one or more antibodies that bind to a marker selected from the group consisting of CALCR, CMKOR1, CXCR4, GPR37, NTN4, RTN4RL1, SEMA3E, SLC40A1, SLC5A9 and TRPA1. In still other embodiments, the reagent cell complexes comprise one or more definitive endoderm cells bound to one or more ligands that bind to a marker selected Table 3. In preferred embodiments, the reagent cell complexes comprise one or more definitive endoderm cells bound to one or more ligands that bind to a marker selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192. In other preferred embodiments, the reagent cell complexes comprise one or more definitive endoderm cells bound to one or more ligands that bind to a marker selected from the group consisting of CALCR, CMKOR1, CXCR4, GPR37, NTN4, RTN4RL1, SEMA3E, SLC40A1, SLC5A9 and TRPA1.

Some embodiments described herein relate to cell cultures and/or cell populations comprising from at least about 5% reagent cell complexes to at least about 95% reagent-cell complexes. In some embodiments the cell cultures or cell populations comprise mammalian cells. In preferred embodiments, the cell cultures or cell populations comprise human cells. For example, certain specific embodiments relate to cell cultures comprising human cells, wherein from at least about 5% to at least about 95% of the human cells are definitive endoderm cells. Other embodiments relate to cell cultures comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or greater than 90% of the human cells are reagent cell complexes. In embodiments where the cell cultures or cell populations comprise human feeder cells, the above percentages are calculated without respect to the human feeder cells in the cell cultures or cell populations. In some embodiments, the reagent cell complexes comprise one or more definitive endoderm cells bound to one or more antibodies that bind to a marker selected from Table 3. In preferred embodiments, the reagent cell complexes comprise one or more definitive endoderm cells bound to one or more antibodies that bind to a marker selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192. In other preferred embodiments, the reagent cell complexes comprise one or more definitive endoderm cells bound to one or more antibodies that bind to a marker selected from the group consisting of CALCR, CMKOR1, CXCR4, GPR37, NTN4, RTN4RL1, SEMA3E, SLC40A1, SLC5A9 and TRPA1. In still other embodiments, the reagent cell complexes comprise one or more definitive endoderm cells bound to one or more ligands that bind to a marker selected Table 3. In preferred embodiments, the reagent cell complexes comprise one or more definitive endoderm cells bound to one or more ligands that bind to a marker selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192. In other preferred embodiments, the reagent cell complexes comprise one or more definitive endoderm cells bound to one or more ligands that bind to a marker selected from the group consisting of CALCR, CMKOR1, CXCR4, GPR37, NTN4, RTN4RL1, SEMA3E, SLC40A1, SLC5A9 and TRPA1.

In some embodiments, the definitive endoderm cells present in the reagent-cell complexes that have been described above express SOX17, CXCR4 and/or one or more other markers selected from Table 3 to a greater extent than OCT4, SPARC, alpha-fetoprotein (AFP), Thrombomodulin (TM) and/or SOX7. In preferred embodiments, the definitive endoderm cells expressing SOX17, CXCR4 and/or one or more other markers selected from Table 3 do not express significant levels or amounts of PDX1 (PDX1-negative). In other embodiments, the definitive endoderm cells present in the reagent-cell complexes that have been described above express one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 to a greater extent than OCT4, SPARC, AFP, TM and/or SOX7. In preferred embodiments, the definitive endoderm cells expressing one or more markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 do not express significant levels or amounts of PDX1 (PDX1-negative). In yet other embodiments, the definitive endoderm cells present in the reagent-cell complexes that have been described above express one or more cell-surface markers selected from the group consisting of CALCR, CMKOR1, CXCR4, GPR37, NTN4, RTN4RL1, SEMA3E, SLC40A1, SLC5A9 and TRPA1. In preferred embodiments, the definitive endoderm cells expressing one or more cell-surface markers selected from the group consisting of CALCR, CMKOR1, CXCR4, GPR37, NTN4, RTN4RL1, SEMA3E, SLC40A1, SLC5A9 and TRPA1.

Additional embodiments described herein relate to compositions, such as cell cultures and/or cell populations, that comprise both pluripotent cells, such as stem cells, and reagent-cell complexes. For example, using the methods described herein, compositions comprising mixtures of hESCs and reagent-cell complexes of definitive endoderm cells can be produced. In some embodiments, compositions comprising at least about 5 reagent-cell complexes for about every 95 pluripotent cells are provided. In other embodiments, compositions comprising at least about 95 reagent-cell complexes for about every 5 pluripotent cells are provided. Additionally, compositions comprising other ratios of reagent-cell complexes cells to pluripotent cells are contemplated. For example, compositions comprising at least about 1 reagent-cell complex for about every 1,000,000 pluripotent cells, at least about 1 reagent-cell complex for about every 100,000 pluripotent cells, at least about 1 reagent-cell complex for about every 10,000 pluripotent cells, at least about 1 reagent-cell complex for about every 1000 pluripotent cells, at least about 1 reagent-cell complex for about every 500 pluripotent cells, at least about 1 reagent-cell complex for about every 100 pluripotent cells, at least about 1 reagent-cell complex for about every 10 pluripotent cells, at least about 1 reagent-cell complex for about every 5 pluripotent cells, at least about 1 reagent-cell complex for about every 2 pluripotent cells, at least about reagent-cell complexes for about every 1 pluripotent cell, at least about 5 reagent-cell complexes for about every 1 pluripotent cell, at least about 10 definitive endoderm cells for about every 1 pluripotent cell, at least about 20 reagent-cell complexes for about every 1 pluripotent cell, at least about 50 reagent-cell complexes for about every 1 pluripotent cell, at least about reagent-cell complexes for about every 1 pluripotent cell, at least about 1000 reagent-cell complexes for about every 1 pluripotent cell, at least about 10,000 reagent-cell complexes for about every 1 pluripotent cell, at least about 100,000 reagent-cell complexes for about every 1 pluripotent cell and at least about 1,000,000 reagent-cell complexes for about every 1 pluripotent cell are contemplated. In some embodiments of the present invention, the pluripotent cells are human pluripotent stem cells. In certain embodiments the stem cells are derived from a morula, the inner cell mass of an embryo or the gonadal ridges of an embryo. In certain other embodiments, the pluripotent cells are derived from the gondal or germ tissues of a multicellular structure that has developed past the embryonic stage.

Identification and Quantitation of Definitive Endoderm Cells

The desirability of detecting or determining the amount of definitive endoderm cells in a cell culture or cell population, and methods of distinguishing this cell type from the other cells in the culture or in the population is readily apparent. Accordingly, certain embodiments described herein relate to reagents and methods for the detection, identification, and quantitation of cell markers whose presence, absence and/or relative expression levels are indicative for definitive endoderm.

Some embodiments provide a method of detecting definitive endoderm cells in a cell population that includes the steps of detecting the expression of at least one of the markers described in Table 3. In some embodiments, the method also includes the step of detecting the expression of at least one marker selected from the group consisting of OCT4, AFP, TM, SPARC and SOX7. In certain embodiments, the expression of one or more markers selected from Table 3 is greater than the expression of OCT4, AFP, TM, SPARC, or SOX7.

As discussed below, expression levels of the markers may be determined by any method known to those skilled in the art, including but not limited to immunocytochemistry or quantitative PCR (Q-PCR). Embodiments of the present invention relate to compositions useful in the detection and quantitation of definitive endoderm cells.

Immunodetection of Definitive Endoderm

In some embodiments, immunochemistry is used to detect the presence, absence, and/or level of expression of proteins encoded by the above-mentioned genes. Accordingly, some embodiments relate to isolated antibodies that bind to certain markers, such as any of the polypeptides encoded by the nucleic acids described in Table 3 including, but not limited to, AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192. Preferred embodiments relate to antibodies that bind to CALCR, CMKOR1, CXCR4, GPR37, NTN4, RTN4RL1, SEMA3E, SLC40A1, SLC5A9 and TRPA1.

The term "antibody" is used in the broadest sense and unless specified specifically covers single monoclonal antibodies (including agonist and antagonist antibodies) and antibody compositions with polyepitopic specificity. The term "antibody" also includes obvious variants, derivatives, analogs, fragments, mimetics, all of which substantially retain the binding characteristics and other properties of the stated antibody.

Monoclonal antibodies (moAbs) refer to antibodies obtained from a population of substantially homogeneous antibodies, i.e., the individual antibodies comprising the population are identical except for possible naturally occurring mutations that may be present in minor amounts. In some embodiments, monoclonal antibodies may be highly specific, being directed against a single epitopic region of an antigen. Furthermore, in contrast to conventional (polyclonal) antibody preparations that typically include different antibodies directed against different determinants (epitopes), each moAb is directed against a single determinant on the antigen. In addition to their specificity, monoclonal antibodies are advantageous in that they can be synthesized by hybridoma culture, uncontaminated by other immunoglobulins.

The modifier "monoclonal" indicates the character of the antibody as being obtained from a substantially homogeneous population of antibodies, and is not to be construed as requiring production of the antibody by any particular method. As described above, the monoclonal antibodies to be used in accordance with the invention may be made by the hybridoma method first described by Kohler et al., Nature, 256:495 (1975), or may be made by recombinant DNA methods (see, e.g., U.S. Pat. No. 4,816,567 to Cabilly et al.). The "monoclonal antibodies" also include clones of antigen-recognition and binding-site containing antibody fragments (Fv clones) isolated from phage antibody libraries using the techniques described in Clackson et al., Nature, 352:624-628 (1991) and Marks et al., J. Mol. Biol., 222: 581-597 (1991), for example.

Furthermore, as described above, in some embodiments, the antibodies can be "antibody fragments," which refer to a portion of an intact antibody comprising the antigen binding site or variable region of the intact antibody, wherein the portion is free of the constant heavy chain domains of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules; (2) single chain polypeptides containing only one light chain variable domain, or a fragment thereof that contains the three CDRs of the light chain variable domain, without an associated heavy chain moiety; and (3) single chain polypeptides containing only one heavy chain variable region, or a fragment thereof containing the three CDRs of the heavy chain variable region, without an associated light chain moiety. In some embodiments, antibody fragments further encompass multispecific or multivalent structures formed from the aforementioned antibody fragments.

It will be appreciated that a wide variety of techniques are useful for the immunodetection of molecules including the markers described herein. For example, flow cytometry, immunomicroscopy, Western blotting, direct and indirect sandwich assays, such as ELISA, Western blotting, and the like. These techniques are described, herein and, for example in Malik and Lillehoj (1994), herein incorporated by reference in its entirety.

Nucleic Acid-Based Detection of Definitive Endoderm

In Other Embodiments, Nucleic Acid Hybridization and/or Amplification techniques are used to detect the presence, absence and/or level of expression of a marker. For example, the amount of transcript produced by certain genetic markers, such as any of the markers listed in Table 3, including but not limited to AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192, can be determined by nucleic acid hybridization techniques, such as, for example, Northern blots, slot blots, RNase protection, in, situ hybridization, and the like. Techniques for the detection and quantitation of specific nucleic acids are well-known to those skilled in the art and are described in, for example, Ausubel et al., (1997), Current Protocols of Molecular Biology, John Wiley and Sons (1997); *Gene transcription: RNA analysis: essential techniques*. 1996. K. Docherty (ed.), Chichester; and Reue, K, *mRNA Quantitation Techniques: Considerations for Experimental Design and Application*, (1998), J. Nutr., 128(11):203 8-2044, each of which is herein incorporated by reference in their entirety. Several sophisticated techniques exist for the sensitive and specific detection nucleic acids In some embodiments, nucleic acid detection techniques such as those described herein are used in combination with nucleic acid amplification techniques. Several nucleic acid amplification techniques are also useful in detection of the presence/absence and/or level of expression markers. The skilled artisan will appreciate that any nucleic acid amplification method that can be adapted to detect expression levels of genes, such as ligase chain reaction (LCR) (See, Wu (1989) *Genomics* 4:560; Landegren (1988) *Science* 241:1077; Barringer (1990) *Gene* 89:117), nucleic acid sequence-based amplification (NASBA), self-sustained sequence replication (3SR) (See, Guatelli (1990) *Proc. Natl. Acad. Sci. USA*, 87:1874), strand displacement amplification (SDA), transcription-mediated amplification (TMA) (See, Kwoh (1989) *Proc. Natl. Acad. Sci. USA* 86:1173), cycling probe technology (CPT), solid phase amplification (SPA), nuclease dependent signal amplification (NDSA), rolling circle amplification technology (RCA), Anchored strand displacement amplification, solid-phase (immobilized) rolling circle amplification, Q Beta replicase amplification and other RNA polymerase mediated techniques (e.g., NASBA, Cangene, Mississauga, Ontario) are useful in the methods described herein. These and other techniques are also described in Berger (1987) *Methods Enzymol*. 152:307-316;

Sambrook, Ausubel, Mullis (1987) U.S. Pat. Nos. 4,683,195 and 4,683,202; Amheim (1990) *C & EN* 36-47; Lomell *J. Clin. Chem.,* 35:1826 (1989); Van Brunt, *Biotechnology,* 8:291-294 (1990); Wu (1989) *Gene* 4:560; Sooknanan (1995) *Biotechnology* 13:563-564. For example, several real-time reverse-transcription-PCR (RT-PCR) based techniques are available that enable mRNA detection and quantitation.

Detection and quantitation of nucleic acids is also known to those skilled in the art. Non-limiting examples of amplification and detection techniques include, for example, TaqMan probe technology (See, European Patent EP 0 543 942), molecular beacon probe technology (See, Tyagi et al., (1996) *Nat. Biotech.* 14:303-308.), Scorpion probe technology (See, Thewell (2000), *Nucl. Acids Res.* 28:3752), nanoparticle probe technology (See, Elghanian, et al. (1997) *Science* 277:1078-1081.) and Amplifluor probe technology (See, U.S. Pat. Nos. 5,866,366; 6,090,592; 6,117,635; and 6,117,986), fluorescence resonance energy transfer (FRET)-based methods such as adjacent hybridization of probes (including probe-probe and probe-primer methods) (See, J. R. Lakowicz, "Principles of Fluorescence Spectroscopy," Kluwer Academic/Plenum Publishers, New York, 1999).

Accordingly, some embodiments of the present invention relate to compositions useful in nucleic acid based techniques for the detection, identification and/or quantitation of definitive endoderm cells in a cell population. Some embodiments relate to composition that include a first oligonucleotide that hybridizes to a first marker, such as those described herein, and a second oligonucleotide that hybridizes to a second marker that other than the first marker, such as those described herein. By way of example, the first and second oligonucleotides can hybridize to different markers selected from Table 3. In preferred embodiments, the first and second oligonucleotides can hybridize to different markers selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192. In other preferred embodiments, the oligonucleotides hybridize to the above markers under stringent conditions.

As used herein, oligonucleotides refer to polynucleotides that are generally at least about 10 nucleotides in length, at least about 12 nucleotides in length, at least about 14 nucleotides in length, at least about 16 nucleotides in length, at least about 18 nucleotides in length, at least about 20 nucleotides in length, at least about 22 nucleotides in length, at least about 24 nucleotides in length, at least about 26 nucleotides in length, at least about 28 nucleotides in length, at least about 30 nucleotides in length, at least about 35 nucleotides in length, at least about 40 nucleotides in length, at least about 45 nucleotides in length, at least about 50 nucleotides in length or greater than 50 nucleotides in length.

It will be appreciated by one skilled in the art that hybridization of the oligonucleotides to marker sequence is achieved by selecting sequences which are at least substantially complementary to the target or reference nucleic acid sequence. In some embodiments, this includes base-pairing of the oligonucleotide target nucleic acid sequence over the entire length of the oligonucleotide sequence. Such sequences can be referred to as "fully complementary" with respect to each other. Where an oligonucleotide is referred to as "substantially complementary" with respect to a nucleic acid sequence herein, the two sequences can be fully complementary, or they may form mismatches upon hybridization, but retain the ability to hybridize under the conditions used to detect the presence marker.

As set forth above, oligonucleotides of the embodiments described herein may be used in an amplification reaction. Accordingly, the compositions may include a polymerase, such as an RNA-dependent DNA polymerase. In some embodiments, the RNA-dependent DNA polymerase is a reverse transciptase. Moloney Murine Leukemia Virus reverse transcriptase and Avian Myeloblastosis Virus (AMV) reverse transcriptase are non-limiting examples of reverse transcriptase enzymes commonly used by those skilled in the art and which are useful in the embodiments described herein. Further embodiments may also include DNA-dependent DNA polymerases, such as Taq polymerase and the like.

Advantageously, the oligonucleotides described herein can include a label, such as a radioactive label, a fluorescent label, or any other type of label that facilitates the detection and/or quantitation of nucleic acid markers, such as those described herein.

In still other embodiments, Q-PCR and immunohistochemical techniques are both used to identify and determine the amount or relative proportions of such markers.

Identification of Factors Capable of Promoting the Differentiation of Definitive Endoderm Cells Certain Screening Methods Described Herein Relate to Methods for identifying at least one differentiation factor that is capable of promoting the differentiation of definitive endoderm cells. In some embodiments of these methods, cell populations comprising definitive endoderm cells, such as human definitive endoderm cells, are obtained. The cell population is then provided with a candidate differentiation factor. At a first time point, which is prior to or at approximately the same time as providing the candidate differentiation factor, expression of a marker is determined. Alternatively, expression of the marker can be determined after providing the candidate differentiation factor. At a second time point, which is subsequent to the first time point and subsequent to the step of providing the candidate differentiation factor to the cell population, expression of the same marker is again determined. Whether the candidate differentiation factor is capable of promoting the differentiation of the definitive endoderm cells is determined by comparing expression of the marker at the first time point with the expression of the marker at the second time point. If expression of the marker at the second time point is increased or decreased as compared to expression of the marker at the first time point, then the candidate differentiation factor is capable of promoting the differentiation of definitive endoderm cells.

Some embodiments of the screening methods described herein utilize cell populations or cell cultures which comprise human definitive endoderm cells. For example, the cell population can be a substantially purified population of human definitive endoderm cells. Alternatively, the cell population can be an enriched population of human definitive endoderm cells, wherein at least about 90%, at least about 91%, at least about 92%, at least about 93%, at least about 94%, at least about 95%, at least about 96%, at least about 97% or greater than at least about 97% of the human cells in the cell population are human definitive endoderm cells. In other embodiments described herein, the cell population comprises human cells wherein at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85% or greater than at least about 85% of the human cells are human definitive endoderm cells. In some embodiments, the cell population includes non-human cells such as non-human feeder cells. In other embodiments, the cell population includes human feeder cells. In such embodiments, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or greater than at least about 95% of the human cells, other than said feeder cells, are human definitive endoderm cells.

In embodiments of the screening methods described herein, the cell population is contacted or otherwise provided with a candidate (test) differentiation factor. The candidate differentiation factor can comprise any molecule that may have the potential to promote the differentiation of human definitive endoderm cells. In some embodiments described herein, the candidate differentiation factor comprises a molecule that is known to be a differentiation factor for one or more types of cells. In alternate embodiments, the candidate differentiation factor comprises a molecule that in not known to promote cell differentiation. In preferred embodiments, the candidate differentiation factor comprises molecule that is not known to promote the differentiation of human definitive endoderm cells.

In some embodiments of the screening methods described herein, the candidate differentiation factor comprises a small molecule. In preferred embodiments, a small molecule is a molecule having a molecular mass of about 10,000 amu or less. In some embodiments, the small molecule comprises a retinoid. In some embodiments, the small molecule comprises retinoic acid.

In other embodiments described herein, the candidate differentiation factor comprises a polypeptide. The polypeptide can be any polypeptide including, but not limited to, a glycoprotein, a lipoprotein, an extracellular matrix protein, a cytokine, a chemokine, a peptide hormone, an interleukin or a growth factor. Preferred polypeptides include growth factors. In some preferred embodiments, the candidate differentiation factors comprises one or more growth factors selected from the group consisting of FGF10, FGF4, FGF2, Wnt3A and Wnt3B.

In some embodiments of the screening methods described herein, the candidate differentiation factors comprise one or more growth factors selected from the group consisting of Amphiregulin, B-lymphocyte stimulator, IL-16, Thymopoietin, TRAIL/Apo-2, Pre B cell colony enhancing factor, Endothelial differentiation-related factor 1 (EDF1), Endothelial monocyte activating polypeptide II, Macrophage migration inhibitory factor (MIF), Natural killer cell enhancing factor (NKEFA), Bone mophogenetic protein 2, Bone mophogenetic protein 8 (osteogeneic protein 2), Bone morphogenic protein 6, Bone morphogenic protein 7, Connective tissue growth factor (CTGF), CGI-149 protein (neuroendocrine differentiation factor), Cytokine A3 (macrophage inflammatory protein 1-alpha), Gliablastoma cell differentiation-related protein (GBDR1), Hepatoma-derived growth factor, Neuromedin U-25 precursor, Vascular endothelial growth factor (VEGF), Vascular endothelial growth factor B (VEGF-B), T-cell specific RANTES precursor, thymic dendritic cell-derived factor 1, Transferrin, Interleukin-1 (IL 1), Interleukin-2 (IL 2), Interleukin-3 (IL 3), Interleukin-4 (IL 4), Interleukin-5 (IL 5), Interleukin-6 (IL 6), Interleukin-7 (IL 7), Interleukin-8 (IL 8), Interleukin-9 (IL 9), Interleukin-10 (IL 10), Interleukin-11 (IL 11), Interleukin-12 (IL 12), Interleukin-13 (IL 13), Granulocyte-colony stimulating factor (G-CSF), Granulocyte macrophage colony stimulating factor (GM-CSF), Macrophage colony stimulating factor (M-CSF), Erythropoietin, Thrombopoietin, Vitamin $D_3$, Epidermal growth factor (EGF), Brain-derived neurotrophic factor, Leukemia inhibitory factor, Thyroid hormone, Basic fibroblast growth factor (bFGF), aFGF, FGF-4, FGF-6, Keratinocyte growth factor (KGF), Platelet-derived growth factor (PDGF), Platelet-derived growth factor-BB, beta nerve growth factor, activin A, Transforming growth factor beta 1 (TGF-β1), Interferon-α, Interferon-β, Interferon-γ, Tumor necrosis factor-α, Tumor necrosis factor-β, Burst promoting activity (BPA), Erythroid promoting activity (EPA), $PGE_2$, insulin growth factor-1 (IGF-1), IGF-II, Neutrophin growth factor (NGF), Neutrophin-3, Neutrophin 4/5, Ciliary neurotrophic factor, Glial-derived nexin, Dexamethasone, β-mercaptoethanol, Retinoic acid, Butylated hydroxyanisole, 5-azacytidine, Amphotericin B, Ascorbic acid, Ascrorbate, isobutylxanthine, indomethacin, β-glycerolphosphate, nicotinamide, DMSO, Thiazolidinediones, TWS119, oxytocin, vasopressin, melanocyte-stimulating hormone, corticortropin, lipotropin, thyrotropin, growth hormone, prolactin, luteinizing hormone, human chorionic gonadotropin, follicle stimulating hormone, corticotropin-releasing factor, gonadotropin-releasing factor, prolactin-releasing factor, prolactin-inhibiting factor, growth-hormone releasing factor, somatostatin, thyrotropin-releasing factor, calcitonin gene-related peptide, parathyroid hormone, glucagon-like peptide 1, glucose-dependent insulinotropic polypeptide, gastrin, secretin, cholecystokinin, motilin, vasoactive intestinal peptide, substance P, pancreatic polypeptide, peptide tyrosine tyrosine, neuropeptide tyrosine, insulin, glucagon, placental lactogen, relaxin, angiotensin II, calctriol, atrial natriuretic peptide, and melatonin. thyroxine, triiodothyronine, calcitonin, estradiol, estrone, progesterone, testosterone, cortisol, corticosterone, aldosterone, epinephrine, norepinepherine, androstiene, calcitriol, collagen, Dexamethasone, β-mercaptoethanol, Retinoic acid, Butylated hydroxyanisole, 5-azacytidine, Amphotericin B, Ascorbic acid, Ascrorbate, isobutylxanthine, indomethacin, β-glycerolphosphate, nicotinamide, DMSO, Thiazolidinediones, and TWS119.

In some embodiments of the screening methods described herein, the candidate differentiation factor is provided to the cell population in one or more concentrations. In some embodiments, the candidate differentiation factor is provided to the cell population so that the concentration of the candidate differentiation factor in the medium surrounding the cells ranges from about 0.1 ng/ml to about 10 mg/ml. In some embodiments, the concentration of the candidate differentiation factor in the medium surrounding the cells ranges from about 1 ng/ml to about 1 mg/ml. In other embodiments, the concentration of the candidate differentiation factor in the medium surrounding the cells ranges from about 10 ng/ml to about 100 ng/ml. In still other embodiments, the concentration of the candidate differentiation factor in the medium surrounding the cells ranges from about 100 ng/ml to about 10 ng/ml. In preferred embodiments, the concentration of the candidate differentiation factor in the medium surrounding the cells is about 5 ng/ml, about 25 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml, about 400 ng/ml, about 425 ng/ml, about 450 ng/ml, about 475 ng/ml, about 500 ng/ml, about 525 ng/ml, about 550 ng/ml, about 575 ng/ml, about 600 ng/ml, about 625 ng/ml, about 650 ng/ml, about 675 ng/ml, about 700 ng/ml, about 725 ng/ml, about 750 ng/ml, about 775 ng/ml, about 800 ng/ml, about 825 ng/ml, about 850 ng/ml, about 875 ng/ml, about 900 ng/ml, about 925 ng/ml, about 950 ng/ml, about 975 ng/ml, about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, about 10 µg/ml, about 11 µg/ml, about 12 µg/ml, about 13 µg/ml, about 14 µg/ml, about 15 µg/ml, about 16 µg/ml, about 17 µg/ml, about 18 µg/ml, about 19 µg/ml, about 20 µg/ml, about 25 µg/ml, about 50 µg/ml, about 75 µg/ml, about 100 µg/ml, about 125 µg/ml, about 150 µg/ml, about 175 µg/ml, about 200 µg/ml, about 250 µg/ml, about 300 µg/ml, about 350 µg/ml, about 400 µg/ml, about 450 µg/ml, about 500 µg/ml, about 550 µg/ml, about 600 µg/ml, about 650 µg/ml, about 700 µg/ml, about 750 µg/ml, about 800 µg/ml, about 850 µg/ml, about 900 µg/ml, about 950 µg/ml, about 1000 µg/ml or greater than about 1000 µg/ml.

In certain embodiments of the screening methods described herein, the cell population is provided with a candidate differentiation factor which comprises any molecule other than foregut differentiation factor. For example, in some embodiments, the cell population is provided with a candidate differentiation factor which comprises any molecule other than a retinoid, a member of the TGFβ superfamily of growth factors, FGF10 or FGF4. In some embodiments, the cell population is provided with a candidate differentiation factor which comprises any molecule other than retinoic acid.

In some embodiments, steps of the screening methods described herein comprise determining expression of at least one marker at a first time point and a second time point. In some of these embodiments, the first time point can be prior to or at approximately the same time as providing the cell population with the candidate differentiation factor. Alternatively, in some embodiments, the first time point is subsequent to providing the cell population with the candidate differentiation factor. In some embodiments, expression of a plurality of markers is determined at a first time point.

Some preferred markers for use in the above embodiments include one or more markers selected from Table 3. In other preferred embodiments, the one or more markers are selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192. In still other preferred embodiments, the one or more markers are selected from the group consisting of CALCR, CMKOR1, CXCR4, GPR37, NTN4, RTN4RL1, SEMA3E, SLC40A1, SLC5A9 and TRPA1.

In addition to determining expression of at least one marker at a first time point, some embodiments of the screening methods described herein contemplate determining expression of at least one marker at a second time point, which is subsequent to the first time point and which is subsequent to providing the cell population with the candidate differentiation factor. In such embodiments, expression of the same marker is determined at both the first and second time points. In some embodiments, expression of a plurality of markers is determined at both the first and second time points. In such embodiments, expression of the same plurality of markers is determined at both the first and second time points. In some embodiments, marker expression is determined at a plurality of time points, each of which is subsequent to the first time point, and each of which is subsequent to providing the cell population with the candidate differentiation factor. In certain embodiments, marker expression is determined by Q-PCR. In other embodiments, marker expression is determined by immunocytochemistry.

Some preferred markers for use in the above embodiments include one or more markers selected from Table 3. In other preferred embodiments, the one or more markers are selected from the group consisting of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192. In still other preferred embodiments, the one or more markers are selected from the group consisting of CALCR, CMKOR1, CXCR4, GPR37, NTN4, RTN4RL1, SEMA3E, SLC40A1, SLC5A9 and TRPA1.

In certain embodiments of the screening methods described herein, the marker having its expression is determined at the first and second time points is a marker that is associated with the differentiation of human definitive endoderm cells to cells which are the precursors of cells which make up tissues and/or organs that are derived from the gut tube. In some embodiments, the tissues and/or organs that are derived from the gut tube comprise terminally differentiated cells. In some embodiments, the marker is indicative of pancreatic cells or pancreatic precursor cells. In preferred embodiments, the marker is pancreatic-duodenal homeobox factor-1 (PDX1). In other embodiments, the marker is homeobox A13 (HOXA13) or homeobox C6 (HOXC6). Additionally, in other embodiments, the marker is indicative of liver cells or liver precursor cells. In certain preferred embodiments, the marker is albumin, hepatocyte specific antigen (HSA) or prospero-related homeobox 1 (PROX1). In other embodiments, the marker is indicative of lung or lung precursor cells. In some preferred embodiments, the marker is thyroid transcription factor 1 (TITF1). In yet other embodiments, the marker is indicative of intestinal or intestinal precursor cells. In additional preferred embodiments, the marker is villin, glucose transporter-2 (GLUT2), apolipoprotein A1 (APOA1), vascular cell adhesion molecule-1 (VACM1), von Willebrand factor (VWF), CXC-type chemokine receptor 4 (CXCR4) or caudal type homeobox transcription factor 2 (CDX2). In still other embodiments, the marker is indicative of stomach or stomach precursor cells. In additional preferred embodiments, the marker is VCAM1, VWF or CXCR4. In other embodiments, the marker is indicative of thyroid or thyroid precursor cells. In such embodiments, the marker is TITF1. In still other embodiments, the marker is indicative of thymus or thymus precursor cells.

In some embodiments of the screening methods described herein, sufficient time is allowed to pass between providing the cell population with the candidate differentiation factor and determining marker expression at the second time point.

Sufficient time between providing the cell population with the candidate differentiation factor and determining expression of the marker at the second time point can be as little as from about 1 hour to as much as about 10 days. In some embodiments, the expression of at least one marker is determined multiple times subsequent to providing the cell population with the candidate differentiation factor. In some embodiments, sufficient time is at least about 1 hour, at least about 6 hours, at least about 12 hours, at least about 18 hours, at least about 24 hours, at least about 30 hours, at least about 36 hours, at least about 42 hours, at least about 48 hours, at least about 54 hours, at least about 60 hours, at least about 66 hours, at least about 72 hours, at least about 78 hours, at least about 84 hours, at least about 90 hours, at least about 96 hours, at least about 102 hours, at least about 108 hours, at least about 114 hours, at least about 120 hours, at least about 126 hours, at least about 132 hours, at least about 138 hours, at least about 144 hours, at least about 150 hours, at least about 156 hours, at least about 162 hours, at least about 168 hours, at least about 174 hours, at least about 180 hours, at least about 186 hours, at least about 192 hours, at least about 198 hours, at least about 204 hours, at least about 210 hours, at least about 216 hours, at least about 222 hours, at least about 228 hours, at least about 234 hours or at least about 240 hours.

In some embodiments of the methods described herein, it is further determined whether the expression of the marker at the second time point has increased or decreased as compared to the expression of this marker at the first time point. An increase or decrease in the expression of the at least one marker indicates that the candidate differentiation factor is capable of promoting the differentiation of the definitive endoderm cells. Similarly, if expression of a plurality of markers is determined, it is further determined whether the expression of the plurality of markers at the second time point has increased or decreased as compared to the expression of this plurality of markers at the first time point. An increase or decrease in marker expression can be determined by measuring or otherwise evaluating the amount, level or activity of the marker in the cell population at the first and second time points. Such determination can be relative to other markers, for example housekeeping gene expression, or absolute. In certain embodiments, wherein marker expression is increased at the second time point as compared with the first time point, the amount of increase is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of increase is less than 2-fold. In embodiments where marker expression is decreased at the second time point as compared with the first time point, the amount of decrease is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of decrease is less than 2-fold.

In some embodiments of the screening methods described herein, after providing the cell population with a candidate differentiation factor, the human definitive endoderm cells differentiate into one or more cell types of the definitive endoderm lineage. In some embodiments, after providing the cell population with a candidate differentiation factor, the human definitive endoderm cells differentiate into cells that are derived from the gut tube. Such cells include, but are not limited to, cells of the pancreas, liver, lungs, stomach, intestine, thyroid, thymus, pharynx, gallbladder and urinary bladder as well as precursors of such cells. Additionally, these cells can further develop into higher order structures such as tissues and/or organs.

Having generally described this invention, a further understanding can be obtained by reference to certain specific examples which are provided herein for purposes of illustration only, and are not intended to be limiting.

EXAMPLE 1

Human ES Cells

For our studies of endoderm development we employed human embryonic stem cells, which are pluripotent and can divide seemingly indefinitely in culture while maintaining a normal karyotype. ES cells were derived from the 5-day-old embryo inner cell mass using either immunological or mechanical methods for isolation. In particular, the human embryonic stem cell line hESCyt-25 was derived from a supernumerary frozen embryo from an in vitro fertilization cycle following informed consent by the patient. Upon thawing the hatched blastocyst was plated on mouse embryonic fibroblasts (MEF), in ES medium (DMEM, 20% FBS, non essential amino acids, beta-mercaptoethanol, and FGF2). The embryo adhered to the culture dish and after approximately two weeks, regions of undifferentiated hESCs were transferred to new dishes with MEFs. Transfer was accomplished with mechanical cutting and a brief digestion with dispase, followed by mechanical removal of the cell clusters, washing and re-plating. Since derivation, hESCyt-25 has been serially passaged over 100 times. We employed the hESCyt-25 human embryonic stem cell line as our starting material for the production of definitive endoderm.

It will be appreciated by those of skill in the art that stem cells or other pluripotent cells can also be used as starting material for the differentiation procedures described herein. For example, cells obtained from embryonic gonadal ridges, which can be isolated by methods known in the art, can be used as pluripotent cellular starting material.

EXAMPLE 2 hESCyt-25 Characterization

The human embryonic stem cell line, hESCyt-25 has maintained a normal morphology, karyotype, growth and self-renewal properties over 18 months in culture. This cell line displays strong immunoreactivity for the OCT4, SSEA-4 and TRA-1-60 antigens, all of which, are characteristic of undifferentiated hESCs and displays alkaline phosphatase activity as well as a morphology identical to other established hESC lines. Furthermore, the human stem cell line, hESCyt-25, also readily forms embryoid bodies (EBs) when cultured in suspension. As a demonstration of its pluripotent nature, hESCyT-25 differentiates into various cell types that represent the three principal germ layers. Ectoderm production was demonstrated by Q-PCR for ZIC1 as well as immunocytochemistry (ICC) for nestin and more mature neuronal markers. Immunocytochemical staining for β-III tubulin was observed in clusters of elongated cells, characteristic of early neurons. Previously, we treated EBs in suspension with retinoic acid, to induce differentiation of pluripotent stem cells to visceral endoderm (VE), an extraembryonic lineage. Treated cells expressed high levels of α-fetoprotein (AFP) and SOX7, two markers of VE, by 54 hours of treatment. Cells differentiated in monolayer expressed AFP in sporadic patches as demonstrated by immunocytochemical staining. As will be described below, the hESCyT-25 cell line was also capable of forming definitive endoderm, as validated by real-time quantitative polymerase chain reaction (Q-PCR) and immunocytochemistry for SOX17 and HNF3beta in the absence of AFP and SOX7 expression. To demonstrate differentiation to mesoderm, differentiating EBs were analyzed for Brachyury gene expression at several time points. Brachyury expression increased progressively over the course of the experiment. In view of the foregoing, the hESCyT-25 line is pluripotent as shown by the ability to form cells representing the three germ layers as well as extraembryonic lineages.

EXAMPLE 3

Production of SOX17 Antibody

A primary obstacle to the identification of definitive endoderm in hESC cultures is the lack of appropriate tools. We therefore undertook the production of an antibody raised against human SOX17 protein.

The marker SOX17 is expressed throughout the definitive endoderm as it forms during gastrulation and its expression is maintained in the gut tube (although levels of expression vary along the A-P axis) until around the onset of organogenesis. SOX17 is also expressed in a subset of extra-embryonic endoderm cells. No expression of this protein has been observed in mesoderm or ectoderm. It has now been discovered that SOX17 is an appropriate marker for the definitive endoderm lineage when used in conjunction with markers to exclude extra-embryonic lineages.

As described in detail herein, the SOX17 antibody was utilized to specifically examine effects of various treatments and differentiation procedures aimed at the production of SOX17 positive definitive endoderm cells. Other antibodies reactive to AFP, SPARC and Thrombomodulin were also employed to rule out the production of visceral and parietal endoderm (extra-embryonic endoderm).

Figure 2:
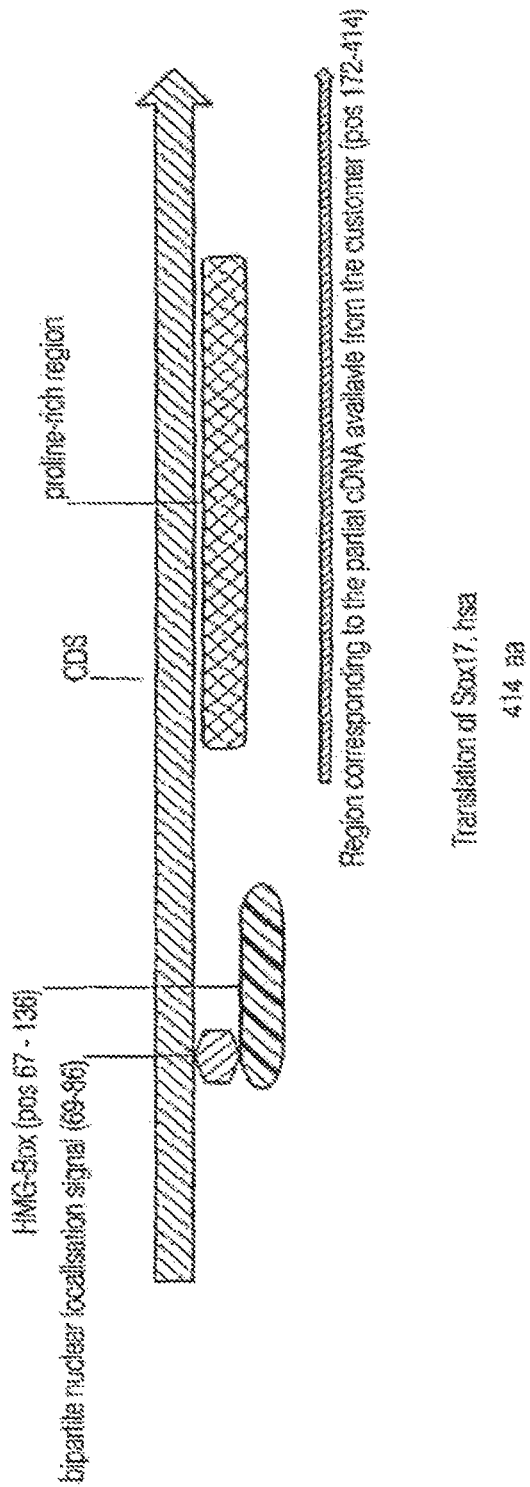
FIG. 2 is a diagram of the human SOX17 cDNA which displays the positions of conserved motifs and highlights the region used for the immunization procedure by GENOVAC.

In order to produce an antibody against SOX17, a portion of the human SOX17 cDNA (SEQ ID NO: 1) corresponding to amino acids 172-414 (SEQ ID NO: 2) in the carboxyterminal end of the SOX17 protein (FIG. 2) was used for genetic immunization in rats at the antibody production company, GENOVAC (Freiberg, Germany), according to procedures developed there. Procedures for genetic immunization can be found in U.S. Pat. Nos. 5,830,876, 5,817, 637, 6,165,993 and 6,261,281 as well as International Patent Application Publication Nos. WO00/29442 and WO99/13915, the disclosures of which are incorporated herein by reference in their entireties.

Other suitable methods for genetic immunization are also described in the non-patent literature. For example, Barry et al. describe the production of monoclonal antibodies by genetic immunization in *Biotechniques* 16: 616-620, 1994, the disclosure of which is incorporated herein by reference in its entirety. Specific examples of genetic immunization methods to produce antibodies against specific proteins can be found, for example, in Costaglia et al., (1998) Genetic immunization against the human thyrotropin receptor causes thyroiditis and allows production of monoclonal antibodies recognizing the native receptor, *J. Immunol.* 160: 1458-1465; Kilpatrick et al (1998) Gene gun delivered DNA-based immunizations mediate rapid production of murine monoclonal antibodies to the Flt-3 receptor, *Hybridoma* 17: 569-576; Schmolke et al., (1998) Identification of hepatitis G virus particles in human serum by E2-specific monoclonal antibodies generated by DNA immunization, *J. Virol.* 72: 4541-4545; Krasemann et al., (1999) Generation of monoclonal antibodies against proteins with an unconventional nucleic acid-based immunization strategy, *J. Biotechnol.* 73: 119-129; and Ulivieri et al., (1996) Generation of a monoclonal antibody to a defined portion of the *Heliobacter pylori* vacuolating cytotoxin by DNA immunization, *J. Biotechnol.* 51: 191-194, the disclosures of which are incorporated herein by reference in their entireties.

Figure 3:
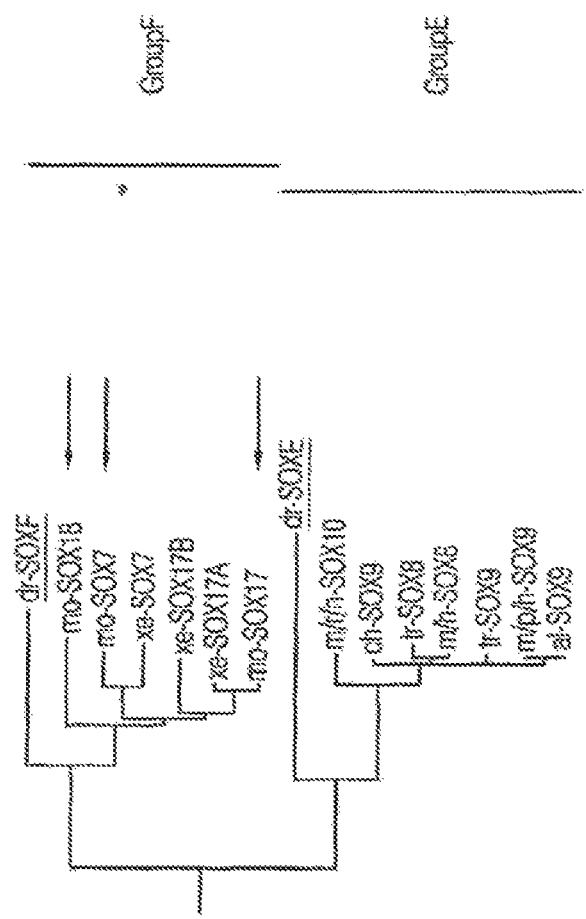
FIG. 3 is a relational dendrogram illustrating that SOX17 is most closely related to SOX7 and somewhat less to SOX18. The SOX17 proteins are more closely related among species homologs than to other members of the SOX group F subfamily within the same species.

SOX7 and SOX18 are the closest Sox family relatives to SOX17 as depicted in the relational dendrogram shown in FIG. 3. We employed the human SOX7 polypeptide as a negative control to demonstrate that the SOX17 antibody is specific for SOX17 and does not react with its closest family member. In particular, to demonstrate that the antibody produced by genetic immunization is specific for SOX17, SOX7 and other proteins were expressed in human fibroblasts, and then, analyzed for cross reactivity with the SOX17 antibody by Western blot and ICC. For example, the following methods were utilized for the production of the SOX17, SOX7 and EGFP expression vectors, their transfection into human fibroblasts and analysis by Western blot. Expression vectors employed for the production of SOX17, SOX7, and EGFP were pCMV6 (OriGene Technologies, Inc., Rockville, Md.), pCMV-SPORT6 (Invitrogen, Carlsbad, Calif.) and pEGFP-N1 (Clonetech, Palo Alto, Calif.), respectively. For protein production, telomerase immortalized MDX human fibroblasts were transiently transfected with supercoiled DNA in the presence of Lipofectamine 2000 (Invitrogen, Carlsbad, Calif.). Total cellular lysates were collected 36 hours post-transfection in 50 mM TRIS-HCl (pH 8), 150 mM NaCl, 0.1% SDS, 0.5% deoxycholate, containing a cocktail of protease inhibitors (Roche Diagnostics Corporation, Indianapolis, Ind.). Western blot analysis of 100 µg of cellular proteins, separated by SDS-PAGE on NuPAGE (4-12% gradient polyacrylamide, Invitrogen, Carlsbad, Calif.), and transferred by electro-blotting onto PDVF membranes (Hercules, Calif.), were probed with a 1/1000 dilution of the rat SOX17 anti-serum in 10 mM TRIS-HCl (pH 8), 150 mM NaCl, 10% BSA, 0.05% Tween-20 (Sigma, St. Louis, Mo.), followed by Alkaline Phosphatase conjugated anti-rat IgG (Jackson ImmunoResearch Laboratories, West Grove, Pa.), and revealed through Vector Black Alkaline Phosphatase staining (Vector Laboratories, Burlingame, Calif.). The proteins size standard used was wide range color markers (Sigma, St. Louis, Mo.).

Figure 4:
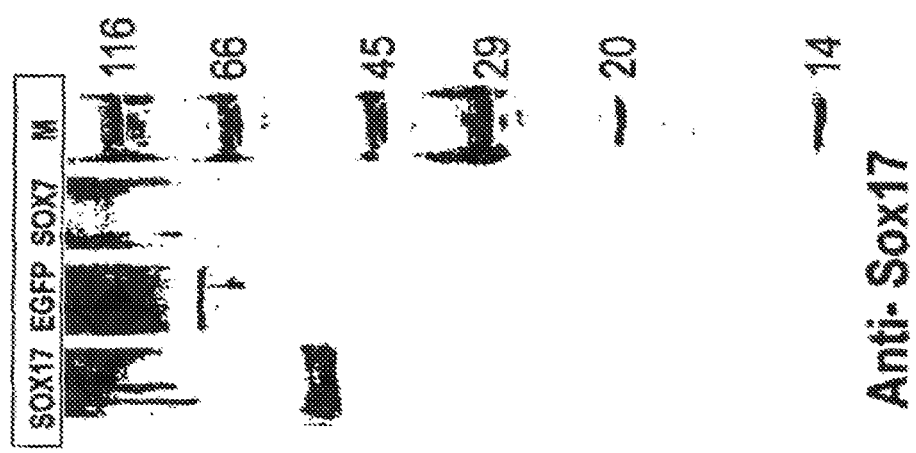
FIG. 4 is a Western blot probed with the rat anti-SOX17 antibody. This blot demonstrates the specificity of this antibody for human SOX17 protein over-expressed in fibroblasts (lane 1) and a lack of immunoreactivity with EGFP (lane 2) or the most closely related SOX family member, SOX7 (lane 3).

In FIG. 4, protein extracts made from human fibroblast cells that were transiently transfected with SOX17, SOX7 or EGFP cDNA's were probed on Western blots with the SOX17 antibody. Only the protein extract from hSOX17 transfected cells produced a band of ~51 Kda which closely matched the predicted 46 Kda molecular weight of the human SOX17 protein. There was no reactivity of the SOX17 antibody to extracts made from either human SOX7 or EGFP transfected cells. Furthermore, the SOX17 antibody clearly labeled the nuclei of human fibroblast cells transfected with the hSOX17 expression construct but did not label cells transfected with EGFP alone. As such, the SOX17 antibody exhibits specificity by ICC.

EXAMPLE 4

Validation of SOX17 Antibody as a Marker of Definitive Endoderm

Figure 5:
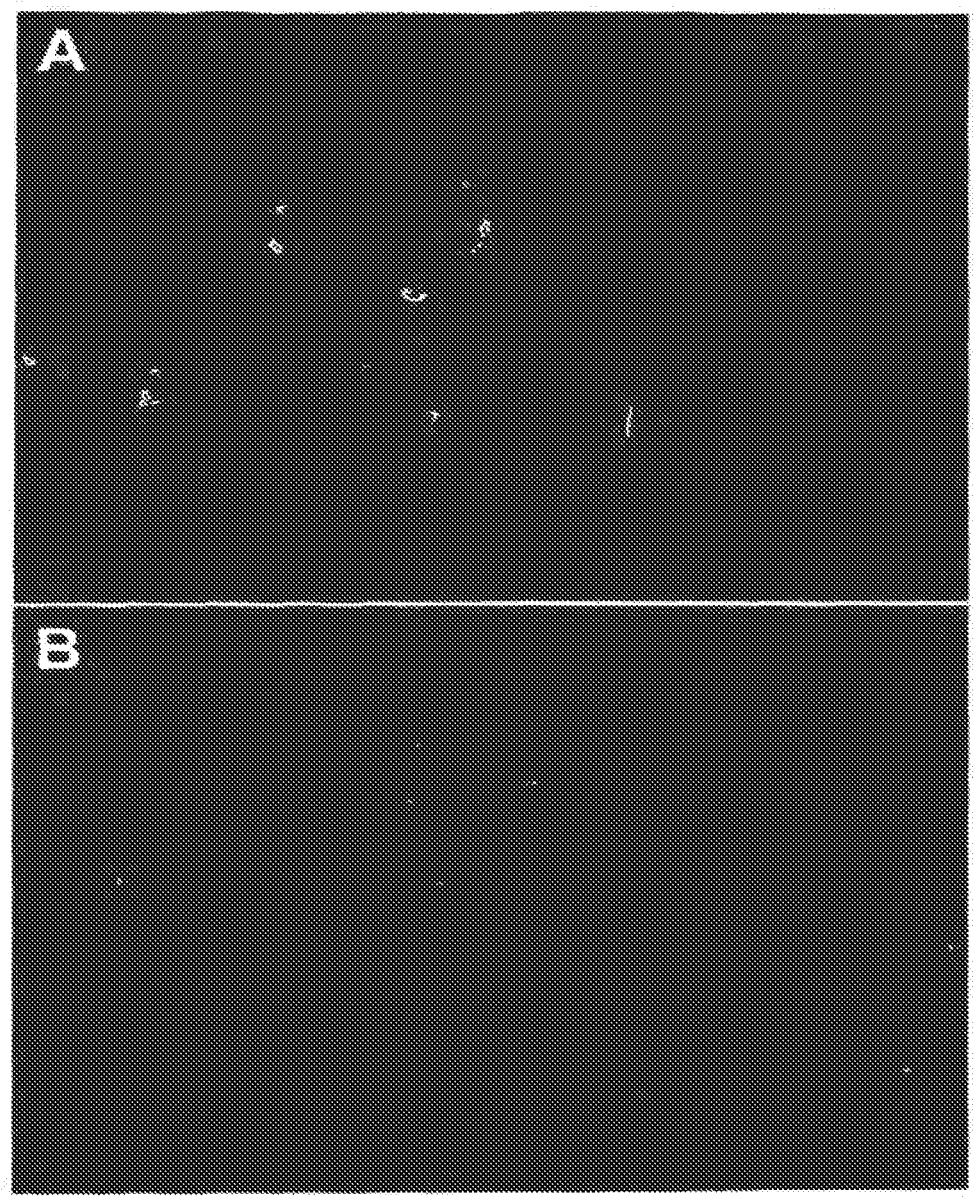
FIGS. 5A-B are micrographs showing a cluster of SOX17+ cells that display a significant number of AFP+ co-labeled cells (A). This is in striking contrast to other SOX17+ clusters (B) where little or no AFP+ cells are observed.
Figure 6:
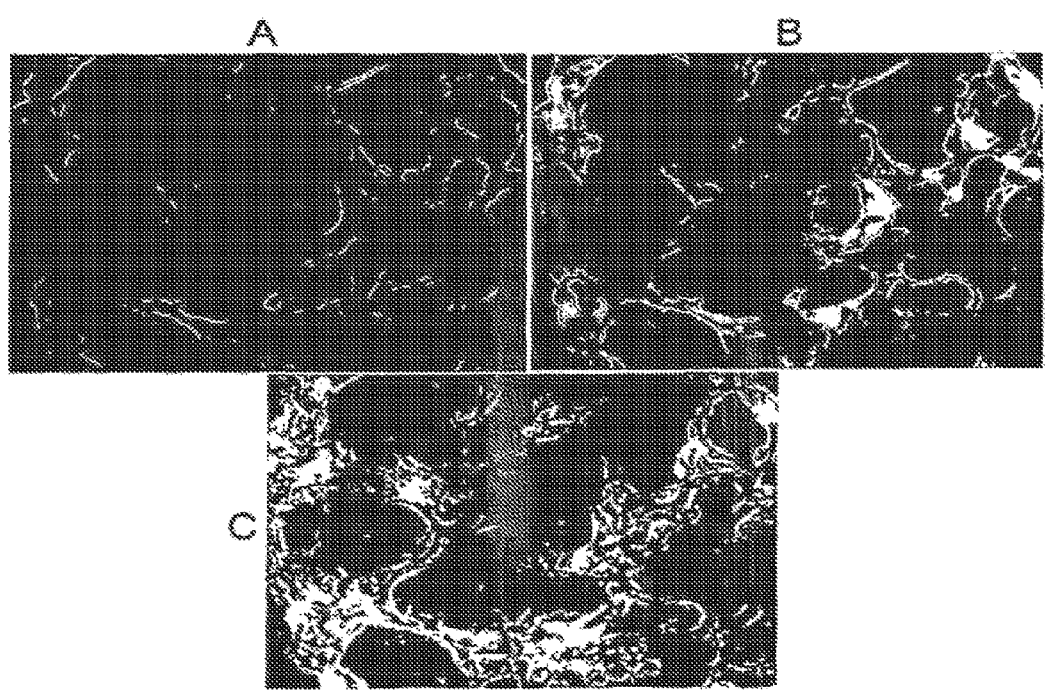
FIGS. 6A-C are micrographs showing parietal endoderm and SOX17. Panel A shows immunocytochemistry for human Thrombomodulin (TM) protein located on the cell surface of parietal endoderm cells in randomly differentiated cultures of hES cells. Panel B is the identical field shown in A double-labeled for TM and SOX17. Panel C is the phase contrast image of the same field with DAPI labeled nuclei. Note the complete correlation of DAPI labeled nuclei and SOX17 labeling.

As evidence that the SOX17 antibody is specific for human SOX17 protein and furthermore marks definitive endoderm, partially differentiated hESCs were co-labeled with SOX17 and AFP antibodies. It has been demonstrated that SOX17, SOX7, which is a closely related member of the SOX gene family subgroup F (FIG. 3), and AFP are each expressed in visceral endoderm. However, AFP and SOX7 are not expressed in definitive endoderm cells at levels detectable by ICC, and thus, they be can employed as negative markers for bonifide definitive endoderm cells. It was shown that SOX17 antibody labels populations of cells that exist as discrete groupings of cells or are intermingled with AFP positive cells. In particular, FIG. 5A shows that small numbers of SOX17 cells were co-labeled with AFP; however, regions were also found where there were little or no AFP+ cells in the field of SOX17+ cells (FIG. 5B). Similarly, since parietal endoderm has also been reported to express SOX17, antibody co-labeling with SOX17 together with the parietal markers SPARC and/or Thrombomodulin (TM) can be used to identify the SOX17+ cells which are parietal endoderm. As shown in FIGS. 6A-C, Thrombomodulin and SOX17 co-labelled parietal endoderm cells were produced by random differentiation of hES cells.

In view of the above cell labelling experiments, the identity of a definitive endoderm cell can be established by the marker profile SOX17$^{hi}$/AFP$^{lo}$/[TM$^{lo}$ or SPARC$^{lo}$]. In other words, the expression of the SOX17 marker is greater than the expression of the AFP marker, which is characteristic of visceral endoderm, and the TM or SPARC markers, which are characteristic of parietal endoderm. Accordingly, those cells positive for SOX17 but negative for AFP and negative for TM or SPARC are definitive endoderm.

Figure 7:
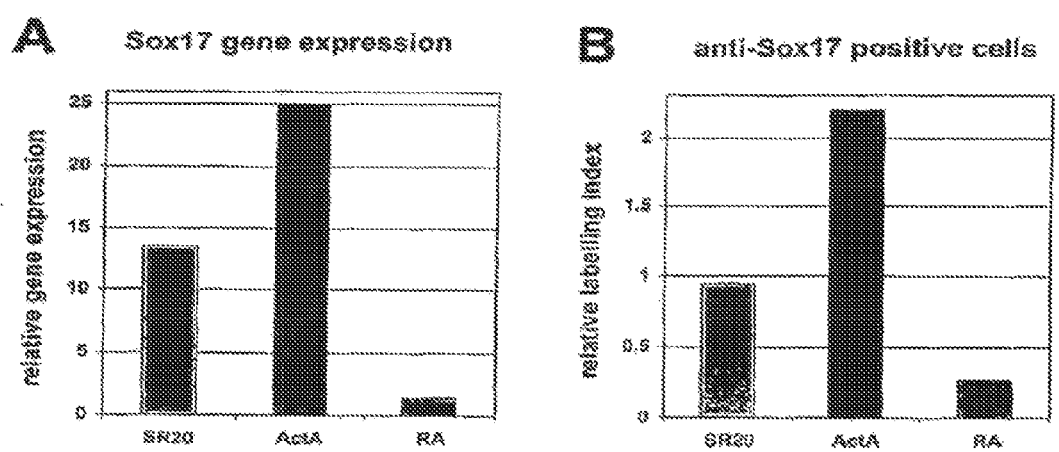
FIGS. 7A-B are bar charts showing SOX17 gene expression by quantitative PCR (Q-PCR) and anti-SOX17 positive cells by SOX17-specific antibody. Panel A shows that activin A increases SOX17 gene expression while retinoic acid (RA) strongly suppresses SOX17 expression relative to the undifferentiated control media (SR20). Panel B shows the identical pattern as well as a similar magnitude of these changes is reflected in SOX17$^+$ cell number, indicating that Q-PCR measurement of SOX17 gene expression is very reflective of changes at the single cell level.
Figure 8:
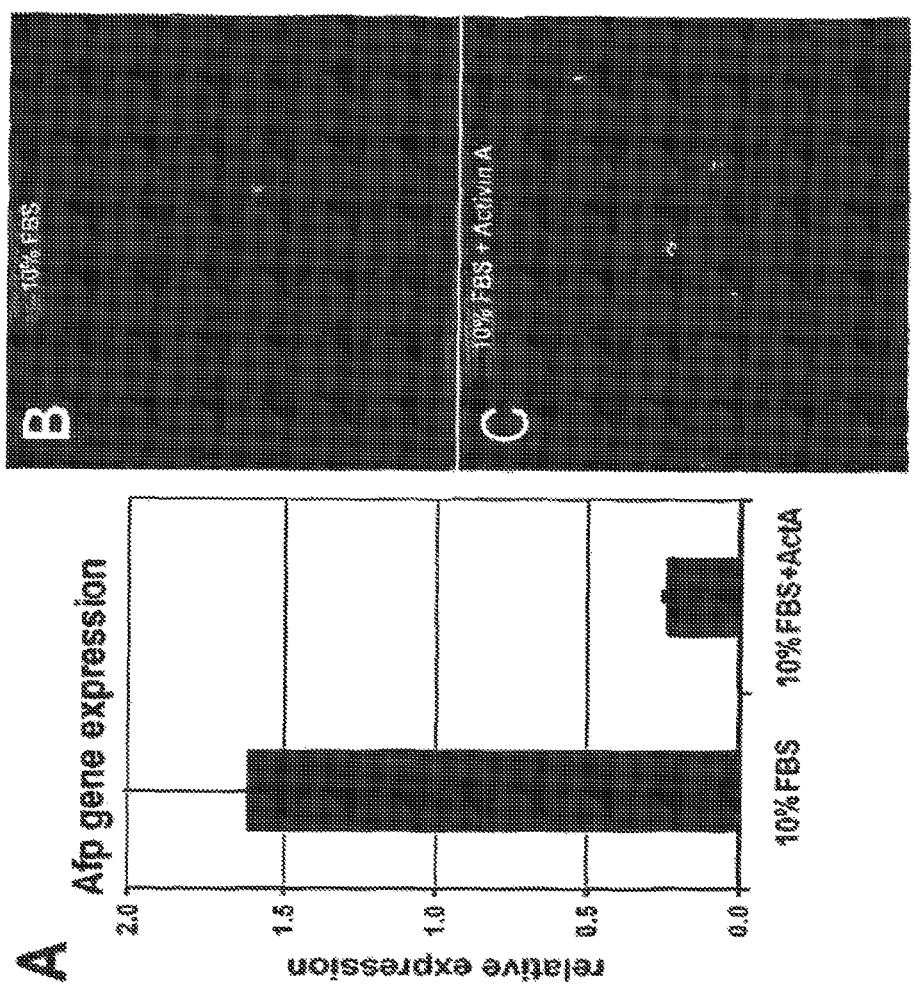
FIG. 8A is a bar chart which shows that a culture of differentiating hESCs in the presence of activin A maintains a low level of AFP gene expression while cells allowed to randomly differentiate in 10% fetal bovine serum (FBS) exhibit a strong upregulation of AFP. The difference in expression levels is approximately 7-fold.
FIGS. 8B-C are images of two micrographs showing that the suppression of AFP expression by activin A is also evident at the single cell level as indicated by the very rare and small clusters of AFP$^+$ cells observed in activin A treatment conditions (bottom) relative to 10% FBS alone (top).
Figure 9:
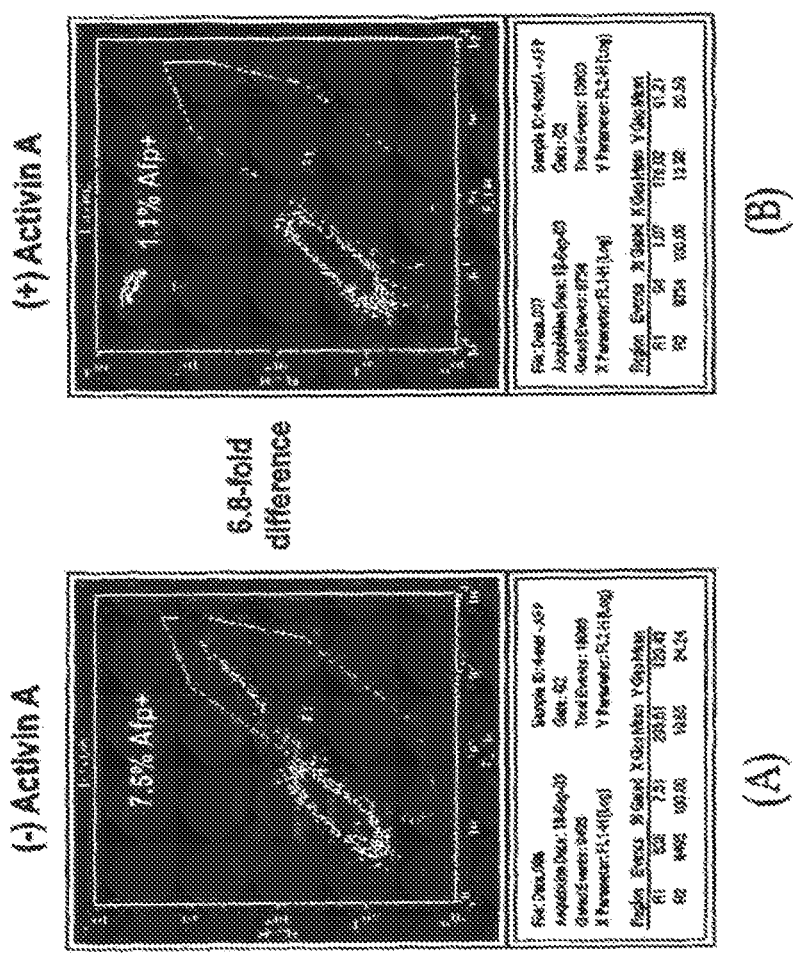
FIGS. 9A-B are comparative images showing the quantitation of the AFP$^+$ cell number using flow cytometry. This figure demonstrates that the magnitude of change in AFP gene expression (FIG. 8A) in the presence (right panel) and absence (left panel) of activin A exactly corresponds to the number of AFP$^+$ cells, further supporting the utility of Q-PCR analyses to indicate changes occurring at the individual cell level.
Figure 10:
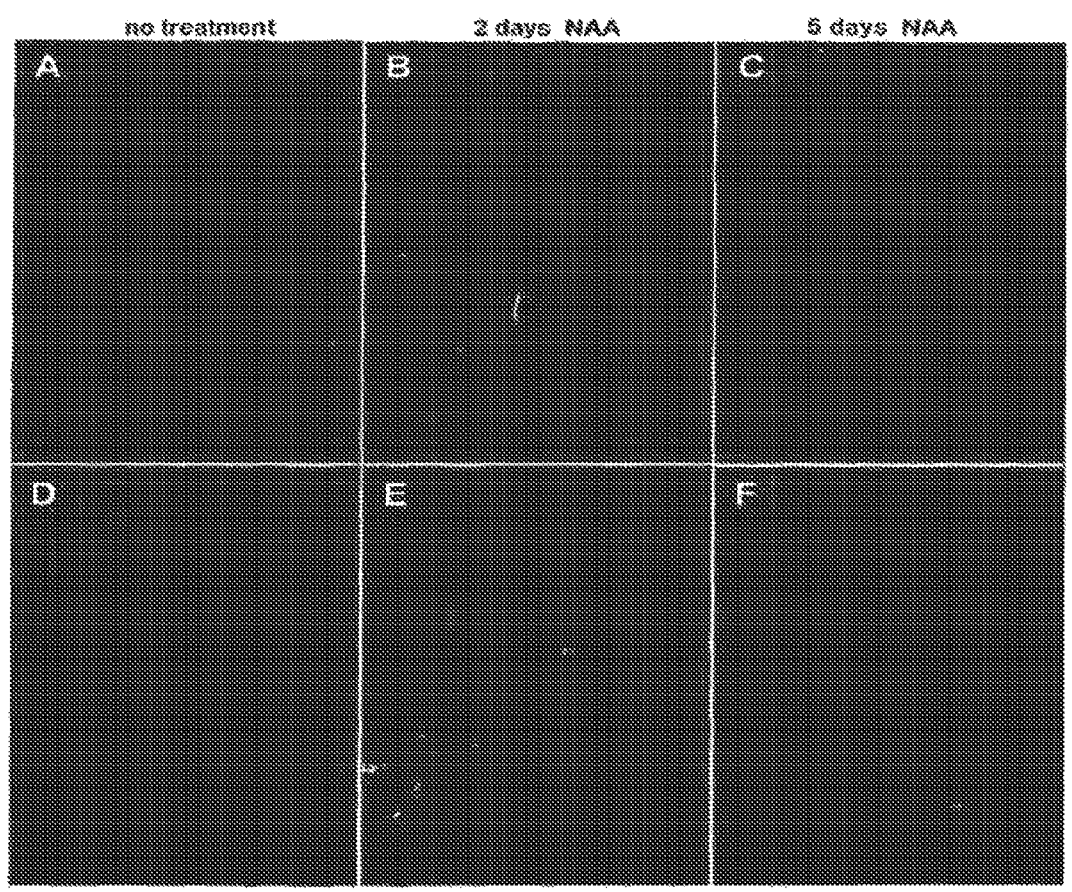
FIGS. 10A-F are micrographs which show that exposure of hESCs to nodal, activin A and activin B (NAA) yields a striking increase in the number of SOX17$^+$ cells over the period of 5 days (A-C). By comparing to the relative abundance of SOX17$^+$ cells to the total number of cells present in each field, as indicated by DAPI stained nuclei (D-F), it can be seen that approximately 30-50% of all cells are immunoreactive for SOX17 after five days treatment with NAA.
Figure 11:
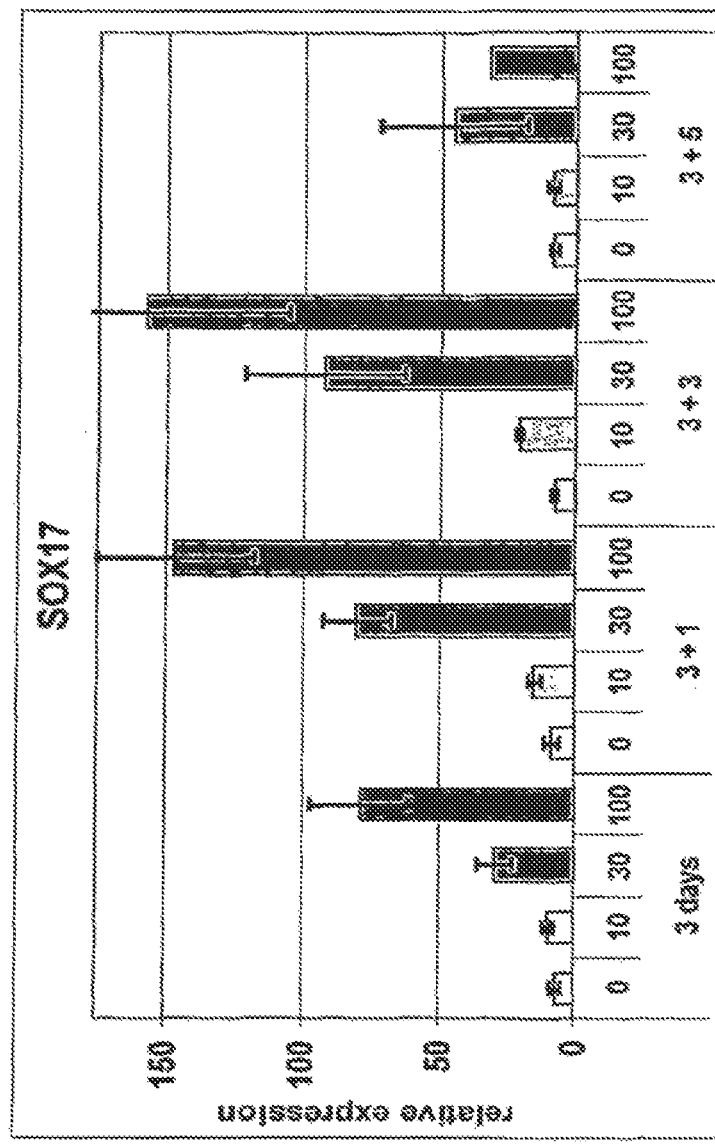
FIG. 11 is a bar chart which demonstrates that activin A (0, 10, 30 or 100 ng/ml) dose-dependently increases SOX17 gene expression in differentiating hESCs. Increased expression is already robust after 3 days of treatment on adherent cultures and continues through subsequent 1, 3 and 5 days of suspension culture as well.
Figure 12:
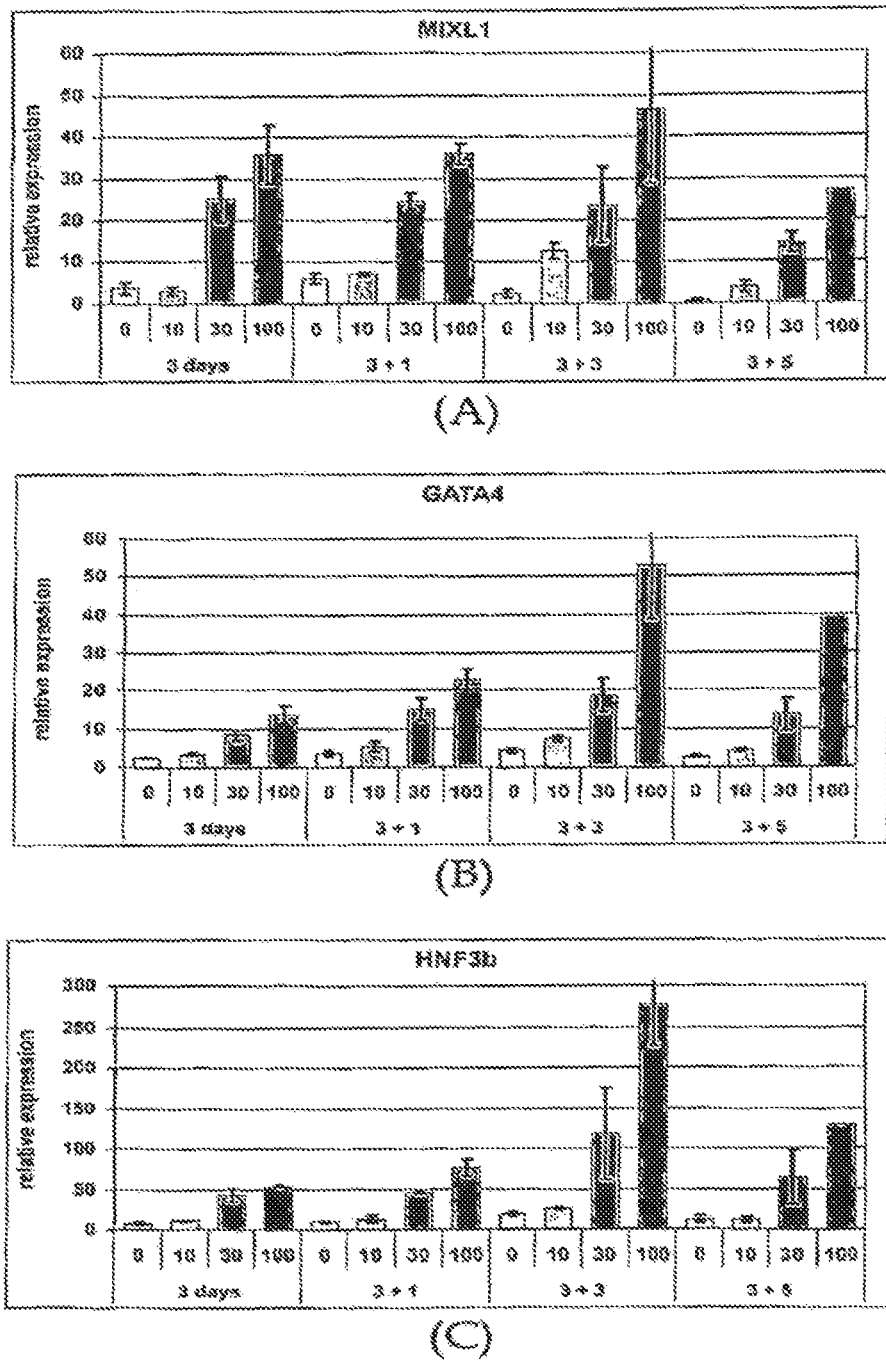
FIGS. 12A-C are bar charts which demonstrate the effect of activin A on the expression of MIXL1 (panel A), GATA4 (panel B) and HNF3b (panel C). Activin A dose-dependent increases are also observed for three other markers of definitive endoderm; MIXL1, GATA4 and HNF3b. The magnitudes of increased expression in response to activin dose are strikingly similar to those observed for SOX17, strongly indicating that activin A is specifying a population of cells that co-express all four genes (SOX17$^+$, MIXL1$^+$, GATA4$^+$ and HNF3b$^+$).
Figure 13:
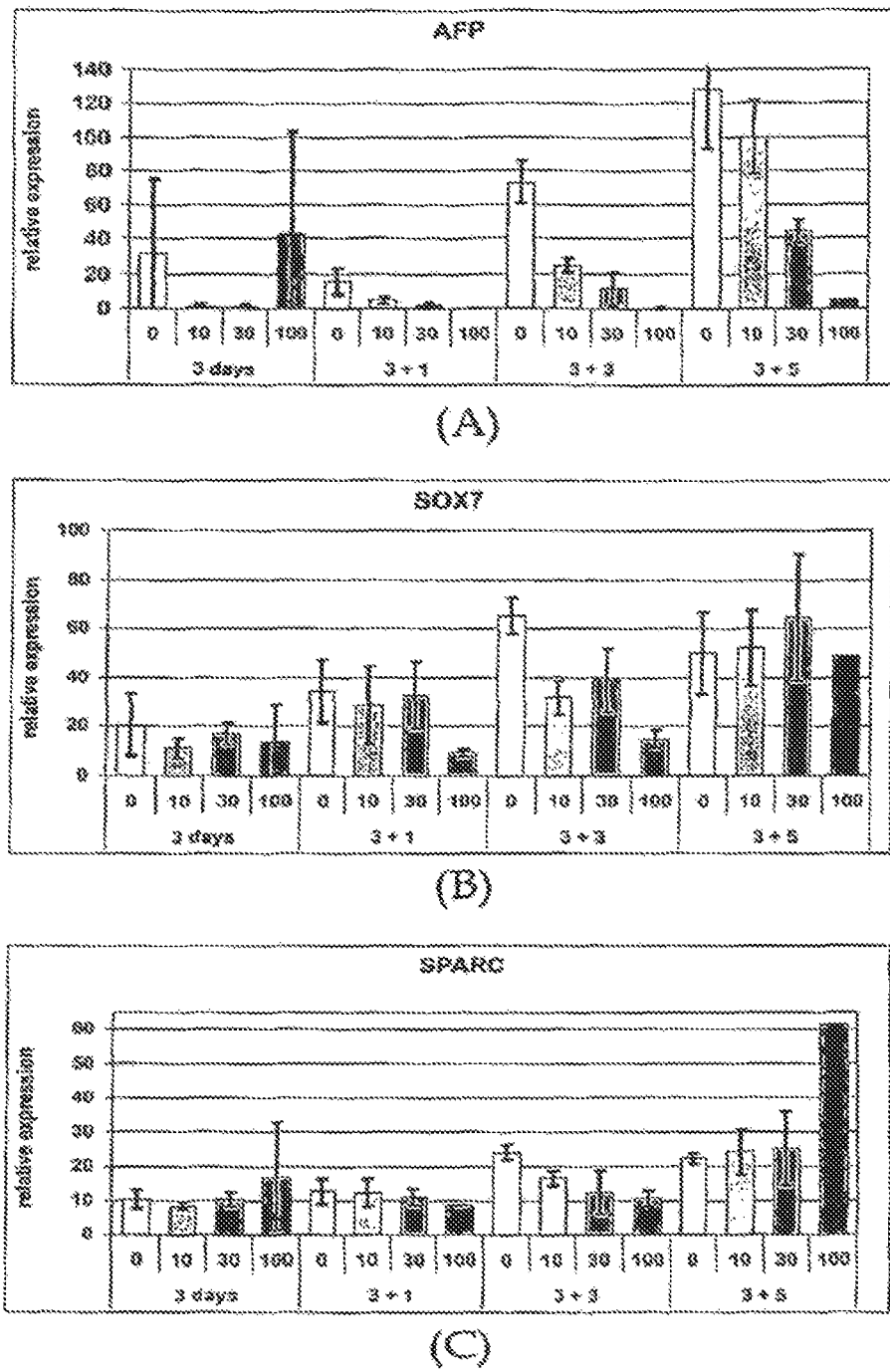
FIGS. 13A-C are bar charts which demonstrate the effect of activin A on the expression of AFP (panel A), SOX7 (panel B) and SPARC (panel C). There is an activin A dose-dependent decrease in expression of the visceral endoderm marker AFP. Markers of primitive endoderm (SOX7) and parietal endoderm (SPARC) remain either unchanged or exhibit suppression at some time points indicating that activin A does not act to specify these extra-embryonic endoderm cell types. This further supports the fact that the increased expression of SOX17, MIXL1, GATA4, and HNF3b are due to an increase in the number of definitive endoderm cells in response to activin A.
Figure 14:
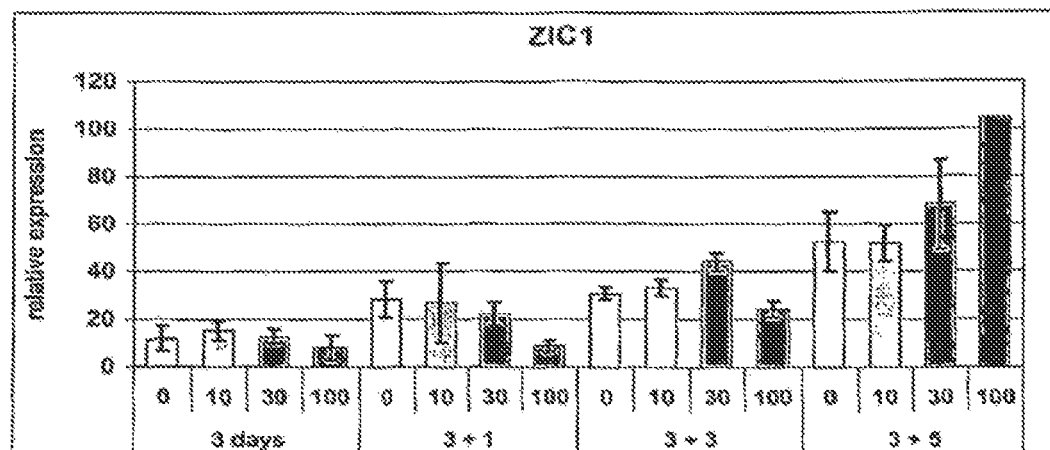
FIGS. 14A-B are bar charts showing the effect of activin A on ZIC1 (panel A) and Brachyury expression (panel B) Consistent expression of the neural marker ZIC1 demonstrates that there is not a dose-dependent effect of activin A on neural differentiation. There is a notable suppression of mesoderm differentiation mediated by 100 ng/ml of activin A treatment as indicated by the decreased expression of brachyury. This is likely the result of the increased specification of definitive endoderm from the mesendoderm precursors. Lower levels of activin A treatment (10 and 30 ng/ml) maintain the expression of brachyury at later time points of differentiation relative to untreated control cultures.
Figure 14:
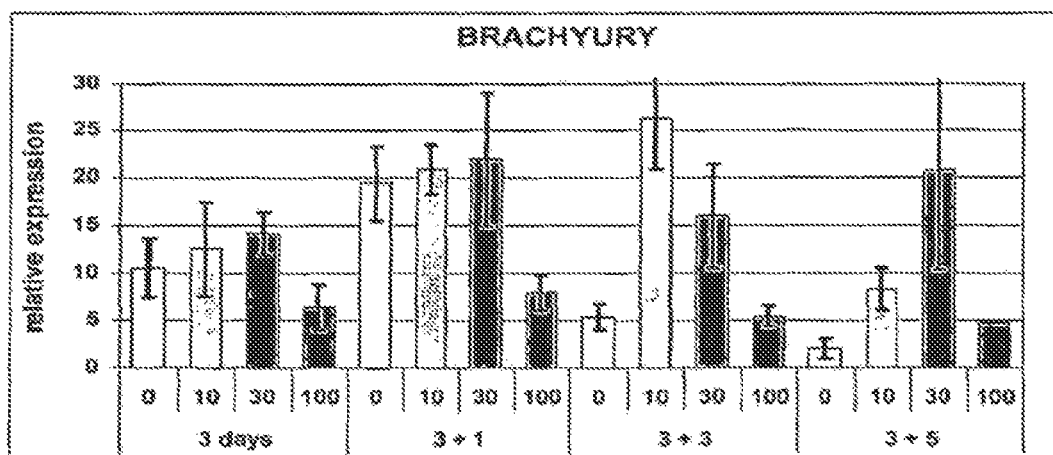

As a further evidence of the specificity of the specificity of the SOX17$^{hi}$/AFP$^{lo}$/TM$^{lo}$/SPARC$^{lo}$ marker profile as predictive of definitive endoderm, SOX17 and AFP gene expression was quantitatively compared to the relative number of antibody labeled cells. As shown in FIG. 7A, hESCs treated with retinoic acid (visceral endoderm inducer), or Activin A (definitive endoderm inducer), resulted in a 10-fold difference in the level of SOX17 mRNA expression. This result mirrored the 10-fold difference in SOX17 antibody-labeled cell number (FIG. 7B). Furthermore, as shown in FIG. 8A, Activin A treatment of hESCs suppressed AFP gene expression by 6.8-fold in comparison to no treatment. This was visually reflected by a dramatic decrease in the number of AFP labeled cells in these cultures as shown in FIGS. 8B-C. To quantify this further, it was demonstrated that this approximately 7-fold decrease in AFP gene expression was the result of a similar 7-fold decrease in AFP antibody-labeled cell number as measured by flow cytometry (FIGS. 9A-B). This result is extremely significant in that it indicates that quantitative changes in gene expression as seen by Q-PCR mirror changes in cell type specification as observed by antibody staining.

Incubation of hESCs in the presence of Nodal family members (Nodal, Activin A and Activin B-NAA) resulted in a significant increase in SOX17 antibody-labeled cells over time. By 5 days of continuous activin treatment greater than 50% of the cells were labeled with SOX17 (FIGS. 1A-F). There were few or no cells labeled with AFP after 5 days of activin treatment.

In summary, the antibody produced against the carboxy-terminal 242 amino acids of the human SOX17 protein identified human SOX17 protein on Western blots but did not recognize SOX7, it's closest Sox family relative. The SOX17 antibody recognized a subset of cells in differentiating hESC cultures that were primarily SOX17+/AFP$^{lo/-}$ (greater than 95% of labeled cells) as well as a small percentage (<5%) of cells that co-label for SOX17 and AFP (visceral endoderm). Treatment of hESC cultures with activins resulted in a marked elevation of SOX17 gene expression as well as SOX17 labeled cells and dramatically suppressed the expression of AFP mRNA and the number of cells labeled with AFP antibody.

EXAMPLE 5

Q-PCR Gene Expression Assay

In the following experiments, real-time quantitative RT-PCR (Q-PCR) was the primary assay used for screening the effects of various treatments on hESC differentiation. In particular, real-time measurements of gene expression were analyzed for multiple marker genes at multiple time points by Q-PCR. Marker genes characteristic of the desired as well as undesired cell types were evaluated to gain a better understanding of the overall dynamics of the cellular populations. The strength of Q-PCR analysis includes its extreme sensitivity and relative ease of developing the necessary markers, as the genome sequence is readily available. Furthermore, the extremely high sensitivity of Q-PCR permits detection of gene expression from a relatively small number of cells within a much larger population. In addition, the ability to detect very low levels of gene expression provides indications for "differentiation bias" within the population. The bias towards a particular differentiation pathway, prior to the overt differentiation of those cellular phenotypes, is unrecognizable using immunocytochemical techniques. For this reason, Q-PCR provides a method of analysis that is at least complementary and potentially much superior to immunocytochemical techniques for screening the success of differentiation treatments. Additionally, Q-PCR provides a mechanism by which to evaluate the success of a differentiation protocol in a quantitative format at semi-high throughput scales of analysis.

The approach taken here was to perform relative quantitation using SYBR Green chemistry on a Rotor Gene 3000 instrument (Corbett Research) and a two-step RT-PCR format. Such an approach allowed for the banking of cDNA samples for analysis of additional marker genes in the future, thus avoiding variability in the reverse transcription efficiency between samples.

Primers were designed to lie over exon-exon boundaries or span introns of at least 800 bp when possible, as this has been empirically determined to eliminate amplification from contaminating genomic DNA. When marker genes were employed that do not contain introns or they possess pseudogenes, DNase I treatment of RNA samples was performed.

We routinely used Q-PCR to measure the gene expression of multiple markers of target and non-target cell types in order to provide a broad profile description of gene expression in cell samples. The markers relevant for the early phases of hESC differentiation (specifically ectoderm, mesoderm, definitive endoderm and extra-embryonic endoderm) and for which validated primer sets are available are provided below in Table 1. The human specificity of these primer sets has also been demonstrated. This is an important fact since the hESCs were often grown on mouse feeder layers. Most typically, triplicate samples were taken for each condition and independently analyzed in duplicate to assess the biological variability associated with each quantitative determination.

To generate PCR template, total RNA was isolated using RNeasy (Qiagen) and quantitated using RiboGreen (Molecular Probes). Reverse transcription from 350-500 ng of total RNA was carried out using the iScript reverse transcriptase kit (BioRad), which contains a mix of oligo-dT and random primers. Each 20 μL reaction was subsequently diluted up to 100 μL total volume and 3 μL was used in each 10 μL Q-PCR reaction containing 400 nM forward and reverse primers and 5 μL 2× SYBR Green master mix (Qiagen). Two step cycling parameters were used employing a 5 second denature at 85-94° C. (specifically selected according to the melting temp of the amplicon for each primer set) followed by a 45 second anneal/extend at 60° C. Fluorescence data was collected during the last 15 seconds of each extension phase. A three point, 10-fold dilution series was used to generate the standard curve for each run and cycle thresholds (Ct's) were converted to quantitative values based on this standard curve. The quantitated values for each sample were normalized to housekeeping gene performance and then average and standard deviations were calculated for triplicate samples. At the conclusion of PCR cycling, a melt curve analysis was performed to ascertain the specificity of the reaction. A single specific product was indicated by a single peak at the $T_m$ appropriate for that PCR amplicon. In addition, reactions performed without reverse transcriptase served as the negative control and do not amplify.

A first step in establishing the Q-PCR methodology was validation of appropriate housekeeping genes (HGs) in the experimental system. Since the HG was used to normalize across samples for the RNA input, RNA integrity and RT efficiency, it was of value that the HG exhibited a constant level of expression over time in all sample types in order for the normalization to be meaningful. We measured the expression levels of Cyclophilin G, hypoxanthine phosphoribosyltransferase 1 (HPRT), beta-2-microglobulin, hydroxymethylbiane synthase (HMBS), TATA-binding protein (TBP), and glucuronidase beta (GUS) in differentiating hESCs. Our results indicated that beta-2-microglobulin expression levels increased over the course of differentiation and therefore we excluded the use of this gene for normalization. The other genes exhibited consistent expression levels over time as well as across treatments. We routinely used both Cyclophilin G and GUS to calculate a normalization factor for all samples. The use of multiple HGs simultaneously reduces the variability inherent to the normalization process and increases the reliability of the relative gene expression values.

After obtaining genes for use in normalization, Q-PCR was then utilized to determine the relative gene expression levels of many marker genes across samples receiving different experimental treatments. The marker genes employed have been chosen because they exhibit enrichment in specific populations representative of the early germ layers and in particular have focused on sets of genes that are differentially expressed in definitive endoderm and extra-embryonic endoderm. These genes as well as their relative enrichment profiles are highlighted in Table 1.

TABLE 1

| Germ Layer | Gene | Expression Domains |
| --- | --- | --- |
| Endoderm | SOX17 | definitive, visceral and parietal endoderm |
| | MIXL1 | endoderm and mesoderm |
| | GATA4 | definitive and primitive endoderm |
| | HNF3b | definitive endoderm and primitive endoderm, mesoderm, neural plate |
| | GSC | endoderm and mesoderm |
| | SOX7 | visceral endoderm |

TABLE 1-continued

| Germ Layer | Gene | Expression Domains |
| --- | --- | --- |
| Extra-embryonic | AFP | visceral endoderm, liver |
| | SPARC | parietal endoderm |
| | TM | parietal endoderm/trophectoderm |
| Ectoderm | ZIC1 | neural tube, neural progenitors |
| Mesoderm | BRACH | nascent mesoderm |

Since many genes are expressed in more than one germ layer it is useful to quantitatively compare expression levels of many genes within the same experiment. SOX17 is expressed in definitive endoderm and to a smaller extent in visceral and parietal endoderm. SOX7 and AFP are expressed in visceral endoderm at this early developmental time point. SPARC and TM are expressed in parietal endoderm and Brachyury is expressed in early mesoderm.

Definitive endoderm cells were predicted to express high levels of SOX17 mRNA and low levels of AFP and SOX7 (visceral endoderm), SPARC (parietal endoderm) and Brachyury (mesoderm). In addition, ZIC1 was used here to further rule out induction of early ectoderm. Finally, GATA4 and HNF3b were expressed in both definitive and extra-embryonic endoderm, and thus, correlate with SOX17 expression in definitive endoderm (Table 1). A representative experiment is shown in FIGS. 11-14 which demonstrates how the marker genes described in Table 1 correlate with each other among the various samples, thus highlighting specific patterns of differentiation to definitive endoderm and extra-embryonic endoderm as well as to mesodermal and neural cell types.

In view of the above data it is clear that increasing doses of activin resulted in increasing SOX17 gene expression. Further this SOX17 expression predominantly represented definitive endoderm as opposed to extra-embryonic endoderm. This conclusion stems from the observation that SOX17 gene expression was inversely correlated with AFP, SOX7, and SPARC gene expression.

EXAMPLE 6

Directed Differentiation of Human ES Cells to Definitive Endoderm

Human ES Cell Cultures Will Randomly Differentiate if they are Cultured under conditions that do not actively maintain their undifferentiated state. This heterogeneous differentiation results in production of extra-embryonic endoderm cells comprised of both parietal and visceral endoderm (AFP, SPARC and SOX7 expression) as well as early ectodermal and mesodermal derivatives as marked by ZIC1 and Nestin (ectoderm) and Brachyury (mesoderm) expression. Definitive endoderm cell appearance has not traditionally been examined or specified for lack of specific antibody markers in ES cell cultures. As such, and by default, early definitive endoderm production in ES cell cultures has not been well studied. Since no good antibody reagents for definitive endoderm cells have been available, most of the characterization has focused on ectoderm and extra-embryonic endoderm. Overall, there are significantly greater numbers of extra-embryonic and neurectodermal cell types in comparison to SOX17$^{hi}$ definitive endoderm cells in randomly differentiated ES cell cultures.

As undifferentiated hESC colonies expand on a bed of fibroblast feeders the edges of the colony take on alternative morphologies that are distinct from those cells residing within the interior of the colony. Many of these outer edge cells can be distinguished by their less uniform, larger cell body morphology and by the expression of higher levels of OCT4. It has been described that as ES cells begin to differentiate they alter the levels of OCT4 expression up or down relative to undifferentiated ES cells. Alteration of OCT4 levels above or below the undifferentiated threshold may signify the initial stages of differentiation away from the pluripotent state.

When undifferentiated colonies were examined by SOX17 immunocytochemistry, occasionally small 10-15-cell clusters of SOX17-positive cells were detected at random locations on the periphery and at the junctions between undifferentiated ESC colonies. As noted above, these scattered pockets of outer colony edges appeared to be some of the first cells to differentiate away from the classical ESC morphology as the colony expanded in size and became more crowded. Younger, smaller fully undifferentiated colonies (<1 mm; 4-5 days old) showed no SOX17 positive cells within or at the edges of the colonies while older, larger colonies (1-2 mm diameter, >5 days old) had sporadic isolated patches of SOX17 positive, AFP negative cells at the periphery of some colonies or in regions interior to the edge that were differentiated away from classical hESC morphology described previously. Given that this was the first development of an effective SOX17 antibody, definitive endoderm cells generated in such early "undifferentiated" ESC cultures have never been previously demonstrated.

Figure 15:
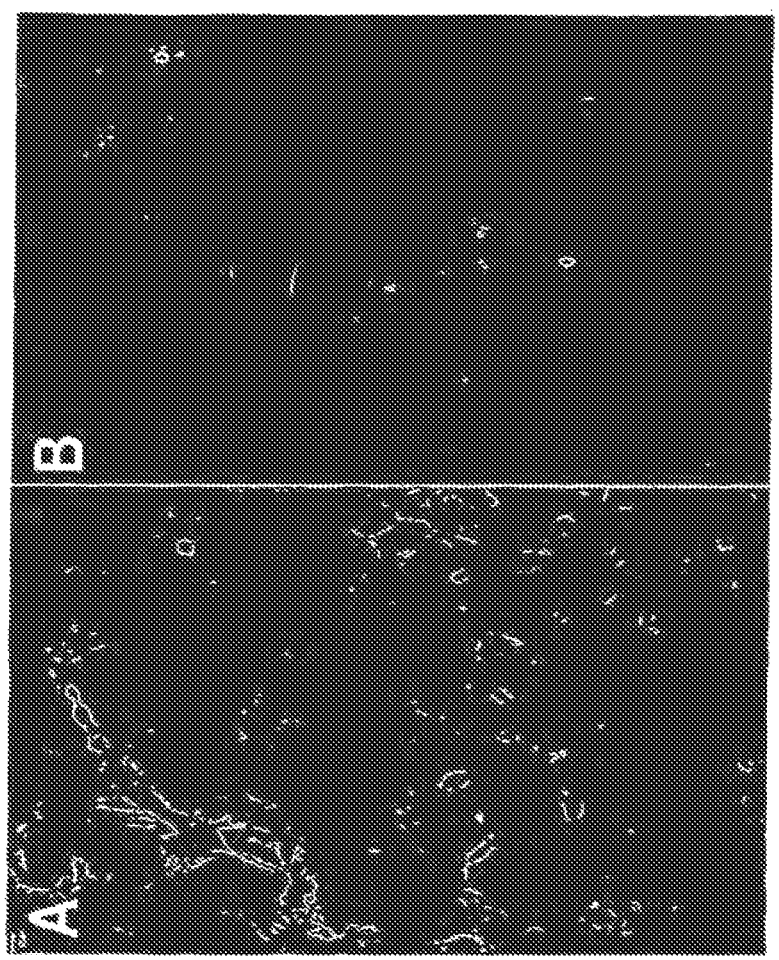
FIGS. 15A-B are micrographs showing decreased parietal endoderm differentiation in response to treatment with activins. Regions of TM$^{hi}$ parietal endoderm are found through the culture (A) when differentiated in serum alone, while differentiation to TM$^+$ cells is scarce when activins are included (B) and overall intensity of TM immunoreactivity is lower.
Figure 16:
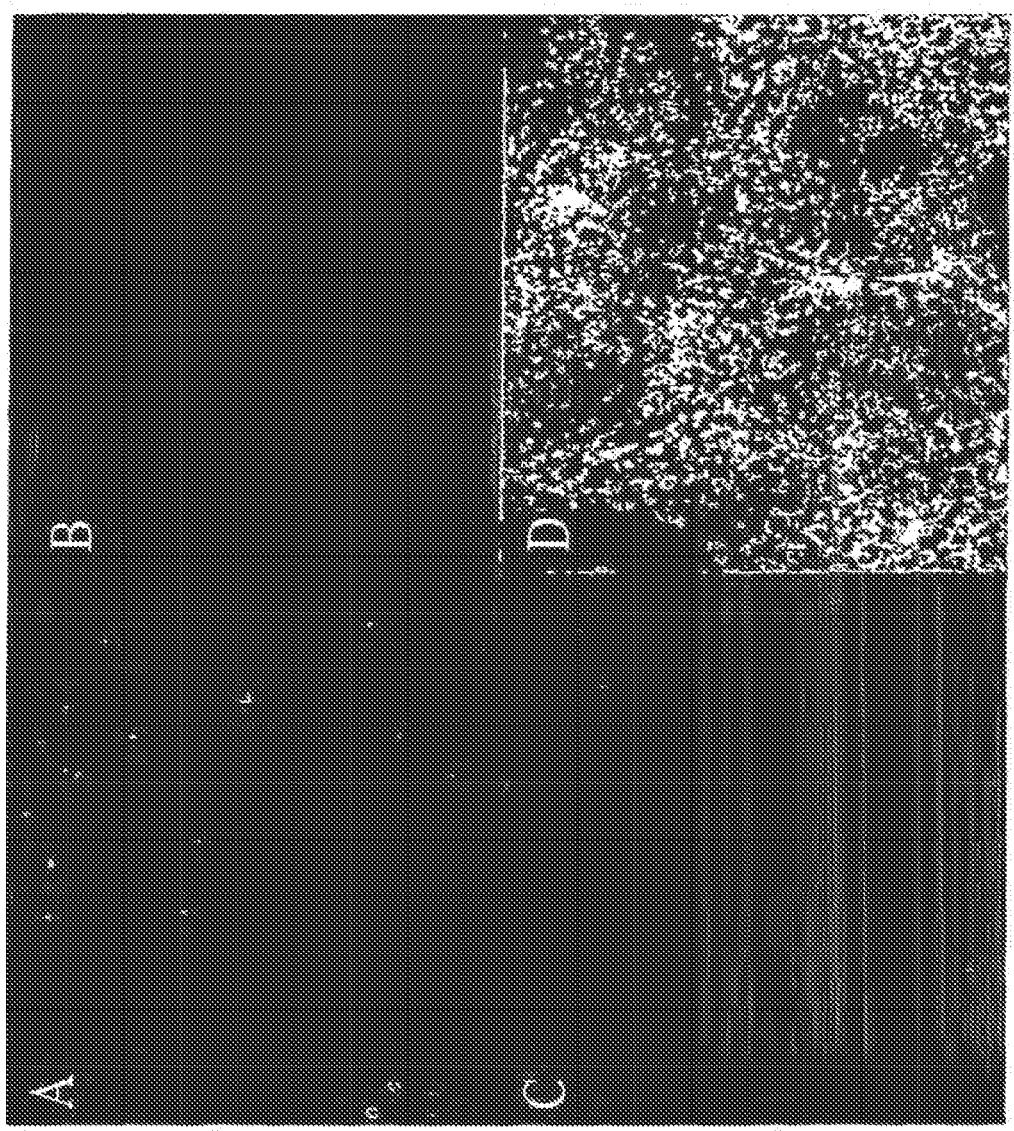
FIGS. 16A-D are micrographs which show marker expression in response to treatment with activin A and activin B. hESCs were treated for four consecutive days with activin A and activin B and triple labeled with SOX17, AFP and TM antibodies. Panel A—SOX17; Panel B—AFP; Panel C—TM; and Panel D—Phase/DAPI. Notice the numerous SOX17 positive cells (A) associated with the complete absence of AFP (B) and TM (C) immunoreactivity.
Figure 17:
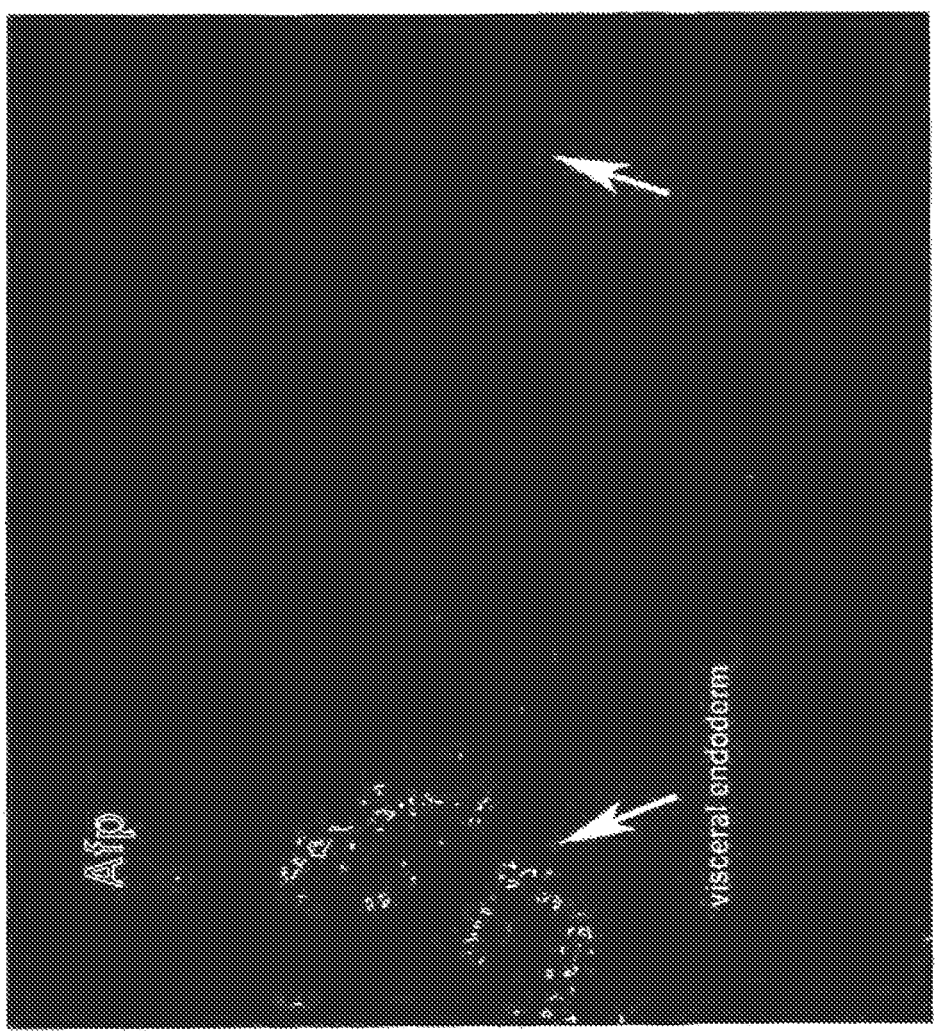
FIG. 17 is a micrograph showing the appearance of definitive endoderm and visceral endoderm in vitro from hESCs. The regions of visceral endoderm are identified by AFP$^{hi}$/SOX17$^{lo/-}$ while definitive endoderm displays the complete opposite profile, SOX17$^{hi}$/AFP$^{lo/-}$. This field was selectively chosen due to the proximity of these two regions to each other. However, there are numerous times when SOX17$^{hi}$/AFP$^{lo/-}$ regions are observed in absolute isolation from any regions of AFP$^{hi}$ cells, suggesting the separate origination of the definitive endoderm cells from visceral endoderm cells.
Figure 18:
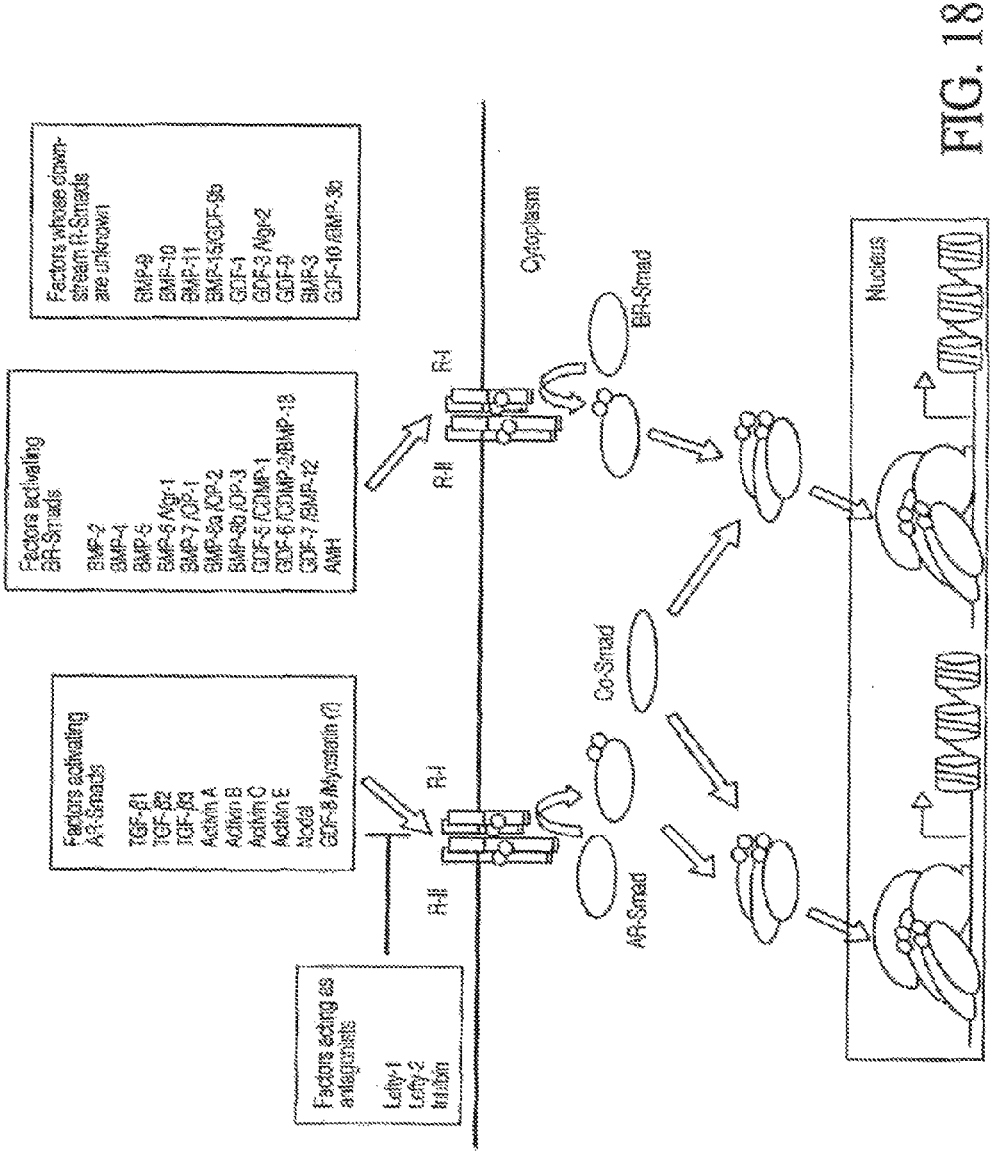
FIG. 18 is a diagram depicting the TGFβ family of ligands and receptors. Factors activating AR Smads and BR Smads are useful in the production of definitive endoderm from human embryonic stem cells (see, *J Cell Physiol.* 187:265-76).

Based on negative correlations of SOX17 and SPARC gene expression levels by Q-PCR, the vast majority of these SOX17 positive, AFP negative cells will be negative for parietal markers by antibody co-labeling. This was specifically demonstrated for TM-expressing parietal endoderm cells as shown in FIGS. 15A-B. Exposure to Nodal factors Activin A and B resulted in a dramatic decrease in the intensity to TM expression and the number of TM positive cells. By triple labeling using SOX17, AFP and TM antibodies on an activin treated culture, clusters of SOX17 positive cells which were also negative for AFP and TM were observed (FIGS. 16A-D). These are the first cellular demonstrations of SOX17 positive definitive endoderm cells in differentiating ESC cultures (FIGS. 16A-D and 17).

With the SOX17 antibody and Q-PCR tools described above we have explored a number of procedures capable of efficiently programming ESCs to become SOX17$^{hi}$/AFP$^{lo}$/SPARC/TM$^{lo}$ definitive endoderm cells. We applied a variety of differentiation protocols aimed at increasing the number and proliferative capacity of these cells as measured at the population level by Q-PCR for SOX17 gene expression and at the level of individual cells by antibody labeling of SOX17 protein.

We were the first to analyze and describe the effect of TGFβ family growth factors, such as Nodal/activin/BMP, for use in creating definitive endoderm cells from embryonic stem cells in in vitro cell cultures. In typical experiments, Activin A, Activin B, BMP or combinations of these growth factors were added to cultures of undifferentiated human stem cell line hESCyt-25 to begin the differentiation process.

Figure 19:
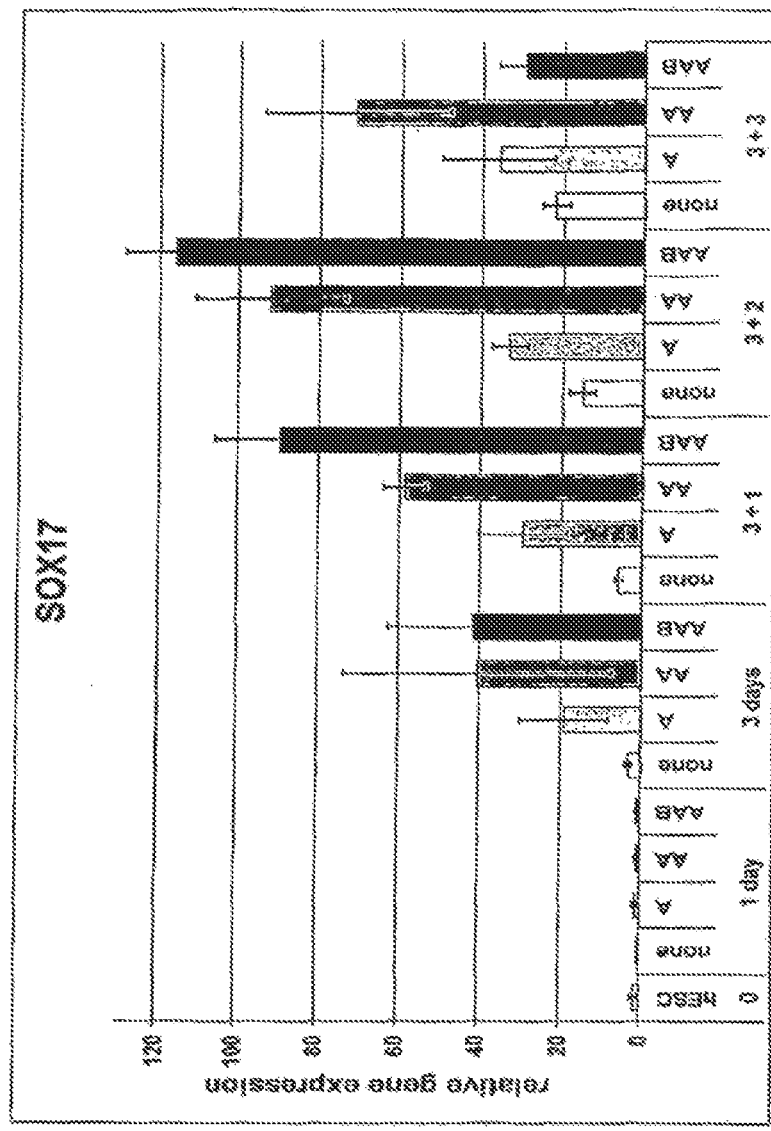
FIG. 19 is a bar chart showing the induction of SOX17 expression over time as a result of treatment with individual and combinations of TGFβ factors.

As shown in FIG. 19, addition of Activin A at 100 ng/ml resulted in a 19-fold induction of SOX17 gene expression vs. undifferentiated hESCs by day 4 of differentiation. Adding Activin B, a second member of the activin family, together with Activin A, resulted in a 37-fold induction over undifferentiated hESCs by day 4 of combined activin treatment. Finally, adding a third member of the TGFβ family from the Nodal/Activin and BMP subgroups, BMP4, together with Activin A and Activin B, increased the fold induction to 57 times that of undifferentiated hESCs (FIG. 19). When SOX17 induction with activins and BMP was compared to no factor medium controls 5-, 10-, and 15-fold inductions resulted at the 4-day time point. By five days of triple treatment with Activins A, B and BMP, SOX17 was induced more than 70 times higher than hESCs. These data indicate that higher doses and longer treatment times of the Nodal/activin TGFβ family members results in increased expression of SOX17.

Nodal and related molecules Activin A, B and BMP facilitate the expression of SOX17 and definitive endoderm formation in vivo or in vitro. Furthermore, addition of BMP results in an improved SOX17 induction possibly through the further induction of Cripto, the Nodal co-receptor.

We have demonstrated that the combination of Activins A and B together with BMP4 result in additive increases in SOX17 induction and hence definitive endoderm formation. BMP4 addition for prolonged periods (>4 days), in combination with Activin A and B may induce SOX17 in parietal and visceral endoderm as well as definitive endoderm. In some embodiments of the present invention, it is therefore valuable to remove BMP4 from the treatment within 4 days of addition.

Figure 20:
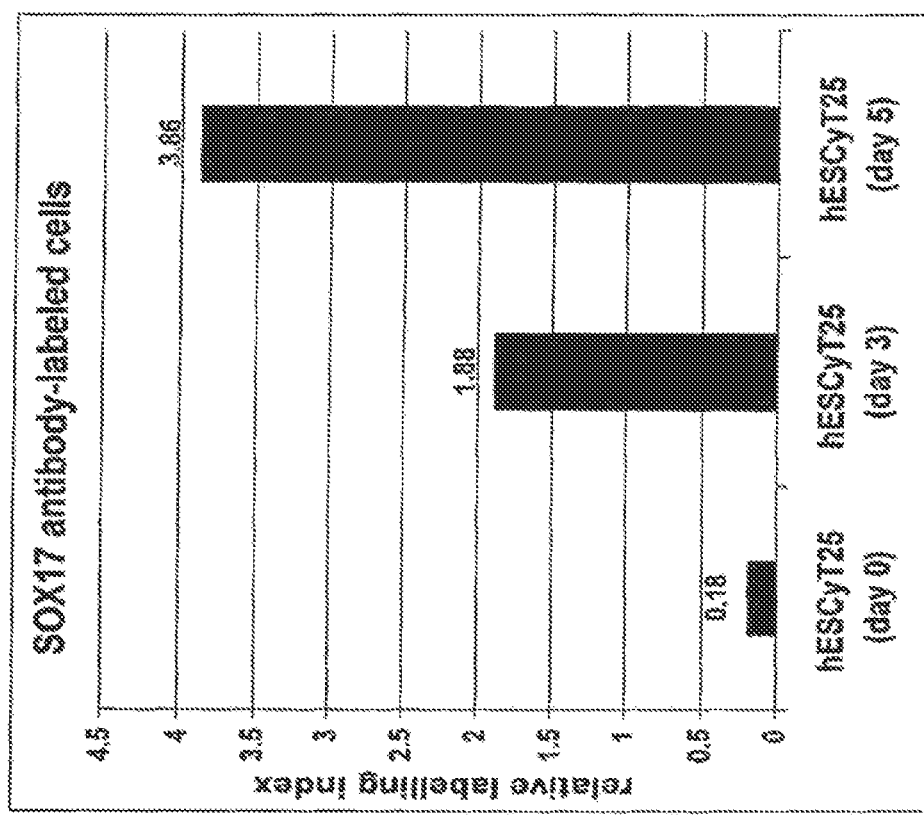
FIG. 20 is a bar chart showing the increase in SOX17$^+$ cell number with time as a result of treatment with combinations of TGFβ factors.
Figure 21:
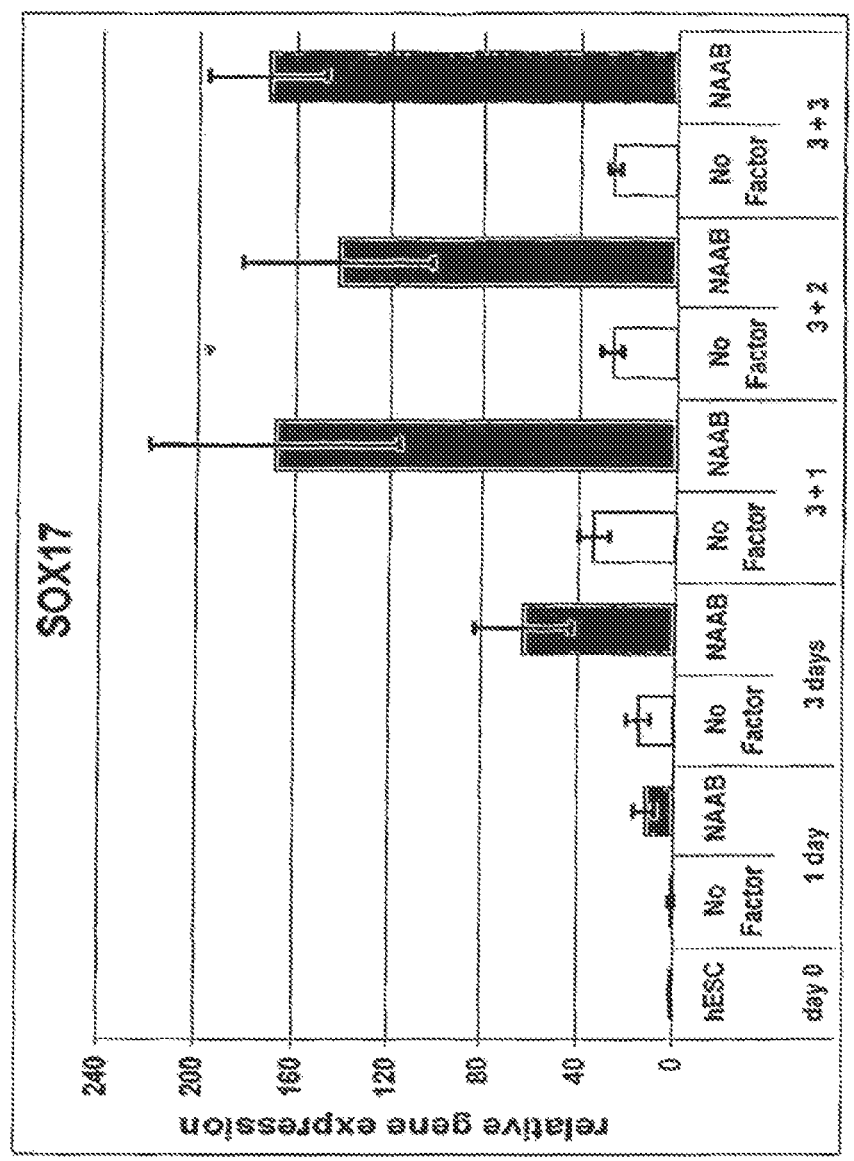
FIG. 21 is a bar chart showing induction of SOX17 expression over time as a result of treatment with combinations of TGFβ factors.
Figure 22:
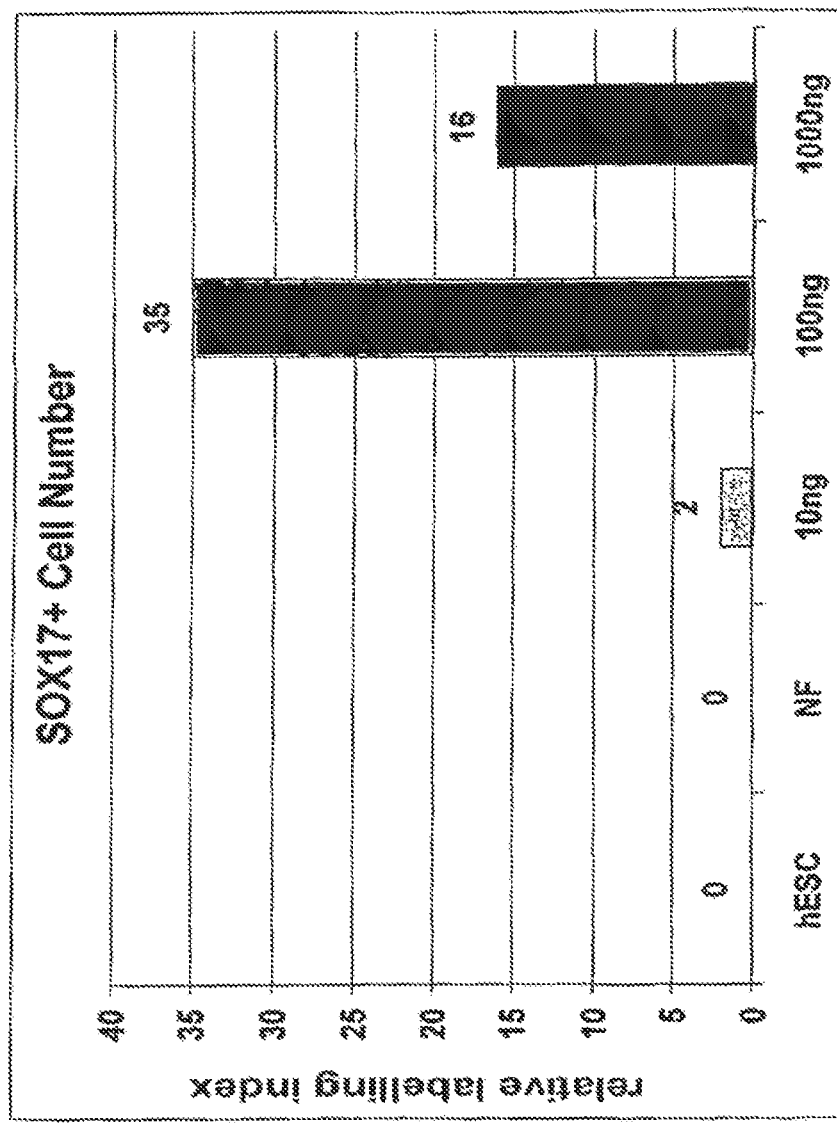
FIG. 22 is a bar chart showing that activin A induces a dose-dependent increase in SOX17$^+$ cell number.

To determine the effect of TGFβ factor treatment at the individual cell level, a time course of TGFβ factor addition was examined using SOX17 antibody labeling. As previously shown in FIGS. 10A-F, there was a dramatic increase in the relative number of SOX17 labeled cells over time. The relative quantitation (FIG. 20) shows more than a 20-fold increase in SOX17-labeled cells. This result indicates that both the numbers of cells as well SOX17 gene expression level are increasing with time of TGFβ factor exposure. As shown in FIG. 21, after four days of exposure to Nodal, Activin A, Activin B and BMP4, the level of SOX17 induction reached 168-fold over undifferentiated hESCs. FIG. 22 shows that the relative number of SOX17-positive cells was also dose responsive. Activin A doses of 100 ng/mL or more were capable of potently inducing SOX17 gene expression and cell number.

Figure 23:
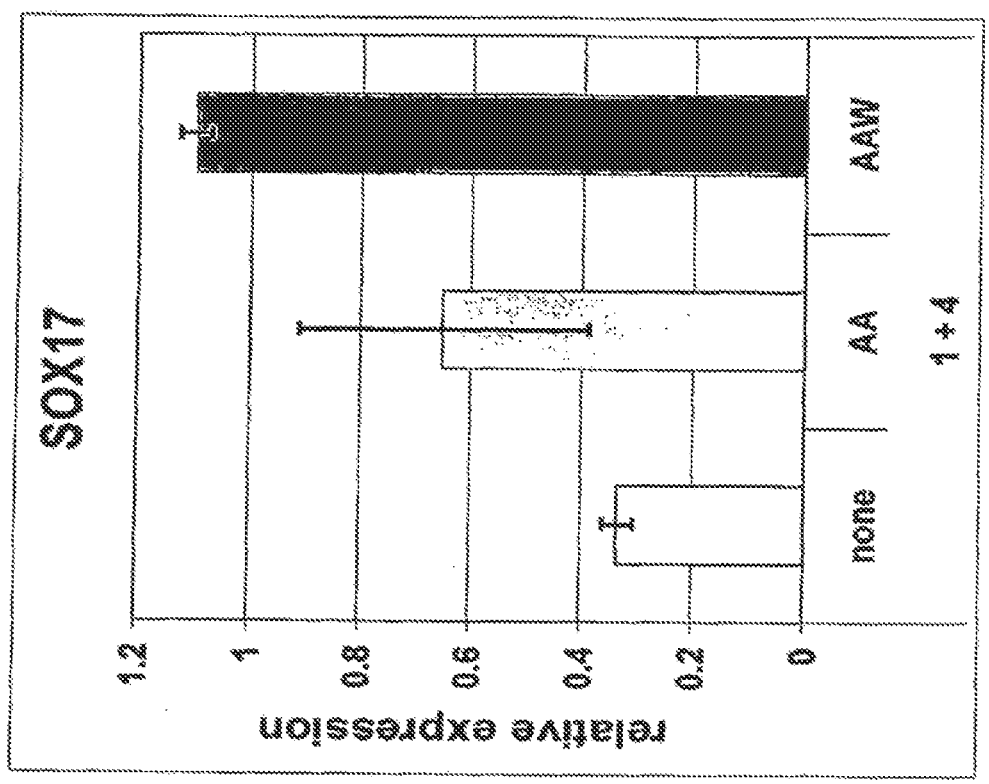
FIG. 23 is a bar chart showing that addition of Wnt3a to activin A and activin B treated cultures increases SOX17 expression above the levels induced by activin A and activin B alone.

In addition to the TGFβ family members, the Wnt family of molecules may play a role in specification and/or maintenance of definitive endoderm. The use of Wnt molecules was also beneficial for the differentiation of hESCs to definitive endoderm as indicted by the increased SOX17 gene expression in samples that were treated with activins plus Wnt3a over that of activins alone (FIG. 23).

Figure 24:
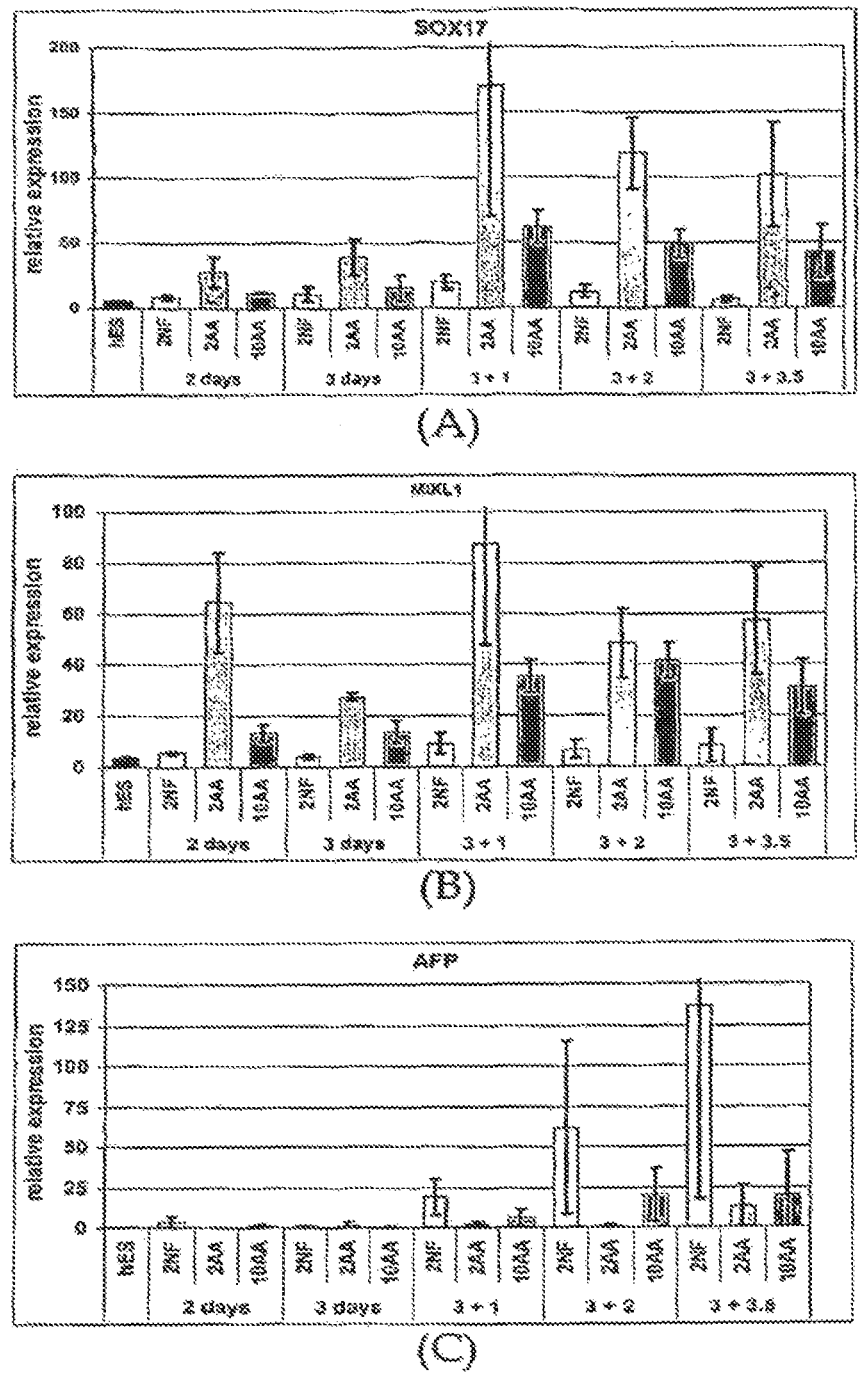
FIGS. 24A-C are bar charts showing differentiation to definitive endoderm is enhanced in low FBS conditions. Treatment of hESCs with activins A and B in media containing 2% FBS (2AA) yields a 2-3 times greater level of SOX17 expression as compared to the same treatment in 10% FBS media (10AA) (panel A). Induction of the definitive endoderm marker MIXL1 (panel B) is also affected in the same way and the suppression of AFP (visceral endoderm) (panel C) is greater in 2% FBS than in 10% FBS conditions.
Figure 25:
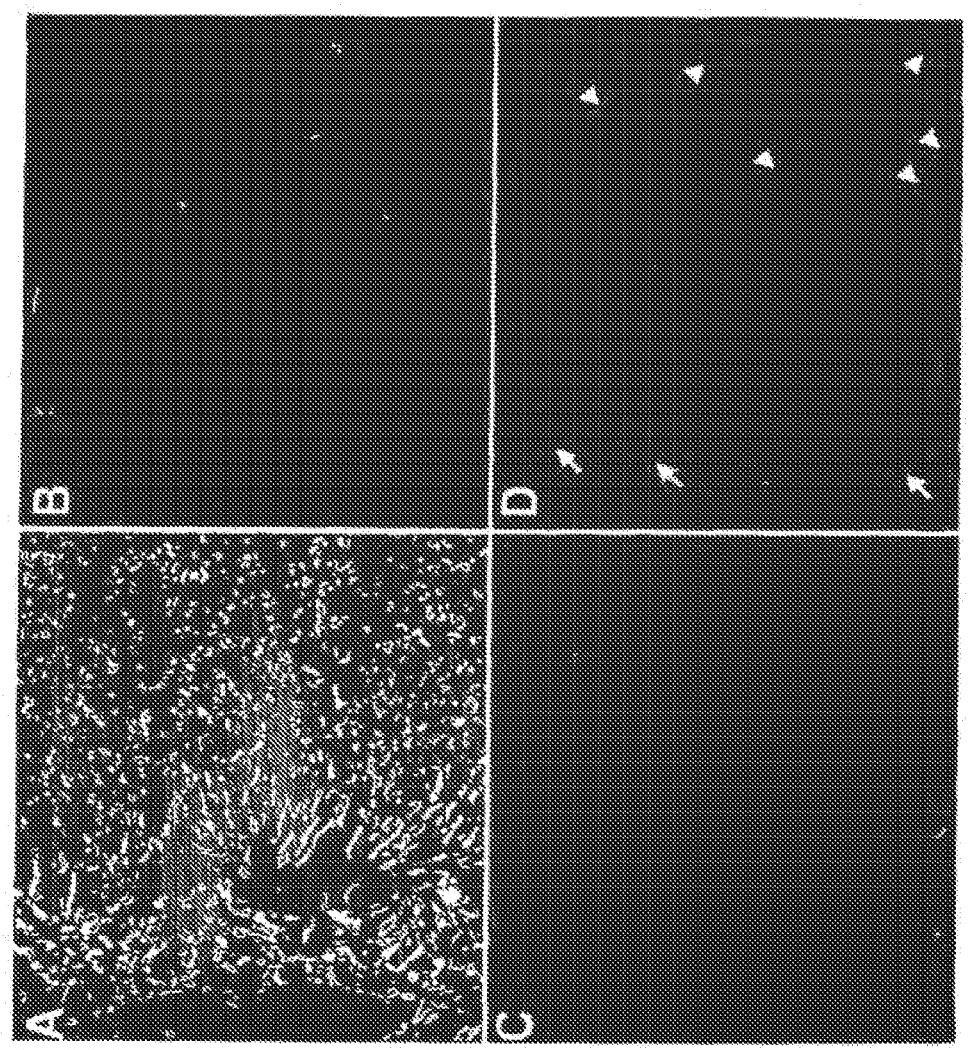
FIGS. 25A-D are micrographs which show SOX17$^+$ cells are dividing in culture. SOX17 immunoreactive cells are present at the differentiating edge of an hESC colony (C, D) and are labeled with proliferating cell nuclear antigen (PCNA) (panel B) yet are not co-labeled with OCT4 (panel C). In addition, clear mitotic figures can be seen by DAPI labeling of nuclei in both SOX17$^+$ cells (arrows) as well as OCT4$^+$, undifferentiated hESCs (arrowheads) (D).

All of the experiments described above were performed using tissue culture medium containing 10% serum with added factors. Surprisingly, we discovered that the concentration of serum had an effect on the level of SOX17 expression in the presence of added activins as shown in FIGS. 24A-C. When serum levels were reduced from 10% to 2%, SOX17 expression tripled in the presence of Activins A and B.

Finally, we demonstrated that activin induced SOX17$^+$ cells divide in culture as depicted in FIGS. 25A-D. The arrows show cells labeled with SOX17/PCNA/DAPI that are in mitosis as evidenced by the PCNA/DAPI-labeled mitotic plate pattern and the phase contrast mitotic profile.

EXAMPLE 7

Chemokine Receptor 4 (CXCR4) Expression Correlates with Markers for Definitive Endoderm and not Markers for Mesoderm, Ectoderm or Visceral Endoderm As described above, ESCs can be induced to differentiate to the definitive endoderm germ layer by the application of cytokines of the TGFβ family and more specifically of the activin/nodal subfamily. Additionally, we have shown that the proportion of fetal bovine serum (FBS) in the differentiation culture medium effects the efficiency of definitive endoderm differentiation from ESCs. This effect is such that at a given concentration of activin A in the medium, higher levels of FBS will inhibit maximal differentiation to definitive endoderm. In the absence of exogenous activin A, differentiation of ESCs to the definitive endoderm lineage is very inefficient and the FBS concentration has much milder effects on the differentiation process of ESCs.

In these experiments, hESCs were differentiated by growing in RPMI medium (Invitrogen, Carlsbad, Calif.; cat#61870-036) supplemented with 0.5%, 2.0% or 10% FBS and either with or without 100 ng/mL activin A for 6 days. In addition, a gradient of FBS ranging from 0.5% to 2.0% over the first three days of differentiation was also used in conjunction with 100 ng/mL of activin A. After the 6 days, replicate samples were collected from each culture condition and analyzed for relative gene expression by real-time quantitative PCR. The remaining cells were fixed for immunofluorescent detection of SOX17 protein.

Figure 26:
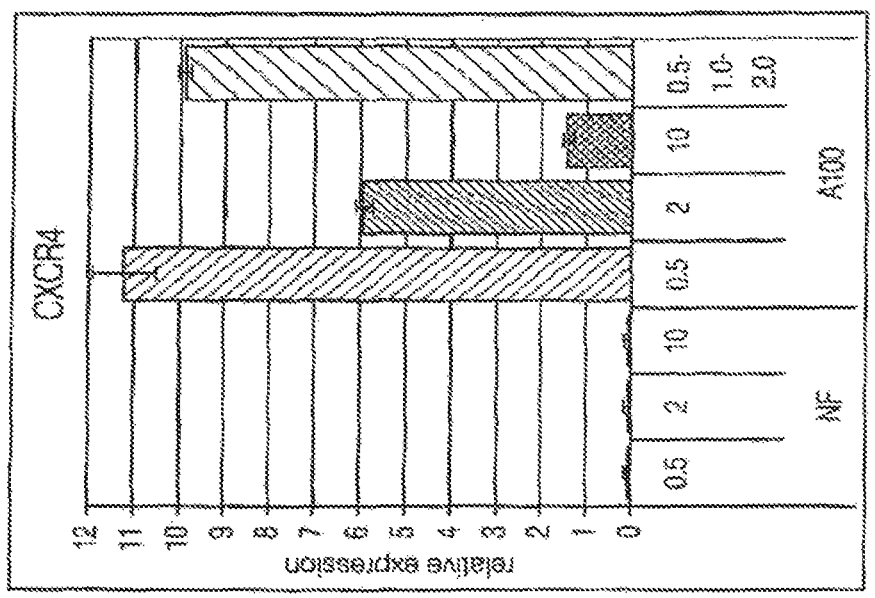
FIG. 26 is a bar chart showing the relative expression level of CXCR4 in differentiating hESCs under various media conditions.
Figure 27:
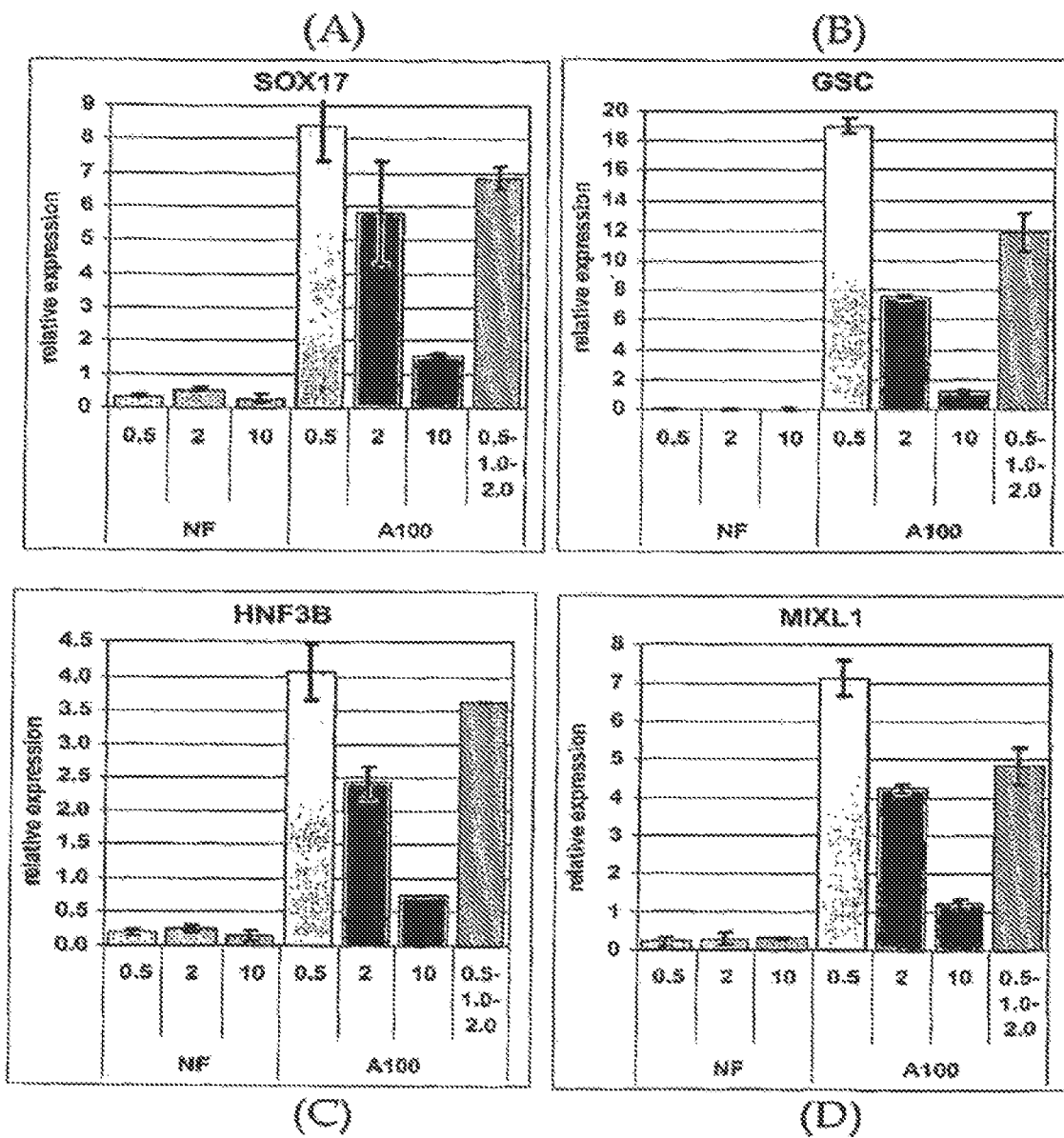
FIGS. 27A-D are bar charts that show how a panel of definitive endoderm markers share a very similar pattern of expression to CXCR4 across the same differentiation treatments displayed in FIG. 26.

The expression levels of CXCR4 varied dramatically across the 7 culture conditions used (FIG. 26). In general, CXCR4 expression was high in activin A treated cultures (A100) and low in those which did not receive exogenous activin A (NF). In addition, among the A100 treated cultures, CXCR4 expression was highest when FBS concentration was lowest. There was a remarkable decrease in CXCR4 level in the 10% FBS condition such that the relative expression was more in line with the conditions that did not receive activin A (NF).

As described above, expression of the SOX17, GSC, MIXL1, and HNF3β genes is consistent with the characterization of a cell as definitive endoderm. The relative expression of these four genes across the 7 differentiation conditions mirrors that of CXCR4 (FIGS. 27A-D). This demonstrates that CXCR4 is also a marker of definitive endoderm.

Ectoderm and mesoderm lineages can be distinguished from definitive endoderm by their expression of various markers. Early mesoderm expresses the genes Brachyury and MOX1 while nascent neuro-ectoderm expresses SOX1 and ZIC1. FIGS. 28A-D demonstrate that the cultures which did not receive exogenous activin A were preferentially enriched for mesoderm and ectoderm gene expression and that among the activin A treated cultures, the 10% FBS condition also had increased levels of mesoderm and ectoderm marker expression. These patterns of expression were inverse to that of CXCR4 and indicated that CXCR4 was not highly expressed in mesoderm or ectoderm derived from ESCs at this developmental time period.

Figure 28:
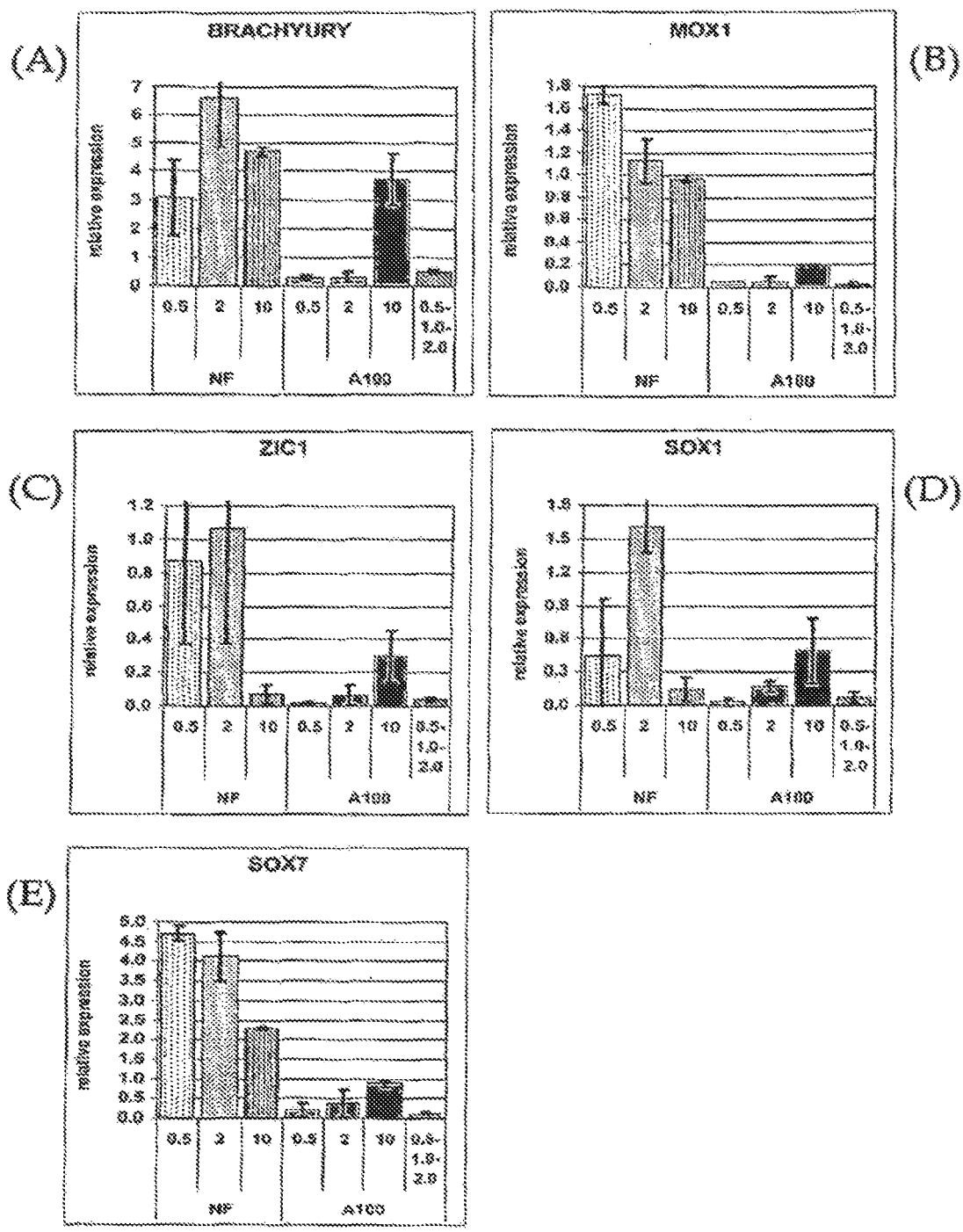
FIGS. 28A-E are bar charts showing how markers for mesoderm (BRACHYURY, MOX1), ectoderm (SOX1, ZIC1) and visceral endoderm (SOX7) exhibit an inverse relationship to CXCR4 expression across the same treatments displayed in FIG. 26.

Early during mammalian development, differentiation to extra-embryonic lineages also occurs. Of particular relevance here is the differentiation of visceral endoderm that shares the expression of many genes in common with definitive endoderm, including SOX17. To distinguish definitive endoderm from extra-embryonic visceral endoderm one should examine a marker that is distinct between these two. SOX7 represents a marker that is expressed in the visceral endoderm but not in the definitive endoderm lineage. Thus, culture conditions that exhibit robust SOX17 gene expression in the absence of SOX7 expression are likely to contain definitive and not visceral endoderm. It is shown in FIG. 28E that SOX7 was highly expressed in cultures that did not receive activin A, SOX7 also exhibited increased expression even in the presence of activin A when FBS was included at 10%. This pattern is the inverse of the CXCR4 expression pattern and suggests that CXCR4 is not highly expressed in visceral endoderm.

Figure 29:
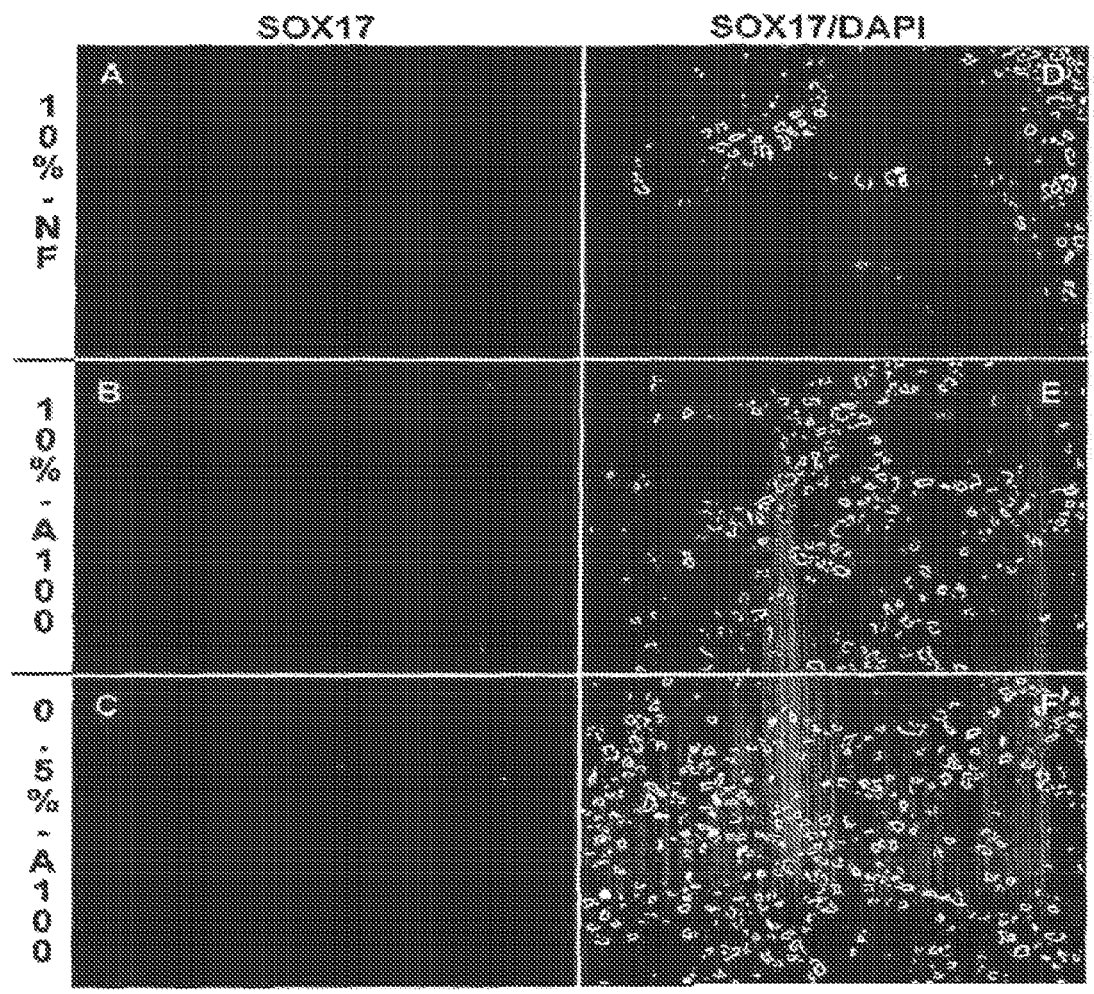
FIGS. 29A-F are micrographs that show the relative difference in SOX17 immunoreactive cells across three of the media conditions displayed in FIGS. 26-28.

The relative number of SOX17 immunoreactive (SOX17$^+$) cells present in each of the differentiation conditions mentioned above was also determined. When hESCs were differentiated in the presence of high dose activin A and low FBS concentration (0.5%-2.0%) SOX17$^+$ cells were ubiquitously distributed throughout the culture. When high dose activin A was used but FBS was included at 10% (v/v), the SOX17$^+$ cells appeared at much lower frequency and always appeared in isolated clusters rather than evenly distributed throughout the culture (FIGS. 29A and C as well as B and E). A further decrease in SOX17$^+$ cells was seen when no exogenous activin A was used. Under these conditions the SOX17$^+$ cells also appeared in clusters and these clusters were smaller and much more rare than those found in the high activin A, low FBS treatment (FIGS. 29 C and F). These results demonstrate that the CXCR4 expression patterns not only correspond to definitive endoderm gene expression but also to the number of definitive endoderm cells in each condition.

EXAMPLE 8

Differentiation Conditions that Enrich for Definitive Endoderm Increase the Proportion of CXCR4 Positive Cells The dose of activin A also effects the efficiency at which definitive endoderm can be derived from ESCs. This example demonstrates that increasing the dose of activin A increases the proportion of CXCR4$^+$ cells in the culture.

hESCs were differentiated in RPMI media supplemented with 0.5%-2% FBS (increased from 0.5% to 1.0% to 2.0% over the first 3 days of differentiation) and either 0, 10, or 100 ng/mL of activin A. After 7 days of differentiation the cells were dissociated in PBS without Ca$^{2+}$/Mg$^{2+}$ containing 2% FBS and 2 mM (EDTA) for 5 minutes at room temperature. The cells were filtered through 35 um nylon filters, counted and pelleted. Pellets were resuspended in a small volume of 50% human serum/50% normal donkey serum and incubated for 2 minutes on ice to block non-specific antibody binding sites. To this, 1 μL of mouse anti-CXCR4 antibody (Abcam, cat#ab10403-100) was added per 50 μL (containing approximately 10$^5$ cells) and labeling proceeded for 45 minutes on ice. Cells were washed by adding 5 mL of PBS containing 2% human serum (buffer) and pelleted. A second wash with 5 mL of buffer was completed then cells were resuspended in 50 μL buffer per 10$^5$ cells. Secondary antibody (FITC conjugated donkey anti-mouse; Jackson ImmunoResearch, cat#715-096-151) was added at 5 μg/mL final concentration and allowed to label for 30 minutes followed by two washes in buffer as above. Cells were resuspended at 5×10$^6$ cells/mL in buffer and analyzed and sorted using a FACS Vantage (Beckton Dickenson) by the staff at the flow cytometry core facility (The Scripps Research Institute). Cells were collected directly into RLT lysis buffer (Qiagen) for subsequent isolation of total RNA for gene expression analysis by real-time quantitative PCR.

Figure 30:
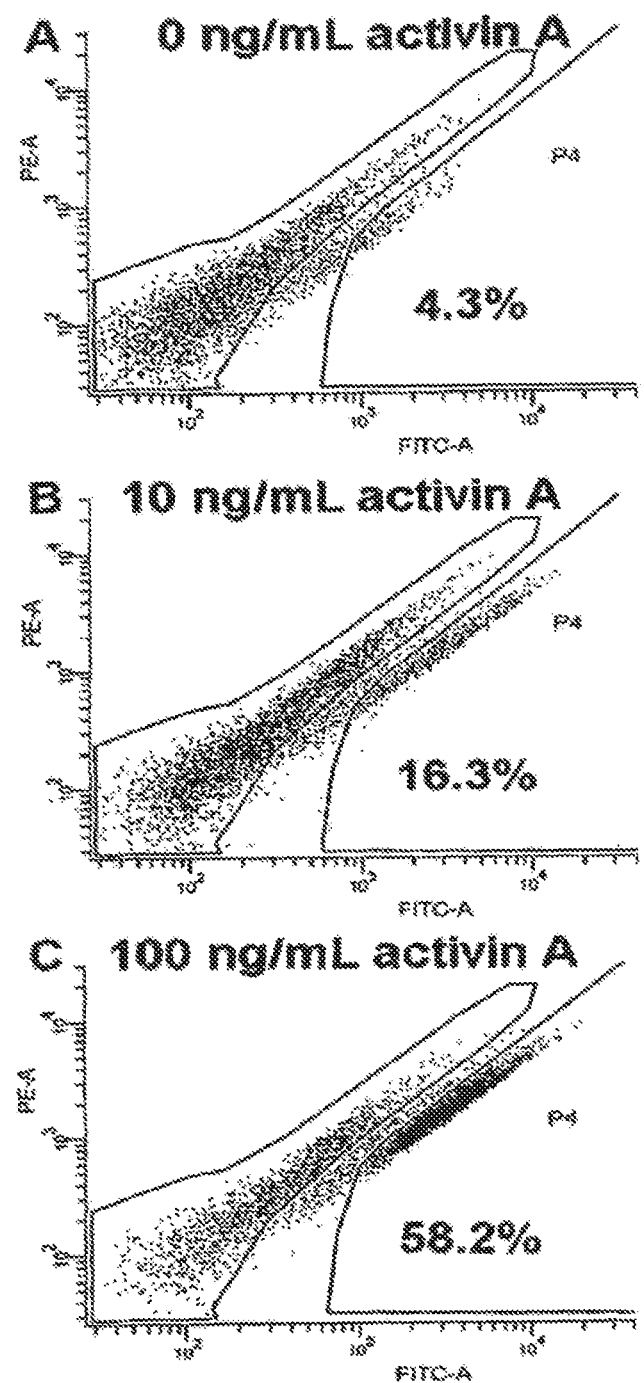
FIGS. 30A-C are flow cytometry dot plots that demonstrate the increase in CXCR4$^+$ cell number with increasing concentration of activin A added to the differentiation media.
Figure 31:
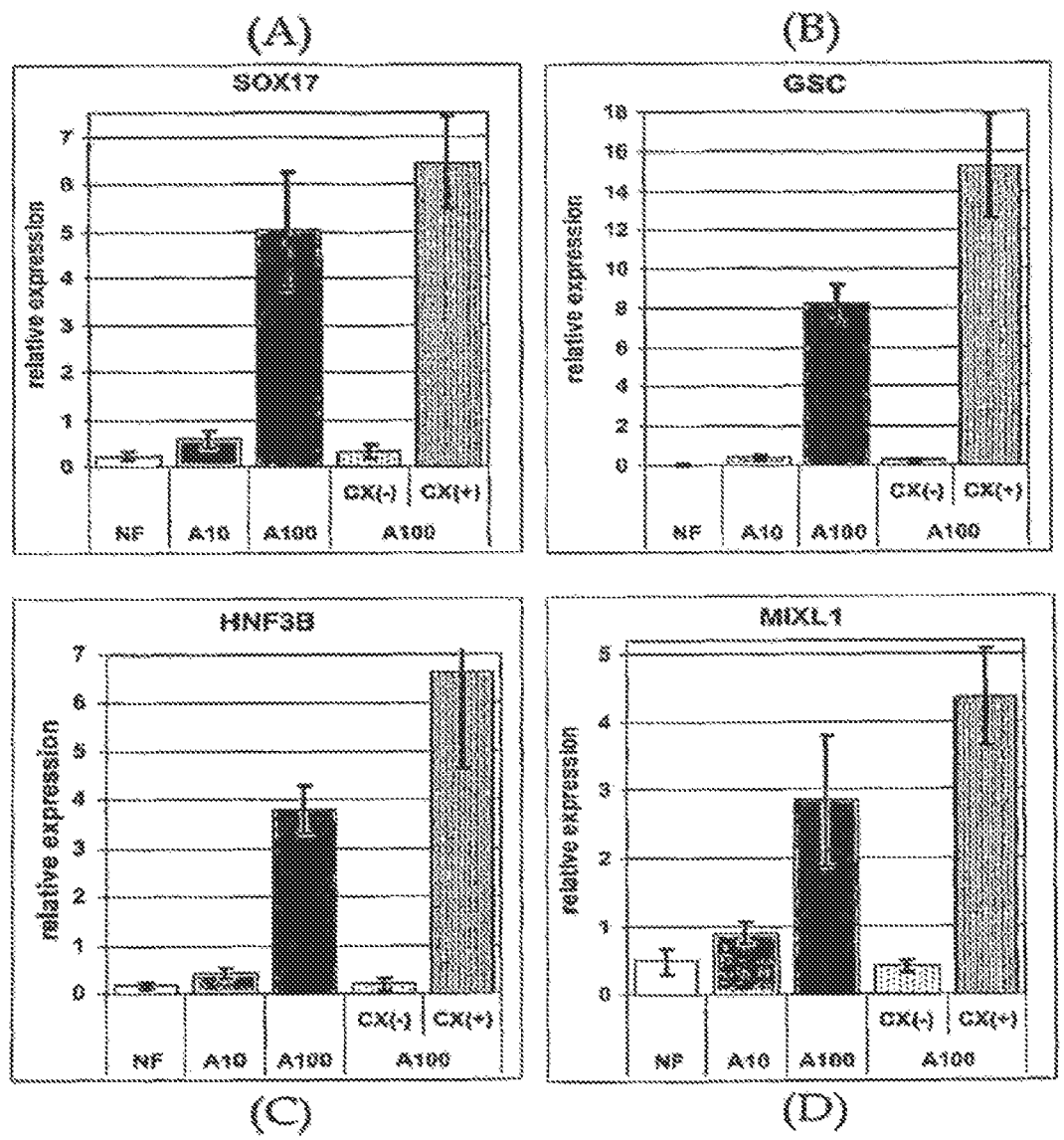
FIGS. 31A-D are bar charts that show the CXCR4$^+$ cells isolated from the high dose activin A treatment (A100-CX+) are even further enriched for definitive endoderm markers than the parent population (A100).

The number of CXCR4$^+$ cells as determined by flow cytometry were observed to increase dramatically as the dose of activin A was increased in the differentiation culture media (FIGS. 30A-C). The CXCR4$^+$ cells were those falling within the R4 gate and this gate was set using a secondary antibody-only control for which 0.2% of events were located in the R4 gate. The dramatically increased numbers of CXCR4+ cells correlates with a robust increase in definitive endoderm gene expression as activin A dose is increased (FIGS. 31A-D).

EXAMPLE 9

Isolation of CXCR4 Positive Cells Enriches for Definitive Endoderm Gene Expression and Depletes Cells Expressing Markers of Mesoderm, Ectoderm and Visceral Endoderm The CXCR4+ and CXCR4− cells identified in Example 8 above were collected and analyzed for relative gene expression and the gene expression of the parent populations was determined simultaneously.

Figure 32:
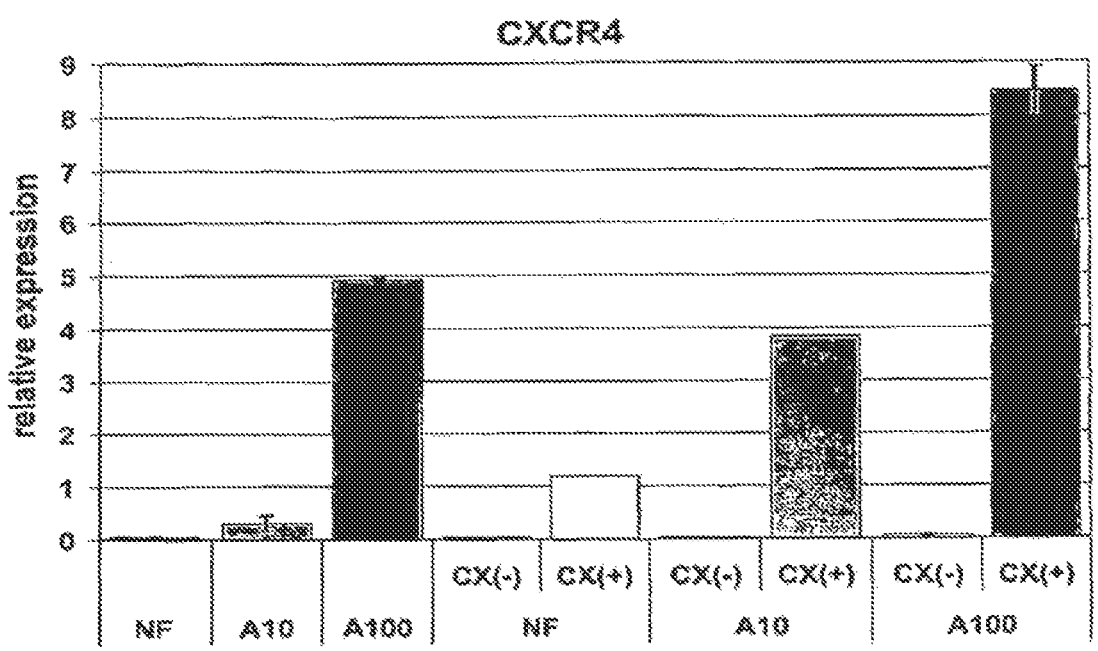
FIG. 32 is a bar chart showing gene expression from CXCR4$^+$ and CXCR4$^-$ cells isolated using fluorescence-activated cell sorting (FACS) as well as gene expression in the parent populations. This demonstrates that the CXCR4+ cells contain essentially all the CXCR4 gene expression present in each parent population and the CXCR4− populations contain very little or no CXCR4 gene expression.
Figure 33:
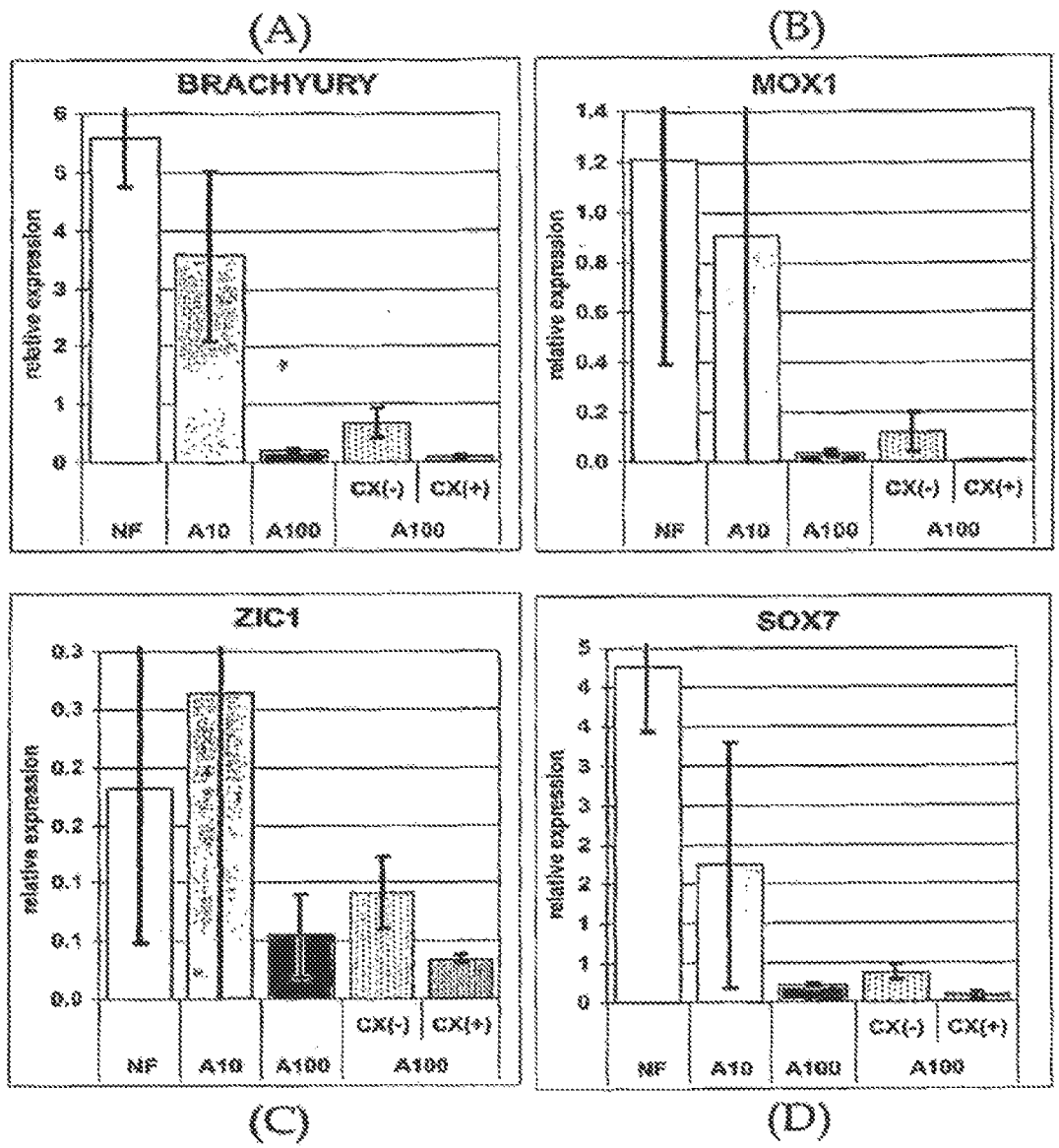
FIGS. 33A-D are bar charts that demonstrate the depletion of mesoderm (BRACHYURY, MOX1), ectoderm (ZIC1) and visceral endoderm (SOX7) gene expression in the CXCR4+ cells isolated from the high dose activin A treatment which is already suppressed in expression of these non-definitive endoderm markers.

The relative levels of CXCR4 gene expression was dramatically increased with increasing dose of activin A (FIG. 32). This correlated very well with the activin A dose-dependent increase of CXCR4+ cells (FIGS. 30A-C). It is also clear that isolation of the CXCR4+ cells from each population accounted for nearly all of the CXCR4 gene expression in that population. This demonstrates the efficiency of the FACS method for collecting these cells.

Gene expression analysis revealed that the CXCR4+ cells contain not only the majority of the CXCR4 gene expression, but they also contained other gene expression for markers of definitive endoderm. As shown in FIGS. 31A-D, the CXCR4+ cells were further enriched over the parent A100 population for SOX17, GSC, HNF3B, and MIXL1. In addition, the CXCR4− fraction contained very little gene expression for these definitive endoderm markers. Moreover, the CXCR4+ and CXCR4− populations displayed the inverse pattern of gene expression for markers of mesoderm, ectoderm and extra-embryonic endoderm. FIGS. 33A-D shows that the CXCR4+ cells were depleted for gene expression of Brachyury, MOX1, ZIC1, and SOX7 relative to the A100 parent population. This A100 parent population was already low in expression of these markers relative to the low dose or no activin A conditions. These results show that the isolation of CXCR4+ cells from hESCs differentiated in the presence of high activin A yields a population that is highly enriched for and substantially pure definitive endoderm.

EXAMPLE 10

Quantitation of Definitive Endoderm Cells in a Cell Population Using CXCR4

To confirm the quantitation of the proportion of definitive endoderm cells present in a cell culture or cell population as determined previously herein and as determined in U.S. Provisional Patent Application No. 60/532,004, entitled DEFINITIVE ENDODERM, filed Dec. 23, 2003, the disclosure of which is incorporated herein by reference in its entirety, cells expressing CXCR4 and other markers of definitive endoderm were analyzed by FACS.

Using the methods such as those described in the above Examples, hESCs were differentiated to produce definitive endoderm. In particular, to increase yield and purity expressed in differentiating cell cultures, the serum concentration of the medium was controlled as follows: 0.2% FBS on day 1, 1.0% FBS on day 2 and 2.0% FBS on days 3-6. Differentiated cultures were sorted by FACS using three cell surface epitopes, E-Cadherin, CXCR4, and Thrombomodulin. Sorted cell populations were then analyzed by Q-PCR to determine relative expression levels of markers for definitive and extraembryonic-endoderm as well as other cell types. CXCR4 sorted cells taken from optimally differentiated cultures resulted in the isolation of definitive endoderm cells that were >98% pure.

Table 2 shows the results of a marker analysis for a definitive endoderm culture that was differentiated from hESCs using the methods described herein.

TABLE 2

Composition of Definitive Endoderm Cultures

| Marker(s) | Percent of culture | Percent Definitive Endoderm | Percent Extraembryonic endododerm | Percent hES cells |
| --- | --- | --- | --- | --- |
| SOX17 | 70-80 | 100 | | |
| Thrombomodulin | <2 | 0 | 75 | |
| AFP | <1 | 0 | 25 | |
| CXCR4 | 70-80 | 100 | 0 | |
| ECAD | 10 | 0 | | 100 |
| other (ECAD neg.) | 10-22 | | | |
| Total | 100 | 100 | 100 | 100 |

In particular, Table 2 indicates that CXCR4 and SOX17 positive cells (endoderm) comprised from 70%-80% of the cells in the cell culture. Of these SOX17-expressing cells, less than 2% expressed TM (parietal endoderm) and less than 1% expressed AFP (visceral endoderm). After subtracting the proportion of TM-positive and AFP-positive cells (combined parietal and visceral endoderm; 3% total) from the proportion of SOX17/CXCR4 positive cells, it can be seen that about 67% to about 77% of the cell culture was definitive endoderm. Approximately 10% of the cells were positive for E-Cadherin (ECAD), which is a marker for hESCs, and about 10-20% of the cells were of other cell types.

We have discovered that the purity of definitive endoderm in the differentiating cell cultures that are obtained prior to FACS separation can be improved as compared to the above-described low serum procedure by maintaining the FBS concentration at ≤0.5% throughout the 5-6 day differentiation procedure. However, maintaining the cell culture at ≤0.5% throughout the 5-6 day differentiation procedure also results in a reduced number of total definitive endoderm cells that are produced.

Definitive endoderm cells produced by methods described herein have been maintained and expanded in culture in the presence of activin for greater than 50 days without appreciable differentiation. In such cases, SOX17, CXCR4, MIXL1, GATA4, HNF3β expression is maintained over the culture period. Additionally, TM, SPARC, OCT4, AFP, SOX7, ZIC1 and BRACH were not detected in these cultures. It is likely that such cells can be maintained and expanded in culture for substantially longer than 50 days without appreciable differentiation.

EXAMPLE 11

Additional Markers of Definitive Endoderm Cells

In the following experiment, RNA was isolated from purified definitive endoderm and human embryonic stem cell populations. Gene expression was then analyzed by gene chip analysis of the RNA from each purified population. Q-PCR was also performed to further investigate the potential of genes expressed in definitive endoderm, but not in embryonic stem cells, as a marker for definitive endoderm.

Human embryonic stem cells (hESCs) were maintained in DMEM/F12 media supplemented with 20% KnockOut Serum Replacement, 4 ng/mL recombinant human basic fibroblast growth factor (bFGF), 0.1 mM 2-mercaptoethanol, L-glutamine, non-essential amino acids and penicillin/streptomycin. hESCs were differentiated to definitive endoderm by culturing for 5 days in RPMI media supplemented with 100 ng/mL of recombinant human activin A, fetal bovine serum (FBS), and penicillin/streptomycin. The concentration of FBS was varied each day as follows: 0.1% (first day), 0.2% (second day), 2% (days 3-5).

Cells were isolated by fluorescence activated cell sorting (FACS) in order to obtain purified populations of hESCs and definitive endoderm for gene expression analysis. Immunopurification was achieved for hESCs using SSEA4 antigen (R&D Systems, cat#FAB1435P) and for definitive endoderm using CXCR4 (R&D Systems, cat#FAB170P). Cells were dissociated using trypsin/EDTA (Invitrogen, cat#25300-054), washed in phosphate buffered saline (PBS) containing 2% human serum and resuspended in 100% human serum on ice for 10 minutes to block non-specific binding. Staining was carried out for 30 minutes on ice by adding 200 µL of phycoerythrin-conjugated antibody to $5 \times 10^6$ cells in 800 µL human serum. Cells were washed twice with 8 mL of PBS buffer and resuspended in 1 mL of the same. FACS isolation was carried out by the core facility of The Scripps Research Institute using a FACS Vantage (BD Biosciences). Cells were collected directly into RLT lysis buffer and RNA was isolated by RNeasy according to the manufacturers instructions (Qiagen).

Purified RNA was submitted in duplicate to Expression Analysis (Durham, N.C.) for generation of the expression profile data using the Affymetrix platform and U133 Plus 2.0 high-density oligonucleotide arrays. Data presented is a group comparison that identifies genes differentially expressed between the two populations, hESCs and definitive endoderm.

Genes that exhibited an upward change in expression level over that found in hESCs are described in Table 3. The "Gene_Symbol" column refers to the unique name given to the gene by the HUGO Gene Nomenclature Committee. The "Raw Fold Change" column refers to the fold difference in signal for each gene in definitive endoderm compared to hESCs. The "Unigene," "LocusLink," and "OMIM" columns refer to identifiers that are descriptive and functional annotations derived from current National Center for Biotechnology Information (NCBI) releases of the UniGene, LocusLink, OMIM, and HomoloGene publicly available databases. The column entitled "SeqDerivedFrom" provides the Genbank Accession Number for a primary database sequence, such as a fragment of a chromosome, from which the listed gene was derived. The column entitled "Gene Descriptor" provides a description of the function of the polypeptide that is encoded by the gene named in the first column.

TABLE 3

Up-regulated markers in definitive endoderm

| Gene_Symbol | Raw Fold Change | Unigene | Locus-Link | OMIM | SeqDerived-From | Gene Descriptor |
| --- | --- | --- | --- | --- | --- | --- |
| ABCB4 | 5.22 | Hs.73812 | 5244 | 171060 | BC020618 | ATP-binding cassette, sub-family B (MDR/TAP), member 4 |
| ABCC4 | 7.18 | Hs.307915 | 10257 | 605250 | AI948503 | ATP-binding cassette, sub-family C (CFTR/MRP), member 4 |
| ABI2 | 5.95 | Hs.387906 | 10152 | 606442 | AF070566 | abl interactor 2 |
| ACADL | 7.09 | Hs.430108 | 33 | 201460 | NM_001608 | acyl-Coenzyme A dehydrogenase, long chain |
| ACE2 | 26.83 | Hs.178098 | 59272 | 300335 | NM_021804 | angiotensin I converting enzyme (peptidyl-dipeptidase A) 2 |
| ACOX3 | 13.04 | Hs.12773 | 8310 | 603402 | BF055171 | acyl-Coenzyme A oxidase 3, pristanoyl |
| ACPP | 7.06 | Hs.388677 | 55 | 171790 | AI659898 | acid phosphatase, prostate |
| ACSL1 | 14.73 | Hs.406678 | 2180 | 152425 | NM_021122 | acyl-CoA synthetase long-chain family member 1 |
| ACSL3 | 6.01 | Hs.268012 | 2181 | 602371 | BF512846 | acyl-CoA synthetase long-chain family member 3 |
| ACTA1 | 8.03 | Hs.1288 | 58 | 102610 | NM_001100 | actin, alpha 1, skeletal muscle |
| ADAM19 | 6.68 | Hs.289368 | 8728 | 603640 | Y13786 | a disintegrin and metalloproteinase domain 19 (meltrin beta) |
| ADAMTS18 | 17.65 | Hs.188746 | 170692 | 607512 | AI733120 | a disintegrin-like and metalloprotease (reprolysin type) with thrombospondin type 1 motif, 18 |
| ADAMTS9 | 16.19 | Hs.318751 | 56999 | 605421 | AF488803 | a disintegrin-like and metalloprotease (reprolysin type) with thrombospondin type 1 motif, 9 |
| ADRA1B | 5.21 | Hs.416813 | 147 | 104220 | NM_000679 | adrenergic, alpha-1B-, receptor |
| AGPAT3 | 53.81 | Hs.443657 | 56894 | | AI337300 | 1-acylglycerol-3-phosphate O-acyltransferase 3 |
| AHI1 | 6.21 | Hs.273294 | 54806 | | AV658469 | Abelson helper integration site |
| AIP1 | 6.21 | Hs.22599 | 9863 | 606382 | NM_012301 | atrophin-1 interacting protein 1 |
| ALAD | 5.43 | Hs.1227 | 210 | 125270 | BC000977 | aminolevulinate, delta-, dehydratase |
| AMHR2 | 9.46 | Hs.437877 | 269 | 600956 | NM_020547 | anti-Mullerian hormone receptor, type II |
| ANGPT2 | 13.75 | Hs.115181 | 285 | 601922 | NM_001147 | angiopoietin 2 |
| ANGPTL1 | 6.19 | Hs.304398 | 9068 | 603874 | BF002046 | angiopoietin-like 1 |
| ANK2 | 10.11 | Hs.409783 | 287 | 106410 | AF131823 | ankyrin 2, neuronal |
| ANKH | 26.52 | Hs.156727 | 56172 | 605145 | NM_019847 | ankylosis, progressive homolog (mouse) |
| ANKRD6 | 14.01 | Hs.30991 | 22881 | | NM_014942 | ankyrin repeat domain 6 |
| ANXA3 | 5.06 | Hs.442733 | 306 | 106490 | M63310 | annexin A3 |
| APC | 6.40 | Hs.75081 | 324 | 175100 | NM_000038 | adenomatosis polyposis coli |
| APOA1 | 15.05 | Hs.93194 | 335 | 107680 | X02162 | apolipoprotein A-I |
| APOA2 | 33.51 | Hs.237658 | 336 | 107670 | NM_001643 | apolipoprotein A-II |
| APOBEC3G | 15.76 | Hs.286849 | 60489 | 607113 | NM_021822 | apolipoprotein B mRNA editing enzyme, catalytic polypeptide-like 3G |
| APOC1 | 5.13 | Hs.268571 | 341 | 107710 | NM_001645 | apolipoprotein C-I |
| APOL3 | 5.88 | Hs.241535 | 80833 | 607253 | NM_014349 | apolipoprotein L, 3 |
| ARF4L | 15.64 | Hs.183153 | 379 | 600732 | NM_001661 | ADP-ribosylation factor 4-like |
| ARG99 | 5.44 | Hs.528689 | 83857 | | AU151239 | ARG99 protein |
| ARHGAP18 | 18.34 | Hs.413282 | 93663 | | AU158022 | Rho GTPase activating protein 18 |
| ARHGAP24 | 10.96 | Hs.442801 | 83478 | | AI743534 | Rho GTPase activating protein 24 |

TABLE 3-continued

Up-regulated markers in definitive endoderm

| Gene_Symbol | Raw Fold Change | Unigene | Locus-Link | OMIM | SeqDerived-From | Gene Descriptor |
|---|---|---|---|---|---|---|
| ARHGEF4 | 5.19 | Hs.6066 | 50649 | 605216 | NM_015320 | Rho guanine nucleotide exchange factor (GEF) 4 |
| ARHGEF7 | 5.10 | Hs.172813 | 8874 | 605477 | AL831814 | Rho guanine nucleotide exchange factor (GEF) 7 |
| ARK5 | 8.63 | Hs.200598 | 9891 | 608130 | NM_014840 | AMP-activated protein kinase family member 5 |
| ARMCX1 | 5.24 | Hs.9728 | 51309 | 300362 | NM_016608 | armadillo repeat containing, X-linked 1 |
| ARRB1 | 13.03 | Hs.112278 | 408 | 107940 | NM_004041 | arrestin, beta 1 |
| ARSE | 7.26 | Hs.386975 | 415 | 300180 | NM_000047 | arylsulfatase E (chondrodysplasia punctata 1) |
| ASAM | 7.31 | Hs.135121 | 79827 |  | BG112263 | adipocyte-specific adhesion molecule |
| ASB4 | 10.03 | Hs.413226 | 51666 | 605761 | BE220587 | ankyrin repeat and SOCS box-containing 4 |
| ASB5 | 47.32 | Hs.352364 | 140458 |  | BF589787 | ankyrin repeat and SOCS box-containing 5 |
| AUTS2 | 13.27 | Hs.296720 | 26053 | 607270 | AI417756 | autism susceptibility candidate 2 |
| BCAR3 | 5.47 | Hs.201993 | 8412 | 604704 | NM_003567 | breast cancer anti-estrogen resistance 3 |
| BCAT2 | 7.68 | Hs.512670 | 587 | 113530 | AK023909 | branched chain aminotransferase 2, mitochondrial |
| BCL2L14 | 8.79 | Hs.11962 | 79370 | 606126 | AI554912 | BCL2-like 14 (apoptosis facilitator) |
| BCL7C | 7.80 | Hs.303197 | 9274 | 605847 | NM_004765 | B-cell CLL/lymphoma 7C |
| BHLHB5 | 7.16 | Hs.388788 | 27319 |  | AL134708 | basic helix-loop-helix domain containing, class B, 5 |
| BIRC3 | 7.41 | Hs.127799 | 330 | 601721 | U37546 | baculoviral IAP repeat-containing 3 |
| BMP2 | 7.76 | Hs.73853 | 650 | 112261 | NM_001200 | bone morphogenetic protein 2 |
| BMPER | 5.53 | Hs.71730 | 168667 | 608699 | AI423201 | BMP-binding endothelial regulator precursor protein |
| BMPR2 | 6.05 | Hs.53250 | 659 | 600799 | AI457436 | bone morphogenetic protein receptor, type II (serine/threonine kinase) |
| BRUNOL4 | 10.60 | Hs.435976 | 56853 |  | AI697701 | bruno-like 4, RNA binding protein (*Drosophila*) |
| BSPRY | 6.56 | Hs.108502 | 54836 |  | NM_017688 | B-box and SPRY domain containing |
| BTG2 | 5.88 | Hs.75462 | 7832 | 601597 | NM_006763 | BTG family, member 2 |
| BTK | 5.13 | Hs.159494 | 695 | 300300 | NM_000061 | Bruton agammaglobulinemia tyrosine kinase |
| C10orf39 | 9.09 | Hs.106254 | 282973 |  | AL137551 | chromosome 10 open reading frame 39 |
| C10orf94 | 12.58 | Hs.311003 | 93426 |  | BC034821 | chromosome 10 open reading frame 94 |
| C11orf21 | 5.13 | Hs.272100 | 29125 |  | BM547346 | chromosome 11 open reading frame 21 |
| C13orf25 | 7.13 |  | 407975 |  | AF339828 | chromosome 13 open reading frame 25 |
| C14orf139 | 13.95 | Hs.41502 | 79686 |  | NM_024633 | chromosome 14 open reading frame 139 |
| C18orf1 | 5.05 | Hs.285091 | 753 | 606571 | AW008505 | chromosome 18 open reading frame 1 |
| C18orf14 | 17.69 | Hs.146025 | 79839 |  | NM_024781 | chromosome 18 open reading frame 14 |
| C20orf56 | 36.01 |  | 140828 |  | AL121722 | chromosome 20 open reading frame 56 |
| C21orf105 | 10.03 | Hs.386685 | 90625 |  | BC005107 | chromosome 21 open reading frame 105 |
| C21orf129 | 77.87 | Hs.350679 | 150135 |  | NM_152506 | chromosome 21 open reading frame 129 |
| C21orf2 | 6.17 | Hs.155361 | 755 | 603191 | U84569 | chromosome 21 open reading frame 2 |
| C21orf29 | 5.57 | Hs.473997 | 54084 |  | BC021197 | chromosome 21 open reading frame 29 |
| C21orf30 | 6.67 | Hs.222909 | 54083 |  | AL117578 | chromosome 21 open reading frame 30 |
| C5 | 15.16 | Hs.1281 | 727 | 120900 | NM_001735 | complement component 5 |
| C5orf13 | 6.29 | Hs.508741 | 9315 | 607332 | AI733949 | chromosome 5 open reading frame 13 |
| C6orf164 | 9.47 |  | 63914 |  | NM_022084 | chromosome 6 open reading frame 164 |
| C6orf182 | 11.05 | Hs.375746 | 285753 |  | BE567344 | chromosome 6 open reading frame 182 |
| C6orf4 | 6.58 | Hs.437508 | 10758 | 607043 | AI916498 | chromosome 6 open reading frame 4 |
| C6orf52 | 9.39 |  | 347744 |  | AW103116 | chromosome 6 open reading frame 52 |
| C6orf54 | 6.13 | Hs.225962 | 26236 |  | AB016900 | chromosome 6 open reading frame 54 |
| C6orf60 | 21.05 | Hs.20537 | 79632 |  | AJ420563 | chromosome 6 open reading frame 60 |
| C6orf97 | 5.47 | Hs.287738 | 80129 |  | NM_025059 | chromosome 6 open reading frame 97 |
| C8orf13 | 8.66 | Hs.318791 | 83648 |  | BE856336 | chromosome 8 open reading frame 13 |
| C8orf6 | 7.04 | Hs.291342 | 203081 |  | NM_145656 | chromosome 8 open reading frame 6 |
| C9orf154 | 22.03 | Hs.119947 | 158326 |  | AI824037 | chromosome 9 open reading frame 154 |
| C9orf52 | 10.19 | Hs.49605 | 158219 |  | AW001030 | chromosome 9 open reading frame 52 |
| C9orf64 | 12.97 | Hs.208914 | 84267 |  | AW983691 | chromosome 9 open reading frame 64 |
| C9orf66 | 8.78 | Hs.190877 | 157983 |  | NM_152569 | chromosome 9 open reading frame 66 |
| C9orf71 | 7.44 | Hs.96641 | 169693 |  | AW271796 | chromosome 9 open reading frame 71 |
| CALB1 | 11.26 | Hs.65425 | 793 | 114050 | NM_004929 | calbindin 1, 28 kDa |
| CALCR | 38.31 | Hs.640 | 799 | 114131 | NM_001742 | calcitonin receptor |
| CAMK2D | 7.15 | Hs.111460 | 817 | 607708 | BF797381 | calcium/calmodulin-dependent protein kinase (CaM kinase) II delta |
| CAP2 | 5.83 | Hs.296341 | 10486 |  | N90755 | CAP, adenylate cyclase-associated protein, 2 (yeast) |
| CASK | 9.64 | Hs.288196 | 8573 | 300172 | AI659225 | calcium/calmodulin-dependent serine protein kinase (MAGUK family) |
| CASP1 | 9.90 | Hs.2490 | 834 | 147678 | AI719655 | caspase 1, apoptosis-related cysteine protease (interleukin 1, beta, convertase) |
| CBLB | 5.96 | Hs.436986 | 868 | 604491 | NM_004351 | Cas-Br-M (murine) ecotropic retroviral transforming sequence b |
| CCKBR | 27.45 | Hs.203 | 887 | 118445 | BC000740 | cholecystokinin B receptor |
| CCL2 | 111.46 | Hs.303649 | 6347 | 158105 | S69738 | chemokine (C-C motif) ligand 2 |
| CCR4 | 5.70 | Hs.506129 | 1233 | 604836 | NM_005508 | chemokine (C-C motif) receptor 4 |
| CD163 | 9.73 | Hs.74076 | 9332 | 605545 | Z22969 | CD163 antigen |
| CD44 | 5.25 | Hs.306278 | 960 | 107269 | AW851559 | CD44 antigen (homing function and Indian blood group system) |
| CD80 | 8.85 | Hs.838 | 941 | 112203 | AY081815 | CD80 antigen (CD28 antigen ligand 1, B7-1 antigen) |
| CD99 | 5.86 | Hs.283477 | 4267 | 313470/ | U82164 | CD99 antigen |
| CDGAP | 10.17 | Hs.300670 | 57514 |  | AB033030 | KIAA1204 protein |
| CDH12 | 9.44 | Hs.333997 | 1010 | 600562 | L33477 | cadherin 12, type 2 (N-cadherin 2) |
| CDH2 | 8.85 | Hs.334131 | 1000 | 114020 | NM_001792 | cadherin 2, type 1, N-cadherin (neuronal) |
| CDK5R2 | 5.13 | Hs.158460 | 8941 | 603764 | R51311 | cyclin-dependent kinase 5, regulatory subunit 2 (p39) |
| CDKN2B | 8.45 | Hs.72901 | 1030 | 600431 | AW444761 | cyclin-dependent kinase inhibitor 2B (p15, inhibits CDK4) |

TABLE 3-continued

Up-regulated markers in definitive endoderm

| Gene_Symbol | Raw Fold Change | Unigene | Locus-Link | OMIM | SeqDerived-From | Gene Descriptor |
|---|---|---|---|---|---|---|
| CDW92 | 5.10 | Hs.414728 | 23446 | 606105 | AW444881 | CDW92 antigen |
| CER1 | 33.04 | Hs.248204 | 9350 | 603777 | NM_005454 | cerberus 1 homolog, cysteine knot superfamily (*Xenopus laevis*) |
| CFLAR | 21.93 | Hs.355724 | 8837 | 603599 | AF005775 | CASP8 and FADD-like apoptosis regulator |
| CFTR | 5.50 | Hs.411882 | 1080 | 602421 | S64699 | cystic fibrosis transmembrane conductance regulator, ATP-binding cassette (sub-family C, member 7) |
| CGI-38 | 19.67 | Hs.412685 | 51673 | | NM_016140 | brain specific protein |
| CLDN1 | 7.32 | Hs.7327 | 9076 | 603718 | AF101051 | claudin 1 |
| CLDN11 | 7.86 | Hs.31595 | 5010 | 601326 | AW264204 | claudin 11 (oligodendrocyte transmembrane protein) |
| CMKOR1 | 53.39 | Hs.231853 | 57007 | | AI817041 | chemokine orphan receptor 1 |
| CNTN3 | 7.56 | Hs.512593 | 5067 | 601325 | BE221817 | contactin 3 (plasmacytoma associated) |
| CNTN4 | 5.13 | Hs.121115 | 152330 | 607280 | R42166 | contactin 4 |
| COL22A1 | 5.12 | Hs.116394 | 169044 | | BE349115 | collagen, type XXII, alpha 1 |
| COL4A3 | 9.58 | Hs.407817 | 1285 | 120070 | AI694562 | collagen, type IV, alpha 3 (Goodpasture antigen) |
| COL5A2 | 6.62 | Hs.283393 | 1290 | 120190 | NM_000393 | collagen, type V, alpha 2 |
| COL8A1 | 11.41 | Hs.114599 | 1295 | 120251 | AL359062 | collagen, type VIII, alpha 1 |
| COL9A2 | 7.94 | Hs.418012 | 1298 | 120260 | AI733465 | collagen, type IX, alpha 2 |
| COLEC12 | 24.49 | Hs.29423 | 81035 | 607621 | NM_030781 | collectin sub-family member 12 |
| CPE | 13.90 | Hs.75360 | 1363 | 114855 | NM_001873 | carboxypeptidase E |
| CPXCR1 | 5.03 | Hs.458292 | 53336 | | AK098646 | CPX chromosome region, candidate 1 |
| CRIP1 | 50.56 | | 1396 | 123875 | NM_001311 | cysteine-rich protein 1 (intestinal) |
| CST1 | 6.20 | Hs.123114 | 1469 | 123855 | NM_001898 | cystatin SN |
| CTSH | 5.20 | Hs.114931 | 1512 | 116820 | NM_004390 | cathepsin H |
| CXCR4 | 55.31 | Hs.421986 | 7852 | 162643 | AJ224869 | chemokine (C—X—C motif) receptor 4 |
| CXorf1 | 54.35 | Hs.106688 | 9142 | | NM_004709 | chromosome X open reading frame 1 |
| CYLC1 | 11.56 | Hs.444230 | 1538 | 603121 | Z22780 | cylicin, basic protein of sperm head cytoskeleton 1 |
| CYP27A1 | 19.84 | Hs.82568 | 1593 | 606530 | NM_000784 | cytochrome P450, family 27, subfamily A, polypeptide 1 |
| DACT2 | 11.72 | Hs.248294 | 168002 | | AF318336 | dapper homolog 2, antagonist of beta-catenin (*xenopus*) |
| DDC | 8.62 | Hs.408106 | 1644 | 107930 | NM_000790 | dopa decarboxylase (aromatic L-amino acid decarboxylase) |
| DDIT4L | 5.33 | Hs.107515 | 115265 | 607730 | AA528140 | DNA-damage-inducible transcript 4-like |
| DIO3 | 33.07 | Hs.49322 | 1735 | 601038 | NM_001362 | deiodinase, iodothyronine, type III |
| DIO3OS | 59.10 | Hs.406958 | 64150 | 608523 | AF305836 | deiodinase, iodothyronine, type III opposite strand |
| DIRAS2 | 8.07 | Hs.165636 | 54769 | 607863 | NM_017594 | DIRAS family, GTP-binding RAS-like 2 |
| dJ222E13.1 | 28.34 | Hs.301947 | 253190 | | AL590118 | kraken-like |
| DKFZp434C184 | 5.73 | Hs.531492 | 399474 | | N63821 | cDNA DKFZp434C184 gene |
| DKFZp564I1922 | 6.26 | Hs.72157 | 25878 | | AF245505 | adlican |
| DKFZp566F0947 | 7.27 | Hs.220597 | 94023 | | AL137518 | hypothetical gene DKFZp566F0947 |
| DKFZP586M1120 | 5.29 | Hs.159068 | 83450 | | BC040276 | hypothetical protein DKFZp586M1120 |
| DLC1 | 13.62 | Hs.8700 | 10395 | 604258 | AA524250 | deleted in liver cancer 1 |
| DLEC1 | 9.06 | Hs.277589 | 9940 | 604050 | NM_007337 | deleted in lung and esophageal cancer 1 |
| DLEU2 | 8.62 | Hs.446406 | 8847 | 605766 | AF264787 | deleted in lymphocytic leukemia, 2 |
| DLG5 | 5.88 | Hs.500245 | 9231 | 604090 | AI809998 | discs, large homolog 5 (*Drosophila*) |
| DNAH14 | 7.14 | Hs.381271 | 1772 | 603341 | U61741 | dynein, axonemal, heavy polypeptide 14 |
| DNAJC6 | 9.80 | Hs.129587 | 9829 | 608375 | AV729634 | DnaJ (Hsp40) homolog, subfamily C, member 6 |
| DNAJD1 | 6.48 | Hs.438830 | 29103 | | NM_013238 | DnaJ (Hsp40) homolog, subfamily D, member 1 |
| DNMT3L | 14.53 | Hs.157237 | 29947 | 606588 | NM_013369 | DNA (cytosine-5-)-methyltransferase 3-like |
| DOCK5 | 5.24 | Hs.383002 | 80005 | | AL832744 | dedicator of cytokinesis 5 |
| DOCK8 | 16.36 | Hs.528687 | 81704 | | AL161725 | dedicator of cytokinesis 8 |
| DPYD | 33.20 | Hs.1602 | 1806 | 274270 | NM_000110 | dihydropyrimidine dehydrogenase |
| DSCAM | 8.25 | Hs.49002 | 1826 | 602523 | BE503065 | Down syndrome cell adhesion molecule |
| DSCAML1 | 5.56 | Hs.397966 | 57453 | | AK025940 | Down syndrome cell adhesion molecule like 1 |
| DSCR6 | 21.62 | Hs.254560 | 53820 | | NM_018962 | Down syndrome critical region gene 6 |
| DUSP4 | 22.18 | Hs.417962 | 1846 | 602747 | NM_001394 | dual specificity phosphatase 4 |
| EB-1 | 162.04 | Hs.372732 | 56899 | 607815 | AW005572 | E2a-Pbx1-associated protein |
| EBAF | 14.86 | Hs.25195 | 7044 | 601877 | NM_003240 | endometrial bleeding associated factor (left-right determination, factor A; transforming growth factor beta superfamily) |
| EBI2 | 5.68 | Hs.784 | 1880 | 605741 | NM_004951 | Epstein-Barr virus induced gene 2 (lymphocyte-Specific G protein-coupled receptor) |
| ED1 | 8.13 | Hs.105407 | 1896 | 300451 | NM_001399 | ectodermal dysplasia 1, anhidrotic |
| EDG3 | 20.71 | Hs.353892 | 1903 | 601965 | NM_005226 | endothelial differentiation, sphingolipid G-protein-coupled receptor, 3 |
| EDG3 | 12.22 | Hs.4257 | 1903 | 601965 | AA534817 | endothelial differentiation, sphingolipid G-protein-coupled receptor, 3 |
| EDNRA | 5.58 | Hs.211202 | 1909 | 131243 | AU118882 | endothelin receptor type A |
| EGF | 13.71 | Hs.419815 | 1950 | 131530 | NM_001963 | epidermal growth factor (beta-urogastrone) |
| EHHADH | 85.52 | Hs.432443 | 1962 | 607037 | NM_001966 | enoyl-Coenzyme A, hydratase/3-hydroxyacyl Coenzyme A dehydrogenase |
| EIF5A2 | 5.20 | Hs.164144 | 56648 | 605782 | AV747725 | eukaryotic translation initiation factor 5A2 |
| ELMO1 | 7.28 | Hs.444695 | 9844 | 606420 | NM_014800 | engulfment and cell motility 1 (ced-12 homolog, *C. elegans*) |
| ELOVL2 | 70.71 | Hs.246107 | 54898 | | BF508639 | elongation of very long chain fatty acids (FEN1/Elo2, SUR4/Elo3, yeast)-like 2 |
| EMR2 | 5.66 | Hs.137354 | 30817 | 606100 | NM_013447 | egf-like module containing, mucin-like, hormone receptor-like 2 |
| ENPEP | 10.17 | Hs.435765 | 2028 | 138297 | L12468 | glutamyl aminopeptidase (aminopeptidase A) |
| EOMES | 16.02 | Hs.147279 | 8320 | 604615 | NM_005442 | eomesodermin homolog (*Xenopus laevis*) |
| EPHB3 | 8.99 | Hs.2913 | 2049 | 601839 | NM_004443 | EphB3 |
| EPOR | 6.92 | Hs.127826 | 2057 | 133171 | BU727288 | erythropoietin receptor |
| EPSTI1 | 34.25 | Hs.343800 | 94240 | 607441 | AA633203 | epithelial stromal interaction 1 (breast) |

TABLE 3-continued

Up-regulated markers in definitive endoderm

| Gene_Symbol | Raw Fold Change | Unigene | Locus-Link | OMIM | SeqDerived-From | Gene Descriptor |
|---|---|---|---|---|---|---|
| ERBB4 | 6.35 | Hs.1939 | 2066 | 600543 | NM_005235 | v-erb-a erythroblastic leukemia viral oncogene homolog 4 (avian) |
| ERO1LB | 5.94 | Hs.424926 | 56605 | | NM_019891 | ERO1-like beta (S. cerevisiae) |
| ETS2 | 6.96 | Hs.292477 | 2114 | 164740 | AL575509 | v-ets erythroblastosis virus E26 oncogene homolog 2 (avian) |
| EVC | 26.80 | Hs.28051 | 2121 | 604831 | NM_014556 | Ellis van Creveld syndrome |
| FAM13C1 | 5.24 | Hs.311205 | 220965 | | BC036453 | family with sequence similarity 13, member C1 |
| FAM38B | 5.63 | Hs.293907 | 63895 | | AW269818 | family with sequence similarity 38, member B |
| FANK1 | 9.17 | Hs.352591 | 92565 | | AU143929 | fibronectin type 3 and ankyrin repeat domains 1 |
| FBS1 | 7.33 | Hs.247186 | 64319 | 608601 | AW134523 | fibrosin 1 |
| FBXL14 | 7.12 | Hs.367956 | 144699 | | NM_152441 | F-box and leucine-rich repeat protein 14 |
| FBXL8 | 10.33 | Hs.75486 | 55336 | | NM_018378 | F-box and leucine-rich repeat protein 8 |
| FBXO32 | 5.70 | Hs.403933 | 114907 | 606604 | BF244402 | F-box only protein 32 |
| FBXO4 | 6.29 | Hs.437345 | 26272 | | NM_018007 | F-box only protein 4 |
| FCGR2A | 6.65 | Hs.352642 | 2212 | 146790 | AF416711 | Fc fragment of IgG, low affinity IIa, receptor for (CD32) |
| FER1L3 | 15.13 | Hs.362731 | 26509 | 604603 | AF207990 | fer-1-like 3, myoferlin (C. elegans) |
| FES | 9.36 | Hs.7636 | 2242 | 190030 | NM_002005 | feline sarcoma oncogene |
| FGD6 | 5.11 | Hs.170623 | 55785 | | AK026881 | FYVE, RhoGEF and PH domain containing 6 |
| FGF17 | 107.07 | Hs.248192 | 8822 | 603725 | NM_003867 | fibroblast growth factor 17 |
| FGF8 | 14.46 | Hs.57710 | 2253 | 600483 | NM_006119 | fibroblast growth factor 8 (androgen-induced) |
| FKBP9 | 5.00 | Hs.497972 | 11328 | | AL050187 | FK506 binding protein 9, 63 kDa |
| FLJ10312 | 30.88 | Hs.183114 | 79822 | | NM_030672 | hypothetical protein FLJ10312 |
| FLJ10970 | 50.86 | Hs.173233 | 55273 | | NM_018286 | hypothetical protein FLJ10970 |
| FLJ10996 | 10.14 | Hs.98324 | 54520 | | AA504256 | hypothetical protein FLJ10996 |
| FLJ11082 | 8.96 | Hs.31792 | 55296 | | NM_018317 | hypothetical protein FLJ11082 |
| FLJ11155 | 9.25 | Hs.176227 | 55314 | | AW173720 | hypothetical protein FLJ11155 |
| FLJ11175 | 5.55 | Hs.33368 | 55784 | | AI052257 | hypothetical protein FLJ11175 |
| FLJ11506 | 5.76 | Hs.254642 | 79719 | | AL136715 | hypothetical protein FLJ11506 |
| FLJ12476 | 16.70 | Hs.88144 | 64799 | | NM_022784 | hypothetical protein FLJ12476 |
| FLJ13231 | 8.43 | Hs.156148 | 65250 | | NM_023073 | hypothetical protein FLJ13231 |
| FLJ13330 | 6.67 | Hs.193048 | 80161 | | NM_025091 | hypothetical protein FLJ13330 |
| FLJ13373 | 6.74 | Hs.494757 | 387751 | | AL833700 | very large inducible GTPase 1 |
| FLJ13725 | 5.66 | Hs.152717 | 79567 | | NM_024519 | hypothetical protein FLJ13725 |
| FLJ14721 | 5.09 | Hs.144655 | 84915 | | BE551088 | hypothetical protein FLJ14721 |
| FLJ20014 | 13.09 | Hs.129563 | 54785 | | NM_017622 | hypothetical protein FLJ20014 |
| FLJ20265 | 5.65 | Hs.7099 | 54872 | | AV650183 | hypothetical protein FLJ20265 |
| FLJ20489 | 5.47 | Hs.438867 | 55652 | | AW149696 | hypothetical protein FLJ20489 |
| FLJ21069 | 10.30 | Hs.341806 | 79745 | | NM_024692 | hypothetical protein FLJ21069 |
| FLJ21195 | 83.56 | Hs.207407 | 64388 | | BF064262 | protein related to DAN and cerberus |
| FLJ22028 | 5.58 | Hs.192570 | 79912 | | AI554909 | hypothetical protein FLJ22028 |
| FLJ22471 | 34.33 | Hs.387266 | 80212 | | NM_025140 | limkain beta 2 |
| FLJ22527 | 34.12 | Hs.113009 | 79781 | | W52934 | hypothetical protein FLJ22527 |
| FLJ23091 | 7.90 | Hs.297792 | 79971 | | AL534095 | putative NFkB activating protein 373 |
| FLJ23514 | 46.65 | Hs.144913 | 60494 | | NM_021827 | hypothetical protein FLJ23514 |
| FLJ23554 | 5.34 | Hs.164705 | 79864 | | NM_024806 | hypothetical protein FLJ23554 |
| FLJ25348 | 6.51 | Hs.62604 | 90853 | | AK096192 | hypothetical protein FLJ25348 |
| FLJ30672 | 5.97 | | 158696 | | NM_153016 | hypothetical protein FLJ30672 |
| FLJ31842 | 21.12 | Hs.84522 | 148534 | | AI004375 | hypothetical protein FLJ31842 |
| FLJ32949 | 5.81 | Hs.484250 | 283417 | | AA758751 | hypothetical protein FLJ32949 |
| FLJ34222 | 5.82 | | 284350 | | AA180985 | hypothetical protein FLJ34222 |
| FLJ36004 | 5.56 | Hs.369235 | 160492 | | NM_152590 | hypothetical protein FLJ36004 |
| FLJ37451 | 15.44 | Hs.153485 | 284161 | | R46180 | hypothetical protein FLJ37451 |
| FLJ39502 | 16.72 | Hs.99104 | 285025 | | NM_173648 | hypothetical protein FLJ39502 |
| FLJ39963 | 20.67 | Hs.512228 | 349075 | | AK097282 | hypothetical protein FLJ39963 |
| FLJ90650 | 5.67 | Hs.98288 | 206338 | | AI246369 | laeverin |
| FLJ90661 | 5.71 | Hs.256632 | 146547 | | NM_173502 | hypothetical protein FLJ90661 |
| FMN2 | 25.08 | Hs.24889 | 56776 | 606373 | BC014364 | formin 2 |
| FMO5 | 6.81 | Hs.396595 | 2330 | 603957 | NM_001461 | flavin containing monooxygenase 5 |
| FNBP2 | 7.60 | Hs.5003 | 23380 | 606524 | AI263819 | formin binding protein 2 |
| FOXA1 | 8.62 | Hs.163484 | 3169 | 602294 | NM_004496 | forkhead box A1 |
| FOXA2 | 252.32 | Hs.155651 | 3170 | 600288 | AB028021 | forkhead box A2 |
| FOXC1 | 9.62 | Hs.348883 | 2296 | 601090 | NM_001453 | forkhead box C1 |
| FOXI1 | 25.76 | Hs.87236 | 2299 | 601093 | NM_012188 | forkhead box I1 |
| FOXQ1 | 43.02 | Hs.297452 | 94234 | | AI676059 | forkhead box Q1 |
| FUBP3 | 5.53 | Hs.98751 | 8939 | 603536 | AW085489 | far upstream element (FUSE) binding protein 3 |
| FZD5 | 10.18 | Hs.152251 | 7855 | 601723 | NM_003468 | frizzled homolog 5 (Drosophila) |
| FZD8 | 37.68 | Hs.302634 | 8325 | 606146 | AL121749 | frizzled homolog 8 (Drosophila) |
| GAL3ST1 | 7.31 | Hs.17958 | 9514 | 602300 | NM_004861 | galactose-3-O-sulfotransferase 1 |
| GATA3 | 13.22 | Hs.169946 | 2625 | 131320 | AI796169 | GATA binding protein 3 |
| GATA4 | 44.12 | Hs.243987 | 2626 | 600576 | AV700724 | GATA binding protein 4 |
| GATA6 | 24.26 | Hs.50924 | 2627 | 601656 | D87811 | GATA binding protein 6 |
| GATM | 5.63 | Hs.75335 | 2628 | 602360 | NM_001482 | glycine amidinotransferase (L-arginine:glycine amidinotransferase) |
| GBA | 5.30 | Hs.282997 | 2629 | 606463 | D13287 | glucosidase, beta; acid (includes glucosylceramidase) |
| GDF15 | 5.06 | Hs.296638 | 9518 | 605312 | AA129612 | growth differentiation factor 15 |
| GJA4 | 13.38 | Hs.296310 | 2701 | 121012 | NM_002060 | gap junction protein, alpha 4, 37 kDa (connexin 37) |
| GJB3 | 7.07 | Hs.415770 | 2707 | 603324 | BF060667 | gap junction protein, beta 3, 31 kDa (connexin 31) |

TABLE 3-continued

Up-regulated markers in definitive endoderm

| Gene_Symbol | Raw Fold Change | Unigene | Locus-Link | OMIM | SeqDerived-From | Gene Descriptor |
|---|---|---|---|---|---|---|
| GMPR | 5.80 | Hs.1435 | 2766 | 139265 | NM_006877 | guanosine monophosphate reductase |
| GNG2 | 9.92 | Hs.112928 | 54331 | 606981 | AK026424 | guanine nucleotide binding protein (G protein), gamma 2 |
| GPC6 | 6.51 | Hs.508411 | 10082 | 604404 | AI651255 | glypican 6 |
| GPM6A | 15.76 | Hs.75819 | 2823 | 601275 | D49958 | glycoprotein M6A |
| GPR115 | 6.03 | Hs.150131 | 221393 | | W67511 | G protein-coupled receptor 115 |
| GPR126 | 8.44 | Hs.419170 | 57211 | | AL033377 | G protein-coupled receptor 126 |
| GPR2 | 7.86 | Hs.278446 | 2826 | 600240 | NM_016602 | G protein-coupled receptor 2 |
| GPR37 | 33.44 | Hs.406094 | 2861 | 602583 | U87460 | G protein-coupled receptor 37 (endothelin receptor type B-like) |
| GPR39 | 15.38 | Hs.512073 | 2863 | 602886 | AV717094 | G protein-coupled receptor 39 |
| GPR49 | 21.48 | Hs.166705 | 8549 | 606667 | AL524520 | G protein-coupled receptor 49 |
| GPR81 | 6.22 | Hs.326712 | 27198 | 606923 | AF345568 | G protein-coupled receptor 81 |
| GPSM2 | 16.16 | Hs.278338 | 29899 | | NM_013296 | G-protein signalling modulator 2 (AGS3-like, C. elegans) |
| GREB1 | 5.95 | Hs.438037 | 9687 | | NM_014668 | GREB1 protein |
| GRK7 | 5.60 | Hs.351818 | 131890 | 606987 | NM_139209 | G protein-coupled receptor kinase 7 |
| GRP | 19.11 | Hs.153444 | 2922 | 137260 | NM_002091 | gastrin-releasing peptide |
| GSC | 524.27 | Hs.440438 | 145258 | 138890 | AY177407 | goosecoid |
| GW112 | 11.00 | Hs.273321 | 10562 | | AL390736 | differentially expressed in hematopoietic lineages |
| H2AFY | 29.04 | Hs.75258 | 9555 | | AF044286 | H2A histone family, member Y |
| HAS2 | 7.56 | Hs.159226 | 3037 | 601636 | AI374739 | hyaluronan synthase 2 |
| HCN1 | 14.55 | Hs.353176 | 348980 | 602780 | BM682352 | hyperpolarization activated cyclic nucleotide-gated potassium channel 1 |
| Hes4 | 6.20 | Hs.154029 | 57801 | 608060 | NM_021170 | bHLH factor Hes4 |
| HGF | 5.02 | Hs.396530 | 3082 | 142409 | U46010 | hepatocyte growth factor (hepapoietin A; scatter factor) |
| HHEX | 6.58 | Hs.118651 | 3087 | 604420 | Z21533 | hematopoietically expressed homeobox |
| HIPK2 | 20.25 | Hs.397465 | 28996 | 606868 | AF207702 | homeodomain interacting protein kinase 2 |
| HLXB9 | 18.27 | Hs.37035 | 3110 | 142994 | AI738662 | homeo box HB9 |
| HNF4A | 38.25 | Hs.54424 | 3172 | 600281 | AI032108 | hepatocyte nuclear factor 4, alpha |
| HOXD13 | 15.68 | Hs.152414 | 3239 | 142989 | NM_000523 | homeo box D13 |
| HP | 14.05 | Hs.403931 | 3240 | 140100 | NM_005143 | haptoglobin |
| HSD17B1 | 6.50 | Hs.448861 | 3292 | 109684 | NM_000413 | hydroxysteroid (17-beta) dehydrogenase 1 |
| HTATIP2 | 5.54 | Hs.90753 | 10553 | 605628 | BG153401 | HIV-1 Tat interactive protein 2, 30 kDa |
| ICOSL | 5.24 | Hs.14155 | 23308 | 605717 | AL355690 | inducible T-cell co-stimulator ligand |
| IFIT5 | 6.36 | Hs.252839 | 24138 | | NM_012420 | interferon-induced protein with tetratricopeptide repeats 5 |
| IGFBP6 | 20.26 | Hs.274313 | 3489 | 146735 | NM_002178 | insulin-like growth factor binding protein 6 |
| IHH | 5.76 | Hs.115274 | 3549 | 600726 | AA628967 | Indian hedgehog homolog (Drosophila) |
| IL18R1 | 25.01 | Hs.159301 | 8809 | 604494 | NM_003855 | interleukin 18 receptor 1 |
| IL1R1 | 5.36 | Hs.82112 | 3554 | 147810 | NM_000877 | interleukin 1 receptor, type I |
| IMAP1 | 47.52 | Hs.159955 | 170575 | 608084 | BC029442 | immunity associated protein 1 |
| ITGA1 | 6.58 | Hs.439320 | 3672 | 192968 | BG619261 | integrin, alpha 1 |
| ITGA5 | 5.66 | Hs.149609 | 3678 | 135620 | NM_002205 | integrin, alpha 5 (fibronectin receptor, alpha polypeptide) |
| ITGA9 | 13.12 | Hs.222 | 3680 | 603963 | AI479176 | integrin, alpha 9 |
| ITPKB | 19.74 | Hs.78877 | 3707 | 147522 | AA348410 | inositol 1,4,5-trisphosphate 3-kinase B |
| JMJD3 | 12.61 | Hs.103915 | 23135 | | AI830331 | jumonji domain containing 3 |
| KCNG1 | 12.30 | Hs.118695 | 3755 | 603788 | AI332979 | potassium voltage-gated channel, subfamily G, member 1 |
| KCNH8 | 13.59 | Hs.410629 | 131096 | | NM_144633 | potassium voltage-gated channel, subfamily H (eag-related), member 8 |
| KCNJ3 | 22.66 | Hs.199776 | 3760 | 601534 | AK026384 | potassium inwardly-rectifying channel, subfamily J, member 3 |
| KCNK1 | 6.73 | Hs.376874 | 3775 | 601745 | AL833343 | potassium channel, subfamily K, member 1 |
| KCNK12 | 7.71 | Hs.252617 | 56660 | 607366 | NM_022055 | potassium channel, subfamily K, member 12 |
| KCNV2 | 26.04 | Hs.441357 | 169522 | 607604 | AI206888 | potassium channel, subfamily V, member 2 |
| KIAA0258 | 6.12 | Hs.47313 | 9827 | | AI690081 | KIAA0258 |
| KIAA0318 | 5.49 | Hs.225014 | 23504 | | BE549770 | RIM binding protein 2 |
| KIAA0484 | 5.10 | | 57240 | | AA732995 | KIAA0484 protein |
| KIAA0626 | 5.02 | Hs.178121 | 9848 | | NM_021647 | KIAA0626 gene product |
| KIAA0774 | 7.72 | Hs.22201 | 23281 | | AI818409 | KIAA0774 |
| KIAA0792 | 5.85 | Hs.119387 | 9725 | | AW510783 | KIAA0792 gene product |
| KIAA0825 | 5.03 | Hs.194755 | 23004 | | AB020632 | KIAA0825 protein |
| KIAA0882 | 23.04 | Hs.411317 | 23158 | | AI348094 | KIAA0882 protein |
| KIAA0895 | 12.12 | Hs.6224 | 23366 | | AB020702 | KIAA0895 protein |
| KIAA1161 | 11.92 | Hs.181679 | 57462 | | AB032987 | KIAA1161 |
| KIAA1202 | 22.67 | Hs.380697 | 57477 | | AI005420 | KIAA1202 protein |
| KIAA1211 | 5.43 | Hs.205293 | 57482 | | AI991996 | KIAA1211 protein |
| KIAA1447 | 5.19 | Hs.512733 | 57597 | | NM_024696 | KIAA1447 protein |
| KIAA1618 | 5.21 | Hs.437033 | 57714 | | AA976354 | KIAA1618 |
| KIAA1679 | 5.98 | Hs.68533 | 80731 | | AB051466 | KIAA1679 protein |
| KIAA1728 | 7.82 | Hs.437362 | 85461 | | AB051515 | KIAA1728 protein |
| KIAA1729 | 5.19 | Hs.99073 | 85460 | | AI138969 | KIAA1729 protein |
| KIAA1856 | 7.82 | Hs.383245 | 84629 | | AI936523 | KIAA1856 protein |
| KIFC3 | 17.78 | Hs.23131 | 3801 | 604535 | BC001211 | kinesin family member C3 |
| KLF5 | 5.42 | Hs.84728 | 688 | 602903 | AF132818 | Kruppel-like factor 5 (intestinal) |
| KYNU | 12.90 | Hs.444471 | 8942 | 236800 | D55639 | kynureninase (L-kynurenine hydrolase) |
| LAMB3 | 6.26 | Hs.436983 | 3914 | 150310 | L25541 | laminin, beta 3 |
| LAMP3 | 6.00 | Hs.10887 | 27074 | 605883 | NM_014398 | lysosomal-associated membrane protein 3 |
| LEFTB | 10.76 | Hs.278239 | 10637 | 603037 | NM_020997 | left-right determination, factor B |

TABLE 3-continued

Up-regulated markers in definitive endoderm

| Gene_Symbol | Raw Fold Change | Unigene | Locus-Link | OMIM | SeqDerived-From | Gene Descriptor |
|---|---|---|---|---|---|---|
| LEPREL1 | 5.44 | Hs.42824 | 55214 | | NM_018192 | leprecan-like 1 |
| LHX1 | 13.00 | Hs.443727 | 3975 | 601999 | NM_005568 | LIM homeobox 1 |
| LIFR | 10.18 | Hs.446501 | 3977 | 151443 | AA701657 | leukemia inhibitory factor receptor |
| LMLN | 7.70 | Hs.432613 | 89782 | | BF056991 | leishmanolysin-like (metallopeptidase M8 family) |
| LOC128153 | 7.17 | Hs.99214 | 128153 | | AA905508 | hypothetical protein BC014608 |
| LOC131873 | 10.87 | Hs.263560 | 131873 | | AI761416 | hypothetical protein LOC131873 |
| LOC132604 | 6.82 | | 132604 | | BC044793 | GalNAc transferase 10 isoform-like |
| LOC148898 | 5.54 | Hs.61884 | 148898 | | AW298597 | hypothetical protein BC007899 |
| LOC148987 | 7.40 | | 148987 | | BC040313 | hypothetical protein LOC148987 |
| LOC149414 | 11.75 | | 149414 | | AF218941 | formin 2-Like |
| LOC151878 | 7.05 | | 151878 | | AW009761 | hypothetical protein LOC151878 |
| LOC152084 | 5.62 | | 152084 | | BC041967 | hypothetical protein LOC152084 |
| LOC153682 | 25.68 | | 153682 | | AL137383 | hypothetical protein LOC153682 |
| LOC157278 | 21.30 | Hs.363026 | 157278 | | AK074886 | hypothetical protein LOC157278 |
| LOC162073 | 5.32 | Hs.28890 | 162073 | | BC015343 | hypothetical protein LOC162073 |
| LOC199920 | 12.19 | | 199920 | | AI452457 | hypothetical protein LOC199920 |
| LOC201175 | 8.06 | Hs.205326 | 201175 | | AF258593 | hypothetical protein LOC201175 |
| LOC203806 | 5.74 | Hs.256916 | 203806 | | AK092565 | hypothetical protein LOC203806 |
| LOC253012 | 7.75 | Hs.443169 | 253012 | | AA600175 | hypothetical protein LOC253012 |
| LOC253970 | 5.72 | | 253970 | | BE218152 | hypothetical protein LOC253970 |
| LOC283537 | 68.29 | Hs.117167 | 283537 | | AK026720 | hypothetical protein LOC283537 |
| LOC283666 | 6.05 | | 283666 | | AW006185 | hypothetical protein LOC283666 |
| LOC283887 | 5.17 | Hs.171285 | 283887 | | AI215529 | hypothetical protein LOC283887 |
| LOC284001 | 6.04 | Hs.526416 | 284001 | | AF007146 | hypothetical protein LOC284001 |
| LOC284367 | 14.25 | Hs.132045 | 284367 | | AI801574 | hypothetical protein LOC284367 |
| LOC284542 | 14.80 | Hs.61504 | 284542 | | BF060736 | hypothetical protein LOC284542 |
| LOC284561 | 6.01 | | 284561 | | AK023548 | hypothetical protein LOC284561 |
| LOC284615 | 8.69 | | 284615 | | AL359622 | hypothetical protein LOC284615 |
| LOC284739 | 5.97 | Hs.97840 | 284739 | | AL157500 | hypothetical protein LOC284739 |
| LOC284898 | 5.82 | Hs.350813 | 284898 | | BC036876 | hypothetical protein LOC284898 |
| LOC284950 | 6.21 | | 284950 | | AK095038 | hypothetical protein LOC284950 |
| LOC285045 | 5.97 | Hs.434660 | 285045 | | AK095182 | hypothetical protein LOC285045 |
| LOC285878 | 5.63 | | 285878 | | AI420977 | hypothetical protein LOC285878 |
| LOC339005 | 5.02 | Hs.212670 | 339005 | | AI824078 | hypothetical protein LOC339005 |
| LOC348094 | 12.72 | Hs.207157 | 348094 | | AI760630 | hypothetical protein LOC348094 |
| LOC349136 | 7.15 | Hs.174373 | 349136 | | AI968904 | hypothetical protein LOC349136 |
| LOC360030 | 6.38 | Hs.385546 | 360030 | | BC036226 | homeobox C14 |
| LOC375616 | 25.34 | Hs.443744 | 375616 | | AI955614 | kielin-like |
| LOC51066 | 21.78 | Hs.113019 | 51066 | | NM_015931 | fls485 |
| LOC51326 | 5.04 | Hs.416744 | 51326 | | AF493886 | ARF protein |
| LOC90342 | 6.85 | | 90342 | | AL133022 | similar to fer-1 like protein 3 |
| LOC90736 | 9.70 | Hs.415414 | 90736 | | BG285399 | hypothetical protein BC000919 |
| LOC91526 | 7.85 | Hs.11571 | 91526 | | AU157224 | hypothetical protein DKFZp434D2328 |
| LRIG3 | 26.20 | Hs.19669 | 121227 | | AI627704 | leucine-rich repeats and immunoglobulin-like domains 3 |
| LRRFIP1 | 5.61 | Hs.512387 | 9208 | 603256 | BC004958 | leucine rich repeat (in FLII) interacting protein 1 |
| LW-1 | 32.53 | | 51402 | | NM_016153 | LW-1 |
| MADH6 | 6.35 | Hs.153863 | 4091 | 602931 | AI193899 | MAD, mothers against decapentaplegic homolog 6 (*Drosophila*) |
| MAML3 | 8.03 | Hs.310320 | 55534 | | AI569476 | mastermind-like 3 (*Drosophila*) |
| MAN1A1 | 10.19 | Hs.255149 | 4121 | 604344 | BG287153 | mannosidase, alpha, class 1A, member 1 |
| MANEA | 18.25 | Hs.46903 | 79694 | | AI587307 | mannosidase, endo-alpha |
| MAP3K13 | 10.61 | Hs.406946 | 9175 | 604915 | NM_004721 | mitogen-activated protein kinase kinase kinase 13 |
| MAP3K4 | 6.15 | Hs.390428 | 4216 | 602425 | AI633559 | mitogen-activated protein kinase kinase kinase 4 |
| MATN3 | 10.63 | Hs.278461 | 4148 | 602109 | NM_002381 | matrilin 3 |
| MCC | 9.39 | Hs.409515 | 4163 | 159350 | BE967311 | mutated in colorectal cancers |
| MCLC | 13.56 | Hs.93121 | 23155 | | AA406603 | Mid-1-related chloride channel 1 |
| MERTK | 6.55 | Hs.306178 | 10461 | 604705 | NM_006343 | c-mer proto-oncogene tyrosine kinase |
| MGC13057 | 9.53 | Hs.389311 | 84281 | | BC005083 | hypothetical protein MGC13057 |
| MGC14276 | 6.08 | Hs.434283 | 253150 | | BE195670 | hypothetical protein MGC14276 |
| MGC14289 | 5.00 | Hs.152618 | 92092 | | AI188445 | similar to RIKEN cDNA 1200014N16 gene |
| MGC19764 | 6.65 | Hs.14691 | 162394 | | AI435399 | hypothetical protein MGC19764 |
| MGC26989 | 6.83 | Hs.430223 | 254268 | | AL832216 | hypothetical protein MGC26989 |
| MGC33835 | 10.65 | Hs.367947 | 222662 | | BC028630 | hypothetical protein MGC33835 |
| MGC34032 | 16.41 | Hs.213897 | 204962 | | AA001450 | hypothetical protein MGC34032 |
| MGC35130 | 10.58 | Hs.388746 | 148581 | | NM_152489 | hypothetical protein MGC35130 |
| MGC35402 | 6.35 | Hs.146844 | 399669 | | AK096828 | hypothetical protein MGC35402 |
| MGC39518 | 5.83 | Hs.372046 | 285172 | | BC039295 | hypothetical protein MGC39518 |
| MGC39821 | 11.27 | Hs.351906 | 284440 | | BI599587 | hypothetical protein MGC39821 |
| MGC39900 | 8.56 | Hs.422848 | 286527 | | H09657 | hypothetical protein MGC39900 |
| MGC45441 | 9.54 | Hs.36567 | 149473 | | AU153816 | hypothetical protein MGC45441 |
| MGC45594 | 8.34 | Hs.408128 | 284273 | | BC033780 | hypothetical protein MGC45594 |
| MGC46719 | 8.84 | Hs.356109 | 128077 | | AW500180 | hypothetical protein MGC46719 |
| MGC52498 | 8.36 | Hs.424589 | 348378 | | AI202632 | hypothetical protein MGC52498 |
| MGC5395 | 10.77 | Hs.378738 | 79026 | | BG287862 | hypothetical protein MGC5395 |
| MGC8721 | 5.00 | Hs.279921 | 51669 | | AI351653 | hypothetical protein MGC8721 |

TABLE 3-continued

Up-regulated markers in definitive endoderm

| Gene_Symbol | Raw Fold Change | Unigene | Locus-Link | OMIM | SeqDerived-From | Gene Descriptor |
|---|---|---|---|---|---|---|
| MGST2 | 13.23 | Hs.81874 | 4258 | 601733 | NM_002413 | microsomal glutathione S-transferase 2 |
| MIB | 5.49 | Hs.34892 | 57534 | 608677 | BE048628 | DAPK-interacting protein 1 |
| MIDORI | 12.95 | Hs.301242 | 57538 | | AB037751 | likely ortholog of mouse myocytic induction/differentiation originator |
| MIXL1 | 16.37 | Hs.282079 | 83881 | | AF211891 | Mix1 homeobox-like 1 (*Xenopus laevis*) |
| MME | 12.25 | Hs.307734 | 4311 | 120520 | NM_007287 | membrane metallo-endopeptidase (neutral endopeptidase, enkephalinase, CALLA, CD10) |
| MMP14 | 13.59 | Hs.2399 | 4323 | 600754 | NM_004995 | matrix metalloproteinase 14 (membrane-inserted) |
| MMP21 | 6.36 | Hs.314141 | 118856 | 608416 | NM_147191 | matrix metalloproteinase 21 |
| MPRG | 12.47 | Hs.257511 | 54852 | 607781 | AI934557 | membrane progestin receptor gamma |
| MRC1 | 5.02 | Hs.75182 | 4360 | 153618 | NM_002438 | mannose receptor, C type 1 |
| MSMB | 25.23 | Hs.255462 | 4477 | 157145 | NM_002443 | microseminoprotein, beta- |
| MTUS1 | 6.10 | Hs.7946 | 57509 | | AL096842 | mitochondrial tumor suppressor 1 |
| MYBPC1 | 7.33 | Hs.169849 | 4604 | 160794 | BF593509 | myosin binding protein C, slow type |
| MYCT1 | 14.81 | Hs.18160 | 80177 | | AI242583 | myc target 1 |
| MYL4 | 11.75 | Hs.356717 | 4635 | 160770 | X58851 | myosin, light polypeptide 4, alkali; atrial, embryonic |
| MYL7 | 38.38 | Hs.75636 | 58498 | | NM_021223 | myosin, light polypeptide 7, regulatory |
| MYO3A | 6.69 | Hs.148228 | 53904 | 606808 | AA443280 | myosin IIIA |
| MYOCD | 6.86 | Hs.42128 | 93649 | 606127 | AI093327 | myocardin |
| NBL1 | 8.62 | Hs.439671 | 4681 | 600613 | NM_005380 | neuroblastoma, suppression of tumorigenicity 1 |
| NBR2 | 6.10 | Hs.500268 | 10230 | | NM_005821 | neighbor of BRCA1 gene 2 |
| NCR1 | 9.38 | Hs.97084 | 9437 | 604530 | NM_004829 | natural cytotoxicity triggering receptor 1 |
| NEBL | 10.59 | Hs.5025 | 10529 | 605491 | BE502910 | nebulette |
| NEXN | 9.60 | Hs.22370 | 91624 | | AF114264 | nexilin (F actin binding protein) |
| NFASC | 35.64 | Hs.13349 | 23114 | | AI821777 | neurofascin |
| NFATC2 | 6.56 | Hs.356321 | 4773 | 600490 | AI770171 | nuclear factor of activated T-cells, cytoplasmic, calcineurin-dependent 2 |
| NFKBIA | 6.83 | Hs.81328 | 4792 | 164008 | AI078167 | nuclear factor of kappa light polypeptide gene enhancer in B-cells inhibitor, alpha |
| NFKBIL1 | 6.39 | Hs.2764 | 4795 | 601022 | AF097419 | nuclear factor of kappa light polypeptide gene enhancer in B-cells inhibitor-like 1 |
| NODAL | 7.89 | Hs.370414 | 4838 | 601265 | AI050866 | nodal homolog (mouse) |
| NOG | 6.96 | Hs.248201 | 9241 | 602991 | AL575177 | noggin |
| NOL3 | 5.46 | Hs.462911 | 8996 | 605235 | AF043244 | nucleolar protein 3 (apoptosis repressor with CARD domain) |
| NPL | 6.11 | Hs.64896 | 80896 | | AI368358 | N-acetylneuraminate pyruvate lyase (dihydrodipicolinate synthase) |
| NPPB | 35.43 | Hs.219140 | 4879 | 600295 | NM_002521 | natriuretic peptide precursor B |
| NR0B1 | 19.33 | Hs.268490 | 190 | 300473 | NM_000475 | nuclear receptor subfamily 0, group B, member 1 |
| NR3C1 | 6.71 | Hs.126608 | 2908 | 138040 | AI934556 | nuclear receptor subfamily 3, group C, member 1 (glucocorticoid receptor) |
| NRG1 | 15.88 | Hs.453951 | 3084 | 142445 | NM_013959 | neuregulin 1 |
| NRP1 | 14.29 | Hs.173548 | 8829 | 602069 | AF145712 | neuropilin 1 |
| NRTN | 5.20 | Hs.234775 | 4902 | 602018 | AL161995 | neurturin |
| NTN4 | 57.13 | Hs.102541 | 59277 | | AF278532 | netrin 4 |
| NUDT14 | 7.42 | Hs.436170 | 256281 | | AF111170 | nudix (nucleoside diphosphate linked moiety X)-type motif 14 |
| NUDT4 | 13.66 | Hs.355399 | 11163 | | AW511135 | nudix (nucleoside diphosphate linked moiety X)-type motif 4 |
| OMD | 6.06 | Hs.94070 | 4958 | | NM_005014 | osteomodulin |
| OR2A4 | 5.43 | Hs.444988 | 79541 | | AC005587 | olfactory receptor, family 2, subfamily A, member 4 |
| OR51B2 | 5.59 | | 79345 | | AF137396 | olfactory receptor, family 51, subfamily B, member 2 |
| OSTF1 | 5.20 | Hs.47011 | 26578 | | BU929456 | osteoclast stimulating factor 1 |
| P101-PI3K | 5.44 | Hs.278901 | 23533 | | BG236366 | phosphoinositide-3-kinase, regulatory subunit, polypeptide p101 |
| P2RY12 | 9.81 | Hs.444983 | 64805 | 600515 | AA810452 | purinergic receptor P2Y, G-protein coupled, 12 |
| PAG | 18.02 | Hs.266175 | 55824 | 605767 | AK000680 | phosphoprotein associated with glycosphingolipid-enriched microdomains |
| PAX6 | 48.76 | Hs.89506 | 5080 | 607108 | AW088232 | paired box gene 6 (aniridia, keratitis) |
| PCDH10 | 12.50 | Hs.146858 | 57575 | 608286 | AI640307 | protocadherin 10 |
| PCDH7 | 6.54 | Hs.443020 | 5099 | 602988 | BE644809 | BH-protocadherin (brain-heart) |
| PCDHA2 | 6.83 | | 56146 | 606308 | BC003126 | protocadherin alpha 2 |
| PCDHB13 | 6.32 | Hs.283803 | 56123 | 606308 | AA489646 | protocadherin beta 13 |
| PCDHB5 | 10.65 | Hs.119693 | 26167 | 606331 | AF152528 | protocadherin beta 5 |
| PCTP | 6.11 | Hs.285218 | 58488 | 606055 | NM_021213 | phosphatidylcholine transfer protein |
| PDE4D | 8.34 | Hs.28482 | 5144 | 600129 | U50157 | phosphodiesterase 4D, cAMP-specific (phosphodiesterase E3 dunce homolog, *Drosophila*) |
| PDE4DIP | 7.74 | Hs.502577 | 9659 | 608117 | H24473 | phosphodiesterase 4D interacting protein (myomegalin) |
| PDE4DIP | 6.27 | Hs.502582 | 9659 | 608117 | AB007923 | phosphodiesterase 4D interacting protein (myomegalin) |
| PDZK1 | 29.68 | Hs.15456 | 5174 | 603831 | NM_002614 | PDZ domain containing 1 |
| PHLDB2 | 5.43 | Hs.7378 | 90102 | | AK025444 | pleckstrin homology-like domain, family B, member 2 |
| PIGC | 5.04 | Hs.386487 | 5279 | 601730 | AL035301 | phosphatidylinositol glycan, class C |
| PITX2 | 12.09 | Hs.92282 | 5308 | 601542 | NM_000325 | paired-like homeodomain transcription factor 2 |
| PKHD1L1 | 11.52 | Hs.170128 | 93035 | 607843 | AV706971 | polycystic kidney and hepatic disease 1 (autosomal recessive)-like 1 |
| PLA1A | 6.48 | Hs.17752 | 51365 | 607460 | NM_015900 | phospholipase A1 member A |
| PLA2G4D | 5.98 | Hs.380225 | 283748 | | BC034571 | phospholipase A2, group IVD (cytosolic) |
| PLAGL1 | 6.84 | Hs.132911 | 5325 | 603044 | NM_002656 | pleiomorphic adenoma gene-like 1 |
| PLCE1 | 18.17 | Hs.103417 | 51196 | 608414 | NM_016341 | phospholipase C, epsilon 1 |
| PLD1 | 11.78 | Hs.380819 | 5337 | 602382 | AI378587 | phospholipase D1, phophatidylcholine-specific |
| PLXNA2 | 23.20 | Hs.300622 | 5362 | 601054 | AI688418 | plexin A2 |

TABLE 3-continued

Up-regulated markers in definitive endoderm

| Gene_Symbol | Raw Fold Change | Unigene | Locus-Link | OMIM | SeqDerived-From | Gene Descriptor |
|---|---|---|---|---|---|---|
| PLXNA2 | 5.48 | Hs.350065 | 5362 | 601054 | AI694545 | plexin A2 |
| PORCN | 6.62 | Hs.386453 | 64840 | | NM_022825 | porcupine homolog (*Drosophila*) |
| PPAPDC1 | 7.83 | Hs.40479 | 196051 | | BF130943 | phosphatidic acid phosphatase type 2 domain containing 1 |
| PPFIBP2 | 17.00 | Hs.12953 | 8495 | 603142 | AI692180 | PTPRF interacting protein, binding protein 2 (liprin beta 2) |
| PPP1R16B | 8.46 | Hs.45719 | 26051 | | AB020630 | protein phosphatase 1, regulatory (inhibitor) subunit 16B |
| PPP3CC | 10.69 | Hs.75206 | 5533 | 114107 | NM_005605 | protein phosphatase 3 (formerly 2B), catalytic subunit, gamma isoform (calcineurin A gamma) |
| PRDM1 | 13.93 | Hs.381140 | 639 | 603423 | AI692659 | PR domain containing 1, with ZNF domain |
| PREX1 | 6.21 | Hs.437257 | 57580 | 606905 | AL445192 | phosphatidylinositol 3,4,5-trisphosphate-dependent RAC exchanger 1 |
| PRND | 12.95 | Hs.406696 | 23627 | 604263 | AL133396 | prion protein 2 (dublet) |
| PRO0471 | 5.73 | Hs.381337 | 28994 | | AF111846 | PRO0471 protein |
| PRO2012 | 8.53 | Hs.283066 | 55478 | | NM_018614 | hypothetical protein PRO2012 |
| PROS1 | 13.38 | Hs.64016 | 5627 | 176880 | NM_000313 | protein S (alpha) |
| PRSS2 | 205.03 | Hs.435699 | 5646 | | NM_002770 | protease, serine, 3 (mesotrypsin) |
| PRV1 | 24.58 | Hs.232165 | 57126 | 162860 | NM_020406 | polycythemia rubra vera 1 |
| PTGFR | 16.53 | Hs.89418 | 5737 | 600563 | NM_000959 | prostaglandin F receptor (FP) |
| PTPN5 | 6.24 | Hs.79092 | 84867 | 176879 | H29627 | protein tyrosine phosphatase, non-receptor type 5 (striatum-enriched) |
| PTPRM | 18.83 | Hs.154151 | 5797 | 176888 | BC029442 | protein tyrosine phosphatase, receptor type, M |
| QPCT | 8.60 | Hs.79033 | 25797 | 607065 | NM_012413 | glutaminyl-peptide cyclotransferase (glutaminyl cyclase) |
| RAB17 | 20.30 | Hs.44278 | 64284 | | NM_022449 | RAB17, member RAS oncogene family |
| RAB18 | 5.00 | Hs.414357 | 22931 | 602207 | AW367507 | RAB18, member RAS oncogene family |
| RAI1 | 7.07 | Hs.438904 | 10743 | 607642 | BF984830 | retinoic acid induced 1 |
| RARB | 5.89 | Hs.436538 | 5915 | 180220 | NM_000965 | retinoic acid receptor, beta |
| RASGEF1B | 6.86 | Hs.352552 | 153020 | | BC036784 | RasGEF domain family, member 1B |
| RASGRP1 | 7.86 | Hs.189527 | 10125 | 603962 | NM_005739 | RAS guanyl releasing protein 1 (calcium and DAG-regulated) |
| RASSF6 | 5.44 | Hs.158857 | 166824 | | AI167789 | Ras association (RalGDS/AF-6) domain family 6 |
| RBM20 | 11.00 | Hs.116630 | 282996 | | AI539118 | RNA binding motif protein 20 |
| RBM24 | 21.38 | Hs.201619 | 221662 | | AI677701 | RNA binding motif protein 24 |
| RBP5 | 14.34 | Hs.246046 | 83758 | | AY007436 | retinol binding protein 5, cellular |
| RBPMS | 5.21 | Hs.195825 | 11030 | 601558 | AI017095 | RNA binding protein with multiple splicing |
| RGC32 | 27.89 | Hs.76640 | 28984 | | NM_014059 | response gene to complement 32 |
| RGS11 | 7.12 | Hs.65756 | 8786 | 603895 | NM_003834 | regulator of G-protein signalling 11 |
| RGS13 | 5.15 | Hs.17165 | 6003 | 607190 | BC036950 | regulator of G-protein signalling 13 |
| RGS5 | 5.70 | Hs.24950 | 8490 | 603276 | AF159570 | regulator of G-protein signalling 5 |
| RGS8 | 7.50 | Hs.458417 | 85397 | 607189 | R37101 | regulator of G-protein signalling 8 |
| RHOBTB3 | 21.23 | Hs.31653 | 22836 | 607353 | NM_014899 | Rho-related BTB domain containing 3 |
| RIN2 | 7.00 | Hs.446304 | 54453 | | AL136924 | Ras and Rab interactor 2 |
| RNASE1 | 8.63 | Hs.78224 | 6035 | 180440 | NM_002933 | ribonuclease, RNase A family, 1 (pancreatic) |
| RNASE4 | 10.29 | Hs.283749 | 6038 | 601030 | AI761728 | ribonuclease, RNase A family, 4 |
| ROR2 | 10.29 | Hs.208080 | 4920 | 602337 | NM_004560 | receptor tyrosine kinase-like orphan receptor 2 |
| RP26 | 8.04 | Hs.145140 | 375298 | 608381 | AI936034 | retinitis pigmentosa 26 (autosomal recessive) |
| RS1 | 5.49 | Hs.149376 | 6247 | 312700 | AL049684 | retinoschisis (X-linked, juvenile) 1 |
| RTN4RL1 | 60.66 | Hs.22917 | 146760 | | H06251 | reticulon 4 receptor-like 1 |
| RUFY2 | 5.60 | Hs.297044 | 55680 | | NM_017987 | RUN and FYVE domain containing 2 |
| RWDD3 | 9.89 | Hs.196585 | 25950 | | AW295367 | RWD domain containing 3 |
| S100A10 | 6.73 | Hs.143873 | 6281 | 114085 | BF126155 | S100 calcium binding protein A10 (annexin II ligand, calpactin I, light polypeptide (p11)) |
| S100A11 | 7.07 | Hs.417004 | 6282 | 603114 | NM_005620 | S100 calcium binding protein A11 (calgizzarin) |
| S100A13 | 7.21 | Hs.446592 | 6284 | 601989 | NM_005979 | S100 calcium binding protein A13 |
| S100A14 | 26.13 | Hs.288998 | 57402 | 607986 | NM_020672 | S100 calcium binding protein A14 |
| S100A16 | 11.27 | Hs.8182 | 140576 | | AA045184 | S100 calcium binding protein A16 |
| S100A2 | 5.97 | Hs.515713 | 6273 | 176993 | NM_005978 | S100 calcium binding protein A2 |
| S100Z | 12.38 | Hs.352172 | 170591 | | AF437876 | S100Z protein |
| SAMD3 | 12.06 | Hs.440508 | 154075 | | AI129628 | sterile alpha motif domain containing 3 |
| SCA1 | 8.18 | Hs.434961 | 6310 | 601556 | BF438383 | spinocerebellar ataxia 1 (olivopontocerebellar ataxia 1, autosomal dominant, ataxin 1) |
| SCD4 | 6.62 | Hs.379191 | 79966 | 608370 | AL571375 | stearoyl-CoA desaturase 4 |
| SCN11A | 5.98 | Hs.186877 | 11280 | 604385 | AF150882 | sodium channel, voltage-gated, type XI, alpha |
| SEC15L1 | 8.34 | Hs.272374 | 54536 | | AF220217 | SEC15-like 1 (*S. cerevisiae*) |
| SEMA3A | 7.44 | Hs.252451 | 10371 | 603961 | BF102683 | sema domain, immunoglobulin domain (Ig), short basic domain, secreted, (semaphorin) 3A |
| SEMA3E | 135.96 | Hs.528721 | 9723 | | NM_012431 | sema domain, immunoglobulin domain (Ig), short basic domain, secreted, (semaphorin) 3E |
| SEMA5A | 5.42 | Hs.528707 | 9037 | | NM_003966 | sema domain, seven thrombospondin repeats (type 1 and type 1-like), transmembrane domain (TM) and short cytoplasmic domain, (semaphorin) 5A |
| SERHL | 27.81 | Hs.398085 | 94009 | 607979 | AL450314 | serine hydrolase-like |
| SET7 | 5.97 | Hs.160208 | 80854 | 606594 | AK024846 | SET domain-containing protein 7 |
| SGPP1 | 5.85 | Hs.24678 | 81537 | | BE880703 | sphingosine-1-phosphate phosphatase 1 |
| SGSH | 10.71 | Hs.31074 | 6448 | 605270 | NM_000199 | N-sulfoglucosamine sulfohydrolase (sulfamidase) |
| SH3BGR | 8.65 | Hs.47438 | 6450 | 602230 | NM_007341 | SH3 domain binding glutamic acid-rich protein |
| SHOX2 | 12.75 | Hs.55967 | 6474 | 602504 | AF022654 | short stature homeobox 2 |

TABLE 3-continued

Up-regulated markers in definitive endoderm

| Gene_Symbol | Raw Fold Change | Unigene | Locus-Link | OMIM | SeqDerived-From | Gene Descriptor |
|---|---|---|---|---|---|---|
| SHREW1 | 15.74 | Hs.25924 | 55966 | | AA835004 | transmembrane protein SHREW1 |
| SIAT7B | 13.12 | Hs.288215 | 10610 | | NM_006456 | sialyltransferase 7 ((alpha-N-acetylneuraminyl-2,3-beta-galactosyl-1,3)-N-acetyl galactosaminide alpha-2,6-sialyltransferase) B. |
| SIAT8A | 34.34 | Hs.408614 | 6489 | 601123 | L32867 | sialyltransferase 8A (alpha-N-acetylneuraminate: alpha-2,8-sialyltransferase, GD3 synthase) |
| SIAT8B | 7.63 | Hs.302341 | 8128 | 602546 | NM_006011 | sialyltransferase 8B (alpha-2,8-sialyltransferase) |
| SIAT8C | 6.55 | Hs.298923 | 51046 | | NM_015879 | sialyltransferase 8C (alpha2,3Galbeta1,4GlcNAcalpha 2,8-sialyltransferase) |
| SIAT8D | 161.93 | Hs.308628 | 7903 | 602547 | AI422986 | sialyltransferase 8D (alpha-2,8-polysialyltransferase) |
| SIAT9 | 13.35 | Hs.415117 | 8869 | 604402 | AI017540 | sialyltransferase 9 (CMP-NeuAc:lactosylceramide alpha-2,3-sialyltransferase; GM3 synthase) |
| SIGLEC10 | 7.88 | Hs.284813 | 89790 | 606091 | NM_033130 | sialic acid binding Ig-like lectin 10 |
| SIPA1L2 | 5.51 | Hs.406879 | 57568 | | AB037810 | signal-induced proliferation-associated 1 like 2 |
| SLAC2-B | 5.01 | Hs.138380 | 23086 | | AB014524 | SLAC2-B |
| SLC1A1 | 14.09 | Hs.91139 | 6505 | 133550 | AW235061 | solute carrier family 1 (neuronal/epithelial high affinity glutamate transporter, system Xag), member 1 |
| SLC1A7 | 5.45 | Hs.104637 | 6512 | 604471 | NM_006671 | solute carrier family 1 (glutamate transporter), member 7 |
| SLC26A7 | 18.00 | Hs.354013 | 115111 | 608479 | AI758950 | solute carrier family 26, member 7 |
| SLC34A2 | 7.97 | Hs.441716 | 10568 | 604217 | AF146796 | solute carrier family 34 (sodium phosphate), member 2 |
| SLC35A3 | 7.42 | Hs.448979 | 23443 | 605632 | BC005136 | solute carrier family 35 (UDP-N-acetylglucosamine (UDP-GlcNAc) transporter), member A3 |
| SLC35F3 | 11.46 | Hs.158748 | 148641 | | BF968270 | solute carrier family 35, member F3 |
| SLC40A1 | 44.06 | Hs.409875 | 30061 | 604653 | AL136944 | solute carrier family 40 (iron-regulated transporter), member 1 |
| SLC5A9 | 79.96 | Hs.37890 | 200010 | | AI767388 | solute carrier family 5 (sodium/glucose cotransporter), member 9 |
| SLC6A20 | 6.86 | Hs.413095 | 54716 | 605616 | NM_020208 | solute carrier family 6 (neurotransmitter transporter), member 20 |
| SLCO2A1 | 12.84 | Hs.83974 | 6578 | 601460 | NM_005630 | solute carrier organic anion transporter family, member 2A1 |
| SLITRK2 | 13.29 | Hs.320368 | 84631 | | AL109653 | SLIT and NTRK-like family, member 2 |
| SMARCD3 | 7.37 | Hs.444445 | 6604 | 601737 | NM_003078 | SWI/SNF related, matrix associated, actin dependent regulator of chromatin, subfamily d, member 3 |
| SMPD1 | 5.76 | Hs.77813 | 6609 | 607608 | M59917 | sphingomyelin phosphodiesterase 1, acid lysosomal (acid sphingomyelinase) |
| SOCS1 | 5.92 | Hs.50640 | 8651 | 603597 | U88326 | suppressor of cytokine signaling 1 |
| SOCS3 | 9.41 | Hs.436943 | 9021 | 604176 | AI244908 | suppressor of cytokine signaling 3 |
| SORCS1 | 24.07 | Hs.348923 | 114815 | 606283 | AI675836 | sortilin-related VPS10 domain containing receptor 1 |
| SOX17 | 30.20 | Hs.98367 | 64321 | | NM_022454 | SRY (sex determining region Y)-box 17 |
| SOX18 | 10.36 | Hs.8619 | 54345 | 601618 | NM_018419 | SRY (sex determining region Y)-box 18 |
| SPOCK3 | 62.58 | Hs.159425 | 50859 | 607989 | AI808090 | sparc/osteonectin, cwcv and kazal-like domains proteoglycan (testican) 3 |
| SPTAN1 | 5.56 | Hs.387905 | 6709 | 182810 | AK026484 | spectrin, alpha, non-erythrocytic 1 (alpha-fodrin) |
| SRGAP1 | 9.61 | Hs.408259 | 57522 | 606523 | BC029919 | SLIT-ROBO Rho GTPase activating protein 1 |
| SSX2 | 11.44 | Hs.289105 | 6757 | 300192 | BC002818 | synovial sarcoma, X breakpoint 2 |
| SSX3 | 12.43 | Hs.178749 | 10214 | 300325 | NM_021014 | synovial sarcoma, X breakpoint 3 |
| SSX4 | 8.27 | Hs.278632 | 6759 | 300326 | BC005325 | synovial sarcoma, X breakpoint 4 |
| STAT4 | 6.73 | Hs.80642 | 6775 | 600558 | NM_003151 | signal transducer and activator of transcription 4 |
| STC1 | 18.86 | Hs.25590 | 6781 | 601185 | U46768 | stanniocalcin 1 |
| STMN2 | 33.93 | Hs.90005 | 11075 | 600621 | BF967657 | stathmin-like 2 |
| SULF2 | 5.84 | Hs.43857 | 55959 | | AL133001 | sulfatase 2 |
| SULT1E1 | 5.08 | Hs.54576 | 6783 | 600043 | NM_005420 | sulfotransferase family 1E, estrogen-preferring, member 1 |
| SV2B | 16.36 | Hs.8071 | 9899 | 185861 | NM_014848 | synaptic vesicle glycoprotein 2B |
| SYNE1 | 8.40 | Hs.282117 | 23345 | 608441 | AF043290 | spectrin repeat containing, nuclear envelope 1 |
| TAF11 | 5.01 | Hs.83126 | 6882 | 600772 | BQ709323 | TAF11 RNA polymerase II, TATA box binding protein (TBP)-associated factor, 28 kDa |
| TAGLN2 | 9.05 | Hs.406504 | 8407 | 604634 | NM_003564 | transgelin 2 |
| TAIP-2 | 9.08 | Hs.287442 | 80034 | | NM_024969 | TGF-beta induced apotosis protein 2 |
| TAL2 | 6.00 | Hs.247978 | 6887 | 186855 | NM_005421 | T-cell acute lymphocytic leukemia 2 |
| TA-LRRP | 7.71 | Hs.387915 | 23507 | | R41498 | T-cell activation leucine repeat-rich protein |
| TCF2 | 9.87 | Hs.408093 | 6928 | 189907 | NM_000458 | transcription factor 2, hepatic; LF-B3; variant hepatic nuclear factor |
| TDRD7 | 19.46 | Hs.416543 | 23424 | | AW129593 | tudor domain containing 7 |
| TGFB1 | 5.40 | Hs.1103 | 7040 | 190180 | BC000125 | transforming growth factor, beta 1 (Camurati-Engelmann disease) |
| TIMP3 | 5.72 | Hs.245188 | 7078 | 188826 | NM_000362 | tissue inhibitor of metalloproteinase 3 (Sorsby fundus dystrophy, pseudoinflammatory) |
| TIRP | 6.36 | Hs.278391 | 353376 | 608321 | AI400110 | TRIF-related adaptor molecule |
| TLE2 | 8.87 | Hs.332173 | 7089 | 601041 | M99436 | transducin-like enhancer of split 2 (E(sp1) homolog, Drosophila) |
| TM4SF1 | 8.02 | Hs.351316 | 4071 | 191155 | AI189753 | transmembrane 4 superfamily member 1 |
| TM4SF12 | 5.88 | Hs.16529 | 23554 | | NM_012338 | transmembrane 4 superfamily member 12 |
| TMOD1 | 74.09 | Hs.374849 | 7111 | 190930 | NM_003275 | tropomodulin 1 |
| TNFSF10 | 15.05 | Hs.387871 | 8743 | 603598 | NM_003810 | tumor necrosis factor (ligand) superfamily, member 10 |
| TNNC1 | 31.06 | Hs.118845 | 7134 | 191040 | AF020769 | troponin C, slow |
| TPK1 | 5.18 | Hs.127548 | 27010 | 606370 | NM_022445 | thiamin pyrophosphokinase 1 |
| TPTE | 11.46 | Hs.122986 | 7179 | 604336 | AL137389 | transmembrane phosphatase with tensin homology |
| TRADD | 8.22 | Hs.89862 | 8717 | 603500 | NM_003789 | TNFRSF1A-associated via death domain |
| TRDN | 12.67 | Hs.159090 | 10345 | 603283 | AA192306 | triadin |
| TRPA1 | 103.37 | Hs.137674 | 8989 | 604775 | AA502609 | transient receptor potential cation channel, subfamily A, member 1 |
| TRPM4 | 5.00 | Hs.31608 | 54795 | 606936 | NM_017636 | transient receptor potential cation channel, subfamily M, member 4 |

TABLE 3-continued

Up-regulated markers in definitive endoderm

| Gene_Symbol | Raw Fold Change | Unigene | Locus-Link | OMIM | SeqDerived-From | Gene Descriptor |
|---|---|---|---|---|---|---|
| TSGA10 | 6.41 | Hs.416032 | 80705 | 607166 | AY014284 | testis specific, 10 |
| TSHR | 5.96 | Hs.123078 | 7253 | 603372 | BE045816 | thyroid stimulating hormone receptor |
| TSPYL5 | 17.94 | Hs.173094 | 85453 | | AI096375 | TSPY-like 5 |
| TTC3 | 12.26 | Hs.132605 | 7267 | 602259 | AI652848 | tetratricopeptide repeat domain 3 |
| TTLL3 | 7.35 | Hs.511982 | 26140 | | AA534291 | tubulin tyrosine ligase-like family, member 3 |
| TTN | 76.16 | Hs.434384 | 7273 | 188840 | NM_003319 | titin |
| TUBE1 | 8.85 | Hs.34851 | 51175 | 607345 | BE550254 | tubulin, epsilon 1 |
| UBE2J1 | 7.26 | Hs.184325 | 51465 | | N64079 | ubiquitin-conjugating enzyme E2, J1 (UBC6 homolog, yeast) |
| UBXD3 | 5.81 | Hs.432503 | 127733 | | T86344 | UBX domain containing 3 |
| UNC13C | 32.43 | Hs.112921 | 145790 | | AL834407 | unc-13 homolog C (*C. elegans*) |
| UNC93A | 32.18 | Hs.267749 | 54346 | 607995 | AL021331 | unc-93 homolog A (*C. elegans*) |
| UNQ467 | 5.30 | Hs.112457 | 388533 | | W69083 | KIPV467 |
| UNQ827 | 5.08 | Hs.516819 | 400830 | | BE044548 | KFLL827 |
| USP3 | 7.90 | Hs.251636 | 9960 | 604728 | AF077040 | ubiquitin specific protease 3 |
| USP53 | 6.36 | Hs.135457 | 54532 | | AW188464 | ubiquitin specific protease 53 |
| VANGL1 | 7.57 | Hs.99598 | 81839 | | NM_024062 | vang-like 1 (van gogh, *Drosophila*) |
| VCAM1 | 18.40 | Hs.109225 | 7412 | 192225 | NM_001078 | vascular cell adhesion molecule 1 |
| VGCNL1 | 5.61 | Hs.391323 | 259232 | | BE220480 | voltage gated channel like 1 |
| VIL1 | 14.42 | Hs.512713 | 7429 | 193040 | NM_007127 | villin 1 |
| VNN3 | 6.94 | Hs.183656 | 55350 | 606592 | NM_078625 | vanin 3 |
| VPS13C | 6.16 | Hs.328109 | 54832 | | AA828371 | vacuolar protein sorting 13C (yeast) |
| VTN | 6.33 | Hs.2257 | 7448 | 193190 | NM_000638 | vitronectin (serum spreading factor, somatomedin B, complement S-protein) |
| VWF | 13.24 | Hs.440848 | 7450 | 193400 | NM_000552 | von Willebrand factor |
| WASPIP | 5.76 | Hs.401414 | 7456 | 602357 | AW058622 | Wiskott-Aldrich syndrome protein interacting protein |
| WBSCR24 | 6.28 | Hs.126451 | 155382 | | AI521163 | Williams Beuren syndrome chromosome region 24 |
| WDR31 | 6.10 | Hs.133331 | 114983 | | BF589326 | WD repeat domain 31 |
| WFDC2 | 8.49 | Hs.2719 | 10406 | | NM_006103 | WAP four-disulfide core domain 2 |
| WT1 | 19.92 | Hs.1145 | 7490 | 607102 | NM_024426 | Wilms tumor 1 |
| XIST | 5.11 | | 7503 | 314670 | BE644917 | X (inactive)-specific transcript |
| XLHSRF-1 | 10.49 | Hs.9740 | 25981 | | AI004779 | heat shock regulated 1 |
| YAF2 | 12.36 | Hs.348380 | 10138 | 607534 | R56794 | YY1 associated factor 2 |
| YPEL2 | 15.77 | Hs.368672 | 388403 | | BE502982 | yippee-like 2 (*Drosophila*) |
| ZAP70 | 14.98 | Hs.234569 | 7535 | 176947 | AB083211 | zeta-chain (TCR) associated protein kinase 70 kDa |
| ZFPM2 | 6.50 | Hs.106309 | 23414 | 603693 | NM_012082 | zinc finger protein, multitype 2 |
| ZNF148 | 5.13 | Hs.442787 | 7707 | 601897 | AW594167 | zinc finger protein 148 (pHZ-52) |
| ZNF335 | 7.13 | Hs.174193 | 63925 | | NM_022095 | zinc finger protein 335 |
| ZNF396 | 18.81 | Hs.351005 | 252884 | | AF533251 | zinc finger protein 396 |
| ZNF436 | 7.11 | Hs.293798 | 80818 | | AI829509 | zinc finger protein 436 |
| ZNF439 | 5.39 | Hs.378527 | 90594 | | N29327 | zinc finger protein 439 |
| ZNF471 | 7.23 | Hs.230188 | 57573 | | AL042523 | zinc finger protein 471 |
| ZNF533 | 8.23 | Hs.6295 | 151126 | | BC038422 | zinc finger protein 533 |
| ZNF555 | 9.10 | Hs.12471 | 148254 | | AF052118 | zinc finger protein 555 |
| ZNF7 | 8.09 | Hs.2076 | 7553 | 194531 | AI862153 | zinc finger protein 7 (KOX 4, clone HF.16) |
| | 116.51 | Hs.11873 | | | AW167727 | Transcribed sequences |
| | 66.25 | Hs.177968 | | | AI821586 | Transcribed sequence with weak similarity to protein ref: NP_066928.1 (*H. sapiens*) phospholipid scramblase 1 [*Homo sapiens*] |
| | 54.91 | Hs.160418 | | | BF941609 | Transcribed sequences |
| | 52.28 | Hs.444751 | | | AI916532 | Transcribed sequences |
| | 50.21 | Hs.390285 | 401221 | | BC034407 | CDNA clone IMAGE: 5268504, partial cds |
| | 43.32 | Hs.518877 | | | BC014345 | Clone IMAGE: 3935474, mRNA |
| | 42.12 | Hs.446121 | | | AW450381 | Transcribed sequences |
| | 41.67 | Hs.445324 | | | BF513800 | Transcribed sequences |
| | 40.16 | Hs.514745 | | | N63706 | CDNA FLJ41084 fis, clone ADRGL2010974 |
| | 35.98 | Hs.434969 | | | AI917371 | Transcribed sequences |
| | 35.50 | Hs.145404 | 345557 | | AI694325 | Similar to RIKEN cDNA B130016O10 gene (LOC345557), mRNA |
| | 33.79 | Hs.127462 | | | AI190292 | Transcribed sequences |
| | 33.43 | Hs.50850 | | | AI127440 | CDNA FLJ30128 fis, clone BRACE1000124 |
| | 32.63 | Hs.348762 | | | AI143879 | CDNA FLJ25677 fis, clone TST04054 |
| | 30.42 | | | | AI248055 | Consensus includes gb: AI248055/FEA = EST /DB_XREF = gi: 3843452/DB_XREF = est: qh64c02.x1 /CLONE = IMAGE: 1849442/UG = Hs.137263 ESTs |
| | 30.05 | Hs.7888 | | | AW772192 | CDNA FLJ44318 fis, clone TRACH3000780 |
| | 29.77 | Hs.382051 | | | BC014585 | Clone IMAGE: 4047715, mRNA |
| | 29.74 | Hs.446340 | | | AW291402 | Transcribed sequences |
| | 28.51 | Hs.112742 | 401141 | | BF508344 | CDNA clone IMAGE: 6301163, containing frame-shift errors |
| | 28.41 | Hs.118317 | | | AU147152 | CDNA FLJ12088 fis, clone HEMBB1002545 |
| | 27.71 | Hs.360628 | 401154 | | AW873604 | CDNA FLJ42757 fis, clone BRAWH3001712 |
| | 24.86 | Hs.158853 | | | AW274369 | Transcribed sequences |
| | 24.14 | | | | AF009316 | gb: AF009316.1/DB_XREF = gi: 2331119/TID = Hs2.384893.1 /CNT = 1/FEA = mRNA/TIER = ConsEnd/STK = 0/UG = Hs.384893 /UG_TITLE = *Homo sapiens* clone TUB2 Cri-du-chat region mRNA /DEF = *Homo sapiens* clone TUB2 Cri-du-chat region mRNA. |

TABLE 3-continued

Up-regulated markers in definitive endoderm

| Gene_Symbol | Raw Fold Change | Unigene | Locus-Link | OMIM | SeqDerived-From | Gene Descriptor |
|---|---|---|---|---|---|---|
| | 24.04 | Hs.531661 | | | AF088010 | Full length insert cDNA clone YY74E10 |
| | 23.38 | Hs.287436 | | | AU145336 | CDNA FLJ11655 fis, clone HEMBA1004554 |
| | 22.75 | Hs.106975 | | | H10408 | Transcribed sequences |
| | 21.99 | | | | BC037932 | gb: BC037932.1/DB_XREF = gi: 23138809/TID = Hs2.385469.1 /CNT = 2/FEA = mRNA/TIER = ConsEnd/STK = 0/UG = Hs.385469 /UG_TITLE = Homo sapiens, clone IMAGE: 5285165, mRNA /DEF = Homo sapiens, clone IMAGE: 5285165, mRNA. |
| | 21.26 | Hs.451103 | | | BC041486 | CDNA clone IMAGE: 5492202, partial cds |
| | 20.96 | Hs.269873 | | | AF339813 | Clone IMAGE: 297403, mRNA sequence |
| | 20.87 | Hs.113150 | | | AV739182 | Transcribed sequences |
| | 20.10 | Hs.191144 | | | T83380 | Transcribed sequences |
| | 19.98 | Hs.525221 | | | AW291482 | Transcribed sequences |
| | 19.17 | Hs.346735 | | | BE222344 | Clone IMAGE: 3881549, mRNA |
| | 18.97 | Hs.256230 | | | AW418842 | CDNA FLJ31245 fis, clone KIDNE2005062 |
| | 17.92 | Hs.265194 | | | BF223214 | Transcribed sequences |
| | 17.65 | Hs.523019 | | | AI801626 | Transcribed sequence with weak similarity to protein ref: NP_055301.1 (H. sapiens) neuronal thread protein [Homo sapiens] |
| | 16.87 | Hs.121518 | | | BE932011 | Transcribed sequence with strong similarity to protein sp: P00722 (E. coli) BGAL_ECOLI Beta-galactosidase |
| | 16.53 | Hs.126622 | | | AW341701 | Transcribed sequences |
| | 16.52 | Hs.348682 | 401612 | | AL833609 | Similar to mitochondrial carrier triple repeat 1 (LOC401612), mRNA |
| | 16.41 | Hs.201875 | | | BE645480 | Transcribed sequences |
| | 16.35 | Hs.296014 | | | AU148154 | CDNA FLJ14136 fis, clone MAMMA1002744 |
| | 16.33 | Hs.375762 | | | AI955713 | Clone IMAGE: 4828750, mRNA |
| | 16.33 | Hs.390443 | | | BC043538 | Clone IMAGE: 5170153, mRNA |
| | 16.27 | Hs.488530 | | | AF086391 | Full length insert cDNA clone ZD73H04 |
| | 15.79 | Hs.244283 | | | AA018404 | MRNA; cDNA DKFZp686I19109 (from clone DKFZp686I19109) |
| | 15.55 | Hs.519952 | | | AL833685 | MRNA; cDNA DKFZp667O0522 (from clone DKFZp667O0522) |
| | 15.45 | Hs.13188 | | | AW300488 | Human HepG2 partial cDNA, clone hmd5d04m5. |
| | 15.37 | Hs.311250 | | | AL137360 | MRNA; cDNA DKFZp434C0326 (from clone DKFZp43400326) |
| | 15.33 | Hs.96917 | | | BF591483 | Transcribed sequences |
| | 15.15 | Hs.316856 | | | BC040219 | Clone IMAGE: 4818734, mRNA |
| | 15.15 | Hs.505003 | | | BG208091 | CDNA FLJ37414 fis, clone BRAWH1000157 |
| | 15.05 | Hs.126995 | | | BM969275 | CDNA FLJ46728 fis, clone TRACH3019142 |
| | 14.91 | Hs.345792 | | | AI684551 | Transcribed sequence with weak similarity to protein ref: NP_077243.1 (M. musculus) ribosome binding protein 1 isoform mRRp61 [Mus musculus] |
| | 14.91 | Hs.441051 | | | AI769647 | CDNA clone IMAGE: 5296106, partial cds |
| | 14.75 | Hs.526642 | | | H49805 | Transcribed sequences |
| | 14.18 | Hs.264606 | | | AI741597 | Full length insert cDNA clone ZD68B12 |
| | 13.94 | Hs.528540 | 401074 | | BC039495 | Similar to double homeobox protein (LOC401074), mRNA |
| | 13.54 | Hs.241559 | | | AL109791 | MRNA full length insert cDNA clone EUROIMAGE 151432 |
| | 13.49 | Hs.253690 | | | BC042378 | Clone IMAGE: 5277693, mRNA |
| | 13.17 | Hs.291015 | | | AA651631 | Transcribed sequences |
| | 13.13 | Hs.529285 | | | AA588092 | Transcribed sequences |
| | 12.65 | Hs.128439 | | | AI190306 | Transcribed sequences |
| | 12.63 | Hs.435959 | | | BF511336 | Transcribed sequences |
| | 12.55 | Hs.202512 | | | AI697714 | Transcribed sequences |
| | 12.51 | Hs.126918 | | | R15004 | Transcribed sequences |
| | 12.21 | | | | AL832724 | gb: AL832724.1/DB_XREF = gi: 21733304/TID = Hs2.376962.1 /CNT = 1/FEA = mRNA/TIER = ConsEnd/STK = 0/UG = Hs.376962 /UG_TITLE = Homo sapiens mRNA; cDNA DKFZp313I209 (from clone DKFZp313I209)/DEF = Homo sapiens mRNA; cDNA DKFZp313I209 (from clone DKFZp313I209). |
| | 12.16 | Hs.385547 | 390845 | | BC036040 | Similar to KIAA0563-related gene (LOC390845), mRNA |
| | 12.08 | Hs.172778 | | | AB046770 | CDNA FLJ38287 fis, clone FCBBF3008362, moderately similar to PLEXIN 4 PRECURSOR |
| | 12.06 | Hs.446559 | | | BG024649 | Transcribed sequence with strong similarity to protein sp: P00722 (E. coli) BGAL_ECOLI Beta-galactosidase |
| | 11.82 | | | | AK055534 | gb: AK055534.1/DB_XREF = gi: 16550279/TID = Hs2.350858.1 /CNT = 1/FEA = mRNA/TIER = ConsEnd/STK = 0/UG = Hs.350858 /UG_TITLE = Homo sapiens cDNA FLJ30972 fis, clone HEART2000492./DEF = Homo sapiens cDNA FLJ30972 fis, clone HEART2000492. |
| | 11.80 | Hs.348434 | | | BC033956 | Clone IMAGE: 5286779, mRNA |
| | 11.66 | Hs.158528 | | | BF002339 | Transcribed sequences |
| | 11.58 | Hs.110406 | | | AI700341 | Transcribed sequences |
| | 11.57 | Hs.517745 | | | AL359583 | MRNA; cDNA DKFZp547L174 (from clone DKFZp547L174) |
| | 11.54 | Hs.116462 | | | AA639753 | Transcribed sequences |
| | 11.28 | Hs.28391 | | | BF511741 | CDNA FLJ37384 fis, clone BRAMY2026347 |
| | 11.18 | Hs.382361 | | | BC034279 | CDNA clone IMAGE: 4824424, containing frame-shift errors |
| | 11.17 | Hs.143258 | | | BC021687 | Clone IMAGE: 3934974, mRNA |
| | 11.07 | Hs.110286 | | | AA418074 | CDNA FLJ43404 fis, clone OCBBF2017516 |

TABLE 3-continued

Up-regulated markers in definitive endoderm

| Gene_Symbol | Raw Fold Change | Unigene | Locus-Link | OMIM | SeqDerived-From | Gene Descriptor |
|---|---|---|---|---|---|---|
| | 10.97 | Hs.194626 | | | AA916568 | Transcribed sequences |
| | 10.96 | Hs.532249 | | | AL833080 | MRNA; cDNA DKFZp451G2119 (from clone DKFZp451G2119) |
| | 10.96 | Hs.383399 | | | AF113679 | Clone FLB3107 |
| | 10.87 | Hs.108068 | | | BF197757 | Transcribed sequences |
| | 10.80 | Hs.374838 | | | AB002318 | Clone 24641 mRNA sequence |
| | 10.70 | | | | AK024556 | gb: AK024556.1/DB_XREF = gi: 10436865/TID = Hs2.383622.1 /CNT = 1/FEA = mRNA/TIER = ConsEnd/STK = 0/UG = Hs.383622 /UG_TITLE = *Homo sapiens* cDNA: FLJ20903 fis, clone ADSE00222./DEF = *Homo sapiens* cDNA: FLJ20903 fis, clone ADSE00222. |
| | 10.67 | Hs.531632 | | | R43486 | CDNA FLJ33443 fis, clone BRALZ1000103 |
| | 10.61 | Hs.163734 | | | BG028463 | Transcribed sequences |
| | 10.54 | Hs.143134 | | | AW207243 | CDNA FLJ38181 fis, clone FCBBF1000125 |
| | 10.49 | Hs.290853 | | | AW970985 | Transcribed sequences |
| | 10.43 | Hs.447459 | | | AU158588 | CDNA FLJ13756 fis, clone PLACE3000365 |
| | 10.37 | Hs.525111 | | | AW134504 | Transcribed sequence with moderate similarity to protein sp: P39194 (*H. sapiens*) ALU7_HUMAN Alu subfamily SQ sequence contamination warning entry |
| | 10.34 | | | | AK096139 | gb: AK096139.1/DB_XREF = gi: 21755553/TID = Hs2.376171.1 /CNT = 1/FEA = mRNA/TIER = ConsEnd/STK = 0/UG = Hs.376171 /UG_TITLE = *Homo sapiens* cDNA FLJ38820 fis, clone LIVER2008473./DEF = *Homo sapiens* cDNA FLJ38820 fis, clone LIVER2008473. |
| | 10.20 | Hs.314414 | | | BC040901 | Clone IMAGE: 5743779, mRNA |
| | 10.15 | Hs.432615 | | | AW070877 | Transcribed sequences |
| | 10.13 | Hs.176872 | | | AW297742 | Transcribed sequences |
| | 10.05 | | | | AK057525 | gb: AK057525.1/DB_XREF = gi: 16553266/TID = Hs2.401310.1 /CNT = 6/FEA = mRNA/TIER = ConsEnd/STK = 5/UG = Hs.401310 /UG_TITLE = *Homo sapiens* cDNA FLJ32963 fis, clone TESTI2008405./DEF = *Homo sapiens* cDNA FLJ32963 fis, clone TESTI2008405. |
| | 9.91 | | | | BC016356 | gb: BC016356.1/DB_XREF = gi: 18921441/TID = Hs2.382791.1 /CNT = 1/FEA = mRNA/TIER = ConsEnd/STK = 0/UG = Hs.382791 /UG_TITLE = *Homo sapiens*, clone IMAGE: 4093039, mRNA /DEF = *Homo sapiens*, clone IMAGE: 4093039, mRNA. |
| | 9.90 | Hs.283228 | | | BC041378 | CDNA clone IMAGE: 5274693, partial cds |
| | 9.85 | Hs.521517 | | | AY010114 | Unknown mRNA sequence |
| | 9.74 | Hs.16193 | | | BG251521 | MRNA; cDNA DKFZp586B211 (from clone DKFZp586B211) |
| | 9.64 | Hs.116631 | | | N63890 | Transcribed sequences |
| | 9.59 | Hs.130526 | | | AI004009 | Transcribed sequence with moderate similarity to protein sp: P39194 (*H. sapiens*) ALU7_HUMAN Alu subfamily SQ sequence contamination warning entry |
| | 9.50 | Hs.176379 | | | AA913023 | Transcribed sequences |
| | 9.45 | Hs.278177 | | | AA809449 | Transcribed sequence with weak similarity to protein sp: P39191 (*H. sapiens*) ALU4_HUMAN Alu subfamily SB2 sequence contamination warning entry |
| | 9.32 | Hs.101428 | | | AW628575 | Transcribed sequences |
| | 9.25 | Hs.373857 | | | AA551114 | Transcribed sequences |
| | 9.23 | Hs.57773 | | | AA449026 | Transcribed sequences |
| | 9.09 | Hs.46908 | | | AI629041 | Transcribed sequences |
| | 9.08 | Hs.364332 | | | BC042834 | Clone IMAGE: 5314388, mRNA |
| | 9.00 | Hs.22137 | | | AI393695 | MRNA; cDNA DKFZp686O0849 (from clone DKFZp686O0849) |
| | 8.94 | Hs.508368 | | | AF339805 | Clone IMAGE: 248602, mRNA sequence |
| | 8.91 | Hs.129620 | | | AI970133 | Transcribed sequences |
| | 8.84 | Hs.481953 | | | AU144883 | CDNA FLJ11566 fis, clone HEMBA1003273 |
| | 8.78 | Hs.42522 | 255338 | | AI027091 | Clone IMAGE: 4827191, mRNA |
| | 8.78 | Hs.418040 | | | BF476080 | CDNA clone IMAGE: 30367357, partial cds |
| | 8.73 | Hs.60797 | | | AA017302 | Transcribed sequences |
| | 8.70 | Hs.114111 | | | BM021056 | Full length insert cDNA clone YA75D10 |
| | 8.68 | Hs.469666 | | | AL041381 | CDNA FLJ32512 fis, clone SMINT1000075 |
| | 8.63 | Hs.36958 | | | AA496799 | Transcribed sequences |
| | 8.59 | Hs.212298 | | | AW204033 | Transcribed sequence with weak similarity to protein sp: P39189 (*H. sapiens*) ALU2_HUMAN Alu subfamily SB sequence contamination warning entry |
| | 8.57 | Hs.365692 | | | AL691692 | CDNA FLJ20833 fis, clone ADKA02957 |
| | 8.57 | Hs.158209 | | | BE178418 | Transcribed sequence with weak similarity to protein ref: NP_062553.1 (*H. sapiens*) hypothetical protein FLJ11267 [Homo sapiens] |
| | 8.54 | Hs.12533 | | | Z39557 | Clone 23705 mRNA sequence |
| | 8.50 | Hs.499320 | | | AU147518 | CDNA FLJ12203 fis, clone MAMMA1000914 |
| | 8.48 | Hs.150378 | | | BF063236 | Transcribed sequences |
| | 8.47 | Hs.306704 | | | AK024800 | CDNA: FLJ21147 fis, clone CAS09371 |

TABLE 3-continued

Up-regulated markers in definitive endoderm

| Gene_Symbol | Raw Fold Change | Unigene | Locus-Link | OMIM | SeqDerived-From | Gene Descriptor |
|---|---|---|---|---|---|---|
| | 8.41 | | | | AL137313 | Consensus includes gb: AL137313.1/DEF = *Homo sapiens* mRNA; cDNA DKFZp761M10121 (from clone DKFZp761M10121). /FEA = mRNA/DB_XREF = gi: 6807798/UG = Hs.306449 *Homo sapiens* mRNA; cDNA DKFZp761M10121 (from clone DKFZp761M10121) |
| | 8.41 | | | | AK098258 | gb: AK098258.1/DB_XREF = gi: 21758235/TID = Hs2.379809.2 /CNT = 1/FEA = mRNA/TIER = ConsEnd/STK = 0/UG = Hs.379809 /UG_TITLE = *Homo sapiens* cDNA FLJ40939 fis, clone UTERU2008077./DEF = *Homo sapiens* cDNA FLJ40939 fis, clone UTERU2008077. |
| | 8.39 | Hs.136672 | | | BC043227 | CDNA clone IMAGE: 5295530, partial cds |
| | 8.36 | Hs.434253 | | | BC042892 | Clone IMAGE: 4830182, mRNA |
| | 8.36 | Hs.351262 | | | AI950472 | Similar to otoconin 90, clone IMAGE: 4278507, mRNA |
| | 8.32 | Hs.531627 | 400680 | | BE138486 | MRNA; cDNA DKFZp686K1836 (from clone DKFZp686K1836) |
| | 8.31 | Hs.249946 | | | AV700086 | Transcribed sequences |
| | 8.26 | Hs.105500 | | | AA521154 | Transcribed sequences |
| | 8.24 | Hs.444915 | | | AI734054 | Transcribed sequences |
| | 8.21 | Hs.444387 | | | AI051967 | Transcribed sequences |
| | 8.18 | Hs.384618 | | | AF086084 | Full length insert cDNA clone YZ84C01 |
| | 8.18 | Hs.370704 | | | AW104813 | CDNA FLJ36685 fis, clone UTERU2008018 |
| | 8.11 | Hs.192075 | | | AA702409 | Transcribed sequences |
| | 8.10 | Hs.117474 | | | R49146 | CDNA FLJ34491 fis, clone HLUNG2004774 |
| | 8.08 | Hs.492671 | | | AU147969 | CDNA FLJ12341 fis, clone MAMMA1002269 |
| | 8.07 | Hs.421746 | | | CA442689 | CDNA FLJ13866 fis, clone THYRO1001213 |
| | 8.05 | Hs.126024 | | | AL041122 | Transcribed sequence with weak similarity to protein ref: NP_491607.1 (*C. elegans*) C09D4.4a.p [*Caenorhabditis elegans*] |
| | 8.03 | Hs.527657 | | | AL552727 | Transcribed sequences |
| | 8.03 | Hs.133319 | | | BE675108 | Alu repeat mRNA sequence |
| | 8.02 | Hs.51515 | | | AA053967 | MRNA; cDNA DKFZp564G112 (from clone DKFZp564G112) |
| | 8.02 | Hs.155814 | | | N23033 | Transcribed sequence with strong similarity to protein sp: P00722 (*E. coli*) BGAL_ECOLI Beta-galactosidase |
| | 7.98 | Hs.98314 | | | AL553774 | MRNA; cDNA DKFZp586L0120 (from clone DKFZp586L0120) |
| | 7.93 | Hs.408455 | | | AA002022 | MRNA; cDNA DKFZp686J1595 (from clone DKFZp686J1595) |
| | 7.91 | Hs.488293 | | | N74195 | Transcribed sequence with weak similarity to protein ref: NP_079268.1 (*H. sapiens*) hypothetical protein FLJ12547 [Homo sapiens] |
| | 7.89 | Hs.513302 | | | N26569 | MRNA; cDNA DKFZp686H0155 (from clone DKFZp686H0155) |
| | 7.88 | Hs.287413 | | | AU144140 | CDNA FLJ11419 fis, clone HEMBA1000985 |
| | 7.80 | | | | AF009316 | gb: AF009316.1/DB_XREF = gi: 2331119/TID = Hs2.384893.1 /CNT = 1/FEA = mRNA/TIER = ConsEnd/STK = 0/UG = Hs.384893 /UG_TITLE = *Homo sapiens* clone TUB2 Cri-du-chat region mRNA /DEF = *Homo sapiens* clone TUB2 Cri-du-chat region mRNA. |
| | 7.75 | Hs.475627 | | | AU147983 | CDNA FLJ43139 fis, clone CTONG3007444 |
| | 7.71 | Hs.526982 | | | BE674460 | Transcribed sequence with strong similarity to protein pir: S38965 (*H. sapiens*) S38965 mannosyl-oligosaccharide 1,2-alpha-mannosidase |
| | 7.70 | Hs.407197 | | | BC028204 | Clone IMAGE: 5201079, mRNA |
| | 7.68 | Hs.269924 | | | BF435438 | Full length insert cDNA clone YH93B03 |
| | 7.67 | | | | Y16185 | gb: Y16185.1/DB_XREF = gi: 3176023/TID = Hs2.382267.1/CNT = 1 /FEA = mRNA/TIER = ConsEnd/STK = 0/UG = Hs.382267 /UG_TITLE = *Homo sapiens* partial mRNA, ID band56/DEF = *Homo sapiens* partial mRNA, ID band56. |
| | 7.66 | Hs.370466 | | | AI939460 | Transcribed sequences |
| | 7.64 | Hs.459142 | | | CA442342 | Clone IMAGE: 5288686, mRNA |
| | 7.63 | Hs.268597 | | | AK025151 | CDNA: FLJ21498 fis, clone COL05627 |
| | 7.52 | Hs.370312 | | | AI953011 | Transcribed sequences |
| | 7.51 | Hs.277215 | 389659 | | BC028018 | LOC389659 (LOC389659), mRNA |
| | 7.48 | Hs.162518 | | | D80168 | MRNA; cDNA DKFZp686P21116 (from clone DKFZp686P21116) |
| | 7.42 | Hs.118704 | | | AI807197 | Transcribed sequence with weak similarity to protein pir: I38022 (*H. sapiens*) I38022 hypothetical protein - human |
| | 7.35 | Hs.517144 | | | AK091704 | CDNA FLJ34385 fis, clone HCHON1000142 |
| | 7.34 | | | | AI142544 | Consensus includes gb: AI142544/FEA = EST /DB_XREF = gi: 3658903/DB_XREF = est: qb47b03.x1 /CLONE = IMAGE: 1703213/UG = Hs.158950 ESTs |
| | 7.29 | Hs.377660 | | | AI498395 | CDNA FLJ26242 fis, clone DMC00770 |
| | 7.28 | Hs.434610 | | | BC040327 | Clone IMAGE: 4830466, mRNA |
| | 7.26 | Hs.272033 | | | T92908 | Transcribed sequences |
| | 7.26 | Hs.450057 | 344595 | | AI678088 | Clone IMAGE: 5300025, mRNA |
| | 7.26 | Hs.145331 | | | AI252905 | Transcribed sequences |

TABLE 3-continued

Up-regulated markers in definitive endoderm

| Gene_Symbol | Raw Fold Change | Unigene | Locus-Link | OMIM | SeqDerived-From | Gene Descriptor |
|---|---|---|---|---|---|---|
| | 7.24 | | | | AK057525 | gb: AK057525.1/DB_XREF = gi: 16553266/TID = Hs2.401310.1 /CNT = 6/FEA = mRNA/TIER = ConsEnd/STK = 5/UG = Hs.401310 /UG_TITLE = *Homo sapiens* cDNA FLJ32963 fis, clone TESTI2008405./DEF = *Homo sapiens* cDNA FLJ32963 fis, clone TESTI2008405. |
| | 7.22 | | | | AK093656 | gb: AK093656.1/DB_XREF = gi: 21752574/TID = Hs2.232296.1 /CNT = 1/FEA = mRNA/TIER = ConsEnd/STK = 0/UG = Hs.232296 /UG_TITLE = *Homo sapiens* cDNA FLJ36337 fis, clone THYMU2006324./DEF = *Homo sapiens* cDNA FLJ36337 fis, clone THYMU2006324. |
| | 7.22 | | | | AI264125 | Consensus includes gb: AI264125/FEA = EST /DB_XREF = gi: 3872328/DB_XREF = est: qk03a05.x1 /CLONE = IMAGE: 1867856/UG = Hs.299056 ESTs |
| | 7.19 | Hs.531773 | | | AV703843 | CDNA FLJ25185 fis, clone CBR09429 |
| | 7.18 | Hs.132571 | | | AL049337 | MRNA; cDNA DKFZp564P016 (from clone DKFZp564P016) |
| | 7.16 | Hs.46689 | | | AF088007 | Full length insert cDNA clone YY74A01 |
| | 7.12 | Hs.371746 | | | AI125516 | Transcribed sequence with weak similarity to protein pir: VWHU (*H. sapiens*) VWHU von Willebrand factor precursor - human |
| | 7.07 | Hs.105738 | | | AA831943 | Transcribed sequences |
| | 7.03 | Hs.144469 | | | AW663083 | Clone IMAGE: 5285945, mRNA |
| | 7.03 | Hs.469331 | | | AU159040 | CDNA FLJ13833 fis, clone THYRO1000676 |
| | 7.01 | Hs.26346 | | | AI638405 | CDNA FLJ42689 fis, clone BRACE3009701 |
| | 7.00 | Hs.362343 | | | BF207861 | CDNA FLJ41751 fis, clone HSYRA2008154 |
| | 6.98 | Hs.390736 | | | R71245 | Transcribed sequence with weak similarity to protein ref: NP_495786.1 (*C. elegans*) F22B5.10.p [*Caenorhabditis elegans*] |
| | 6.96 | Hs.147030 | | | AI186173 | Transcribed sequence with moderate similarity to protein sp: P00722 (*E. coli*) BGAL_ECOLI Beta-galactosidase |
| | 6.96 | Hs.287562 | | | AK023375 | CDNA FLJ13313 fis, clone OVARC1001489 |
| | 6.91 | Hs.37902 | | | AI808348 | Transcribed sequences |
| | 6.88 | Hs.21248 | | | R40515 | Transcribed sequences |
| | 6.83 | Hs.12853 | | | BF446943 | MRNA; cDNA DKFZp762M127 (from clone DKFZp762M127) |
| | 6.81 | Hs.99836 | | | AI384076 | MRNA; cDNA DKFZp686B0610 (from clone DKFZp686B0610) |
| | 6.79 | Hs.357304 | | | AW103823 | Clone IMAGE: 5266114, mRNA |
| | 6.76 | | | | AF334792 | gb: AF334792.1/DEF = *Homo sapiens* P143 mRNA, complete cds. /FEA = mRNA/PROD = P143/DB_XREF = gi: 12659333 /UG = Hs.307005 *Homo sapiens* P143 mRNA, complete cds /FL = gb: AF334792.1 |
| | 6.75 | Hs.508096 | | | AU157457 | CDNA FLJ11204 fis, clone PLACE1007810 |
| | 6.73 | Hs.407118 | | | AL833266 | MRNA; cDNA DKFZp451G0810 (from clone DKFZp451G0810) |
| | 6.72 | Hs.526497 | | | BC040539 | Clone IMAGE: 5267024, mRNA |
| | 6.68 | Hs.405427 | | | AI283051 | Clone IMAGE: 5175565, mRNA |
| | 6.68 | Hs.201184 | | | BE551395 | Transcribed sequence with weak similarity to protein ref: NP_060265.1 (*H. sapiens*) hypothetical protein FLJ20378 [Homo sapiens] |
| | 6.65 | | | | AF086490 | gb: AF086490.1/DB_XREF = gi: 3483835/TID = Hs2.384576.1 /CNT = 2/FEA = mRNA/TIER = ConsEnd/STK = 1/UG = Hs.384576 /UG_TITLE = *Homo sapiens* full length insert cDNA clone ZD94H12. /DEF = *Homo sapiens* full length insert cDNA clone ZD94H12. |
| | 6.65 | Hs.144759 | | | AI200555 | CDNA FLJ32438 fis, clone SKMUS2001402 |
| | 6.63 | | | | BC039119 | gb: BC039119.1/DB_XREF = gi: 24659569/TID = Hs2.407561.1 /CNT = 2/FEA = mRNA/TIER = ConsEnd/STK = 1/UG = Hs.407561 /UG_TITLE = *Homo sapiens*, clone IMAGE: 4838391, mRNA /DEF = *Homo sapiens*, clone IMAGE: 4838391, mRNA. |
| | 6.61 | Hs.9887 | | | AI683805 | CDNA FLJ36309 fis, clone THYMU2004986 |
| | 6.60 | Hs.445500 | | | AI225238 | Transcribed sequences |
| | 6.55 | Hs.383205 | | | BE276551 | Clone IMAGE: 3050253, mRNA |
| | 6.54 | Hs.484965 | | | AA755296 | MRNA; cDNA DKFZp686P16118 (from clone DKFZp686P16118) |
| | 6.52 | Hs.487431 | | | AA554430 | CDNA FLJ14343 fis, clone THYRO1000916 |
| | 6.50 | Hs.58423 | | | AF086424 | Full length insert cDNA clone ZD78G02 |
| | 6.49 | | | | AL117528 | Consensus includes gb: AL117528.1/DEF = *Homo sapiens* mRNA; cDNA DKFZp434P2450 (from clone DKFZp434P2450). /FEA = mRNA/DB_XREF = gi: 5912054/UG = Hs.306350 *Homo sapiens* mRNA; cDNA DKFZp434P2450 (from clone DKFZp434P2450) |
| | 6.48 | Hs.169068 | | | AU144005 | CDNA FLJ11397 fis, clone HEMBA1000622 |
| | 6.47 | Hs.61590 | | | AI300077 | Transcribed sequences |
| | 6.43 | Hs.369777 | 401176 | | BC043001 | Clone IMAGE: 5297432, mRNA |
| | 6.42 | | | | AF314543 | gb: AF314543.1/DEF = *Homo sapiens* ovarian cancer-related protein 1 (OCR1) mRNA, complete cds./FEA = mRNA /GEN = OCR1/PROD = ovarian cancer-related protein 1 /DB_XREF = gi: 12584148/UG = Hs.307048 *Homo sapiens* ovarian cancer-related protein 1 (OCR1) mRNA, . . . |
| | 6.41 | Hs.21965 | | | AI798981 | Clone IMAGE: 4813782, mRNA |

TABLE 3-continued

Up-regulated markers in definitive endoderm

| Gene_Symbol | Raw Fold Change | Unigene | Locus-Link | OMIM | SeqDerived-From | Gene Descriptor |
|---|---|---|---|---|---|---|
| | 6.39 | | | | NM_025089 | gb: NM_025089.1/DEF = *Homo sapiens* hypothetical protein FLJ23497 (FLJ23497), mRNA./FEA = mRNA/GEN = FLJ23497 /PROD = hypothetical protein FLJ23497/DB_XREF = gi: 13376647 /UG = Hs.288498 hypothetical protein FLJ23497 /FL = gb: NM_025089.1 |
| | 6.36 | Hs.130203 | | | AW301241 | Transcribed sequences |
| | 6.35 | Hs.434203 | | | BC042835 | Clone IMAGE: 4828037, mRNA |
| | 6.35 | | | | AL137305 | Consensus includes gb: AL137305.1/DEF = *Homo sapiens* mRNA; cDNA DKFZp434J197 (from clone DKFZp434J197)./FEA = mRNA /DB_XREF = gi: 6807770/UG = Hs.306447 *Homo sapiens* mRNA; cDNA DKFZp434J197 (from clone DKFZp434J197) |
| | 6.34 | Hs.149442 | | | AI346891 | Transcribed sequences |
| | 6.32 | Hs.385767 | | | BC038784 | Clone IMAGE: 5271697, mRNA |
| | 6.28 | Hs.391856 | | | BG150301 | CDNA FLJ42567 fis, clone BRACE3007559 |
| | 6.24 | Hs.306566 | | | AF090948 | Clone HQ0709 |
| | 6.22 | Hs.385614 | | | BC035176 | Clone IMAGE: 5266012, mRNA |
| | 6.21 | Hs.436589 | | | BC041341 | Clone IMAGE: 5272066, mRNA |
| | 6.20 | Hs.136941 | | | AW182342 | Transcribed sequences |
| | 6.20 | Hs.372303 | | | AW611685 | CDNA FLJ45450 fis, clone BRSTN2002691 |
| | 6.19 | Hs.17892 | | | AA411712 | Transcribed sequences |
| | 6.18 | Hs.133386 | | | AI056872 | Transcribed sequences |
| | 6.15 | Hs.353387 | | | AL832704 | MRNA; cDNA DKFZp313A1935 (from clone DKFZp313A1935) |
| | 6.14 | Hs.22542 | | | N49237 | Clone IMAGE: 5312516, mRNA |
| | 6.09 | Hs.385747 | | | BC038195 | Clone IMAGE: 3918875, mRNA |
| | 6.07 | Hs.49774 | | | AI040744 | Transcribed sequences |
| | 6.06 | Hs.102981 | | | AL122040 | CDNA FLJ43416 fis, clone OCBBF2025730 |
| | 6.05 | Hs.382138 | 400234 | | BC029835 | CDNA FLJ27344 fis, clone TST03461 |
| | 6.02 | Hs.529382 | | | BG236742 | Transcribed sequences |
| | 6.01 | Hs.481773 | | | AK095656 | CDNA FLJ38337 fis, clone FCBBF3026692 |
| | 6.01 | Hs.133107 | | | AW271932 | Transcribed sequences |
| | 6.01 | | | | BC037921 | gb: BC037921.1/DB_XREF = gi: 23138806/TID = Hs2.385471.1 /CNT = 1/FEA = mRNA/TIER = ConsEnd/STK = 0/UG = Hs.385471 /UG_TITLE = *Homo sapiens*, clone IMAGE: 5278633, mRNA /DEF = *Homo sapiens*, clone IMAGE: 5278633, mRNA. |
| | 6.00 | Hs.270027 | | | AI683911 | Transcribed sequence with weak similarity to protein sp: P39194 (*H. sapiens*) ALU7_HUMAN Alu subfamily SQ sequence contamination warning entry |
| | 5.99 | Hs.283417 | | | AI826437 | Transcribed sequences |
| | 5.99 | Hs.365415 | | | BC037799 | Clone IMAGE: 4792036, mRNA |
| | 5.97 | Hs.434573 | | | BQ184537 | Full length insert cDNA clone ZB72E12 |
| | 5.97 | Hs.112916 | | | BF445273 | Transcribed sequences |
| | 5.96 | Hs.530006 | | | BG436225 | CDNA FLJ35202 fis, clone PLACE6018287 |
| | 5.95 | Hs.519717 | | | BM668595 | CDNA FLJ33578 fis, clone BRAMY2011639 |
| | 5.95 | Hs.173400 | | | BF724303 | Transcribed sequences |
| | 5.95 | Hs.27621 | | | BF940761 | CDNA FLJ12815 fis, clone NT2RP2002546 |
| | 5.94 | Hs.326721 | | | AF339788 | Clone IMAGE: 208561, mRNA sequence |
| | 5.93 | | | | BC043264 | gb: BC043264.1/DB_XREF = gi: 27695862/TID = Hs2.434164.1 /CNT = 2/FEA = mRNA/TIER = ConsEnd/STK = 1/UG = Hs.434164 /UG_TITLE = *Homo sapiens*, clone IMAGE: 5296753, mRNA /DEF = *Homo sapiens*, clone IMAGE: 5296753, mRNA. |
| | 5.92 | Hs.406798 | | | AU144676 | CDNA FLJ11533 fis, clone HEMBA1002678 |
| | 5.90 | Hs.128024 | 392659 | | AI798822 | CDNA FLJ27139 fis, clone SPL08682 |
| | 5.90 | Hs.130370 | | | AI130988 | Transcribed sequences |
| | 5.88 | Hs.370869 | | | AW173212 | Transcribed sequences |
| | 5.86 | Hs.71947 | | | AA565852 | MRNA full length insert cDNA clone EUROIMAGE 994183 |
| | 5.86 | Hs.201980 | 400516 | | AI914160 | Hypothetical gene supported by AK126852 (LOC400516), mRNA |
| | 5.84 | Hs.12473 | | | AF052109 | Clone 23927 mRNA sequence |
| | 5.83 | Hs.115122 | | | AA228366 | Transcribed sequences |
| | 5.83 | | | | AU144309 | Consensus includes gb: AU144309/FEA = EST /DB_XREF = gi: 11005830/DB_XREF = est: AU144309 /CLONE = HEMBA1001533/UG = Hs.55830 *Homo sapiens* cDNA FLJ10068 fis, clone HEMBA1001533 |
| | 5.81 | Hs.368488 | | | AA476583 | Transcribed sequences |
| | 5.81 | Hs.362707 | 400648 | | BC031271 | Hypothetical gene supported by BC031271 (LOC400648), mRNA |
| | 5.78 | | | | AF257500 | gb: AF257500.1/DEF = *Homo sapiens* SYTSSX4 fusion protein (SSXTSSX4 fusion) mRNA, complete cds./FEA = mRNA /GEN = SSXTSSX4 fusion/PROD = SYTSSX4 fusion protein /DB_XREF = gi: 11127694/UG = Hs.289105 synovial sarcoma, X breakpoint 2/FL = gb: AF257500.1 . . . |
| | 5.78 | Hs.445792 | | | BC037349 | Clone IMAGE: 5266332, mRNA |
| | 5.77 | Hs.375821 | | | BC031963 | Clone IMAGE: 4838328, mRNA |
| | 5.77 | | | | AA905023 | Consensus includes gb: AA905023/FEA = EST /DB_XREF = gi: 3040146/DB_XREF = est: ok09c06.s1 /CLONE = IMAGE: 1507306/UG = Hs.130769 ESTs |

TABLE 3-continued

Up-regulated markers in definitive endoderm

| Gene_Symbol | Raw Fold Change | Unigene | Locus-Link | OMIM | SeqDerived-From | Gene Descriptor |
|---|---|---|---|---|---|---|
| | 5.76 | Hs.380219 | | | BC034696 | MRNA similar to RIKEN cDNA A030009B12 gene (cDNA clone MGC: 21382 IMAGE: 4746351), complete cds |
| | 5.75 | | | | AK027174 | Consensus includes gb: AK027174.1/DEF = *Homo sapiens* cDNA: FLJ23521 fis, clone LNG04928./FEA = mRNA /DB_XREF = gi: 10440240/UG = Hs.306909 *Homo sapiens* cDNA: FLJ23521 fis, clone LNG04928 |
| | 5.75 | Hs.406106 | | | BG149337 | Transcribed sequences |
| | 5.74 | Hs.200004 | | | AI808303 | Transcribed sequences |
| | 5.72 | Hs.381113 | | | AW576443 | Transcribed sequences |
| | 5.72 | Hs.526474 | | | BC000856 | CDNA: FLJ21331 fis, clone COL02520 |
| | 5.71 | Hs.62929 | | | AI083557 | CDNA FLJ42179 fis, clone THYMU2030796 |
| | 5.71 | Hs.243596 | | | AI807482 | MRNA; cDNA DKFZp686I21166 (from clone DKFZp686I21166) |
| | 5.70 | Hs.100636 | | | AW960145 | CDNA FLJ36210 fis, clone THYMU2000155 |
| | 5.70 | Hs.438377 | | | AK023938 | CDNA FLJ13876 fis, clone THYRO1001401 |
| | 5.68 | Hs.280216 | | | BF510506 | Transcribed sequence with weak similarity to protein sp: P08547 (*H. sapiens*) LIN1_HUMAN LINE-1 REVERSE TRANSCRIPTASE HOMOLOG |
| | 5.68 | Hs.201953 | | | Y10204 | *H. sapiens* mRNA for CD77 protein |
| | 5.67 | Hs.257683 | | | AW572853 | Transcribed sequence with moderate similarity to protein sp: P39190 (*H. sapiens*) ALU3_HUMAN Alu subfamily SB1 sequence contamination warning entry |
| | 5.66 | Hs.401142 | | | AL832260 | MRNA; cDNA DKFZp667G1817 (from clone DKFZp667G1817) |
| | 5.65 | Hs.308222 | 402476 | | BI823265 | CDNA FLJ46106 fis, clone TESTI2026284 |
| | 5.65 | Hs.375072 | | | BC030740 | CDNA clone IMAGE: 4791521, partial cds |
| | 5.64 | Hs.429375 | | | AI272805 | Transcribed sequences |
| | 5.62 | | | | D00267 | Consensus includes gb: D00267/DEF = *Homo sapiens* pseudogene for cytochrome c-like protein, clone pHGC4E1/FEA = CDS /DB_XREF = gi: 219559/UG = Hs.248014 *Homo sapiens* pseudogene for cytochrome c-like protein, clone pHGC4E1 |
| | 5.61 | | | | AI990495 | Consensus includes gb: AI990495/FEA = EST /DB_XREF = gi: 5837376/DB_XREF = est: ws40d02.x1 /CLONE = IMAGE: 2499651/UG = Hs.126809 ESTs |
| | 5.60 | Hs.130260 | | | AI695695 | Transcribed sequences |
| | 5.55 | Hs.107070 | | | H93043 | Transcribed sequences |
| | 5.54 | Hs.501925 | | | AU144382 | CDNA FLJ11476 fis, clone HEMBA1001745 |
| | 5.54 | Hs.98073 | | | AA490685 | CDNA: FLJ22994 fis, clone KAT11918 |
| | 5.53 | Hs.126133 | 389324 | | AI799695 | MRNA; cDNA DKFZp686D0374 (from clone DKFZp686D0374) |
| | 5.52 | Hs.262826 | | | AI218551 | Transcribed sequences |
| | 5.51 | Hs.373571 | | | AA305027 | CDNA FLJ39665 fis, clone SMINT2007294 |
| | 5.50 | Hs.445122 | | | AW291140 | Transcribed sequences |
| | 5.48 | | | | NM_025116 | gb: NM_025116.1/DEF = *Homo sapiens* hypothetical protein FLJ12781 (FLJ12781), mRNA./FEA = mRNA/GEN = FLJ12781 /PROD = hypothetical protein FLJ12781/DB_XREF = gi: 13376692 /UG = Hs.288726 hypothetical protein FLJ12781 /FL = gb: NM_025116.1 |
| | 5.48 | Hs.7309 | | | AA995925 | CDNA FLJ34019 fis, clone FCBBF2002898 |
| | 5.48 | Hs.268818 | | | AF147404 | Full length insert cDNA clone YP01H07 |
| | 5.47 | Hs.433791 | | | AW664964 | Transcribed sequence with weak similarity to protein ref: NP_060312.1 (*H. sapiens*) hypothetical protein FLJ20489 [Homo sapiens] |
| | 5.46 | Hs.432355 | 392551 | | AI080106 | Similar to Ras-related protein Rab-28 (Rab-26) (LOC392551), mRNA |
| | 5.46 | Hs.302631 | | | AW952781 | CDNA clone IMAGE: 5286843, partial cds |
| | 5.45 | Hs.371751 | | | BC044305 | Clone IMAGE: 5174069, mRNA |
| | 5.44 | Hs.434569 | | | BQ707702 | Full length insert cDNA clone YB66H06 |
| | 5.44 | Hs.523914 | | | AI565746 | Full length insert cDNA YH73H08 |
| | 5.44 | Hs.185701 | | | AL109696 | MRNA full length insert cDNA clone EUROIMAGE 21920 |
| | 5.42 | Hs.16370 | | | AW139789 | CDNA FLJ11652 fis, clone HEMBA1004461 |
| | 5.41 | Hs.371436 | | | AW418647 | CDNA FLJ34002 fis, clone FCBBF1000206 |
| | 5.41 | Hs.160900 | | | BI560014 | CDNA FLJ39420 fis, clone PLACE6018769 |
| | 5.41 | Hs.96297 | | | AI051769 | Transcribed sequence with weak similarity to protein ref: NP_055301.1 (*H. sapiens*) neuronal thread protein [*Homo sapiens*] |
| | 5.39 | Hs.356457 | | | AW197431 | Transcribed sequence with moderate similarity to protein sp: P39194 (*H. sapiens*) ALU7_HUMAN Alu subfamily SQ sequence contamination warning entry |
| | 5.39 | | | | BE066040 | Consensus includes gb: BE066040/FEA = EST /DB_XREF = gi: 8410690/DB_XREF = est: RC3-BT0319-240200-015-c01/UG = Hs.292358 ESTs |
| | 5.38 | Hs.448887 | | | AF131798 | Clone 25119 mRNA sequence |
| | 5.37 | Hs.407471 | | | BC034815 | CDNA FLJ25418 fis, clone TST03512 |
| | 5.35 | Hs.4194 | | | AK024956 | CDNA: FLJ21303 fis, clone COL02107 |
| | 5.35 | Hs.432643 | | | AK001829 | CDNA FLJ10967 fis, clone PLACE1000798 |
| | 5.35 | Hs.470154 | | | AK026778 | CDNA: FLJ23125 fis, clone LNG08217 |

TABLE 3-continued

Up-regulated markers in definitive endoderm

| Gene_Symbol | Raw Fold Change | Unigene | Locus-Link | OMIM | SeqDerived-From | Gene Descriptor |
|---|---|---|---|---|---|---|
| | 5.34 | Hs.28803 | | | BE501976 | Transcribed sequence with moderate similarity to protein sp: P39192 (*H. sapiens*) ALU5_HUMAN Alu subfamily SC sequence contamination warning entry |
| | 5.34 | Hs.531894 | | | BC036311 | Clone IMAGE: 4819526, mRNA |
| | 5.34 | Hs.105623 | | | AI038071 | Transcribed sequences |
| | 5.33 | Hs.190060 | | | AI874267 | Transcribed sequences |
| | 5.32 | Hs.452398 | | | AL037998 | CDNA FLJ30740 fis, clone FEBRA2000319 |
| | 5.31 | Hs.356888 | | | AL713714 | MRNA; cDNA DKFZp667C0715 (from clone DKFZp667C0715) |
| | 5.31 | Hs.502632 | | | AK000995 | CDNA FLJ10133 fis, clone HEMBA1003067 |
| | 5.30 | | | | AF118079 | gb: AF118079.1/DEF = *Homo sapiens* PRO1854 mRNA, complete cds./FEA = mRNA/PROD = PRO1854/DB_XREF = gi: 6650803 /UG = Hs.136570 PRO1854 protein/FL = gb: AF118079.1 |
| | 5.30 | Hs.306439 | | | AL122039 | MRNA; cDNA DKFZp434E0572 (from clone DKFZp434E0572) |
| | 5.30 | Hs.437104 | | | AW139588 | Transcribed sequences |
| | 5.30 | Hs.13818 | | | BE675486 | Transcribed sequences |
| | 5.29 | Hs.55378 | | | AI123586 | Transcribed sequences |
| | 5.29 | Hs.105268 | | | BC043176 | CDNA clone IMAGE: 5287441, partial cds |
| | 5.27 | Hs.133160 | 401237 | | H14782 | Clone IMAGE: 5742072, mRNA |
| | 5.25 | Hs.225986 | | | AL050145 | MRNA; cDNA DKFZp586C2020 (from clone DKFZp586C2020) |
| | 5.25 | Hs.416521 | | | BC039533 | Clone IMAGE: 5743964, mRNA |
| | 5.25 | Hs.178803 | | | AA913383 | Transcribed sequences |
| | 5.25 | Hs.88156 | | | BF207870 | Transcribed sequences |
| | 5.25 | Hs.406781 | | | AL137325 | MRNA; cDNA DKFZp434M0835 (from clone DKFZp434M0835) |
| | 5.23 | Hs.355404 | | | AW590614 | Transcribed sequences |
| | 5.22 | Hs.252588 | | | AL359626 | MRNA; cDNA DKFZp564F172 (from clone DKFZp564F172) |
| | 5.21 | Hs.126895 | | | AA932539 | Transcribed sequences |
| | 5.21 | Hs.291564 | | | BE467383 | Transcribed sequence with moderate similarity to protein sp: P39194 (*H. sapiens*) ALU7_HUMAN Alu subfamily SQ sequence contamination warning entry |
| | 5.21 | Hs.197745 | | | AI660254 | Transcribed sequences |
| | 5.21 | Hs.28540 | | | AL050204 | MRNA; cDNA DKFZp586F1223 (from clone DKFZp586F1223) |
| | 5.20 | Hs.400256 | | | AW162768 | CDNA FLJ11478 fis, clone HEMBA1001781 |
| | 5.18 | Hs.272198 | | | AK000798 | CDNA FLJ20791 fis, clone COL01392 |
| | 5.18 | | | | U54734 | gb: U54734.1/DB_XREF = gi: 2724997/TID = Hs2.384853.1/CNT = 1 /FEA = mRNA/TIER = ConsEnd/STK = 1/UG = Hs.384853 /UG_TITLE = Human clone TM029 mRNA sequence./DEF = Human clone TM029 mRNA sequence. |
| | 5.16 | | | | AF143866 | gb: AF143866.1/DB_XREF = gi: 4895008/TID = Hs2.407308.1 /CNT = 2/FEA = mRNA/TIER = ConsEnd/STK = 0/UG = Hs.407308 /UG_TITLE = *Homo sapiens* clone IMAGE: 110987 mRNA sequence /DEF = *Homo sapiens* clone IMAGE: 110987 mRNA sequence. |
| | 5.15 | Hs.252924 | | | AA883831 | Transcribed sequences |
| | 5.14 | Hs.282340 | | | AV646408 | Transcribed sequences |
| | 5.14 | Hs.174067 | | | AI401627 | Transcribed sequences |
| | 5.13 | Hs.439326 | | | AU145365 | CDNA FLJ11662 fis, clone HEMBA1004629 |
| | 5.12 | Hs.43744 | | | AW290940 | CDNA FLJ35131 fis, clone PLACE6008824 |
| | 5.11 | Hs.308017 | | | AI125337 | CDNA FLJ36973 fis, clone BRACE2006249 |
| | 5.11 | Hs.375788 | | | AL713719 | MRNA; cDNA DKFZp667K1916 (from clone DKFZp667K1916) |
| | 5.09 | | | | X79200 | Consensus includes gb: X79200.1/DEF = *Homo spaiens* mRNA for SYT-SSX protein./FEA = mRNA/PROD = SYT-SSX protein /DB_XREF = gi: 531107/UG = Hs.289105 synovial sarcoma, X breakpoint 2 |
| | 5.08 | Hs.376811 | | | AL833811 | MRNA; cDNA DKFZp564G203 (from clone DKFZp564G203) |
| | 5.08 | Hs.531959 | | | BC040680 | Clone IMAGE: 4817893, mRNA |
| | 5.08 | | | | AK024527 | gb: AK024527.1/DB_XREF = gi: 10436829/TID = Hs2.306684.1 /CNT = 1/FEA = mRNA/TIER = ConsEnd/STK = 0/UG = Hs.306684 /UG_TITLE = *Homo sapiens* cDNA: FLJ20874 fis, clone ADKA02818./DEF = *Homo sapiens* cDNA: FLJ20874 fis, clone ADKA02818. |
| | 5.07 | Hs.385644 | | | BC023608 | CDNA clone IMAGE: 4639754, partial cds |
| | 5.06 | Hs.493477 | | | AW301393 | CDNA FLJ10263 fis, clone HEMBB1000991 |
| | 5.05 | Hs.445316 | | | BF509230 | Transcribed sequences |
| | 5.05 | Hs.434344 | | | BC041884 | Clone IMAGE: 5298352, mRNA |
| | 5.02 | Hs.274593 | | | AL162033 | MRNA; cDNA DKFZp434F1872 (from clone DKFZp434F1872) |
| | 5.02 | Hs.531897 | | | AV700891 | Transcribed sequences |
| | 5.01 | Hs.282377 | | | AV647958 | Transcribed sequences |
| | 5.01 | Hs.144510 | | | BF110426 | Transcribed sequences |
| | 5.00 | | | | AL834280 | gb: AL834280.1/DB_XREF = gi: 21739855/TID = Hs2.407106.1 /CNT = 1/FEA = mRNA/TIER = ConsEnd/STK = 0/UG = Hs.407106 /UG_TITLE = *Homo sapiens* mRNA; cDNA DKFZp547J0114 (from clone DKFZp547J0114)/DEF = *Homo sapiens* mRNA; cDNA DKFZp547J0114 (from clone DKFZp547J0114). |

Figure 34:
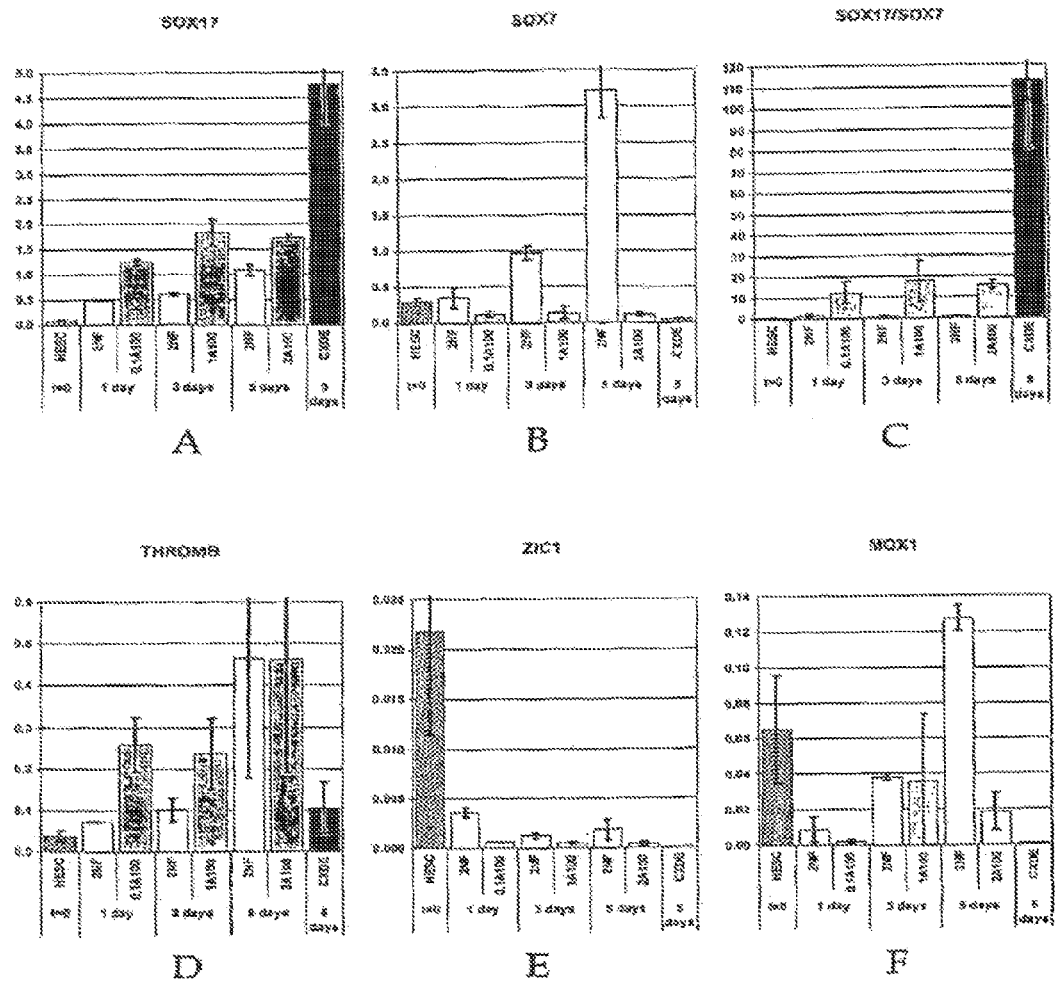
FIGS. 34A-M are bar charts showing the expression patterns of marker genes that can be used to identify definitive endoderm cells. The expression analysis of definitive endoderm markers, FGF17, VWF, CALCR, FOXQ1, CMKOR1 and CRIP1 is shown in panels G-L, respectively. The expression analysis of previously described lineage marking genes, SOX17, SOX7, SOX17/SOX7, TM, ZIC1, and MOX1 is shown in panels A-F, respectively. Panel M shows the expression analysis of CXCR4. With respect to each of panels A-M, the column labeled hESC indicates gene expression from purified human embryonic stem cells; 2NF indicates cells treated with 2% FBS, no activin addition; 0.1A100 indicates cells treated with 0.1% FBS, 100 ng/ml activin A; 1A100 indicates cells treated with 1% FBS, 100 ng/ml activin A; and 2A100 indicates cells treated with 2% FBS, 100 ng/ml activin A.
Figure 34:
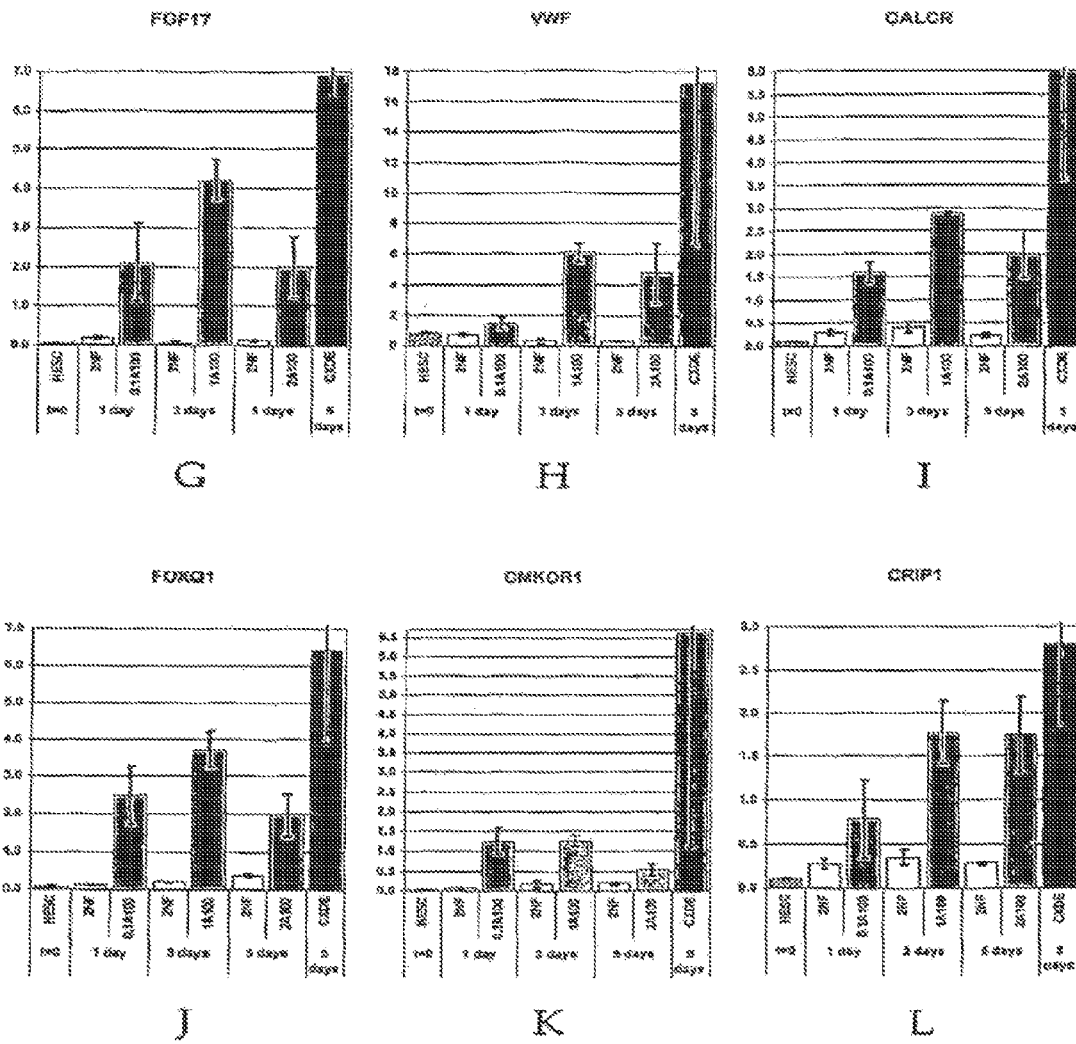
Figure 34:
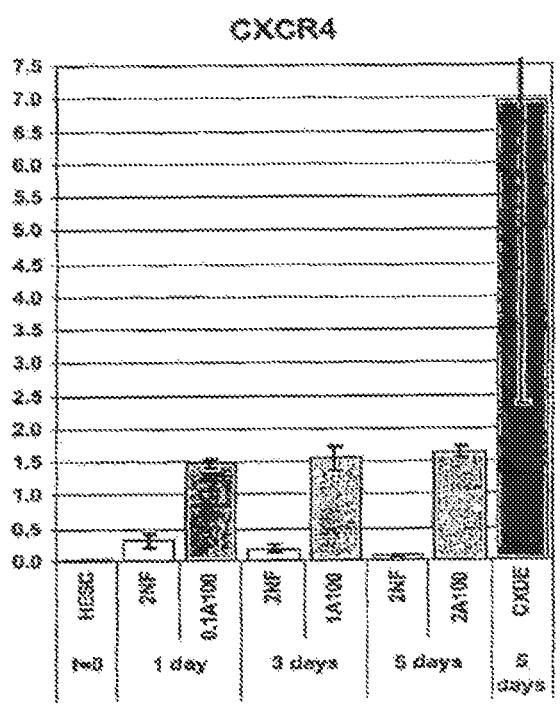

Increased expression of these cell surface markers in definitive endoderm cells as compared to hESCs was confirmed with real time QPCR as previously described. FIGS. 34A-M show the results of QPCR for certain markers. Results are displayed for cell cultures analyzed 1, 3 and 5 days after the addition of 100 ng/ml activin A, CXCR4-expressing definitive endoderm cells purified at the end of the five day differentiation procedure (CXDE), and in purified human embryonic stem cells (HESC). A comparison of FIGS. 34C and G-M demonstrates that the six marker genes, FGF17, VWF, CALCR, FOXQ1, CMKOR1 and CRIP1, exhibit an expression pattern that is almost identical to each other and which is also identical to the pattern of expression of CXCR4 and SOX17/SOX7. As described previously, SOX17 is expressed in both the definitive endoderm as well as in the SOX7-expressing extra-embryonic endoderm. Since SOX7 is not expressed in the definitive endoderm, the ratio of SOX17/SOX7 provides a reliable estimate of definitive endoderm contribution to the SOX17 expression witnessed in the population as a whole. The similarity of panels G-L and M to panel C indicates that FGF17, VWF, CALCR, FOXQ1, CMKOR1 and CRIP1 are likely markers of definitive endoderm and that they are not significantly expressed in extra-embryonic endoderm cells. It will be appreciated that the Q-PCR results described herein can be further confirmed by ICC.

Table 4 describes a subset of genes included in Table 3 that exhibit over 30-fold upward change in expression in definitive endoderm cells as compared to hESCs. Select genes were assayed by Q-PCR, as described above, to verify the gene expression changes found on the gene chip and also to investigate the expression pattern of the genes during a during a time course of hESC differentiation as discussed below. Q-PCR data is presented in the column entitled "QPCR Fold Change," where applicable.

TABLE 4

Highly up-regulated markers in definitive endoderm

| Gene_Symbol | Raw Fold Change | QPCR Fold Change | Unigene | LocusLink | OMIM | SeqDerivedFrom | Gene Descriptor |
| --- | --- | --- | --- | --- | --- | --- | --- |
| AGPAT3 | 53.81 | | Hs.443657 | 56894 | | AI337300 | 1-acylglycerol-3-phosphate O-acyltransferase 3 |
| APOA2 | 33.51 | 47 | Hs.237658 | 336 | 107670 | NM_001643 | apolipoprotein A-II |
| C20orf56 | 36.01 | | | 140828 | | AL121722 | chromosome 20 open reading frame 56 |
| C21orf129 | 77.87 | | Hs.350679 | 150135 | | NM_152506 | chromosome 21 open reading frame 129 |
| CALCR | 38.31 | | Hs.640 | 799 | 114131 | NM_001742 | calcitonin receptor |
| CCL2 | 111.46 | | Hs.303649 | 6347 | 158105 | S69738 | chemokine (C-C motif) ligand 2 |
| CER1 | 33.04 | | Hs.248204 | 9350 | 603777 | NM_005454 | cerberus 1 homolog, cysteine knot superfamily (*Xenopus laevis*) |
| CMKOR1 | 53.39 | 213 | Hs.231853 | 57007 | | AI817041 | chemokine orphan receptor 1 |
| CRIP1 | 50.56 | 28 | | 1396 | 123875 | NM_001311 | cysteine-rich protein 1 (intestinal) |
| CXCR4 | 55.31 | 289 | Hs.421986 | 7852 | 162643 | AJ224869 | chemokine (C-X-C motif) receptor 4 |
| CXorf1 | 54.35 | | Hs.106688 | 9142 | | NM_004709 | chromosome X open reading frame 1 |
| DIO3 | 33.07 | | Hs.49322 | 1735 | 601038 | NM_001362 | deiodinase, iodothyronine, type III |
| DIO3OS | 59.10 | | Hs.406958 | 64150 | 608523 | AF305836 | deiodinase, iodothyronine, type III opposite strand |
| EB-1 | 162.04 | | Hs.372732 | 56899 | 607815 | AW005572 | E2a-Pbx1-associated protein |
| EHHADH | 85.52 | | Hs.432443 | 1962 | 607037 | NM_001966 | enoyl-Coenzyme A, hydratase/3-hydroxyacyl Coenzyme A dehydrogenase |
| ELOVL2 | 70.71 | | Hs.246107 | 54898 | | BF508639 | elongation of very long chain fatty acids (FEN1/Elo2, SUR4/Elo3, yeast)-like 2 |
| EPSTI1 | 34.25 | | Hs.343800 | 94240 | 607441 | AA633203 | epithelial stromal interaction 1 (breast) |
| FGF17 | 107.07 | 166 | Hs.248192 | 8822 | 603725 | NM_003867 | fibroblast growth factor 17 |
| FLJ10970 | 50.86 | | Hs.173233 | 55273 | | NM_018286 | hypothetical protein FLJ10970 |
| FLJ21195 | 83.56 | | Hs.207407 | 64388 | | BF064262 | protein related to DAN and cerberus |
| FLJ22471 | 34.33 | | Hs.387266 | 80212 | | NM_025140 | limkain beta 2 |
| FLJ23514 | 46.65 | | Hs.144913 | 60494 | | NM_021827 | hypothetical protein FLJ23514 |
| FOXA2 | 252.32 | | Hs.155651 | 3170 | 600288 | AB028021 | forkhead box A2 |
| FOXQ1 | 43.02 | 85 | Hs.297452 | 94234 | | AI676059 | forkhead box Q1 |
| GATA4 | 44.12 | 140 | Hs.243987 | 2626 | 600576 | AV700724 | GATA binding protein 4 |
| GPR37 | 33.44 | | Hs.406094 | 2861 | 602583 | U87460 | G protein-coupled receptor 37 (endothelin receptor type B-like) |
| GSC | 524.27 | 596 | Hs.440438 | 145258 | 138890 | AY177407 | goosecoid |
| LOC283537 | 68.29 | | Hs.117167 | 283537 | | AK026720 | hypothetical protein LOC283537 |
| MYL7 | 38.38 | | Hs.75636 | 58498 | | NM_021223 | myosin, light polypeptide 7, regulatory |
| NPPB | 35.43 | | Hs.219140 | 4879 | 600295 | NM_002521 | natriuretic peptide precursor B |
| NTN4 | 57.13 | | Hs.102541 | 59277 | | AF278532 | netrin 4 |
| PRSS2 | 205.03 | | Hs.511525 | 5645 | 601564 | NM_002771 | protease, serine, 2 (trypsin 2) |
| RTN4RL1 | 60.66 | | Hs.22917 | 146760 | | H06251 | reticulon 4 receptor-like 1 |
| SEMA3E | 135.96 | | Hs.528721 | 9723 | | NM_012431 | sema domain, immunoglobulin domain (Ig), short basic domain, secreted, (semaphorin) 3E |
| SIAT8D | 161.93 | | Hs.308628 | 7903 | 602547 | AI422986 | sialyltransferase 8D (alpha-2, 8-polysialyltransferase) |
| SLC5A9 | 79.96 | | Hs.37890 | 200010 | | AI767388 | solute carrier family 5 (sodium/glucose cotransporter), member 9 |
| SLC40A1 | 44.06 | | Hs.409875 | 30061 | 604653 | AL136944 | solute carrier family 40 (iron-regulated transporter), member 1 |
| SOX17 | 30.20 | 61 | Hs.98367 | 64321 | | NM_022454 | SRY (sex determining region Y)-box 17 |
| SPOCK3 | 62.58 | | Hs.159425 | 50859 | 607989 | AI808090 | sparc/osteonectin, cwcv and kazal-like domains proteoglycan (testican) 3 |
| TMOD1 | 74.09 | | Hs.374849 | 7111 | 190930 | NM_003275 | tropomodulin 1 |

TABLE 4-continued

Highly up-regulated markers in definitive endoderm

| Gene_Symbol | Raw Fold Change | QPCR Fold Change | Unigene | LocusLink | OMIM | SeqDerivedFrom | Gene Descriptor |
|---|---|---|---|---|---|---|---|
| TRPA1 | 103.37 | | Hs.137674 | 8989 | 604775 | AA502609 | transient receptor potential cation channel, subfamily A, member 1 |
| TTN | 76.16 | | Hs.434384 | 7273 | 188840 | NM_003319 | titin |
| | 116.51 | | Hs.11873 | | | AW167727 | Transcribed sequences |
| | 66.25 | | Hs.177968 | | | AI821586 | Transcribed sequence with weak similarity to protein ref: NP_066928.1 (*H. sapiens*) phospholipid scramblase 1 [*Homo sapiens*] |
| | 54.91 | | Hs.160418 | | | BF941609 | Transcribed sequences |
| | 52.28 | | Hs.444751 | | | AI916532 | Transcribed sequences |
| | 50.21 | | Hs.390285 | 401221 | | BC034407 | CDNA clone IMAGE: 5268504, partial cds |
| | 40.16 | | Hs.514745 | | | N63706 | CDNA FLJ41084 fis, clone ADRGL2010974 |
| | 30.05 | | Hs.7888 | | | AW772192 | CDNA FLJ44318 fis, clone TRACH3000780 |

Gene products that appear to be localized to the cell surface are described in Table 5. Localization of markers at the cell surface is useful for applications such as enrichment, isolation and/or purification of definitive endoderm cells. Each of the markers described in Table 5 include over a 30-fold increase in expression level in definitive endoderm as compared to hESCs.

DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 is measured by Q-PCR.

TABLE 5

Up-regulated cell Surface markers in definitive endoderm

| Gene_Symbol | Raw Fold Change | QPCR Fold Change | Unigene | LocusLink | OMIM | SeqDerivedFrom | Gene Descriptor |
|---|---|---|---|---|---|---|---|
| CALCR | 38.31 | | Hs.640 | 799 | 114131 | NM_001742 | calcitonin receptor |
| CMKOR1 | 53.39 | 213 | Hs.231853 | 57007 | | AI817041 | chemokine orphan receptor 1 |
| CXCR4 | 55.31 | 289 | Hs.421986 | 7852 | 162643 | AJ224869 | chemokine (C-X-C motif) receptor 4 |
| GPR37 | 33.44 | | Hs.406094 | 2861 | 602583 | U87460 | G protein-coupled receptor 37 (endothelin receptor type B-like) |
| NTN4 | 57.13 | | Hs.102541 | 59277 | | AF278532 | netrin 4 |
| RTN4RL1 | 60.66 | | Hs.22917 | 146760 | | H06251 | reticulon 4 receptor-like 1 |
| SEMA3E | 135.96 | | Hs.528721 | 9723 | | NM_012431 | sema domain, immunoglobulin domain (Ig), short basic domain, secreted, (semaphorin) 3E |
| SLC5A9 | 79.96 | | Hs.37890 | 200010 | | AI767388 | solute carrier family 5 (sodium/glucose cotransporter), member 9 |
| SLC40A1 | 44.06 | | Hs.409875 | 30061 | 604653 | AL136944 | solute carrier family 40 (iron-regulated transporter), member 1 |
| TRPA1 | 103.37 | | Hs.137674 | 8989 | 604775 | AA502609 | transient receptor potential cation channel, subfamily A, member 1 |

EXAMPLE 12

Validation of Definitive Endoderm Markers

Using the methods, such as those described in the above Examples, hESCs are differentiated to produce definitive endoderm. In particular, to increase the yield and purity of definitive endoderm in differentiating cell cultures, the serum concentration of the medium is controlled as follows: 0% FBS on day 1, 0.2% FBS on day 2 and 2.0% FBS on days 3-6. Differentiating cell populations are grown in the presence of 100 ng/ml activin A, whereas non-differentiating control populations are grown in the absence of activin A. Human embryonic cell cultures grown in the presence or absence of activin A and in either 2% serum or 10% serum over the entire 6 day differentiation period are also monitored. Daily samples of each culture are withdrawn and the amount of mRNA transcript produced for each of the markers AGPAT3, APOA2, C20orf56, C21orf129, CALCR, CCL2, CER1, CMKOR1, CRIP1, CXCR4, CXorf1, DIO3, In general, expression levels of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 are high in cultures treated with 100 ng/ml activin A and low in those which do not receive exogenous activin A. Additionally, among activin A treated cultures, expression levels of AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 are highest when FBS concentration is lowest. A decrease in AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 expression levels is seen in the 10% FBS cultures as compared to such expression levels in low serum FSB cultures.

Additionally, the expression profile of AGPAT3, APOA2, C20orf56, C21orf129, CALCR, CCL2, CER1, CMKOR1, CRIP1, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SPOCK3, TMOD1, TRPA1, TTN, AW166727, AI821586, BF941609, AI916532, BC034407, N63706 and AW772192 is consistent with the expression profile of SOX17 and/or CXCR4 under similar conditions over the differentiation period.

The markers AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192 are not substantially expressed in cultures that are allowed to differentiate to mesoderm, ectoderm, or extra-embryonic endoderm.

EXAMPLE 13

Isolation of Definitive Endoderm Cells Using Markers Selected from Table 5

This Example demonstrates the isolation of definitive endoderm cells positive for AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and/or AW772192 in a cell culture by using a cell surface marker selected from CALCR, CMKOR1, CXCR4, GPR37, NTN4, RTN4RL1, SEMA3E, SLC40A1, SLC5A9 and TRPA1.

Using methods, such as those described in the above Examples, hESCs are differentiated to produce definitive endoderm. In particular, to increase yield and purity of definitive endoderm in differentiating cell cultures, the serum concentration of the medium is controlled as follows: 0% FBS on day 1, 0.2% FBS on day 2 and 2.0% FBS on days 3-6. Differentiating cell populations are grown in the presence of 100 ng/ml, 50 ng/ml or 25 ng/ml activin A, whereas non-differentiating control populations are grown in the absence of activin A.

An appropriate amount of labeled antibody that binds to one of the markers listed above is added to a sample of each culture and labeling proceeds on ice. Cells are washed by adding PBS and pelleted. A second wash with buffer is completed then cells are resuspended. Secondary antibody (FITC conjugated secondary antibody is added and allowed to label for about 30 minutes followed by two washes in buffer as above. Cells are resuspended and analyzed and sorted using a FACS. Cells are collected directly into RLT lysis buffer for subsequent isolation of total RNA for gene expression analysis by real-time quantitative PCR.

The number of cells positive for AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and/or AW772192 increase significantly as the dose of activin A is increased in the differentiation culture media. Isolated cell populations are analyzed as described in the Example below.

EXAMPLE 14

Quantitation of Isolated Definitive Endoderm Cells

To quantitate the proportion of definitive endoderm cells present in a cell culture or cell population, cells expressing a cell surface marker selected from CALCR, CMKOR1, CXCR4, GPR37, NTN4, RTN4RL1, SEMA3E, SLC40A1, SLC5A9 and TRPA1 and other markers of definitive endoderm are analyzed by FACS.

Using the methods such as those described in the above Examples, hESCs are differentiated to produce definitive endoderm. In particular, to increase yield and purity of definitive endoderm in differentiating cell cultures, the serum concentration of the medium is controlled as follows: 0% FBS on day 1, 0.2% FBS on day 2 and 2.0% FBS on days 3-6. Differentiated cultures are sorted by FACS using cell surface epitopes, E-Cadherin, Thrombomodulin and one of CALCR, CMKOR1, CXCR4, GPR37, NTN4, RTN4RL1, SEMA3E, SLC40A1, SLC5A9 and TRPA1 as described above. Sorted cell populations are then analyzed by Q-PCR to determine relative expression levels of markers for definitive and extraembryonic endoderm as well as other cell types. Use of any one of the above cell surface markers for isolation results in populations of definitive endoderm cells that are >98% pure.

EXAMPLE 15

Transplantation of Human Definitive Endoderm Cells Under Mouse Kidney Capsule

To demonstrate that the human definitive endoderm cells produced using the methods described herein are capable of responding to differentiation factors so as to produce cells that are derived from the gut tube, such human definitive endoderm cells were subjected to an in vivo differentiation protocol.

Human definitive endoderm cells were produced as described in the foregoing Examples. Such cells were harvested and transplanted under the kidney capsule of immunocompromised mice using standard procedures. After three weeks, the mice were sacrificed and the transplanted tissue was removed, sectioned and subjected to histological and immunocytochemical analysis.

Figure 35:
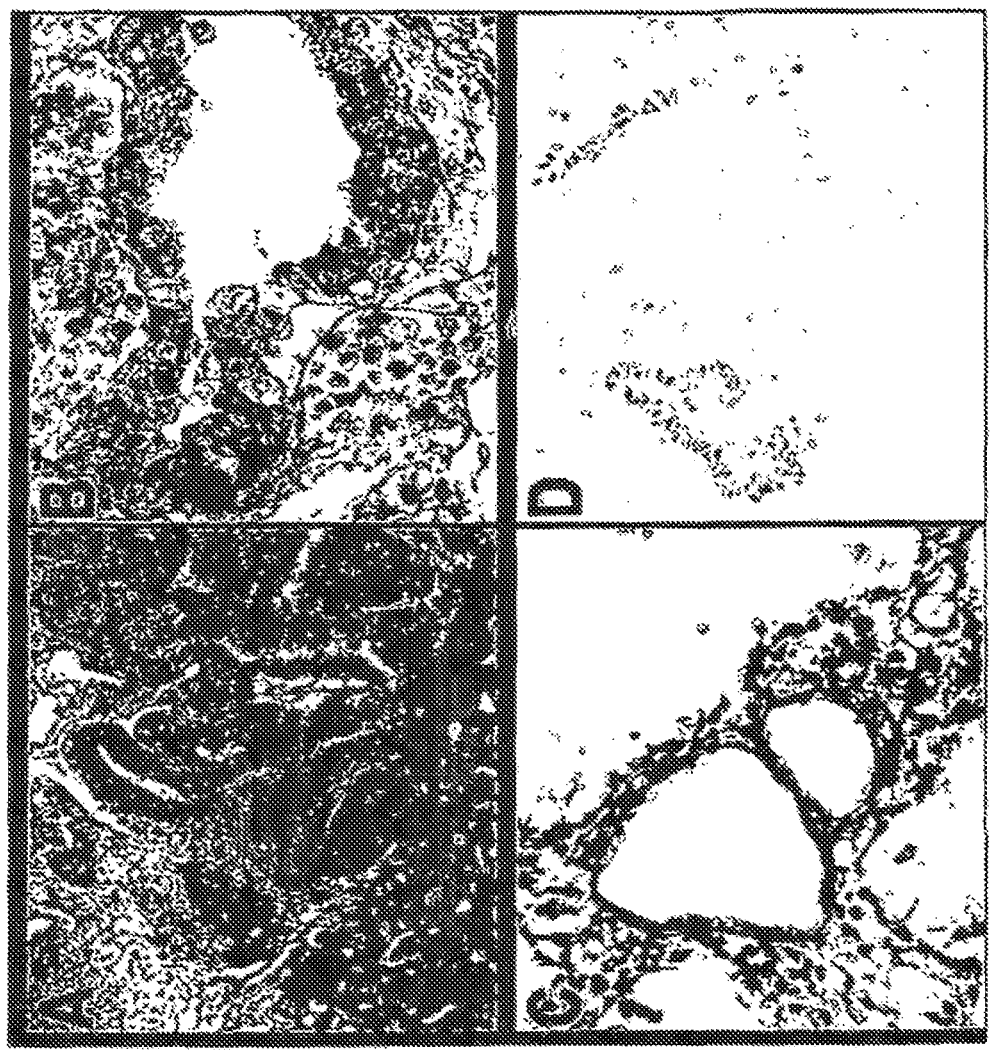
FIGS. 35A-D show the in vivo differentiation of definitive endoderm cells that are transplanted under the kidney capsule of immunocompromised mice. Panels: A—hetatoxylin-eosin staining showing gut-tube-like structures; B—antibody immunoreactivity against hepatocyte specific antigen (liver); C—antibody immunoreactivity against villin (intestine); and D—antibody immunoreactivity against CDX2 (intestine).

FIGS. 35A-D show that after three weeks post-transplantation, the human definitive endoderm cells differentiated into cells and cellular structures derived from the gut tube. In particular, FIG. 35A shows hematoxylin and eosin stained sections of transplanted human definitive endoderm tissue that has differentiated into gut-tube-like structures. FIG. 35B shows a transplanted human definitive endoderm section immunostained with antibody to hepatocyte specific antigen (HSA). This result indicates that the human definitive endoderm cells are capable of differentiating into liver or liver precursor cells. FIGS. 35C and 35D show a transplanted human definitive endoderm section immunostained with antibody to villin and antibody to caudal type homeobox transcription factor 2 (CDX2), respectively. These results indicate that the human definitive endoderm cells are capable of differentiating into intestinal cells or intestinal cell precursors.

EXAMPLE 16

Identification of Differentiation Factors Capable of Promoting the Differentiation of Human Definitive Endoderm Cells In Vitro To exemplify the differentiation factor screening methods described herein, populations of human definitive endoderm cells produced using the methods described herein were separately provided with several candidate differentiation factors while determining the normalized expression levels of certain marker gene products at various time points.

Human definitive endoderm cells were produced as described in the foregoing Examples. In brief, hESCs cells were grown in the presence of 100 ng/ml activin A in low serum RPMI medium for four days, wherein the fetal bovine serum (FBS) concentration on day 1 was 0%, on day 2 was 0.2% and on days 3-4 was 2%. After formation of definitive endoderm, beginning on day 5 and ending on day 10, cell populations maintained in individual plates in RPMI containing 0.2% FBS were treated with one of: Wnt3A at 20 ng/ml, FGF2 at 5 ng/ml or FGF2 at 100 ng/ml. The expression of marker gene products for albumin, PROX1 and TITF1 were quantitated using Q-PCR.

Figure 36:
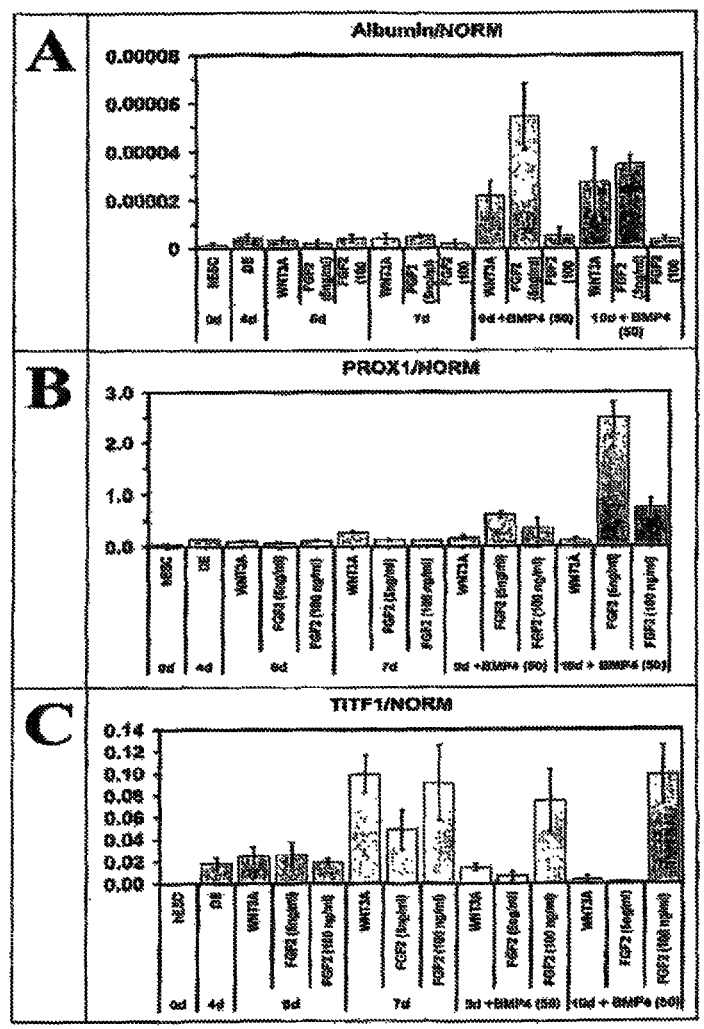
FIGS. 36A-C are charts showing the normalized relative expression levels of markers for liver (albumin and PROX1) and lung (TITF1) tissues in cells contacted with Wnt3A at 20 ng/ml, FGF2 at 5 ng/ml or FGF2 at 100 ng/ml on days 5-10. DE refers to definitive endoderm. Panels: A—albumin, B—PROX1, and C—TITF1.

FIG. 36A shows that expression of the albumin gene product (a marker for liver precursors and liver cells) substantially increased on days 9 and 10 in response to FGF2 at 5 ng/ml as compared to expression in definitive endoderm cells on day 4 prior to treatment with this differentiation factor. Expression of the albumin gene product was also increased in response to 20 ng/ml Wnt3A on days 9 and 10 as compared to expression in untreated definitive endoderm cells, however, the increase was not as large as that observed for the 5 ng/ml FGF2 treatment. Of particular significance is the observation that the expression of the albumin gene product was not increased on days 9 and 10 in response to FGF2 at 100 ng/ml as compared to expression in definitive endoderm cells on day 4. Similar results were seen with the PROX1 marker (a second marker for liver precursors and liver cells) as shown in FIG. 36B. FIG. 36C shows that in cell populations provided with 100 ng/ml FGF2, expression of the TITF1 marker gene substantially increased on days 7, 9 and 10 as compared to expression in definitive endoderm cells on day 4 prior to treatment with this differentiation factor, but FGF2 at 5 ng/ml had very little effect on expression of this gene product as compared to untreated definitive endoderm. TITF1 is a marker expressed in developing lung and thyroid cells. Taken together, the results shown in FIGS. 36A-C indicate that the concentration at which the candidate differentiation factor is provided to the cell population can affect the differentiation fate of definitive endoderm cells in vitro.

The methods, compositions, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

REFERENCES

Numerous literature and patent references have been cited in the present patent application. Each and every reference that is cited in this patent application is incorporated by reference herein in its entirety.

For some references, the complete citation is in the body of the text. For other references the citation in the body of the text is by author and year, the complete citation being as follows:

Alexander, J., Rothenberg, M., Henry, G. L., and Stainier, D. Y. (1999). Casanova plays an early and essential role in endoderm formation in zebrafish. Dev Biol 215, 343-357.

Alexander, J., and Stainier, D. Y. (1999). A molecular pathway leading to endoderm formation in zebrafish. Curr Biol 9, 1147-1157.

Aoki, T. O., Mathieu, J., Saint-Etienne, L., Rebagliati, M. R., Peyrieras, N., and Rosa, F. M. (2002). Regulation of nodal signalling and mesendoderm formation by TARAM-A, a TGFbeta-related type I receptor. Dev Biol 241, 273-288.

Ausubel et al., (1997), Current Protocols of Molecular Biology, John Wiley and Sons, Hoboken, N.J.

Beck, S., Le Good, J. A., Guzman, M., Ben Haim, N., Roy, K., Beermann, F., and Constam, D. B. (2002). Extra-embryonic proteases regulate Nodal signalling during gastrulation. Nat Cell Biol 4, 981-985.

Beddington, R. S., Rashbass, P., and Wilson, V. (1992). Brachyury-a gene affecting mouse gastrulation and early organogenesis. Dev Suppl, 157-165.

Bongso, A., Fong, C. Y., Ng, S. C., and Ratnam, S. (1994). Isolation and culture of inner cell mass cells from human blastocysts. Hum Reprod 9, 2110-2117.

Chang, H., Brown, C. W., and Matzuk, M. M. (2002). Genetic analysis of the mammalian transforming growth factor-beta superfamily. Endocr Rev 23, 787-823.

Conlon, F. L., Lyons, K. M., Takaesu, N., Barth, K. S., Kispert, A., Herrmann, B., and Robertson, E. J. (1994). A primary requirement for nodal in the formation and maintenance of the primitive streak in the mouse. Development 120, 1919-1928.

Dougan, S. T., Warga, R. M., Kane, D. A., Schier, A. F., and Talbot, W. S. (2003). The role of the zebrafish nodal-related genes squint and cyclops in patterning of mesendoderm. Development 130, 1837-1851.

Feldman, B., Gates, M. A., Egan, E. S., Dougan, S. T., Rennebeck, G., Sirotkin, H. I., Schier, A. F., and Talbot, W. S. (1998). Zebrafish organizer development and germ-layer formation require nodal-related signals. Nature 395, 181-185.

Feng, Y., Broder, C. C., Kennedy, P. E., and Berger, E. A. (1996). HIV-1 entry cofactor: functional cDNA cloning of a seven-transmembrane, G protein-coupled receptor. Science 272, 872-877.

Futaki, S., Hayashi, Y., Yamashita, M., Yagi, K., Bono, H., Hayashizaki, Y., Okazaki, Y., and Sekiguchi, K. (2003). Molecular basis of constitutive production of basement membrane components: Gene expression profiles of engelbreth-holm-swarm tumor and F9 embryonal carcinoma cells. J Biol Chem.

Grapin-Botton, A., and Melton, D. A. (2000). Endoderm development: from patterning to organogenesis. Trends Genet 16, 124-130.

Harris, T. M., and Childs, G. (2002). Global gene expression patterns during differentiation of F9 embryonal carcinoma cells into parietal endoderm. Funct Integr Genomics 2, 105-119.

Hogan, B. L. (1996). Bone morphogenetic proteins in development. Curr Opin Genet Dev 6, 432-438.

Hogan, B. L. (1997). Pluripotent embryonic cells and methods of making same (U.S.A., Vanderbilt University).

Howe, C. C., Overton, G. C., Sawicki, J., Solter, D., Stein, P., and Strickland, S. (1988). Expression of SPARC/osteonectin transcript in murine embryos and gonads. Differentiation 37, 20-25.

Hudson, C., Clements, D., Friday, R. V., Stott, D., and Woodland, H. R. (1997). Xsox17alpha and -beta mediate endoderm formation in Xenopus. Cell 91, 397-405.

Imada, M., Imada, S., Iwasaki, H., Kume, A., Yamaguchi, H., and Moore, E. E. (1987). Fetomodulin: marker surface protein of fetal development which is modulatable by cyclic AMP. Dev Biol 122, 483-491.

Kanai-Azuma, M., Kanai, Y., Gad, J. M., Tajima, Y., Taya, C., Kurohmaru, M., Sanai, Y., Yonekawa, H., Yazaki, K., Tam, P. P., and Hayashi, Y. (2002). Depletion of definitive gut endoderm in Sox17-null mutant mice. Development 129, 2367-2379.

Katoh, M. (2002). Expression of human Sox17 in normal tissues and tumors. Int J Mol Med 9, 363-368.

Kikuchi, Y., Agathon, A., Alexander, J., Thisse, C., Waldron, S., Yelon, D., Thisse, B., and Stainier, D. Y. (2001). casanova encodes a novel Sox-related protein necessary and sufficient for early endoderm formation in zebrafish. Genes Dev 15, 1493-1505.

Kim, C. H., and Broxmeyer, H. E. (1999). Chemokines: signal lamps for trafficking of T and B cells for development and effector function. J Leukoc Biol 65, 6-15.

Kimelinan, D., and Griffin, K. J. (2000). Vertebrate mesendoderm induction and patterning. Curr Opin Genet Dev 10, 350-356.

Kubo A, Shinozaki K, Shannon J M, Kouskoff V, Kennedy M, Woo S, Fehling H J, Keller G. (2004) Development of definitive endoderm from embryonic stem cells in culture. Development. 131, 1651-62.

Kumar, A., Novoselov, V., Celeste, A. J., Wolfman, N. M., ten Dijke, P., and Kuehn, M. R. (2001). Nodal signaling uses activin and transforming growth factor-beta receptor-regulated Smads. J Biol Chem 276, 656-661.

Labosky, P. A., Barlowo, D. P., and Hogan, B. L. (1994a). Embryonic germ cell lines and their derivation from mouse primordial germ cells. Ciba Found Symp 182, 157-168; discussion 168-178.

Labosky, P. A., Barlow, D. P., and Hogan, B. L. (1994b). Mouse embryonic germ (EG) cell lines: transmission through the germline and differences in the methylation imprint of insulin-like growth factor 2 receptor (Igf2r) gene compared with embryonic stem (ES) cell lines. Development 120, 3197-3204.

Lickert, H., Kutsch, S., Kanzler, B., Tamai, Y., Taketo, M. M., and Kemler, R. (2002). Formation of multiple hearts in mice following deletion of beta-catenin in the embryonic endoderm. Dev Cell 3, 171-181.

Lu, C. C., Brennan, J., and Robertson, E. J. (2001). From fertilization to gastrulation: axis formation in the mouse embryo. Curr Opin Genet Dev 11, 384-392.

Ma, Q., Jones, D., and Springer, T. A. (1999). The chemokine receptor CXCR4 is required for the retention of B lineage and granulocytic precursors within the bone marrow microenvironment. Immunity 10, 463-471.

Malik V and Lillehoj E (ed.), (1994), Antibody Techniques, Academic Press, Inc. Burlington, Mass.

McGrath K E, Koniski A D, Maltby K M, McGann J K, Palis J. (1999) Embryonic expression and function of the chemokine SDF-1 and its receptor, CXCR4. Dev Biol. 213, 442-56.

Miyazono, K., Kusanagi, K., and Inoue, H, (2001). Divergence and convergence of TGF-beta/BMP signaling. J Cell Physiol 187, 265-276.

Nagasawa, T., Hirota, S., Tachibana, K., Takakura, N., Nishikawa, S., Kitamura, Y., Yoshida, N., Kikutani, H., and Kishimoto, T. (1996). Defects of B-cell lymphopoiesis and bone-marrow myelopoiesis in mice lacking the CXC chemokine PBSF/SDF-1. Nature 382, 635-638.

Niwa, H. (2001). Molecular mechanism to maintain stem cell renewal of ES cells. Cell Struct Funct 26, 137-148.

Ogura, H., Aruga, J., and Mikoshiba, K. (2001). Behavioral abnormalities of Zic1 and Zic2 mutant mice: implications as models for human neurological disorders. Behav Genet 31, 317-324.

Reubinoff, B. E., Pera, M. F., Fong, C. Y., Trounson, A., and Bongso, A. (2000). Embryonic stem cell lines from human blastocysts: somatic differentiation in vitro. Nat Biotechnol 18, 399-404.

Rodaway, A., and Patient, R. (2001). Mesendoderm. an ancient germ Layer? Cell 105, 169-172.

Rodaway, A., Takeda, H., Koshida, S., Broadbent, J., Price, B., Smith, J. C., Patient, R., and Holder, N. (1999). Induction of the mesendoderm in the zebrafish germ ring by yolk cell-derived TGF-beta family signals and discrimination of mesoderm and endoderm by FGF. Development 126, 3067-3078.

Rohr, K. B., Schulte-Merker, S., and Tautz, D. (1999). Zebrafish zic1 expression in brain and somites is affected by BMP and hedgehog signalling. Mech Dev 85, 147-159.

Schier, A. F. (2003). Nodal signaling in vertebrate development. Annu Rev Cell Dev Biol 19, 589-621.

Schoenwolf, G. C., and Smith, J. L. (2000). Gastrulation and early mesodermal patterning in vertebrates. Methods Mol Biol 135, 113-125.

Shamblott, M. J., Axelman, J., Wang, S., Bugg, E. M., Littlefield, J. W., Donovan, P. J., Blumenthal, P. D., Huggins, G. R., and Gearhart, J. D. (1998). Derivation of pluripotent stem cells from cultured human primordial germ cells. Proc Natl Acad Sci USA 95, 13726-13731.

Shapiro, A. M., Lakey, J. R., Ryan, E. A., Korbutt, G. S., Toth, E., Warnock, G. L., Kneteman, N. M., and Rajotte, R. V. (2000). Islet transplantation in seven patients with type 1 diabetes mellitus using a glucocorticoid-free immunosuppressive regimen. N Engl J Med 343, 230-238.

Shapiro, A. M., Ryan, E. A., and Lakey, J. R. (2001a). Pancreatic islet transplantation in the treatment of diabetes mellitus. Best Pract Res Clin Endocrinol Metab 15, 241-264.

Shapiro, J., Ryan, E., Warnock, G. L., Kneteman, N. M., Lakey, J., Korbutt, G. S., and Rajotte, R. V. (2001b). Could fewer islet cells be transplanted in type 1 diabetes? Insulin independence should be dominant force in islet transplantation. Bmj 322, 861.

Shiozawa, M., Hiraoka, Y., Komatsu, N., Ogawa, M., Sakai, Y., and Aiso, S. (1996). Cloning and characterization of *Xenopus* laevis xSox7 cDNA. Biochim Biophys Acta 1309, 73-76.

Smith, J. (1997). Brachyury and the T-box genes. Curr Opin Genet Dev 7, 474-480.

Smith, J. C., Armes, N. A., Conlon, F. L., Tada, M., Umbhauer, M., and Weston, K. M. (1997). Upstream and downstream from Brachyury, a gene required for vertebrate mesoderm formation. Cold Spring Harb Symp Quant Biol 62, 337-346.

Takash, W., Canizares, J., Bonneaud, N., Poulat, F., Mattei, M. G., Jay, P., and Berta, P. (2001). SOX7 transcription factor: sequence, chromosomal localisation, expression, transactivation and interference with Wnt signalling. Nucleic Acids Res 29, 4274-4283.

Taniguchi, K., Hiraoka, Y., Ogawa, M., Sakai, Y., Kido, S., and Aiso, S. (1999). Isolation and characterization of a mouse SRY-related cDNA, mSox7. Biochim Biophys Acta 1445, 225-231.

Technau, U. (2001). Brachyury, the blastopore and the evolution of the mesoderm. Bioessays 23, 788-794.

Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147.

Tremblay, K. D., Hoodless, P. A., Bikoff, E. K., and Robertson, E. J. (2000). Formation of the definitive endoderm in mouse is a Smad2-dependent process. Development 127, 3079-3090.

Vandesompele, J., De Preter, K., Pattyn, F., Poppe, B., Van Roy, N., De Paepe, A., and Speleman, F. (2002). Accurate normalization of real-time quantitative RT-PCR data by geometric averaging of multiple internal control genes. Genome Biol 3, RESEARCH0034.

Varlet, I., Collignon, J., and Robertson, E. J. (1997). nodal expression in the primitive endoderm is required for specification of the anterior axis during mouse gastrulation. Development 124, 1033-1044.

Vincent, S. D., Dunn, N. R., Hayashi, S., Norris, D. P., and Robertson, E. J. (2003). Cell fate decisions within the mouse organizer are governed by graded Nodal signals. Genes Dev 17, 1646-1662.

Weiler-Guettler, H., Aird, W. C., Rayburn, H., Husain, M., and Rosenberg, R. D. (1996). Developmentally regulated gene expression of thrombomodulin in postimplantation mouse embryos. Development 122, 2271-2281.

Weiler-Guettler, H., Yu, K., Soff, G., Gudas, L. J., and Rosenberg, R. D. (1992). Thrombomodulin gene regulation by cAMP and retinoic acid in F9 embryonal carcinoma cells. Proceedings Of The National Academy Of Sciences Of The United States Of America 89, 2155-2159.

Wells, J. M., and Melton, D. A. (1999). Vertebrate endoderm development. Annu Rev Cell Dev Biol 15, 393-410.

Wells, J. M., and Melton, D. A. (2000). Early mouse endoderm is patterned by soluble factors from adjacent germ layers. Development 127, 1563-1572.

Willison, K. (1990). The mouse Brachyury gene and mesoderm formation. Trends Genet 6, 104-105.

Zhao, G. Q. (2003). Consequences of knocking out BMP signaling in the mouse. Genesis 35, 43-56.

Zhou, X., Sasaki, H., Lowe, L., Hogan, B. L., and Kuehn, M. R. (1993). Nodal is a novel TGF-beta-like gene expressed in the mouse node during gastrulation. Nature 361, 543-547.

What is claimed is:

1. An in vitro method of producing cells which express thyroid transcription factor 1 (TITF1) from mammalian definitive endoderm cells comprising the steps of:
   (i) culturing mammalian definitive endoderm cells with an effective amount of Wnt3a for at least 7 days,
   (ii) enriching for cells which express TITF1.

2. The in vitro method of claim 1, wherein step (i) further comprises providing less than 2% serum to the definitive endoderm cells.

* * * * *

SEQUENCE LISTING

```
<160> NUMBER OF SEQ ID NOS: 2

<210> SEQ ID NO 1
<211> LENGTH: 1245
<212> TYPE: DNA
<213> ORGANISM: Homo sapiens

<400> SEQUENCE: 1
atgagcagcc cggatgcggg atacgccagt gacgaccaga gccagaccca gagcgcgctg         60
cccgcggtga tggccgggct gggcccctgc ccctgggccg agtcgctgag ccccatcggg        120
gacatgaagg tgaagggcga ggcgccggcg aacagcggag caccggccgg ggccgcgggc        180
cgagccaagg gcgagtcccg tatccggcgg ccgatgaacg ctttcatggt gtgggctaag        240
gacgagcgca agcggctggc gcagcagaat ccagacctgc acaacgccga gttgagcaag        300
atgctgggca agtcgtggaa ggcgctgacg ctggcggaga agcggccctt cgtggaggag        360
gcagagcggc tgcgcgtgca gcacatgcag gaccacccca actacaagta ccggccgcgg        420
cggcgcaagc aggtgaagcg gctgaagcgg gtggagggcg gcttcctgca cggcctggct        480
gagccgcagg cggccgcgct gggccccgag ggcggccgcg tggccatgga cggcctgggc        540
ctccagttcc ccgagcaggg cttccccgcc ggcccgccgc tgctgcctcc gcacatgggc        600
ggccactacc gcgactgcca gagtctgggc gcgcctccgc tcgacggcta cccgttgccc        660
acgcccgaca cgtccccgct ggacggcgtg gaccccgacc cggctttctt cgccgcccccg       720 atgcccgggg actgcccggc ggccggcacc tacagctacg cgcaggtctc ggactacgct        780
ggccccccgg agcctcccgc cggtcccatg caccccccgac tcggcccaga gcccgcgggt        840
ccctcgattc cgggcctcct ggcgccaccc agcgcccttc acgtgtacta cggcgcgatg        900
ggctcgcccg gggcgggcgg cggcgcgcgc ttccagatgc agccgcaaca ccagcaccag        960
caccagcacc agcaccaccc cccgggcccc ggacagccgt cgcccctcc ggaggcactg       1020 ccctgccggg acggcacgga ccccagtcag cccgccgagc tcctcgggga ggtggaccgc      1080
acggaatttg aacagtatct gcacttcgtg tgcaagcctg agatgggcct ccctaccag       1140 gggcatgact ccggtgtgaa tctccccgac agccacgggg ccatttcctc ggtggtgtcc      1200
gacgccagct ccgcggtata ttactgcaac tatcctgacg tgtga                       1245

<210> SEQ ID NO 2
<211> LENGTH: 414
<212> TYPE: PRT
<213> ORGANISM: Homo sapiens

<400> SEQUENCE: 2
```

-continued

```
Met Ser Ser Pro Asp Ala Gly Tyr Ala Ser Asp Gln Ser Gln Thr
1               5                   10                  15

Gln Ser Ala Leu Pro Ala Val Met Ala Gly Leu Gly Pro Cys Pro Trp
            20                  25                  30

Ala Glu Ser Leu Ser Pro Ile Gly Asp Met Lys Val Lys Gly Glu Ala
                35                  40                  45

Pro Ala Asn Ser Gly Ala Pro Ala Gly Ala Ala Gly Arg Ala Lys Gly
    50                  55                  60

Glu Ser Arg Ile Arg Arg Pro Met Asn Ala Phe Met Val Trp Ala Lys
65                  70                  75                  80

Asp Glu Arg Lys Arg Leu Ala Gln Gln Asn Pro Asp Leu His Asn Ala
                85                  90                  95

Glu Leu Ser Lys Met Leu Gly Lys Ser Trp Lys Ala Leu Thr Leu Ala
                100                 105                 110

Glu Lys Arg Pro Phe Val Glu Glu Ala Glu Arg Leu Arg Val Gln His
            115                 120                 125

Met Gln Asp His Pro Asn Tyr Lys Tyr Arg Pro Arg Arg Arg Lys Gln
    130                 135                 140

Val Lys Arg Leu Lys Arg Val Glu Gly Gly Phe Leu His Gly Leu Ala
145                 150                 155                 160

Glu Pro Gln Ala Ala Ala Leu Gly Pro Glu Gly Gly Arg Val Ala Met
                165                 170                 175

Asp Gly Leu Gly Leu Gln Phe Pro Glu Gln Gly Phe Pro Ala Gly Pro
                180                 185                 190

Pro Leu Leu Pro Pro His Met Gly Gly His Tyr Arg Asp Cys Gln Ser
                195                 200                 205

Leu Gly Ala Pro Pro Leu Asp Gly Tyr Pro Leu Pro Thr Pro Asp Thr
    210                 215                 220

Ser Pro Leu Asp Gly Val Asp Pro Asp Pro Ala Phe Phe Ala Ala Pro
225                 230                 235                 240

Met Pro Gly Asp Cys Pro Ala Ala Gly Thr Tyr Ser Tyr Ala Gln Val
                245                 250                 255

Ser Asp Tyr Ala Gly Pro Pro Glu Pro Pro Ala Gly Pro Met His Pro
                260                 265                 270

Arg Leu Gly Pro Glu Pro Ala Gly Pro Ser Ile Pro Gly Leu Leu Ala
                275                 280                 285

Pro Pro Ser Ala Leu His Val Tyr Tyr Gly Ala Met Gly Ser Pro Gly
                290                 295                 300

Ala Gly Gly Gly Arg Gly Phe Gln Met Gln Pro Gln His Gln His Gln
305                 310                 315                 320

His Gln His Gln His Pro Pro Gly Pro Gly Gln Pro Ser Pro Pro
                325                 330                 335

Pro Glu Ala Leu Pro Cys Arg Asp Gly Thr Asp Pro Ser Gln Pro Ala
                340                 345                 350

Glu Leu Leu Gly Glu Val Asp Arg Thr Glu Phe Glu Gln Tyr Leu His
                355                 360                 365

Phe Val Cys Lys Pro Glu Met Gly Leu Pro Tyr Gln Gly His Asp Ser
                370                 375                 380

Gly Val Asn Leu Pro Asp Ser His Gly Ala Ile Ser Ser Val Val Ser
385                 390                 395                 400

Asp Ala Ser Ser Ala Val Tyr Tyr Cys Asn Tyr Pro Asp Val
                405                 410
```